US011879014B2

(12) United States Patent
Goubier et al.

(10) Patent No.: US 11,879,014 B2
(45) Date of Patent: Jan. 23, 2024

(54) METHOD OF TREATING CANCER OR DEPLETING REGULATORY T CELLS IN A SUBJECT BY ADMINISTERING A HUMAN IGG1 ANTI-CD25 ANTIBODY

(71) Applicants: Tusk Therapeutics Ltd., Hertfordshire (GB); Cancer Research Technology Limited, London (GB)

(72) Inventors: Anne Goubier, Hertfordshire (GB); Josephine Salimu, Hertfordshire (GB); Kevin Moulder, Hertfordshire (GB); Beatriz Goyenechea Corzo, Hertfordshire (GB); Pascal Merchiers, Hertfordshire (GB); Sergio Quezada, London (GB); Karl Peggs, London (GB); Frederick Arce Vargas, London (GB); Isabelle Solomon, London (GB)

(73) Assignees: Tusk Therapeutics Ltd., Hertfordshire (GB); Cancer Research Technology Limited, London (GB)

( * ) Notice: Subject to any disclaimer, the term of this patent is extended or adjusted under 35 U.S.C. 154(b) by 116 days.

(21) Appl. No.: 16/494,962

(22) PCT Filed: Mar. 3, 2018

(86) PCT No.: PCT/EP2018/056312
§ 371 (c)(1),
(2) Date: Sep. 17, 2019

(87) PCT Pub. No.: WO2018/167104
PCT Pub. Date: Sep. 20, 2018

(65) Prior Publication Data
US 2020/0010554 A1 Jan. 9, 2020

(30) Foreign Application Priority Data

Mar. 17, 2017 (EP) ..................................... 17161717
Jul. 6, 2017 (GB) ..................................... 1710879
Sep. 7, 2017 (GB) ..................................... 1714429

(51) Int. Cl.
*C07K 16/28* (2006.01)
*A61K 39/00* (2006.01)
*C07K 14/55* (2006.01)
*A61K 45/06* (2006.01)

(52) U.S. Cl.
CPC .......... *C07K 16/2866* (2013.01); *C07K 14/55* (2013.01); *C07K 16/2818* (2013.01); *A61K 39/0011* (2013.01); *A61K 45/06* (2013.01); *C07K 2317/31* (2013.01); *C07K 2317/52* (2013.01); *C07K 2317/60* (2013.01); *C07K 2317/73* (2013.01); *C07K 2317/76* (2013.01); *C07K 2317/92* (2013.01)

(58) Field of Classification Search
CPC ............ C07K 16/2866; C07K 2317/31; C07K 2317/52; C07K 2317/73; C07K 2317/76; C07K 2317/92
See application file for complete search history.

(56) References Cited

U.S. PATENT DOCUMENTS

| 4,208,479 | A | 6/1980 | Zuk et al. |
|---|---|---|---|
| 8,486,398 | B2 | 7/2013 | Van Ryn et al. |
| 2005/0181375 | A1 | 8/2005 | Aziz et al. |
| 2008/0292620 | A1 | 11/2008 | Damiano et al. |
| 2013/0017168 | A1 | 1/2013 | Gillies et al. |
| 2016/0194627 | A1 | 7/2016 | Smider et al. |

FOREIGN PATENT DOCUMENTS

| CL | 2020/002339 A1 | 4/2021 |
|---|---|---|
| CL | 202000 2338 A1 | 4/2021 |
| CN | 101124244 A | 2/2008 |
| CN | 105121470 A | 12/2015 |
| CO | 2018/008558 A2 | 8/2018 |
| CO | 2019/005922 A2 | 8/2019 |
| CO | 2020/009476 A2 | 10/2020 |
| CO | 2020/009743 A2 | 10/2020 |
| JP | 2006-523433 A | 10/2006 |
| RU | 2391401 C2 | 6/2010 |
| RU | 2598711 C2 | 9/2016 |
| WO | 2004045512 A2 † | 6/2004 |
| WO | WO-2011/035884 A1 | 3/2011 |
| WO | WO-2012/012759 A2 | 1/2012 |
| WO | WO-2014/144935 A2 | 9/2014 |
| WO | WO-2014/145000 A2 | 9/2014 |
| WO | WO-2017/127514 A1 | 7/2017 |
| WO | WO-2018/089420 A1 | 5/2018 |

OTHER PUBLICATIONS

Rubin LA, et al. (Summer 1985) Hybridoma 4(2):91-102. (doi: 10.1089/hyb. 1985.4.91).*
Bannas, P. et al., Nanobodies and Nanobody-Based Human Heavy Chain Antibodies as Antitumor Therapeutics, Frontiers in Immunology, 8(1603): 13 pages (2017).
Chikuma, S. et al., PD-1-Mediated Suppression of IL-2 Production Induces CD8+T Cell Anergy In Vivo, The Journal of Immunology, 182:6682-6689 (2009).
Kiyoshi, M. et al., Structural basis for binding of human IgG1 to its high-affinity human receptor FcγRI, Nature Communications, 6:6866, 11 pages (2015).
Kuhn, D. J. and Dou, Q. P., The role of interleukin-2 receptor alpha in cancer, Frontiers in Bioscience, 10:1462-1474 (2005).

(Continued)

Primary Examiner — Robert S Landsman
(74) Attorney, Agent, or Firm — Choate, Hall & Stewart LLP; Brenda Herschbach Jarrell; Michael L. Vetter

(57) ABSTRACT

The present disclosure relates to use of an anti-CD25 antibody, not inhibiting IL-2-CD25 interaction, with enhanced binding to activating Fc gamma Rs that lead to effective depletion of tumor-infiltrating Treg cells and improved control of established tumors. Combination with anti-programmed cell death protein-1 antibodies further improves tumor rejection.

16 Claims, 65 Drawing Sheets
Specification includes a Sequence Listing.

(56) References Cited

OTHER PUBLICATIONS

Rajan, A. et al., Nivolumab, anti-programmed death-1 (PD-1) monoclonal antibody immunotherapy: Role in advanced cancers, Human Vaccines & Immunotherapeutics, 12(9):2219-2231 (2016).
Shi, Y. et al., Progress in immunotherapy of non-small cell lung cancer, Chinese Oncologist Education, pp. 148-150, (2015).
Simpson, T. et al., Fc-dependent depletion of tumor-infiltrating regulatory T cells co-defines the efficacy of anti-CTLA-4 therapy against melanoma, J. Exp. Med., 210(9):1695-1710 (2013).
Temming, A. et al., Cross-reactivity of mouse IgG subclasses to human Fc gamma receptors: Antibdy deglycosylation only eliminates IgG2b binding, Molecular Immunology, 127:79-86 (2020).
Wark, K. et al., Latest technologies for the enhancement of antibody affinity, Advanced Drug Delivery Reviews, 58(2006):657-670 (2006).
Zhang, M. et al., The Anti-CD25 Monoclonal Antibody 7G7/B6, Armed with the A-Emitter 211At, Provides Effective Radioimmunotherapy for a Murine Model of Leukemia, Cancer Research, 66(16):8227-8232 (2006).
Almagro, J. C. et al., Progress and Challenges in the Design and Clinical Development of Antibodies for Cancer Therapy, Front Immunol., 8:1751 (2018).
Berkowitz, J. L. et al., Safety, efficacy, and pharmacokinetics/pharmacodynamics of daclizumab (anti-CD25) in patients with adult T-cell leukemia/lymphoma, Clinical Immunology 155:176-187 (2014).
Brown, M. et al., Tolerance of single, but not multiple, amino acid replacements in antibody VH CDR 2: a means of minimizing B cell wastage from somatic hypermutation? J. Immunol., 156(9):3285-3291 (1996).
Dekkers, G. et al., Affinity of human IgG subclasses to mouse Fc gamma receptors, MABS, 9(5):767-773 (2017).
Ishida, T. and Ueda, R., Antibody therapy for Adult T-cell leukemia-lymphoma, Int. J. Hematol., 94:443-452 (2011).
Longo, N. et al., Characterization of Ig Gene Somatic Hypermutation in the Absence of Activation-Induced Cytidine Deaminase, The Journal of Immunology, 181:1299-1306 (2008).
Mkrtichyan, M. et al., Anti-PD-1 synergizes with cyclophosphamide to induce potent anti-tumor vaccine effects through novel mechanisms, Eur. J. Immunol., 41:2977-2986 (2011).
Muyldermans, S. et al., Recognition of antigens by single-domain antibody fragments: the superfluous luxury of paired domains, TRENDS in Biochemical Sciences, 26(4):230-235 (2001).
Nelson, A. and Reichert, J., Development trends for therapeutic antibody fragments, Nature Biotechnology, 27:331-337 (2009).
Rentero, I. and Heinis, C., Screening of Large Molecule Diversities by Phage Display, Chimia (Aarau), 65(11):843-845 (2011).
Rijkers, G.T. and Van De Corput, L., Antibody diversity and B cell-mediated immunity, Principles of Immunopharmacology, 2nd Edition, 16 pages (2005).
Rudikoff S. et al., Single Amino Acid Substitution Altering Antigen-Binding Specificity, Proc Natl Acad Sci USA, 79(6):1979-1983 (1982).
Yu, P. et al., Simultaneous inhibition of two regulatory T-cell subsets enhanced Interleukin-15 efficacy in a prostate tumor model, PNAS, 109(16):6187-6192 (2012).
Gül, N. and van Egmond, M., Antibody-Dependent Phagocytosis of Tumor Cells by Macrophages: A Potent Effector Mechanism of Monoclonal Antibody Therapy of Cancer, Cancer Res. 75(23):5008-5013 (2015).
Hoogenbom, Hennie R., Selecting and screening recombinant antibody libraries, Nat Biotechnol, 23:1105-1116 (2005).
Janeway, C. Jr. et al., Immunobiology: The Immune System in Health and Disease, 5th edition, Section 7.8, 17 pages (2001).
Lydard, et al., Immunology, D3 Generation of Diversity, Section D—Antibodies, pp. 76-85 (2011).
Marvin, J. and Lowman, H., Redesigning an antibody fragment for faster association with its antigen, Biochemistry, 42(23):7077-7083 (2003).
Third Party Submissions filed on U.S. Appl. No. 16/494,962 (28 pages).
John C. Morris et al., Receptor-Directed Therapy of T-Cell Leukemias and Lymphomas, 15 pages, Oct. 9, 2008.†

\* cited by examiner
† cited by third party

FIGURE 1
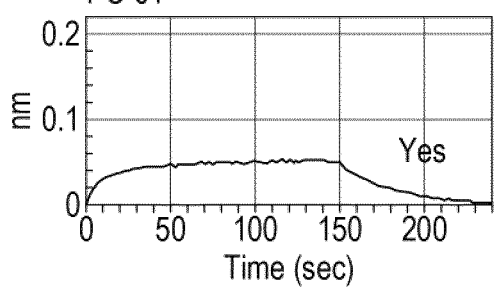
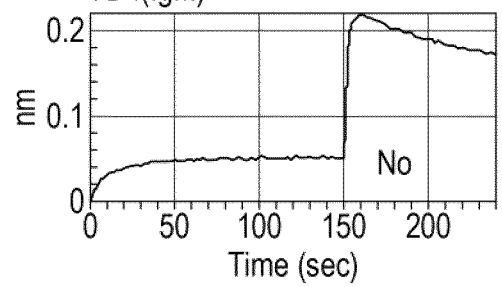
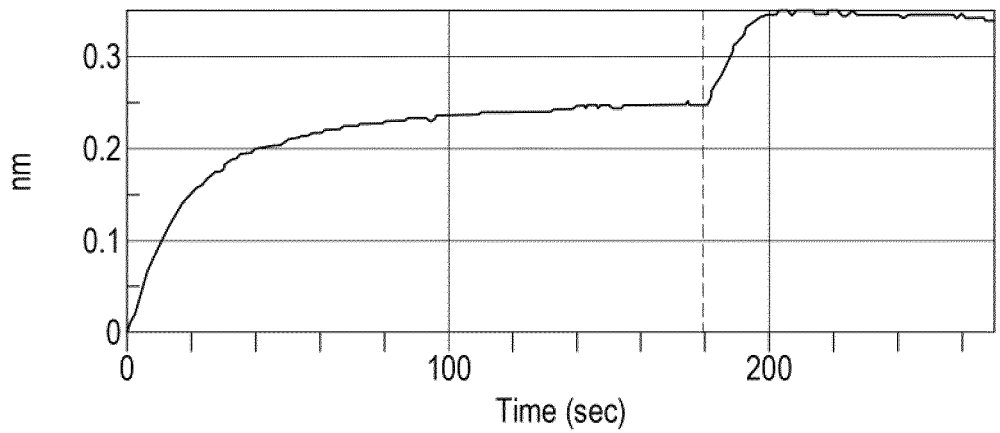
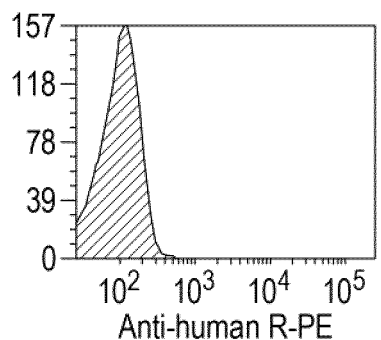
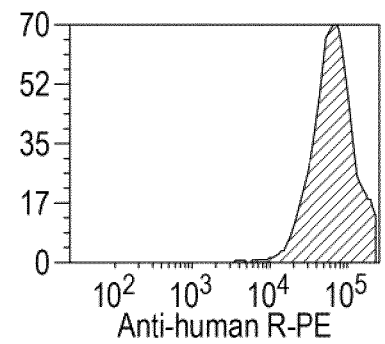
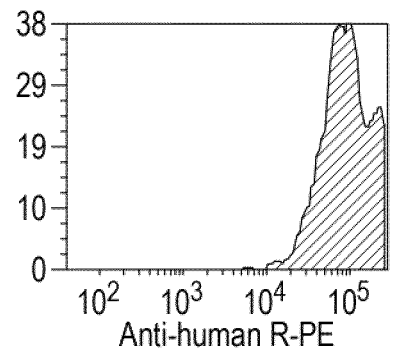

CT26 Model

FIGURE 10

```
         10          20          30          40          50          60
                                                       Epitope 3
MDSYLLMWGL  LTFIMVPGCQ  AELCDDDPPE  IPHATFKAMA  Y[KEGTMLNCE  CKRGFR]RIKS 70          80          90         100         110         120
            Epitopes 4
GSLYMLCTG[N  SSH{SSWDNQC  QCTS}SATR]NT  TKQVTPQPEE  QKERKTTEMQ  SPMQPVDQAS 130         140         150         160         170         180
                     DAC           Epitopes 1              Epitopes 2
LPGHCREPPP  WENEAT[ERIY  HFV]VGQMV{Y[Y  QCVQGYRA]LH}  RGPAE[SVCKM  THGKTR{WTQP}

190         200         210         220         230         240
{QLICTG]EMET  SQFPGEEKPQ  ASPEGRPESE  TSCLVTTTDF  QIQTEMAATM  ETSIFTTEYQ
Epitopes 2 cont.

250         260         270
VAVAGCVFLL  ISVLLLSGLT  WQRRQRKSRR  TI
```

Figure 11
A)
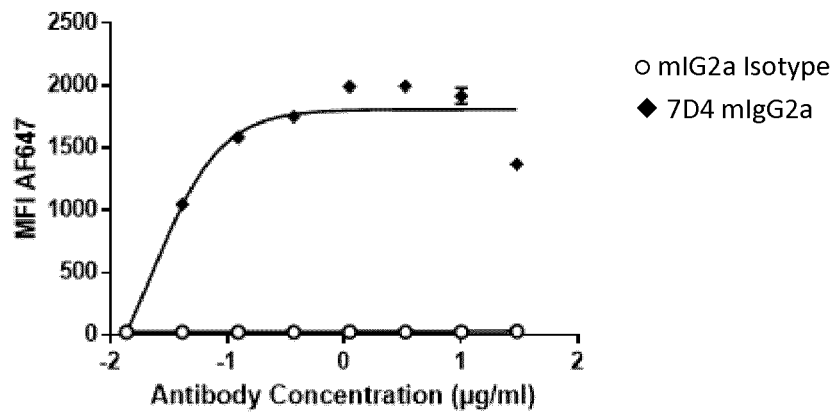
B)
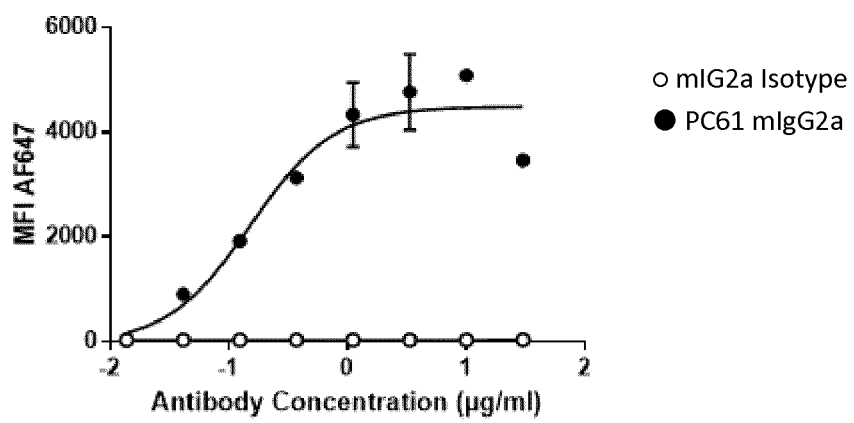
C)
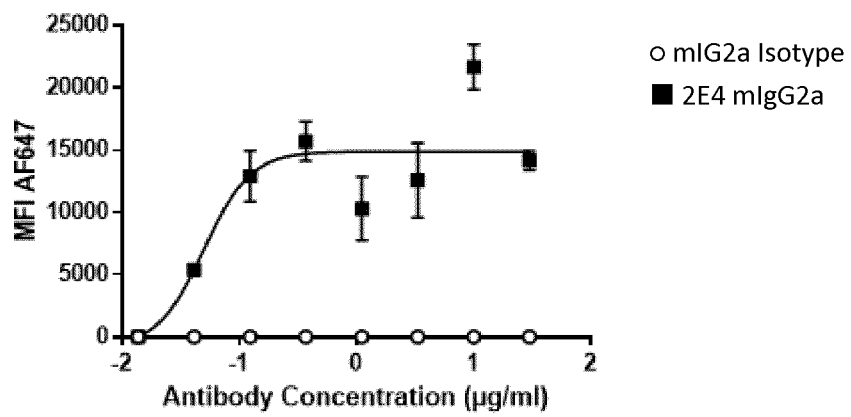

FIGURE 12
A)
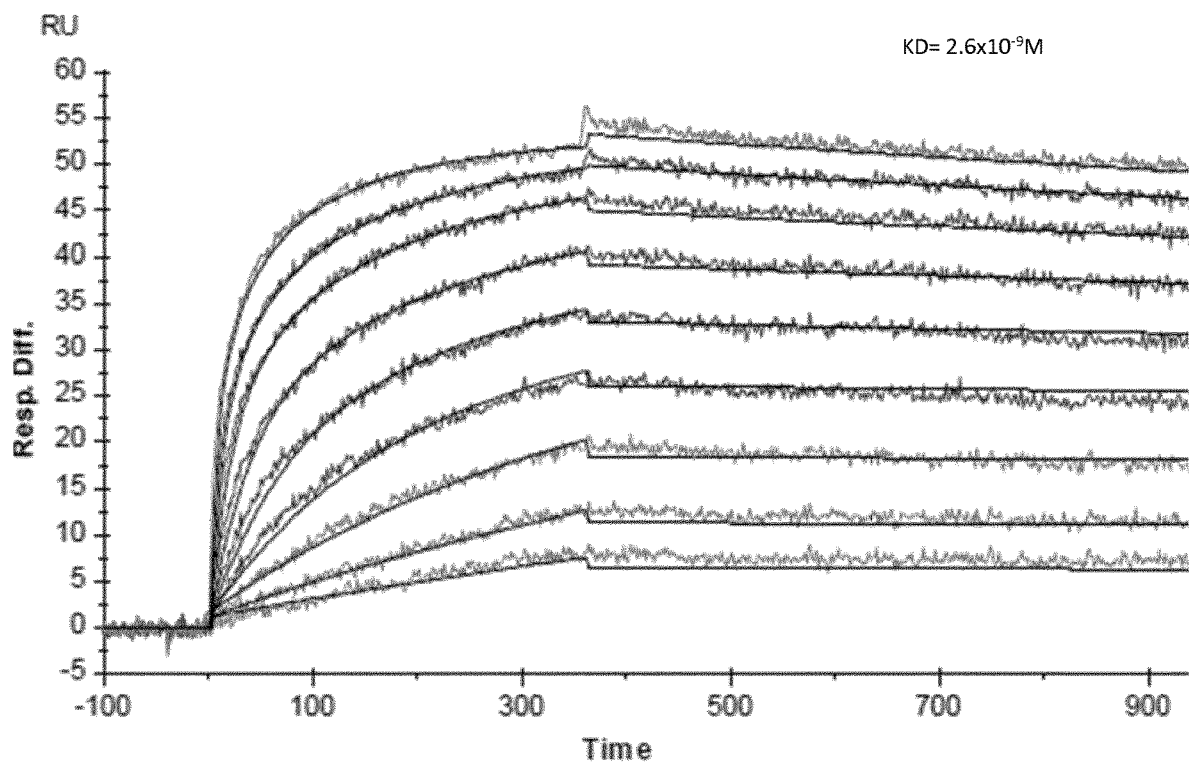
B)
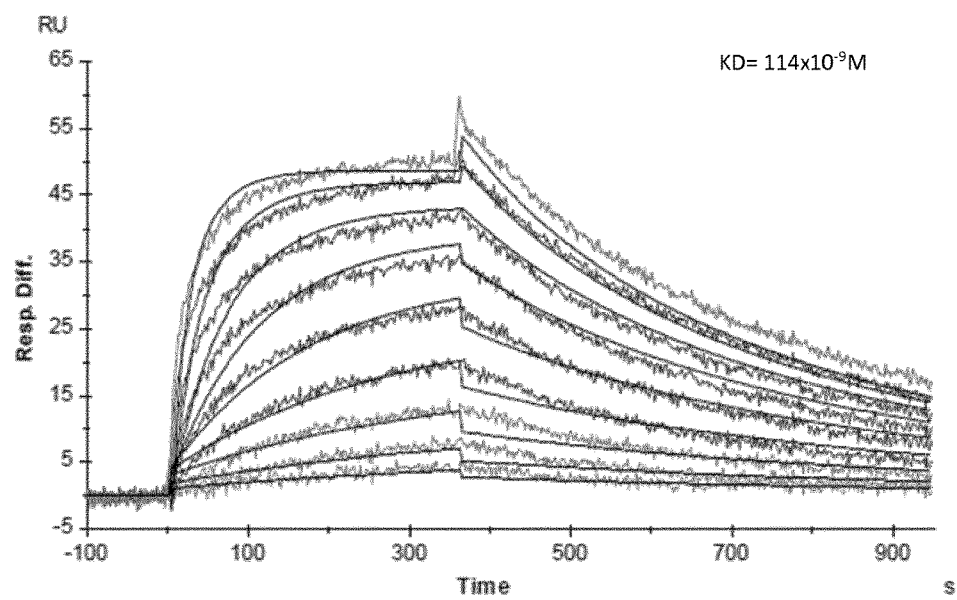

FIGURE 15
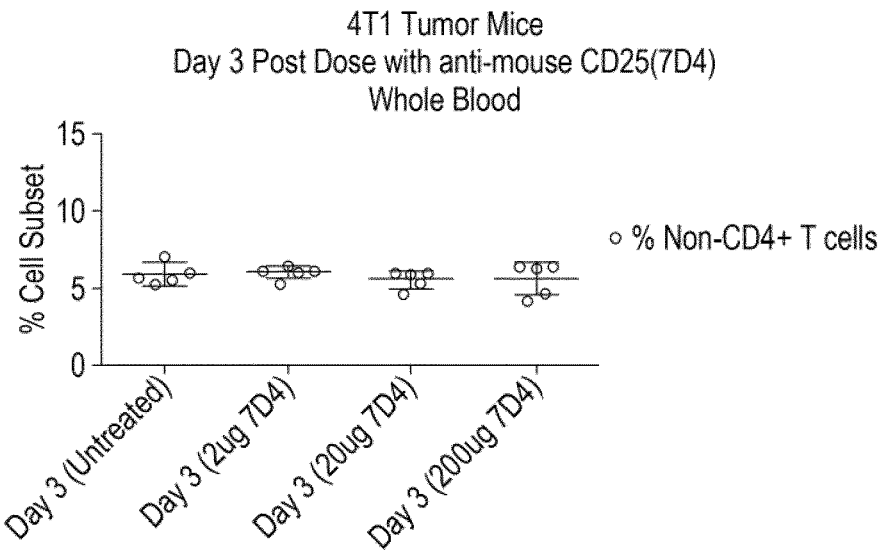
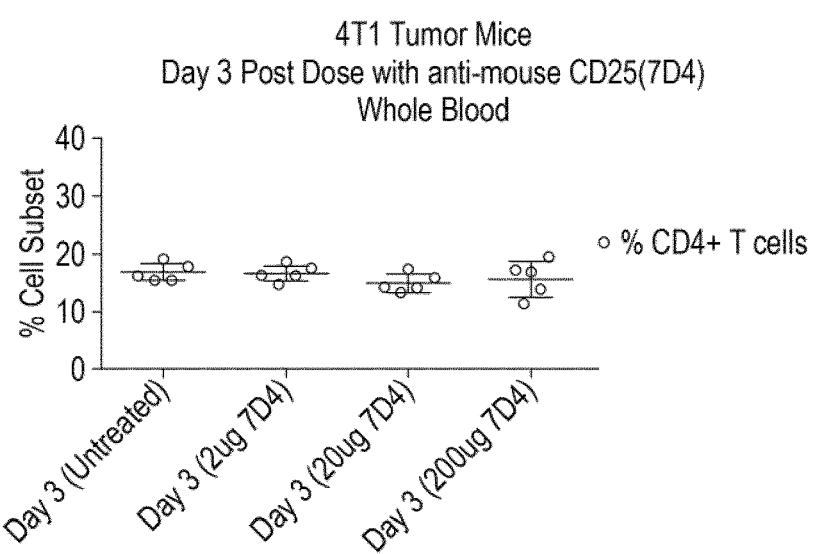
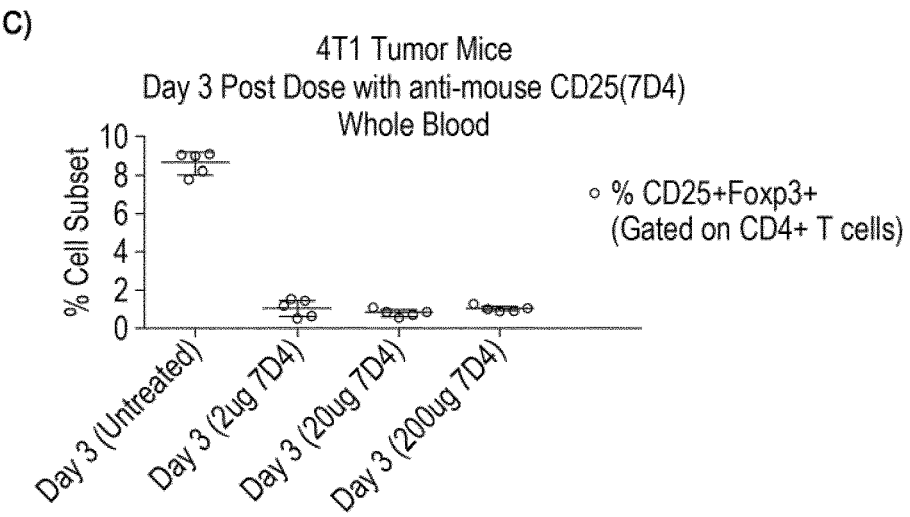

FIGURE 15 cont.
D)
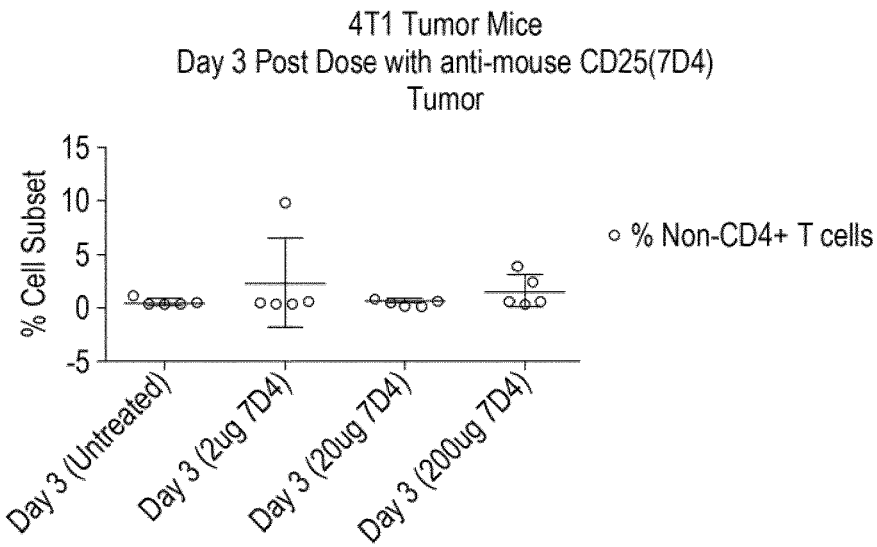
E)
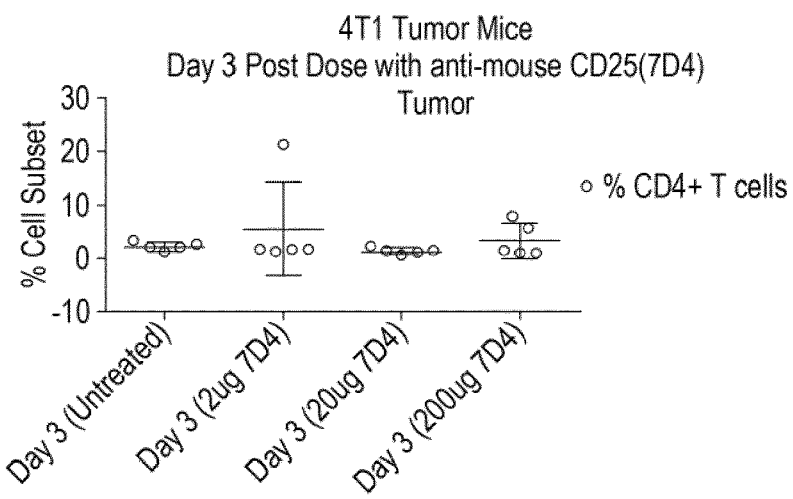
F)
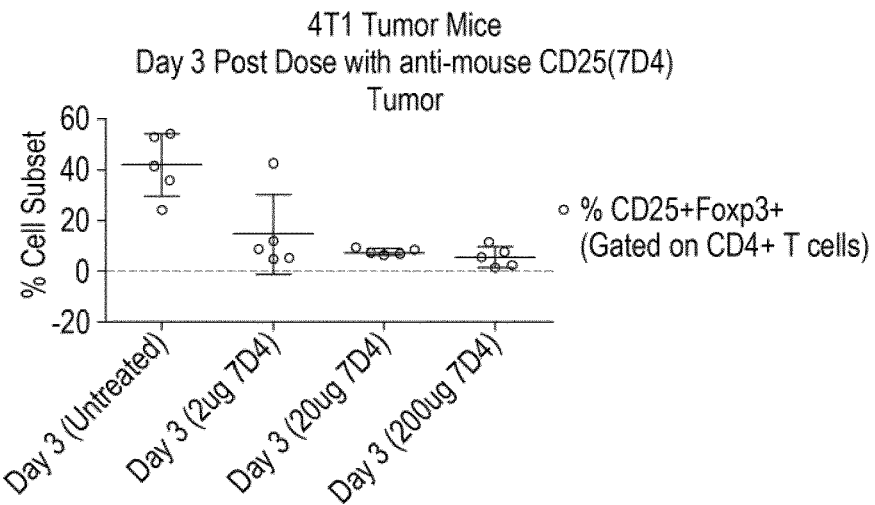

FIGURE 15 cont.
J)
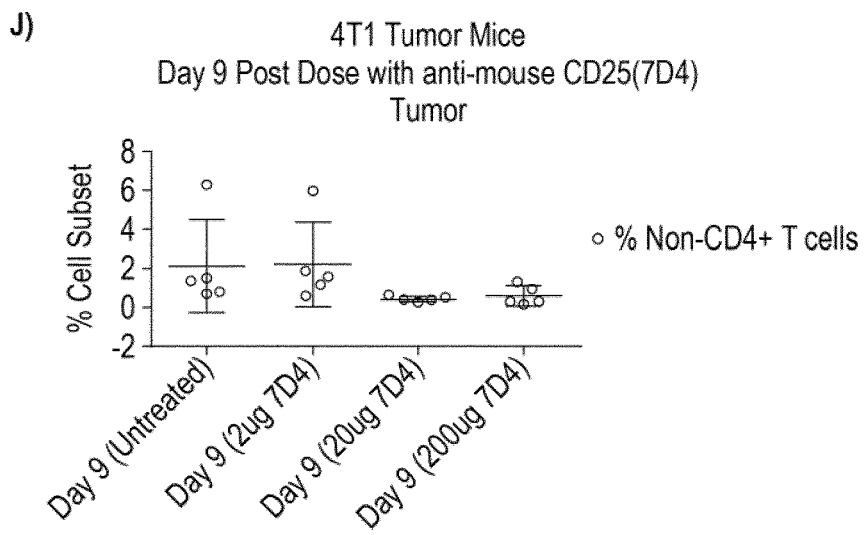
K)
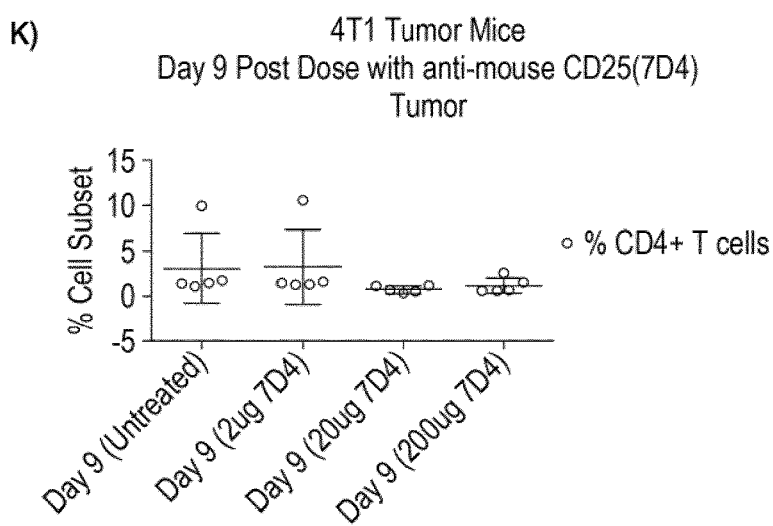
L)
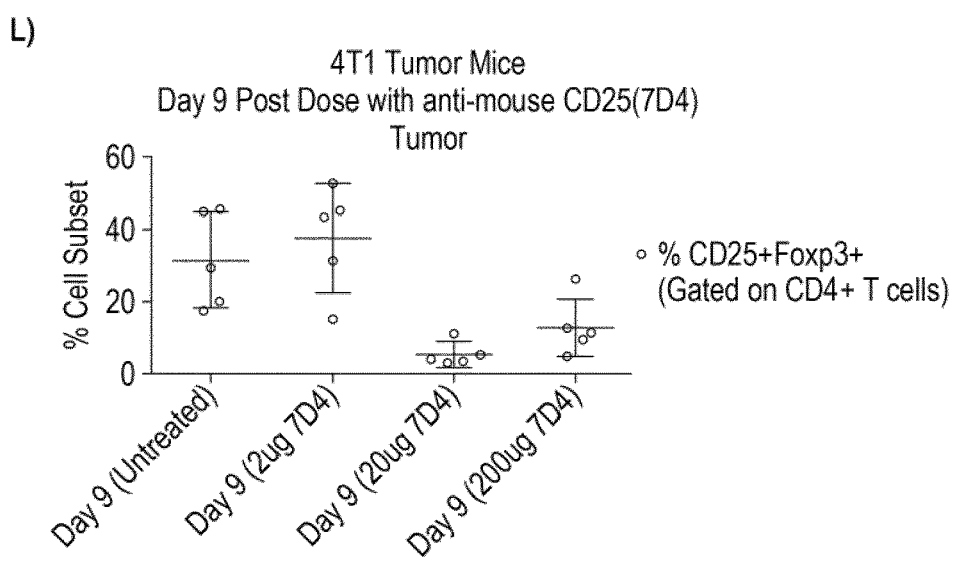

FIGURE 24
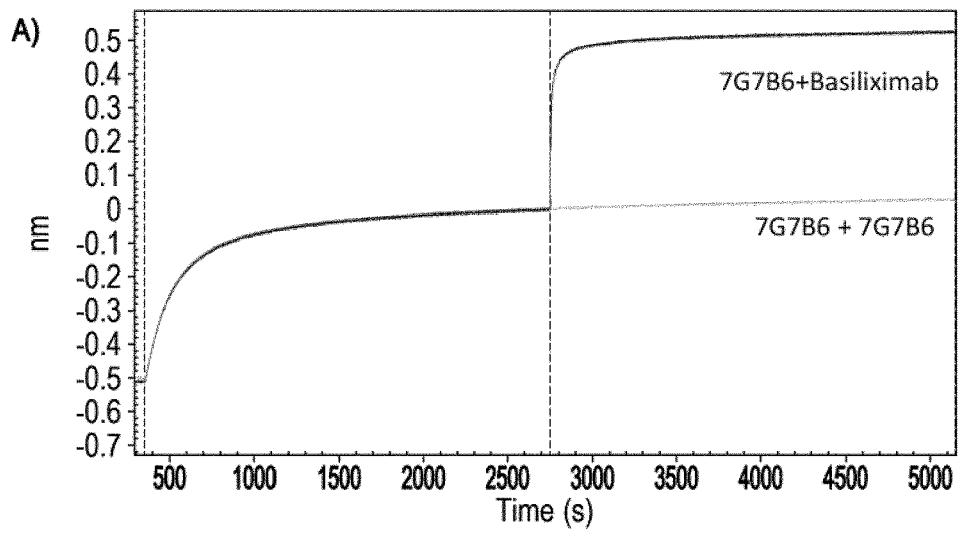
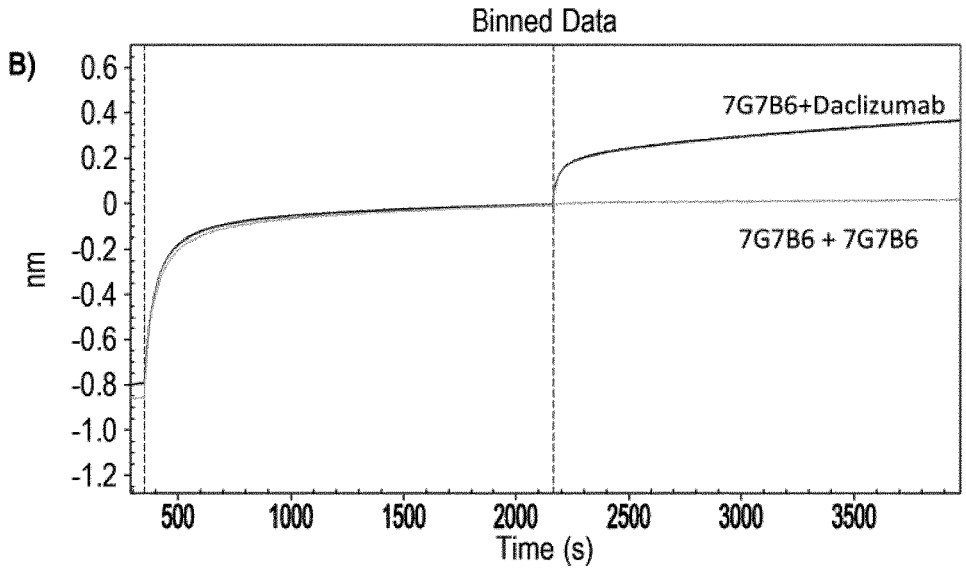
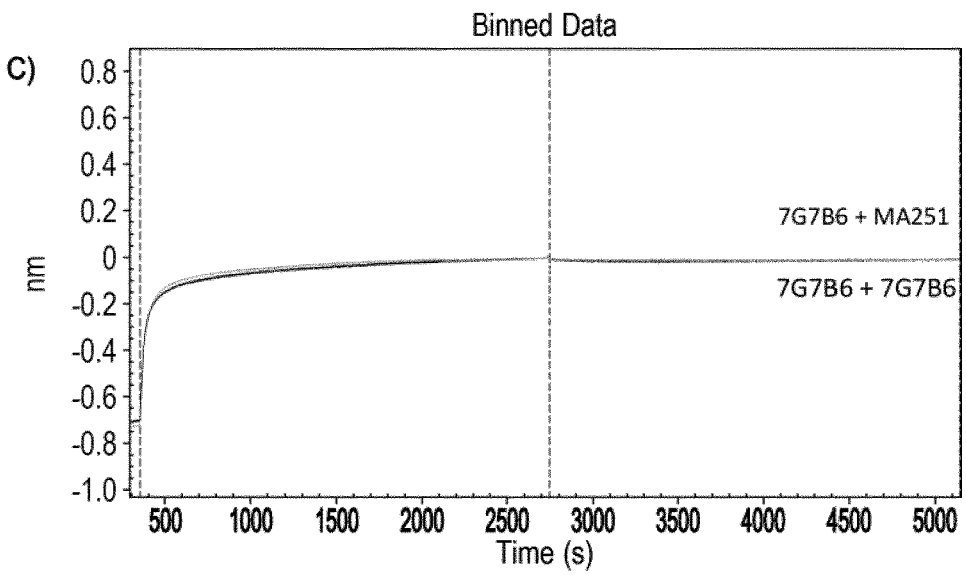

FIGURE 24 cont.
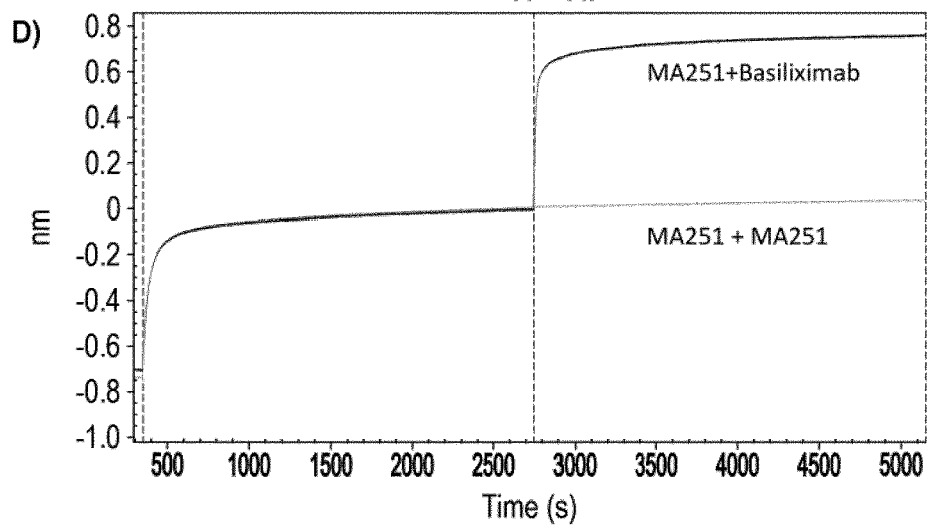
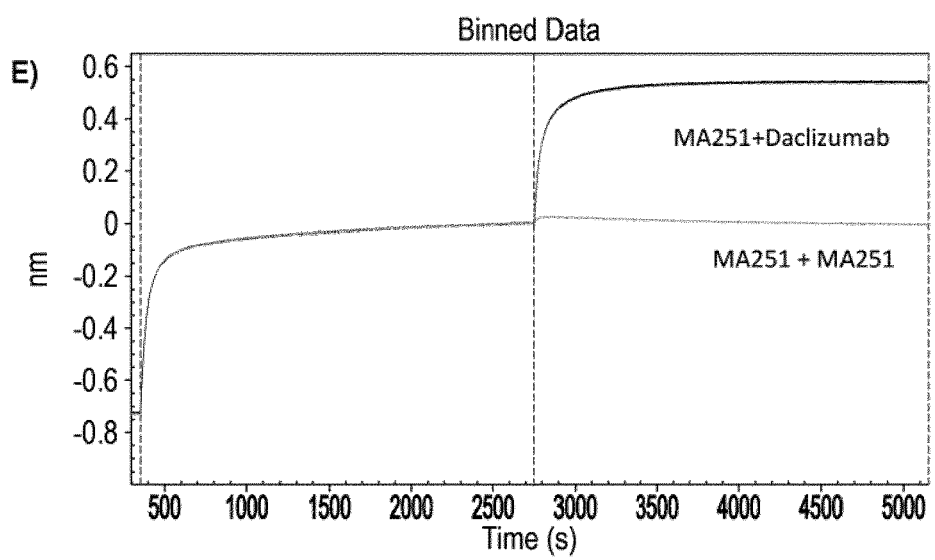
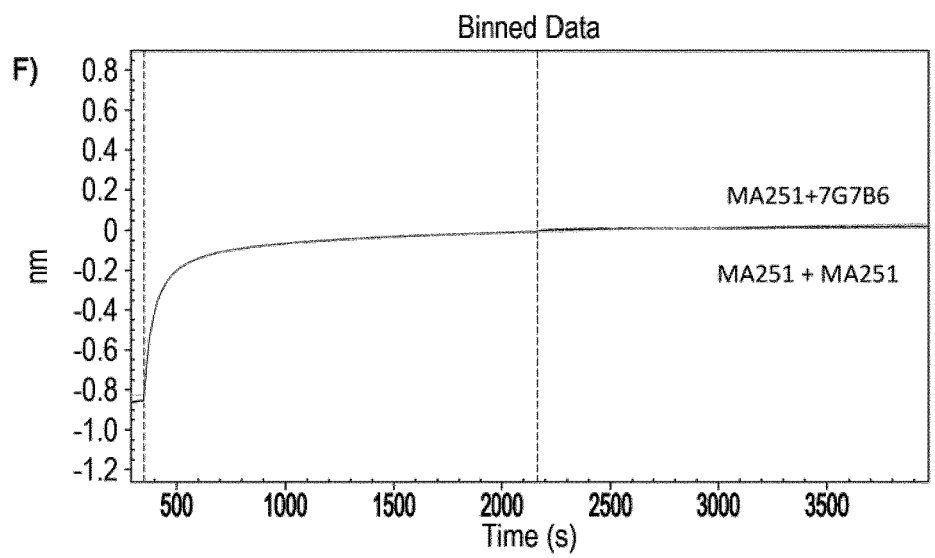

FIGURE 24 cont.
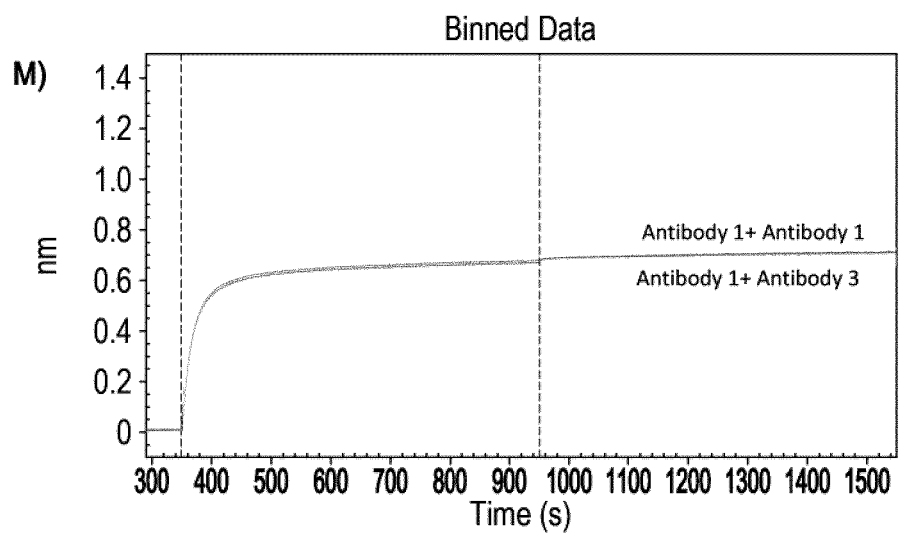
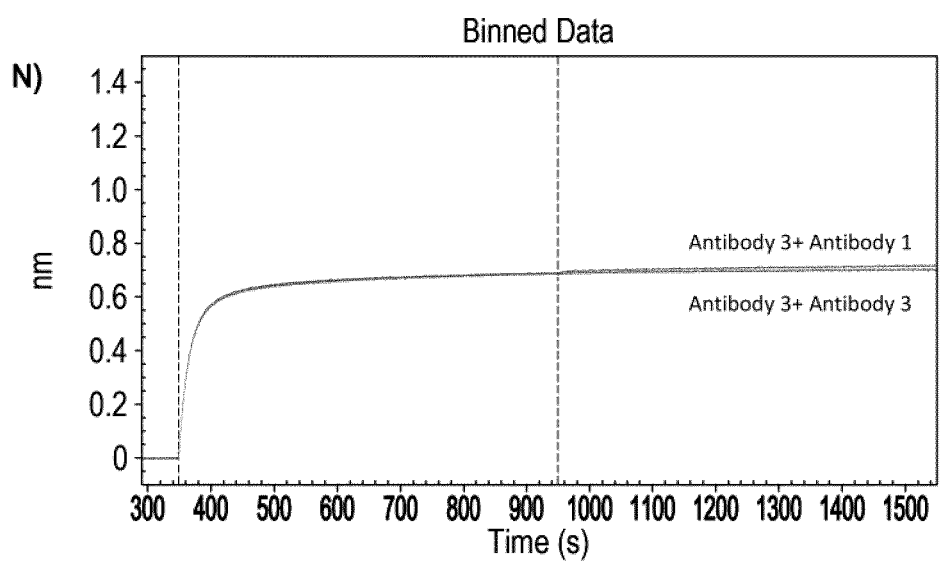

FIGURE 25
A)
Vehicle start palpable tumors
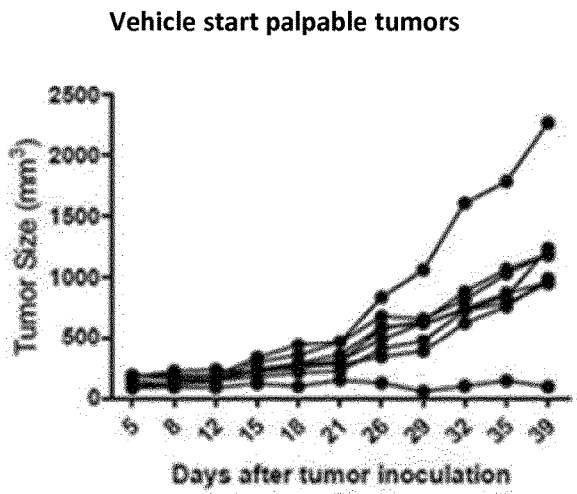
B)
Antibody 1 start palpable tumors
2mg/kg IV TWx2.5 wks
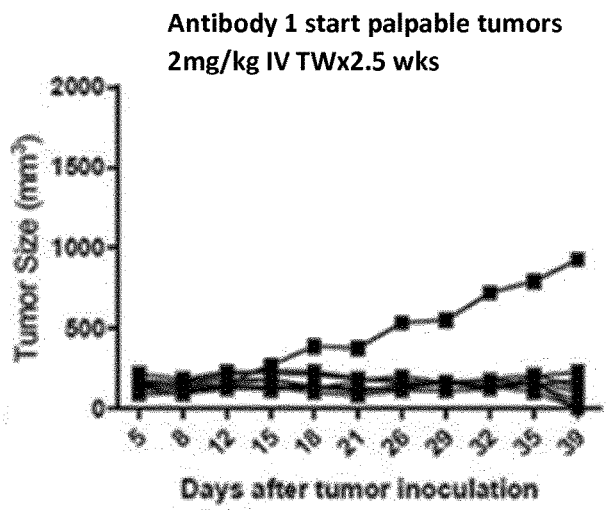
C)
Vehicle start 100-200mm3 tumors IV
TWx2.5 wks
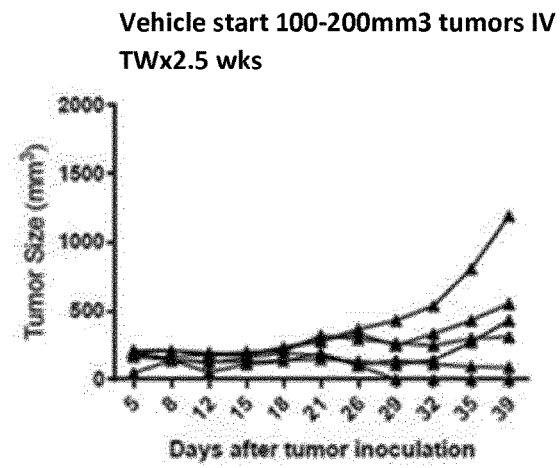
D)
Antibody 1 start 100-200mm3
tumors 2mg/kg IV TWx2.5 wks
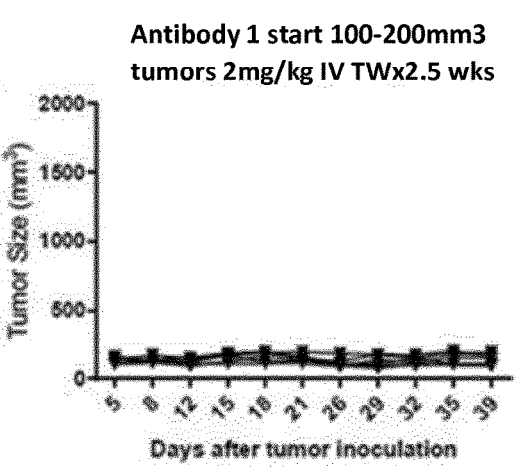
E)
Antibody 1 start 100-200mm3
tumors 10mg/kgIV Q1Dx1
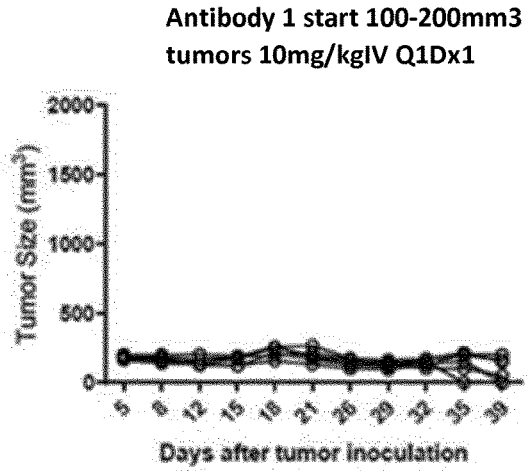

FIGURE 26
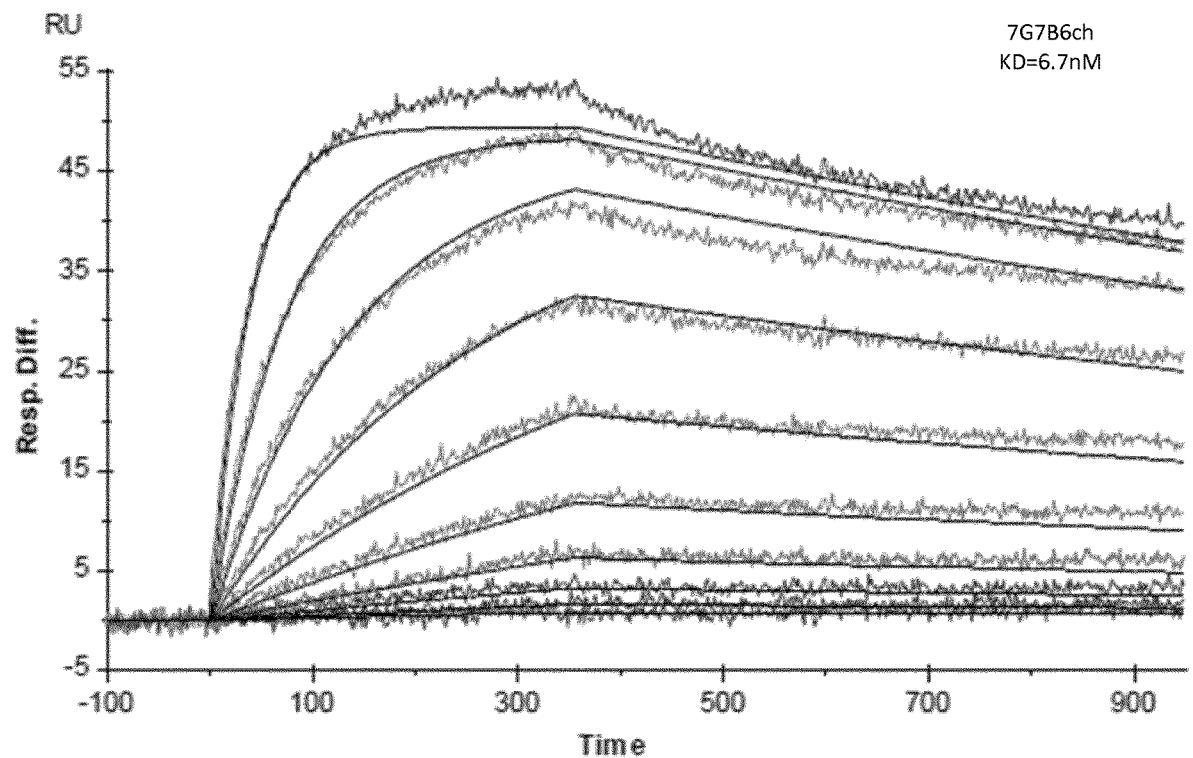
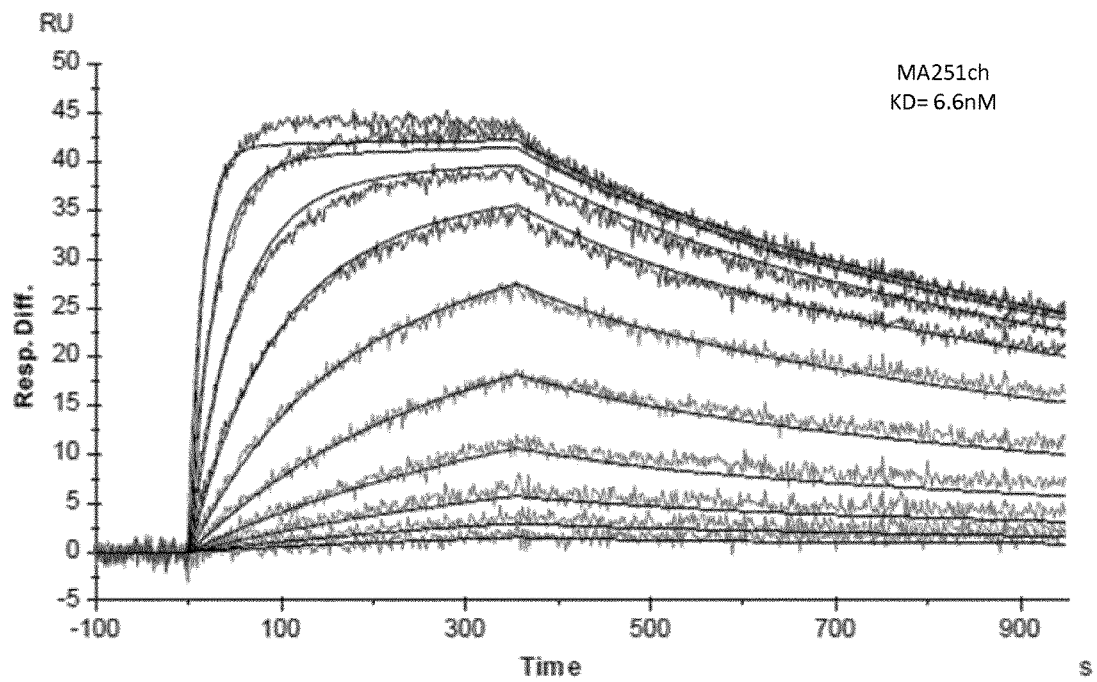

FIGURE 26 cont.
C)
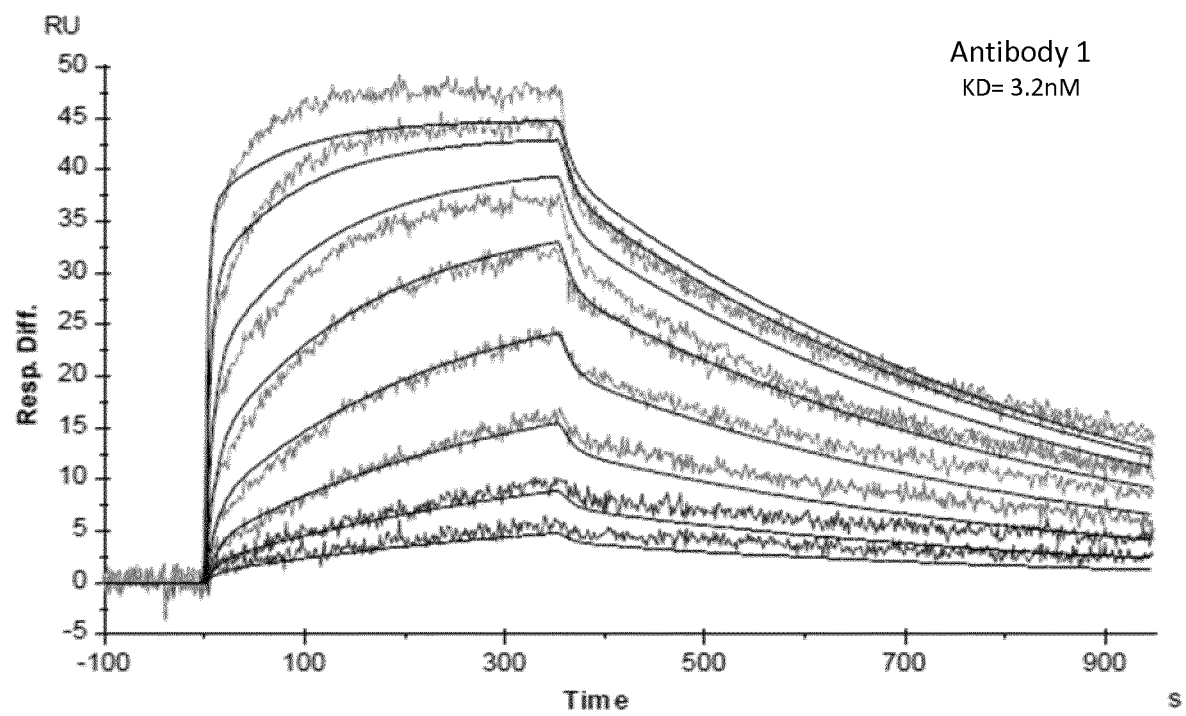
D)
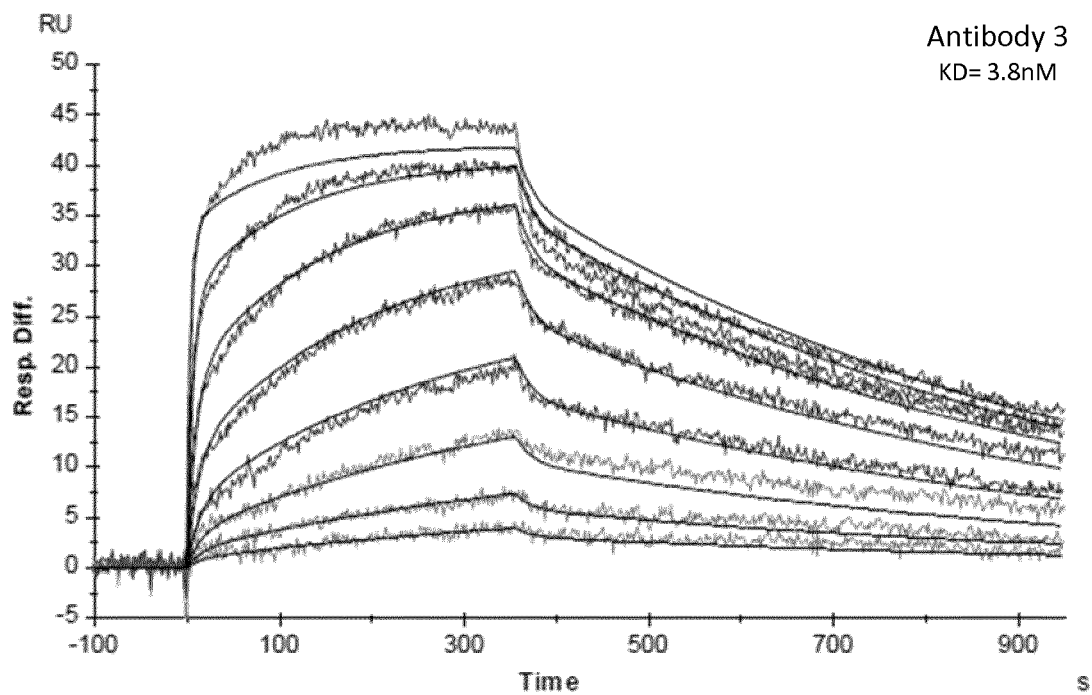

FIGURE 26 cont,
E)
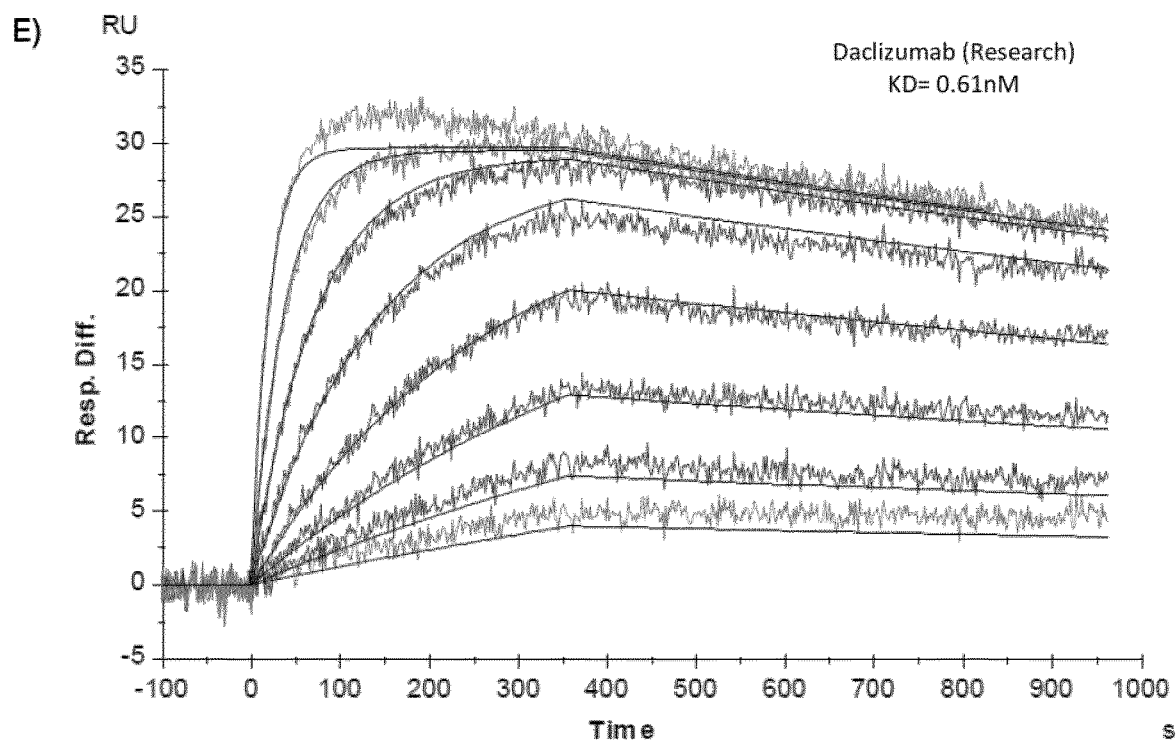
F)
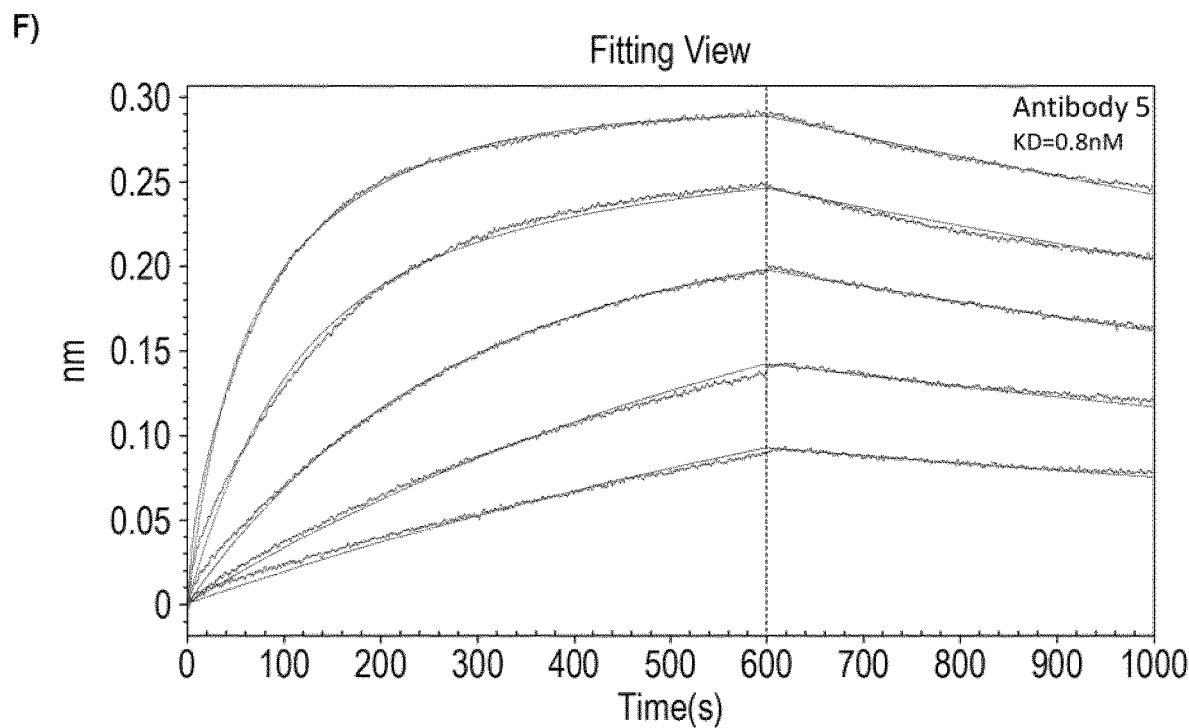

FIGURE 27
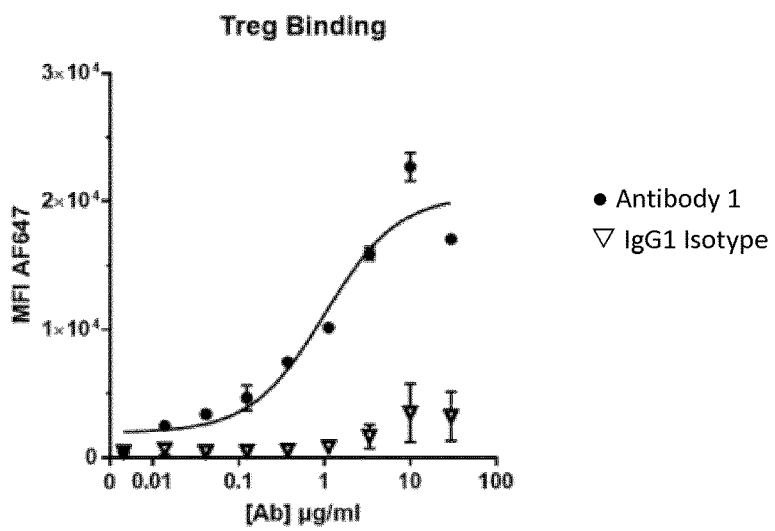
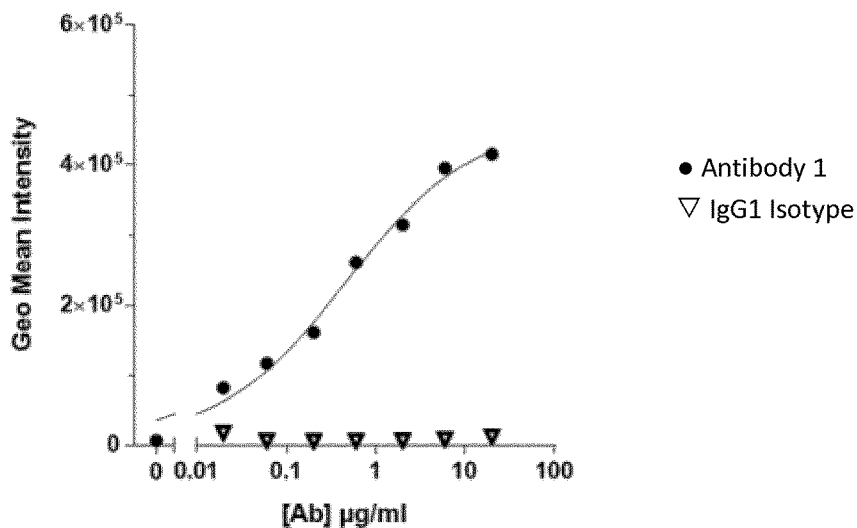
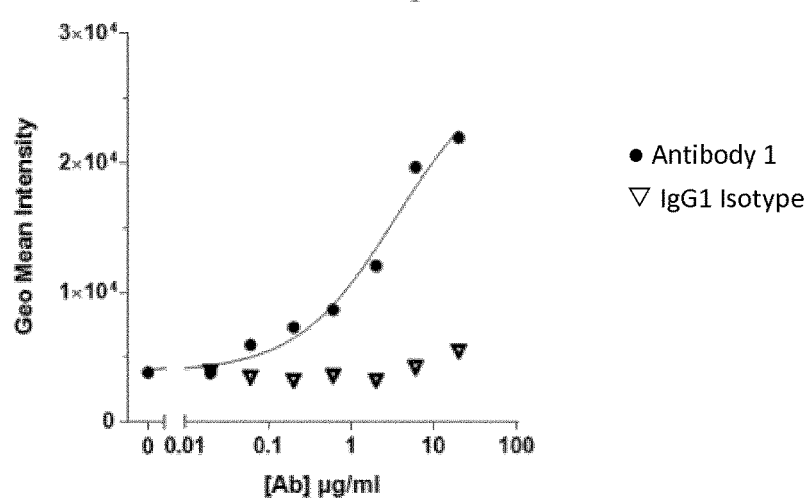

FIGURE 28
A)
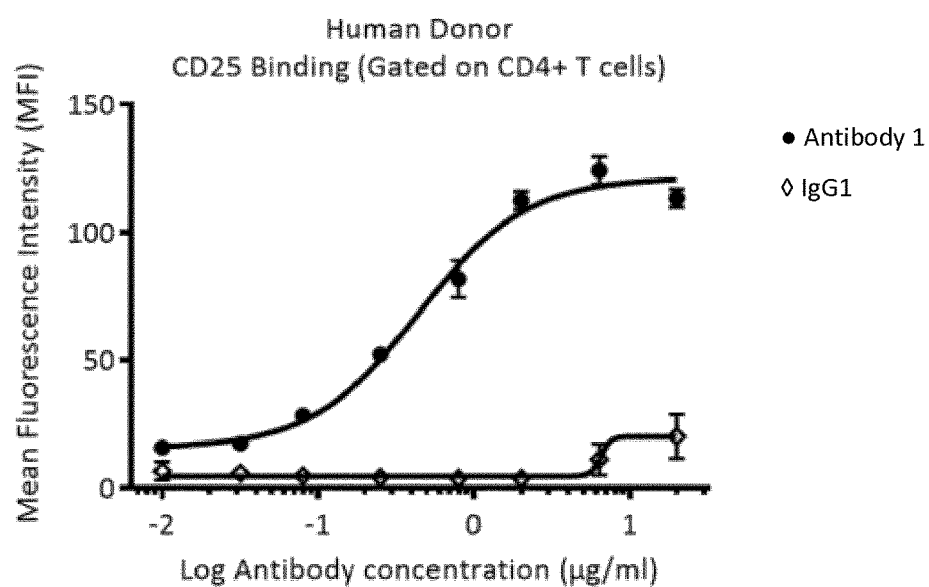
B)
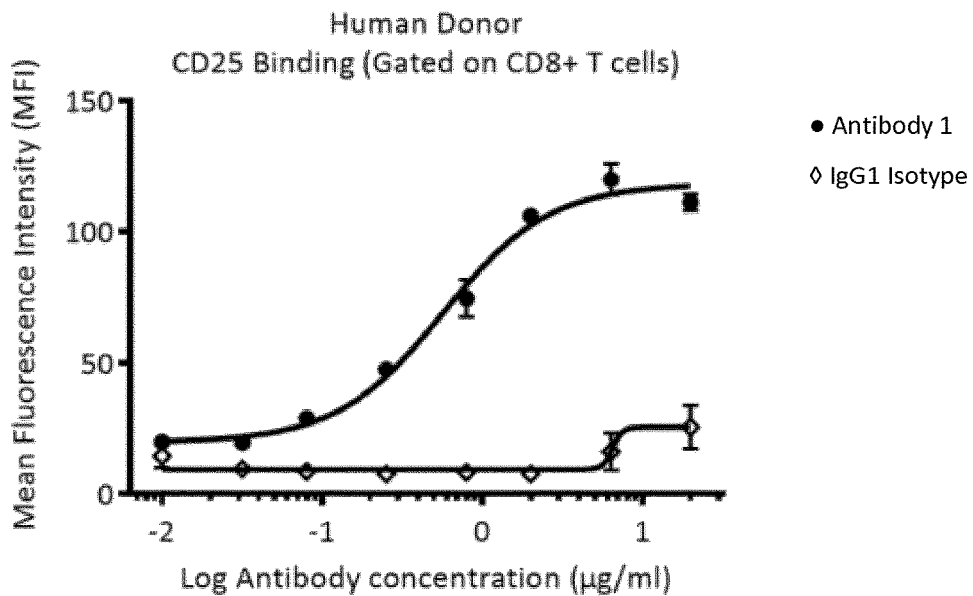

FIGURE 29
Non IL-2 competing Ab (Antibody 1)
A) 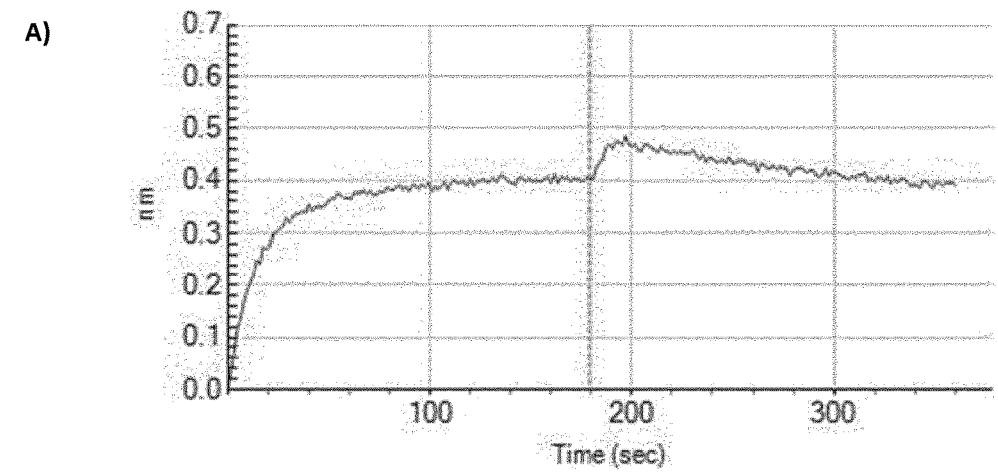
B) IL-2 Competing Ab
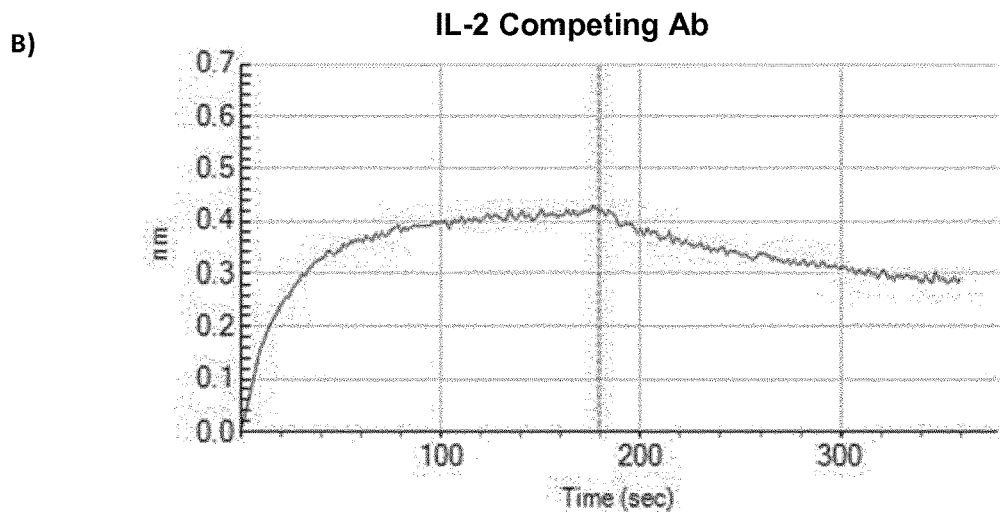
FIGURE 30
Competitive binding to Daclizumab determine via Octet
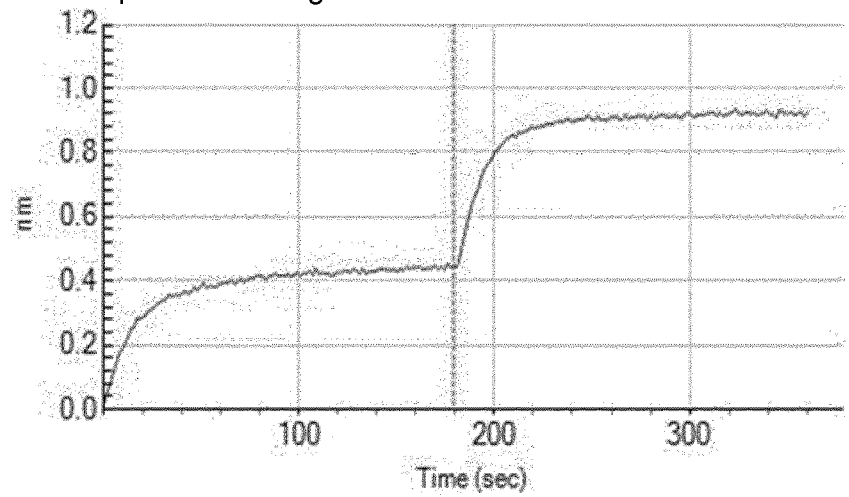

FIGURE 35
A)
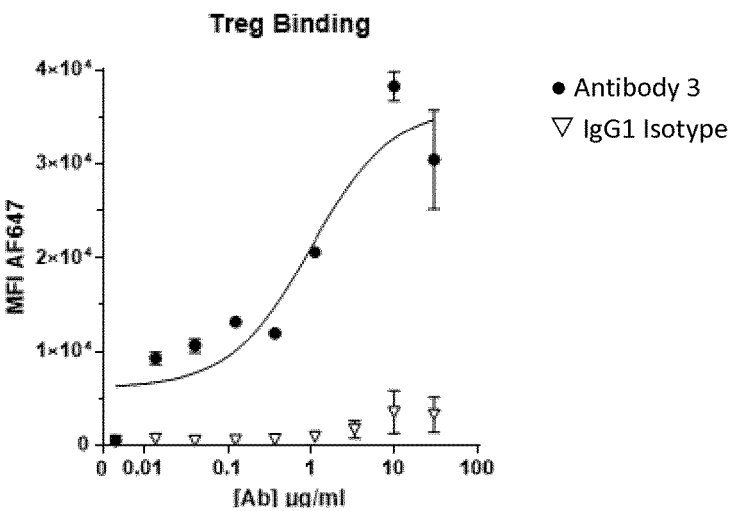
B)
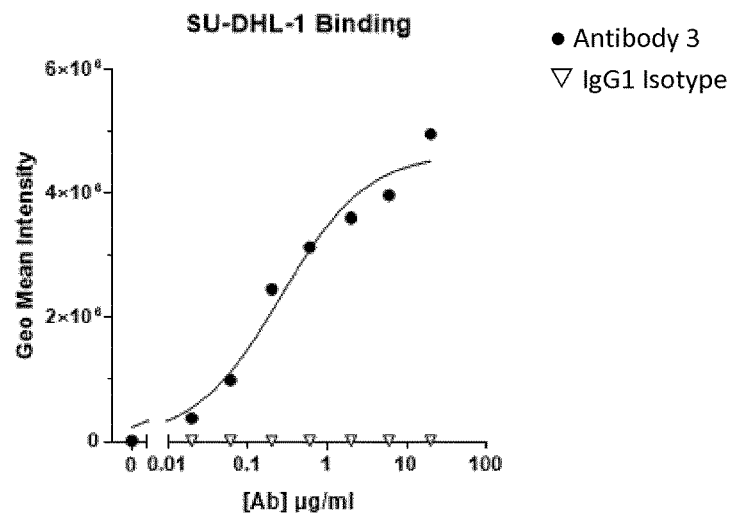
C)
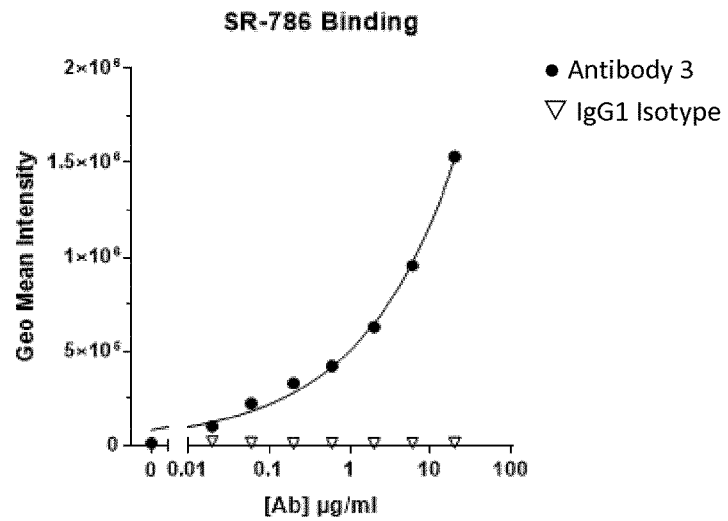

FIGURE 36
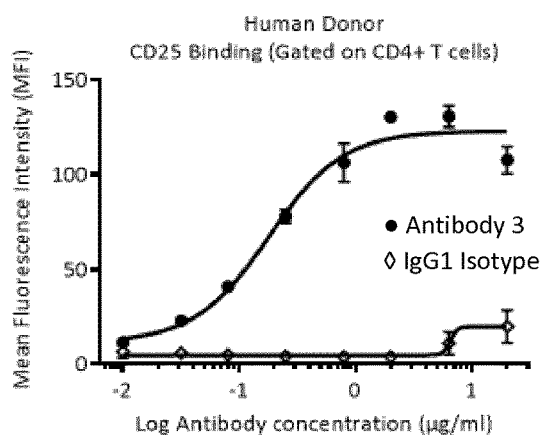
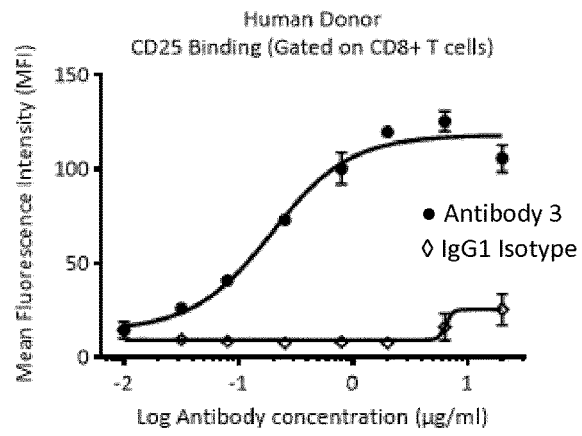
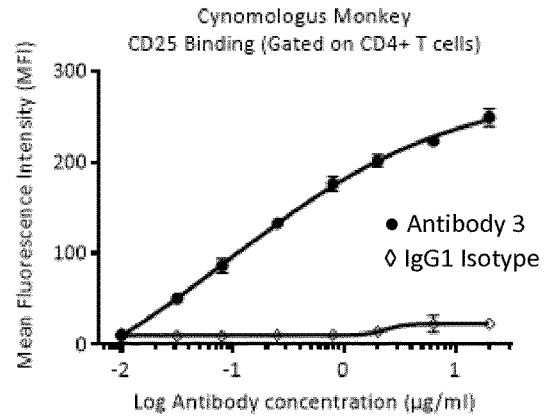
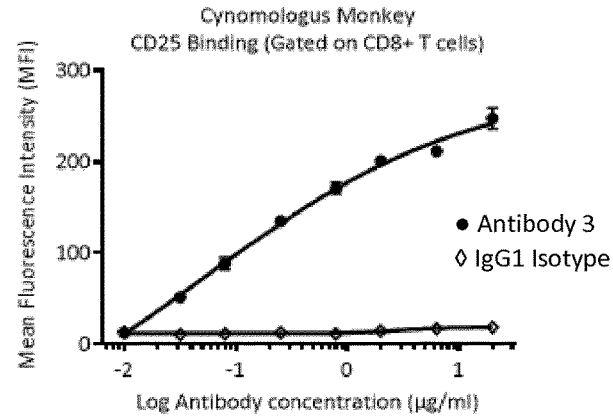

Non IL-2 competing Ab (Antibody 3)

Competitive binding to Daclizumab determine via Octet

FIGURE 40
A)
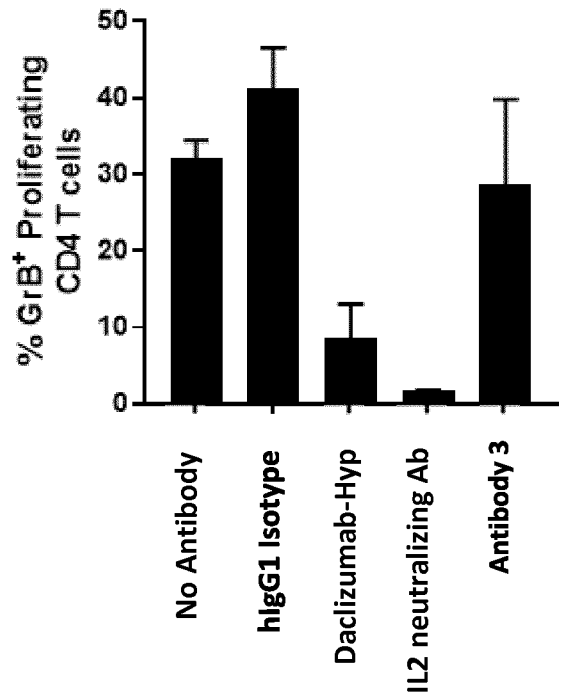
B)
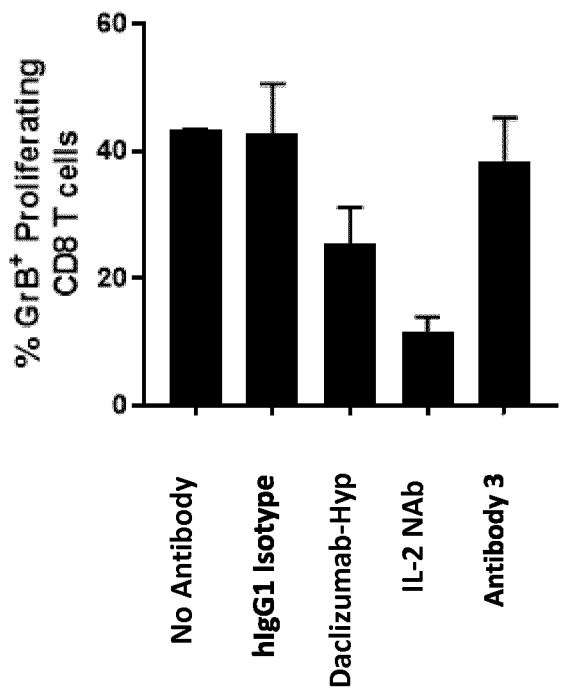

FIGURE 41
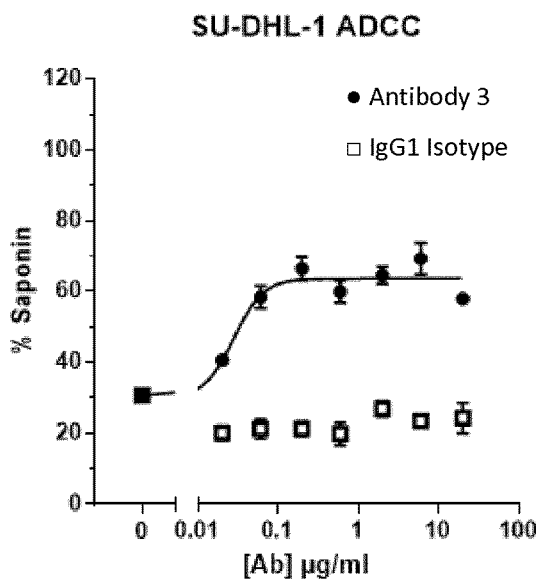
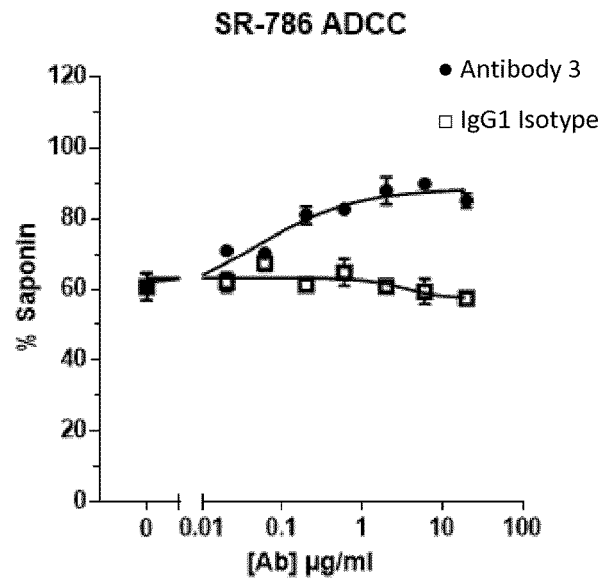
FIGURE 42
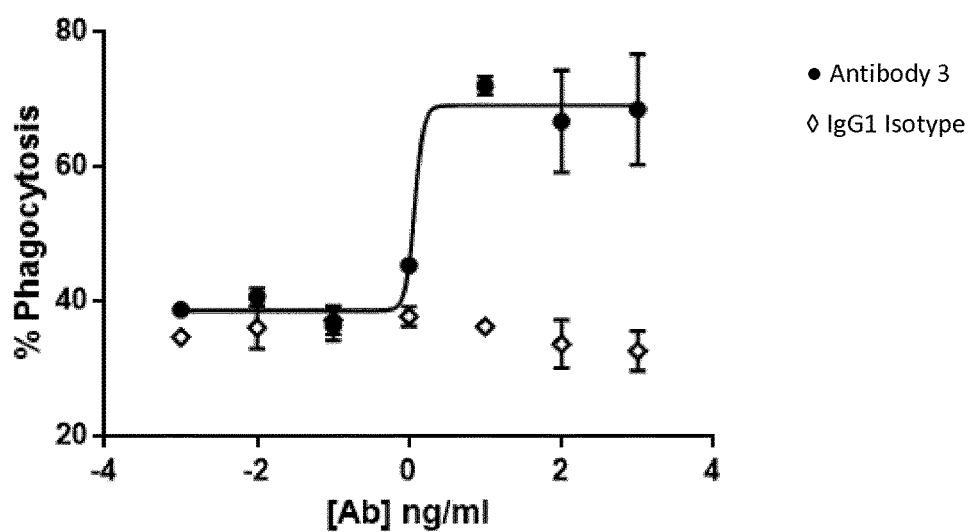

FIGURE 43
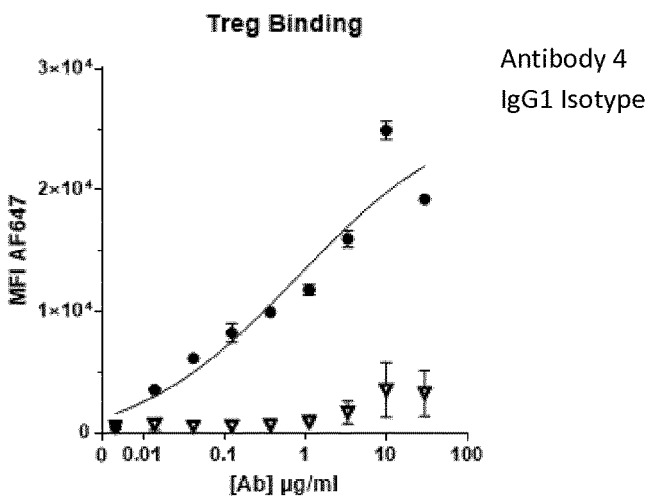
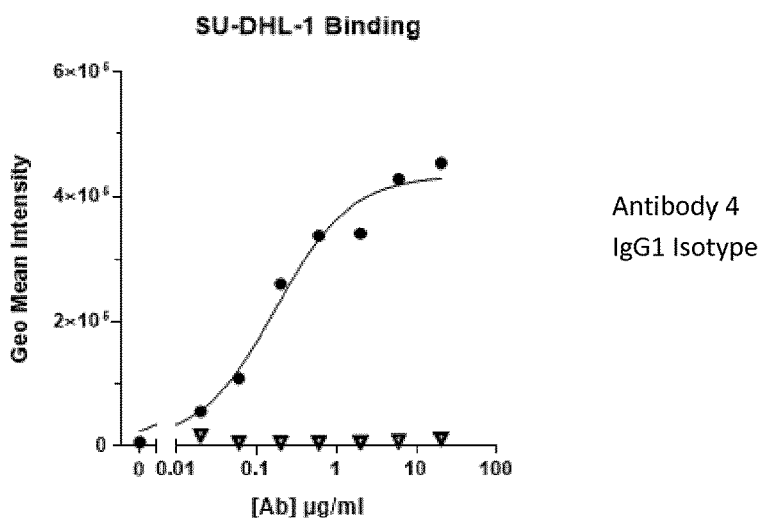
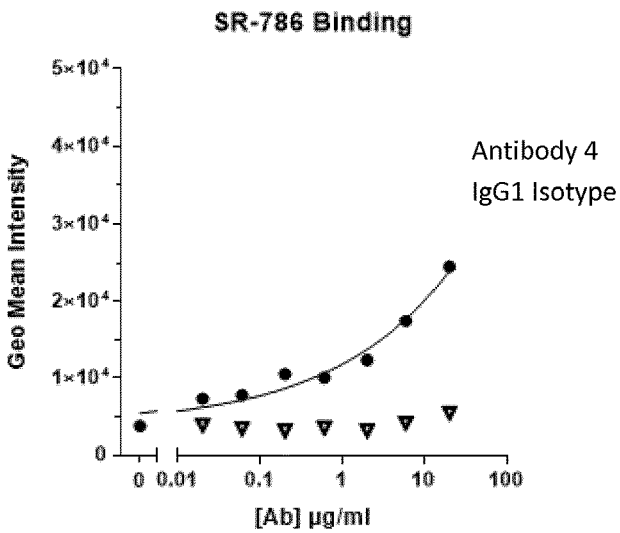

Non IL-2 competing Ab (Antibody 4)

Competitive binding to Daclizumab determine via Octet

IL2 titration

□ No Antibody
Δ IgG1 Isotype
○ Daclizumab
● Antibody 4

FIGURE 48
A)
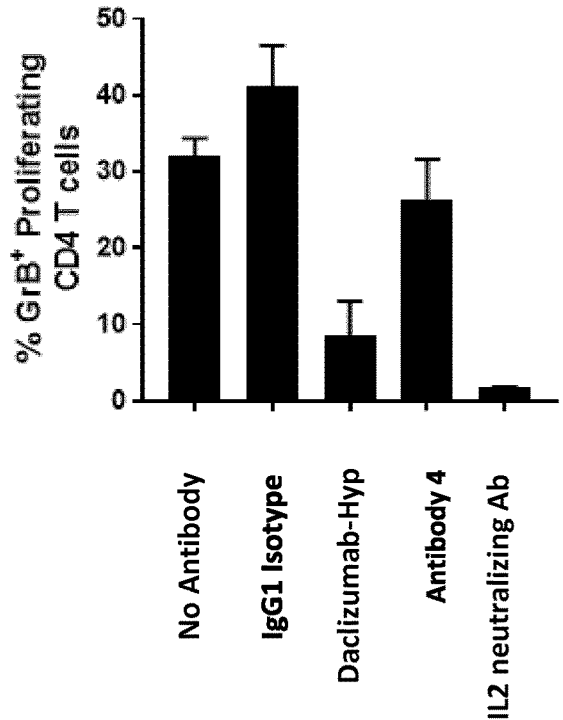
B)
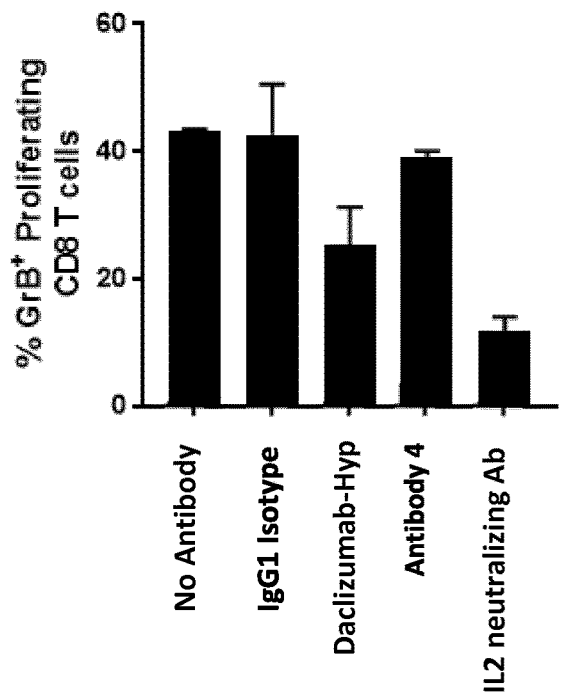

FIGURE 51
A)
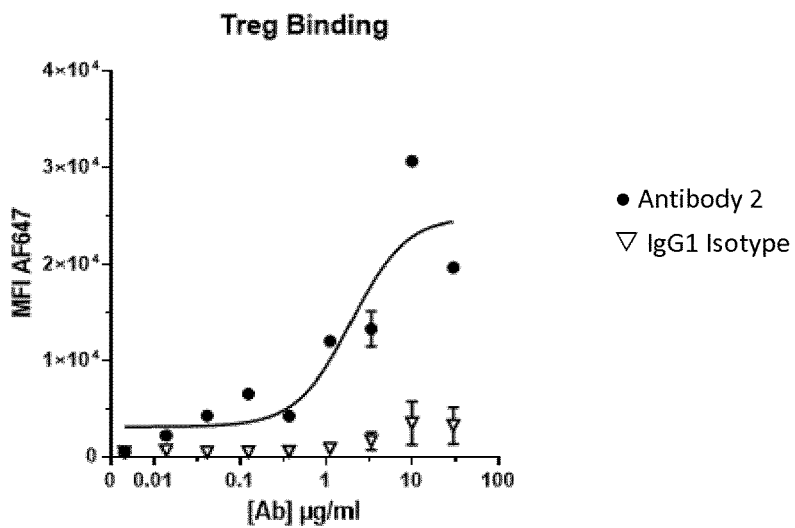
B)
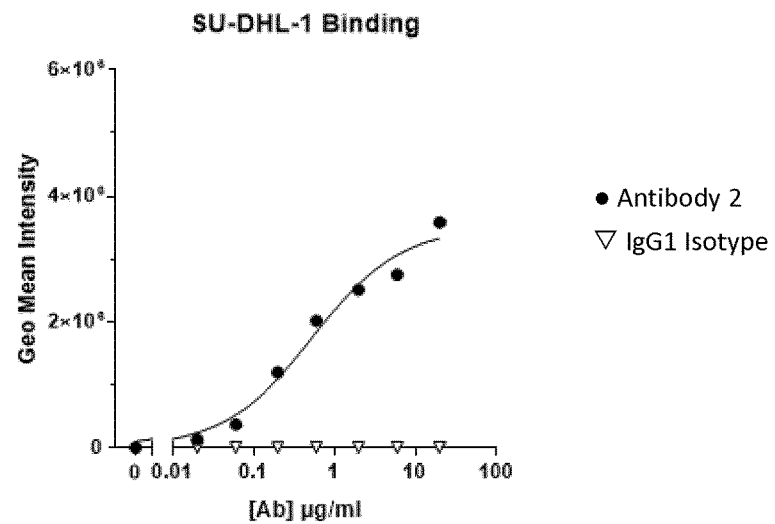
C)
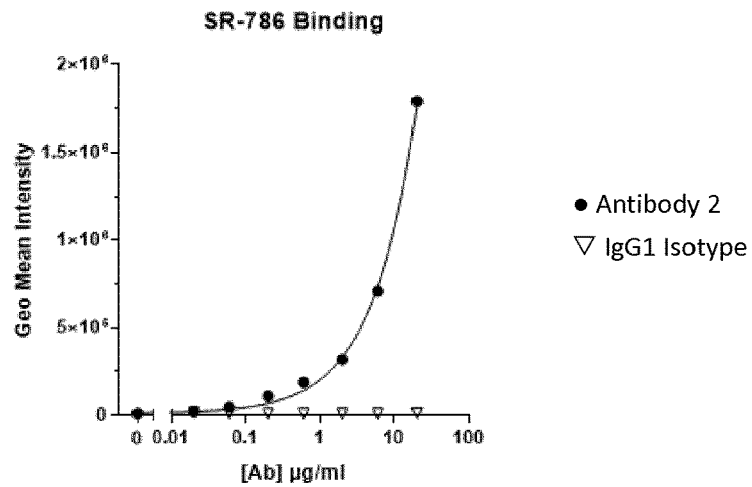

FIGURE 52
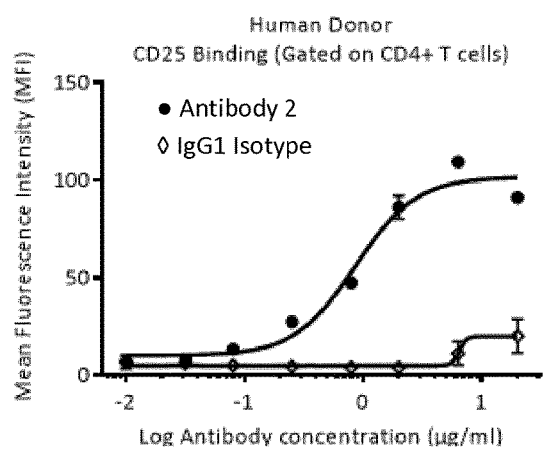
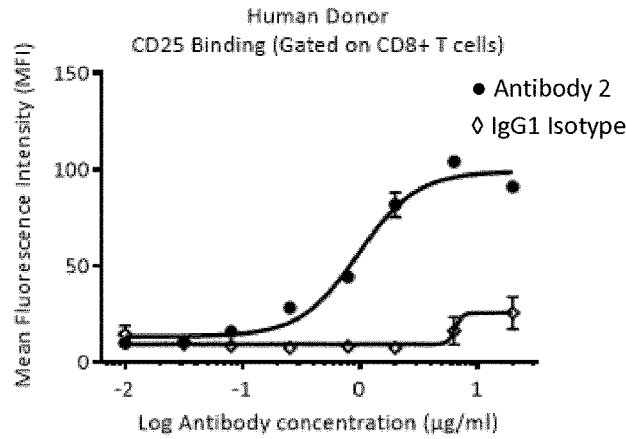
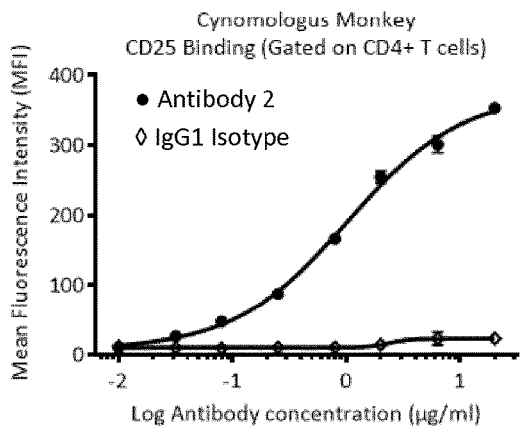
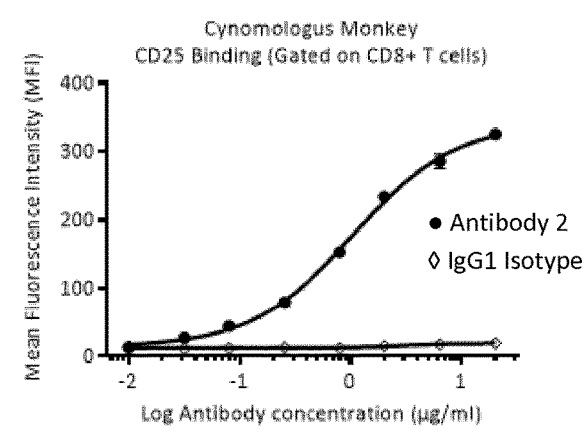

Non IL-2 competing Ab (Antibody 2)

Competitive binding to Daclizumab determine via Octet

IL2 titration

□ No antibody
Δ IgG1 Isotype
○ Daclizumab
● Antibody 2

FIGURE 56
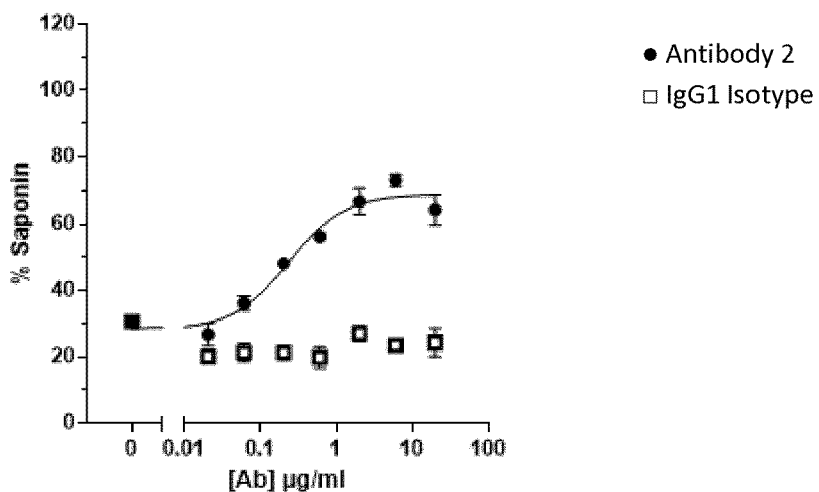
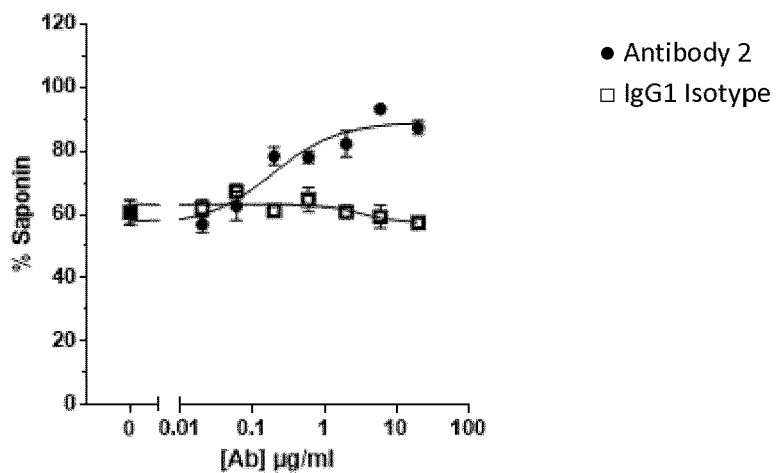
FIGURE 57
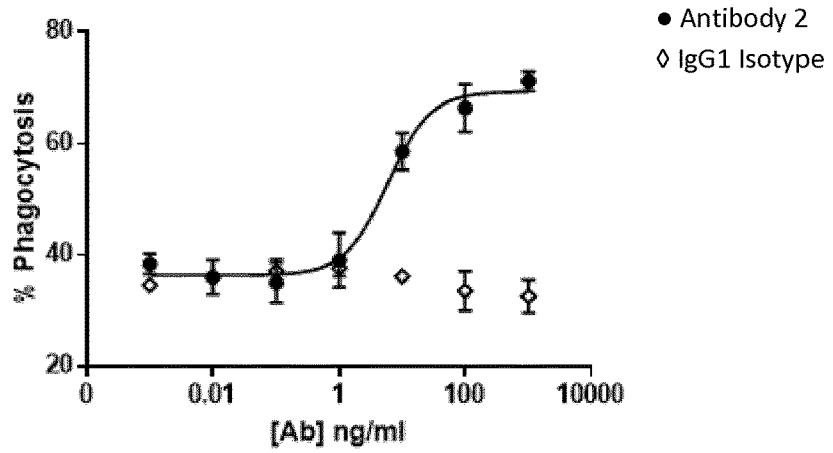

Figure 63
A)
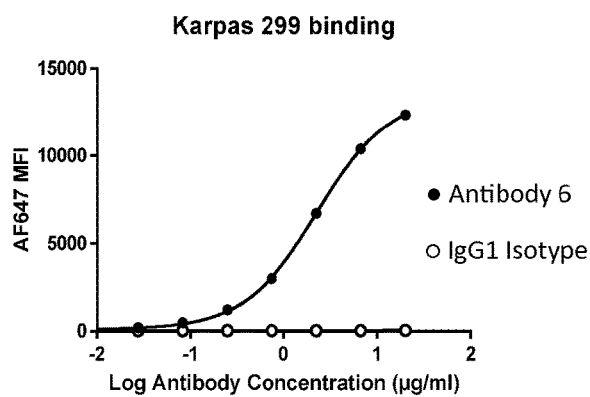
B)
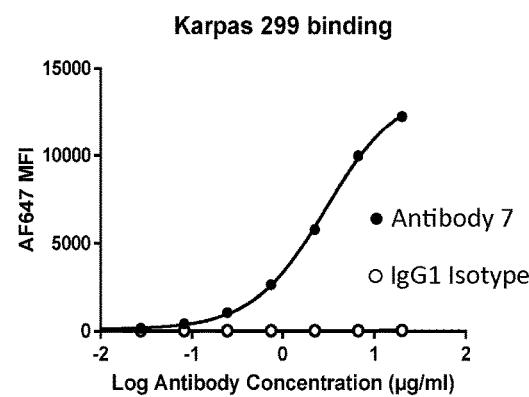
C)
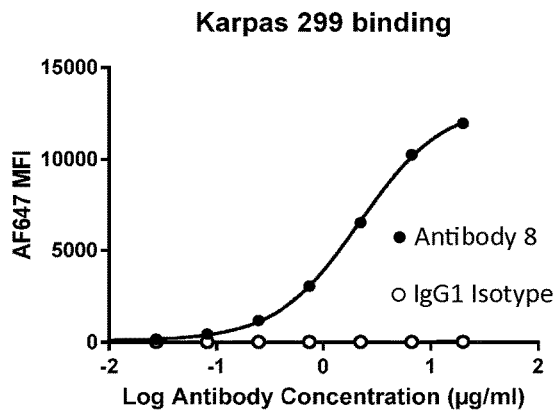
D)
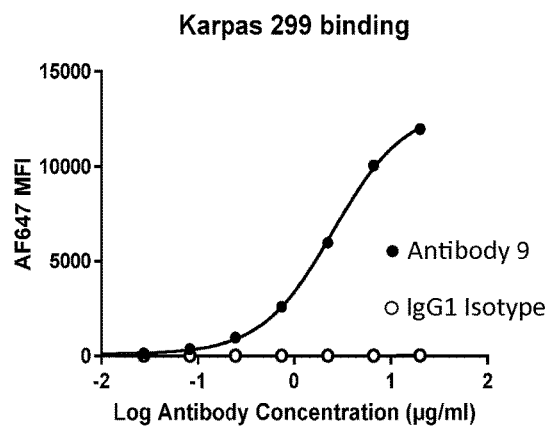

Figure 64
A)
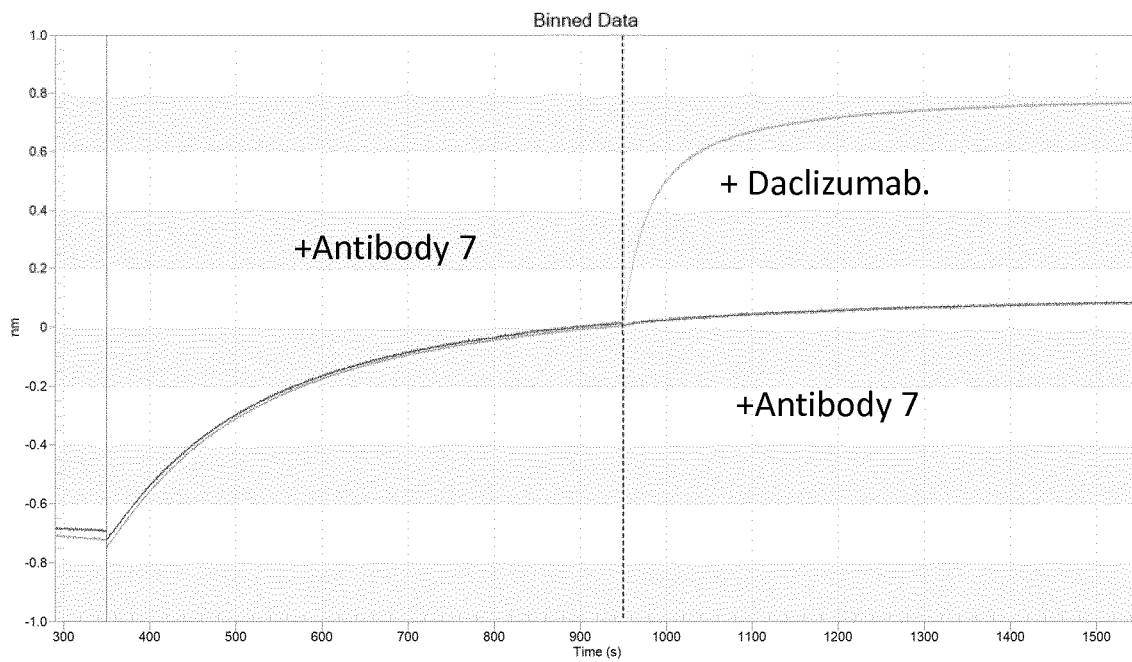
B)
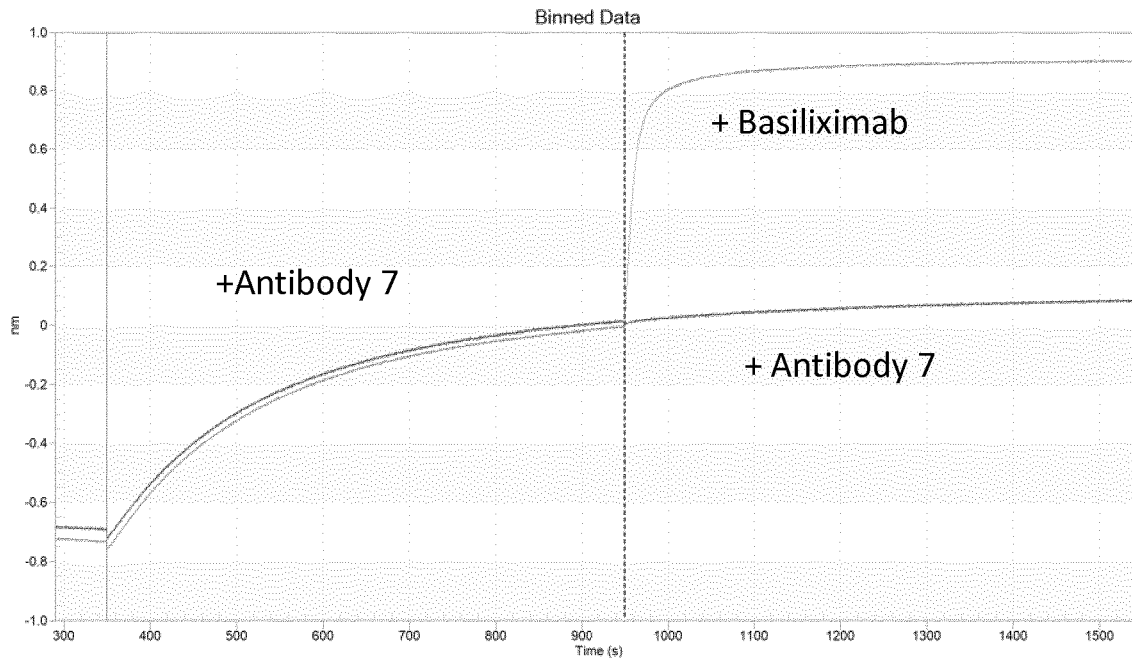

ADCP assay

Figure 68
A)
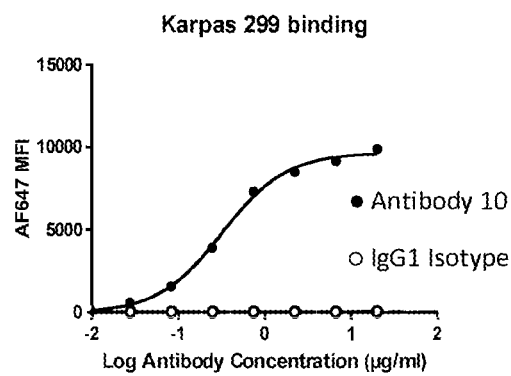
B)
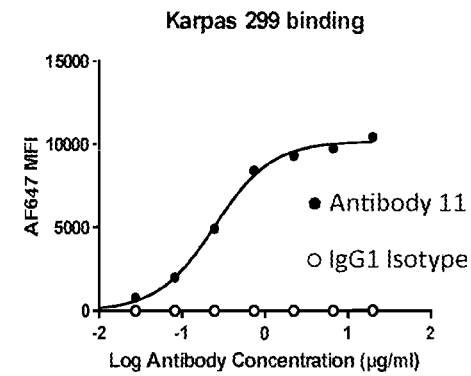
C)
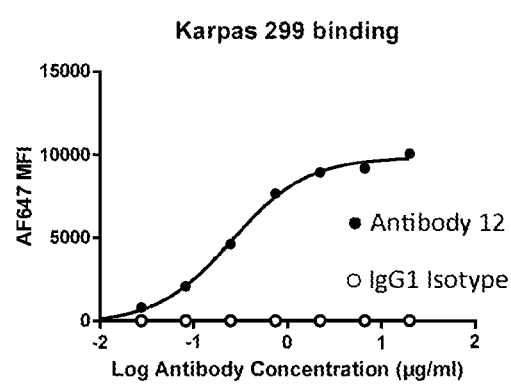
D)
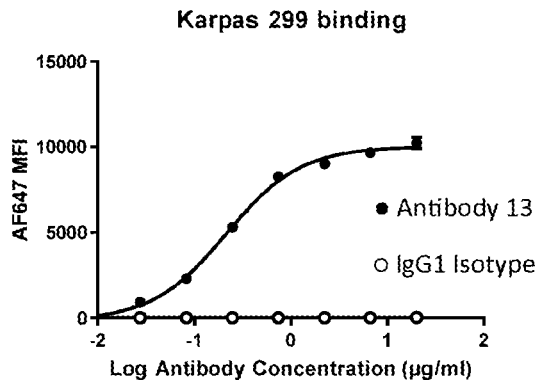
E)
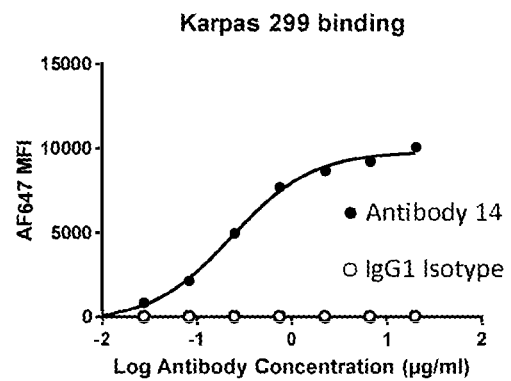
F)
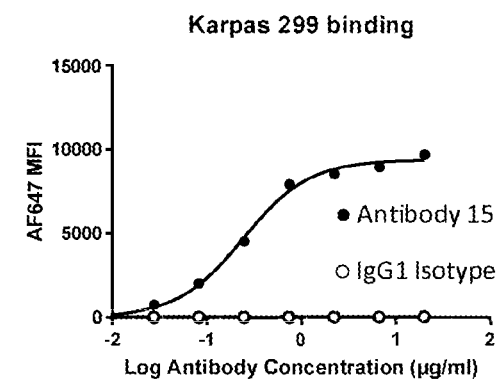

Fig. 68 (Cont.)
G)
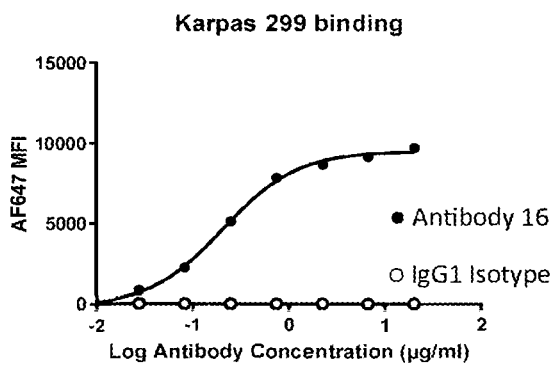
H)
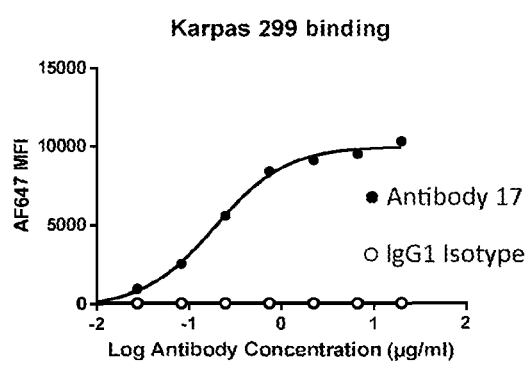
I)
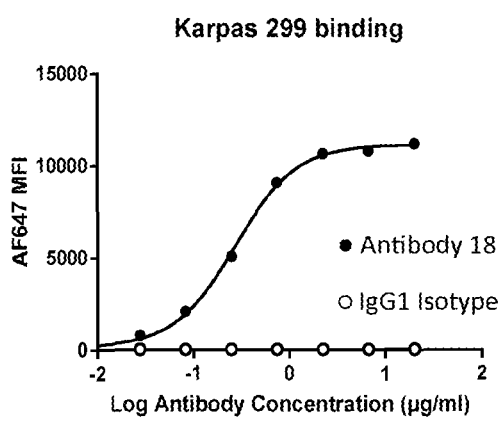
J)
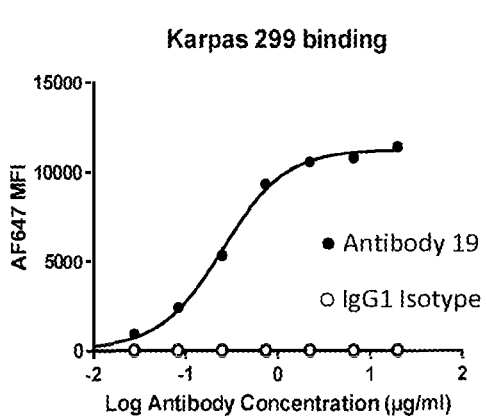
K)
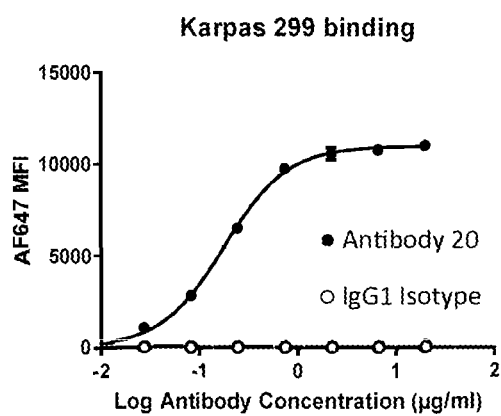
L)
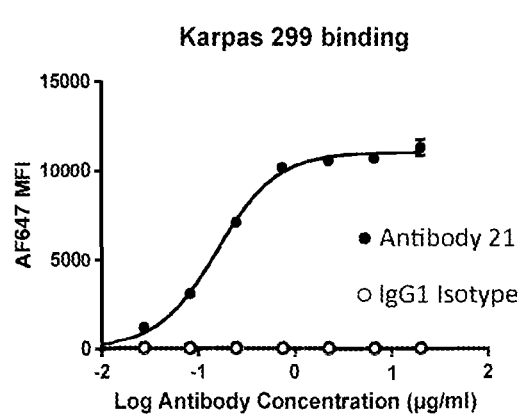

FIGURE 69
A)
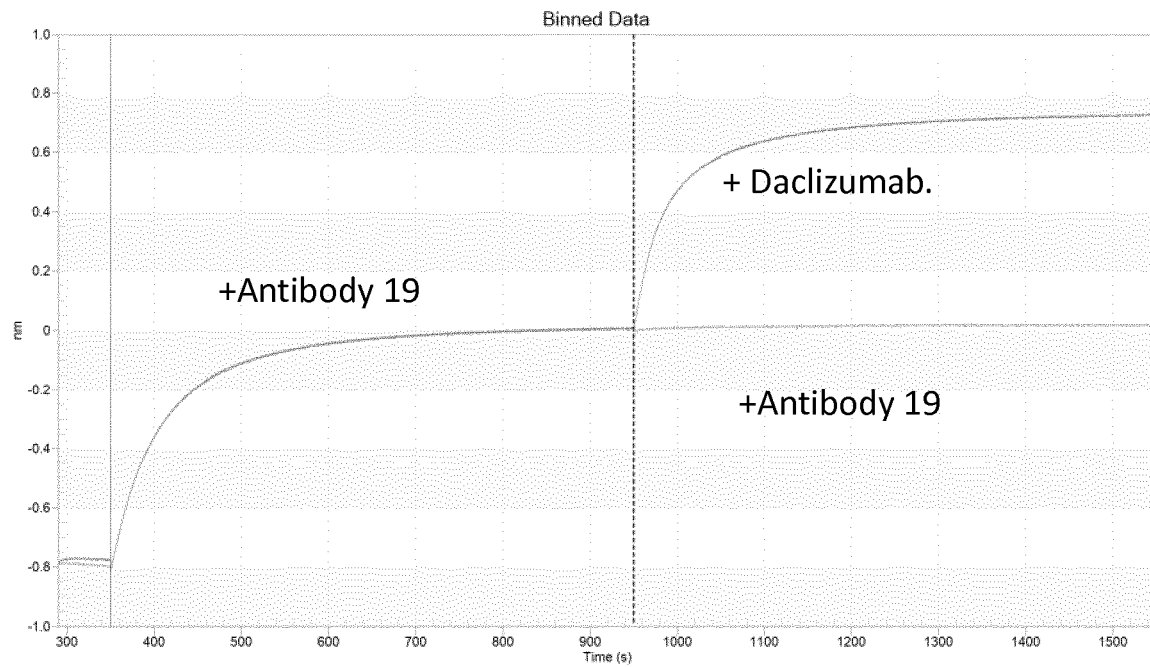
B)
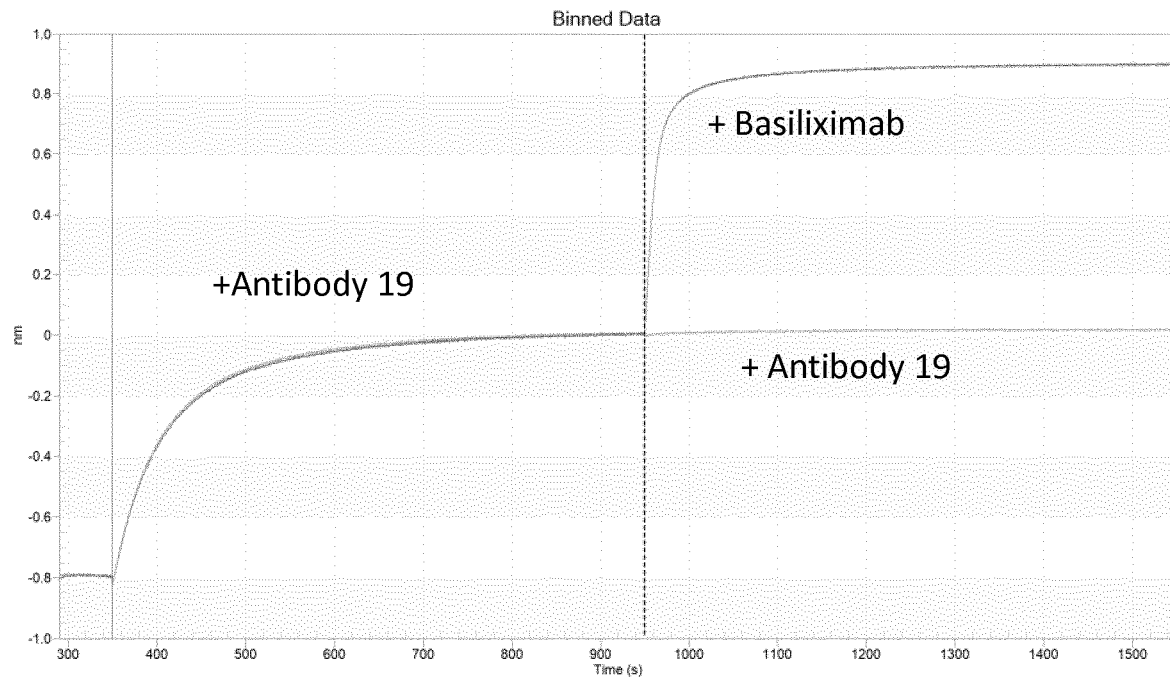

Figure 72
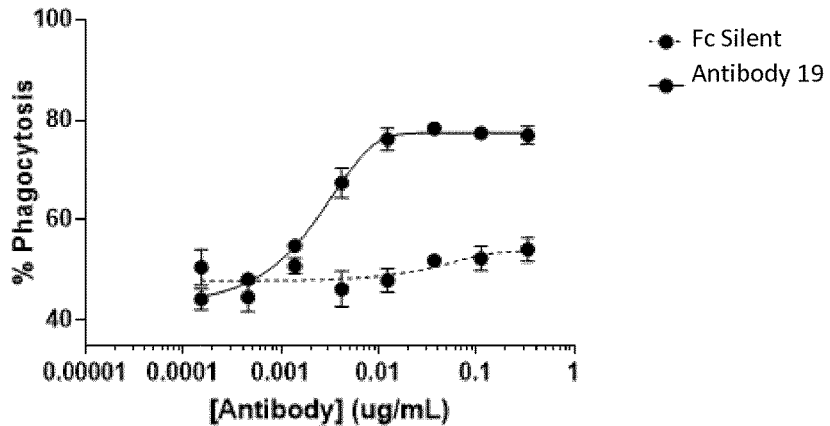
Figure 73
A)
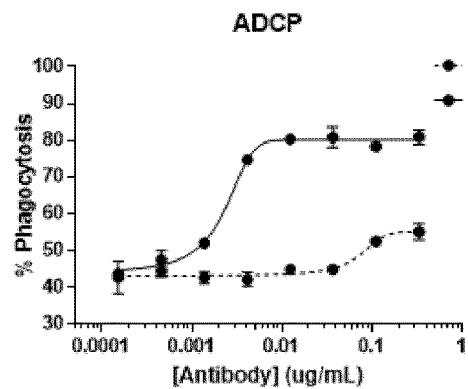
B)
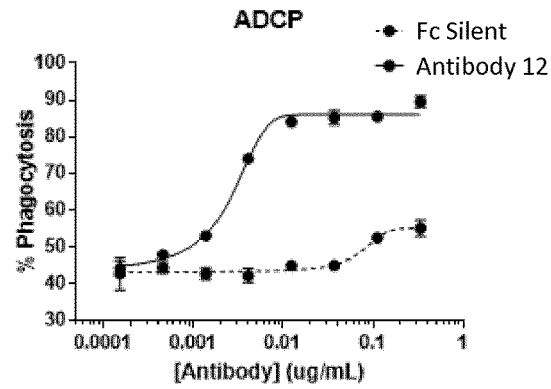
C)
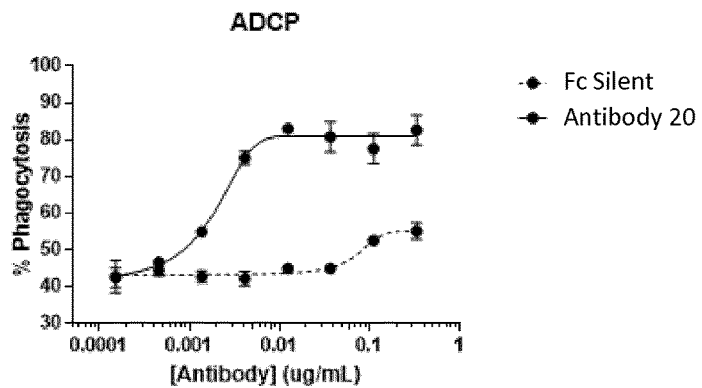

Figure 74
A)
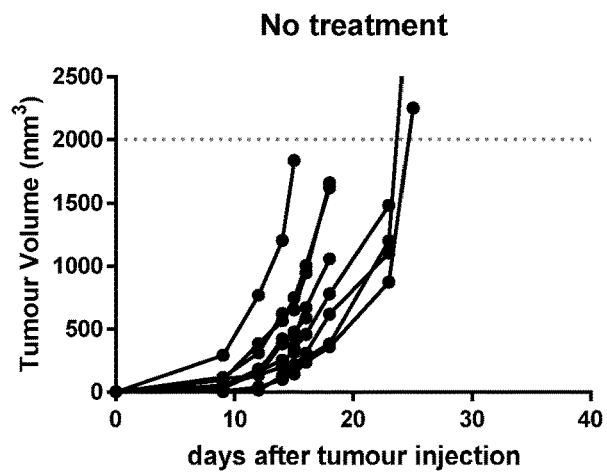
B)
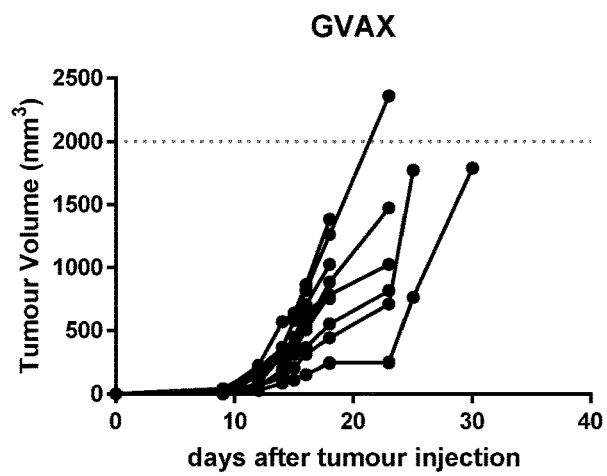
C)
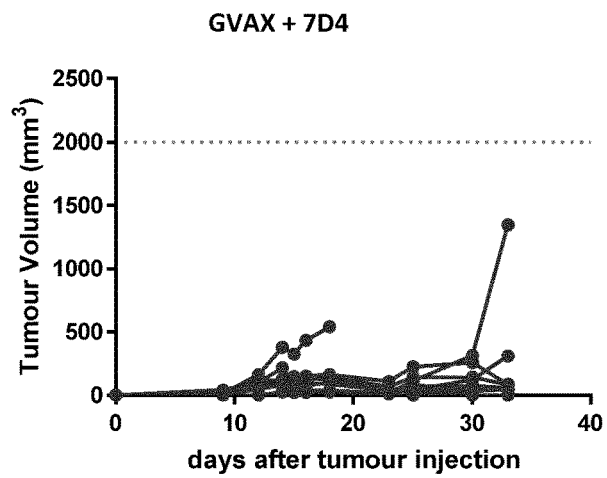

METHOD OF TREATING CANCER OR DEPLETING REGULATORY T CELLS IN A SUBJECT BY ADMINISTERING A HUMAN IGG1 ANTI-CD25 ANTIBODY

CROSS REFERENCE TO RELATED APPLICATIONS

This Application is a national phase entry of PCT/EP2018/056312 filed Mar. 13, 2018 which claims priority to EP 17161717.8 filed Mar. 17, 2017; GB 1710879.6 filed Jul. 6, 2017; and GB 1714429.6 filed Sep. 7, 2017, the entire contents of each of which is hereby incorporated by reference.

SEQUENCE LISTING

The instant application contains a Sequence Listing which has been submitted electronically in ASCII format and is hereby incorporated by reference in its entirety. Said ASCII copy, created on May 27, 2022, is named 2003882-0076_ST25 and is 40,969 bytes in size.

FIELD OF THE INVENTION

The present invention is in the field of cancer immunotherapy, and relates to a method of treating cancer, including a method of treating solid tumours, wherein the method involves the use of an antibody to CD25.

BACKGROUND TO THE INVENTION

Cancer immunotherapy involves the use of a subject's own immune system to treat or prevent cancer. Immunotherapies exploit the fact that cancer cells often have subtly different molecules on their surface that can be detected by the immune system. These molecules, or cancer antigens, are most commonly proteins, but also include molecules such as carbohydrates. Immunotherapy thus involves provocation of the immune system into attacking tumour cells via these target antigens. However, malignant tumours, in particular solid tumours, or haematological cancers can escape immune surveillance by means of various mechanisms both intrinsic to the tumour cell and mediated by components of the tumour microenvironment. Amongst the latter, tumour infiltration by regulatory T cells (Treg cells or Tregs) and, more specifically, an unfavorable balance of effector T cells (Teff) versus Tregs (i.e. a low ratio of Teff to Treg), have been proposed as critical factors (Smyth M et al., 2014, Immunol Cell Biol. 92, 473-4).

Since their discovery, Tregs have been found to be critical in mediating immune homeostasis and promoting the establishment and maintenance of peripheral tolerance. However, in the context of cancer their role is more complex. As cancer cells express both self- and tumour-associated antigens, the presence of Tregs, which seek to dampen effector cell responses, can contribute to tumour progression. The infiltration of Tregs in established tumours therefore represents one of the main obstacles to effective anti-tumour responses and to treatment of cancers in general. Suppression mechanisms employed by Tregs are thought to contribute significantly to the limitation or even failure of current therapies, in particular immunotherapies that rely on induction or potentiation of anti-tumour responses (Onishi H et al, 2012 Anticanc. Res. 32, 997-1003).

Depletion of Tregs as a therapeutic approach for treating cancer is an approach that is supported by studies having shown the contribution of Tregs to tumour establishment and progression in murine models. Moreover, tumour infiltration by Tregs has also been associated with worse prognosis in several human cancers (Shang B et al., 2015, Sci Rep. 5:15179). It has been demonstrated that Treg cells contribute to the establishment and progression of tumours in murine models and that their absence results in delay of tumour progression (Elpek et al., 2007 J Immunol. 178(11):6840-8; Golgher et al., 2002; Eur J Immunol. 32(11):3267-75, Jones et al., 2002 Cancer Immun. 22; 2:1; Onizuka et al., 1999 Cancer Res. 59(13):3128-33.; Shimizu et al., 1999, J Immunol. 163(10):5211-8). In humans, high tumour infiltration by Treg cells and, more importantly, a low ratio of effector T (Teff) cells to Treg cells, is associated with poor outcomes in multiple human cancers (Shang et al., 2015). Conversely, a high Teff/Treg cell ratio is associated with favourable responses to immunotherapy in both humans and mice (Hodi et al., 2008, Proc. Natl. Acad. Sci. USA, 105, 3005-3010; Quezada et al., 2006, J Clin Invest. 116(7):1935-45. However, depletion of Tregs in tumours is complex, and results of studies in this area have been discrepant.

CD25 is one of the potential molecular targets for achieving depletion of Tregs. CD25, also known as the interleukin-2 high-affinity receptor alpha chain (IL-2Ra), is constitutively expressed at high-levels on Treg cells, and it is absent or expressed at low-levels on T effector cells and is thus a promising target for Treg depletion. The IL-2/CD25 interaction has been the object of several studies in murine models, most of them involving the use of PC61, a rat anti-murine CD25 mouse antibody (Setiady Y et al., 2010. Eur J Immunol. 40:780-6), The CD25 binding and functional activities of this antibody have been compared to those of panel of monoclonal antibodies generated by different authors (Lowenthal J. W et al., 1985. J. Immunol., 135, 3988-3994; Moreau, J.-L et al., 1987. Eur. J. Immunol. 17, 929-935; Volk H D et al., 1989 Clin. exp. Immunol. 76, 121-5; Dantal J et al., 1991, Transplantation 52:110-5). While original studies demonstrated prophylactic but not therapeutic activity of PC61, a recent study showed that an Fc optimized version of this anti-CD25 antibody led to intra-tumoral Treg depletion and offers significant therapeutic benefit in several murine tumour models (Vargas A et al., 2017, Immunity 48(6), 577-586). Available anti-CD25 antibodies such as PC61 block or inhibit the binding of IL-2 to CD25, as do many other anti-mouse CD25 antibodies, and most of those disclosed as being anti-human CD25 antibodies; see for instance WO2004/045512, WO 2006/108670, WO1993/011238, WO1990/007861 and WO2017/174331. For example, Basiliximab and Daclizumab are anti-human CD25 antibodies that inhibit the binding of IL-2 to CD25 and have been developed to reduce activation of T-effector cells. Basiliximab is a chimeric mouse-human CD25 antibody currently approved for graft versus host diseases and Daclizumab is a humanized CD25 antibody approved for the treatment of multiple sclerosis. However, other anti-CD25 antibodies still allow the binding of IL-2 to CD25, such as the clone 7D4 (anti-mouse CD25), clone MA251 (anti-human CD25) or 7G7B6 (anti-human CD25) (Rubin et al, 1985, Hybridoma 4(2) 91-102, Tanaka et al, 1986, Microbiol. Immunol 30(4), 373-388). 7G7B6 has been used as a research antibody and suggested as a target moiety to targeting radionuclide to CD25-expressing lymphomas (Zhang et al, 2009, Cancer Biother Radiopharm 24(3), 303-309).

For example, 7D4 is a rat IgM anti-mouse CD25 antibody that has been extensively used to detect CD25-positive cells in the presence of or following the treatment with PC61 or of antibodies having similar binding properties (Onizuka S et al., 1999. Canc Res. 59, 3128-3133). Very few documents disclose any functional property of 7D4-IgM antibody, alone or in comparison with PC61 (Kohm A et al., 2006, J Immunol. 176: 3301-5; Hallett W et al., 2008. Biol Blood Marrow Transplant 14:1088-1099; Fecci P et al., 2006 Clin Cancer Res. 12:4294-4305; McNeill A et al., 2007. Scand J Immunol 65: 63-9; Setiady Y et al., 2010. Eur. J. Immunol. 40: 780-6; Couper K et al., 2007. J Immunol. 178: 4136-4146). Indeed, the prior art does not teach the possibility to adapt or somehow modify the isotype or other structural features of 7D4 in order to obtain an improved antibody to be used in cancer therapy.

However, the ability of 7D4-IgM (as such or as an engineered antibody) or of any anti-human CD25 designed or characterized as having CD25 binding features similar to those of 7D4 for mouse CD25, such as 7G7B6 or M-A251 have not been evaluated in detail with respect to the optimized depletion of Treg cells within tumours, alone or in combination with other antibodies or other anti-cancer compounds. As discussed above the infiltration of Treg cells in tumors, and in particular a low ratio of Teff cells to Treg cells, can lead to poor clinical outcome. CD25 has been identified as a Treg marker and could thus be an interesting target for therapeutic antibodies aiming at depleting Treg. Importantly, CD25 is the alpha subunit of the receptor for IL-2 and IL-2 is a key cytokine for Teff responses. Anti-CD25 antibodies that have undergone clinical testing so far, whilst depleting Treg cells also block IL-2 signalling via CD25. The present inventors have now found that such a blockade of IL-2 signalling limits Teff responses and that an anti-CD25 antibody that does not block the IL2 signalling can effectively deplete Treg cells, whilst still allowing IL-2 to stimulate Teff cells, providing antibodies that exhibit a strong anti-cancer effect. Thus, there is a need in the art for a method of treating cancer involving depletion of Tregs, particularly while still allowing IL-2 to stimulate Teff cells, in particular by using appropriate anti-CD25 antibodies.

SUMMARY OF THE INVENTION

The present invention provides anti-CD25 antibodies and uses of anti-CD25 antibodies that are characterized by structural elements that allow both binding CD25 without substantially blocking the binding of Interleukin 2 (IL-2) to CD25 or signalling of IL-2 via CD25, and depleting efficiently Tregs, in particular within tumours. The structural and functional features of 7D4-IgM (as described with respect to mouse CD25) have been modified in order to provide antibodies that present surprisingly improved features in terms of use for depleting Tregs and efficacy against tumours, alone or in combination with other anti-cancer agents. Structural and functional features of further anti-CD25 antibodies which do not block the binding of interleukin 2 to CD25 (and do not block the signalling of IL2 via CD25) and efficiently deplete Tregs have also been characterised. These findings can be used for defining and generating further anti-human CD25 antibodies that provide comparable effects against tumours in human subjects. References herein to "anti-CD25 antibodies" and the like include antigen-binding fragments thereof, as well as variants (including affinity matured variants), unless the context implies otherwise.

In a main aspect, the present invention provides a method of treating a human subject who has cancer comprising the step of administering an anti-CD25 antibody to a subject, wherein said subject has a tumour (preferably a solid tumour), wherein said antibody does not inhibit the binding of Interleukin-2 (IL-2) to CD25.

References to "does not block", "non-blocking", "non-IL-2 blocking", "without blocking" and similar terminology herein (with respect to the non-blocking of IL-2 binding to CD25 in the presence of the anti-CD25 antibody) include embodiments wherein the anti-CD25 antibody does not block the signalling of IL-2 via CD25. That is, the anti-CD25 antibody of the invention inhibits less than 50% of IL-2 signalling via CD25 compared to IL-2 signalling in the absence of the antibodies. Preferably the anti-CD25 antibody inhibits less than about 40%, 35%, 30%, preferably less than about 25% of IL-2 signalling compared to IL-2 signalling in the absence of the antibodies.

In one embodiment, the anti-CD25 antibody competes with the antibody 7G7B6 for binding to human CD25; and/or competes with the antibody MA251 for binding to human CD25.

In one embodiment, the anti-CD25 antibody binds to the same epitope recognised by antibody 7G7B6 and/or binds to the same epitope recognised by antibody MA251.

In one embodiment the anti-CD25 antibody specifically binds to an epitope of human CD25 wherein the epitope comprises one or more amino acid residues comprised in one or more of the amino acid stretches selected from amino acids 150-163 of SEQ ID NO:1 (YQCVQGYRALHRGP), amino acids 166-186 of SEQ ID NO:1 (SVCKMTHGKTRVVTQPQLICTG), amino acids 42-56 of SEQ ID NO:1 (KEGTMLNCECKRGFR) and amino acids 70-88 of SEQ ID NO:1 (NSSHSSWDNQCQCTSSATR).

Preferably the epitope comprises at least two, at least three, at least four, at least five, at least six, at least seven, at least eight, at least nine, at least ten, at least eleven, at least twelve, at least thirteen, at least fourteen, at least fifteen, at least sixteen, at least seventeen, at least eighteen or more amino acid residues comprised in one of more the amino acid stretches selected from amino acids 150-163 of SEQ ID NO:1 (YQCVQGYRALHRGP), amino acids 166-186 of SEQ ID NO:1 (SVCKMTHGKTRVVTQPQLICTG), amino acids 42-56 of SEQ ID NO:1 (KEGTMLNCECKRGFR) and/or amino acids 70-88 of SEQ ID NO:1 (NSSHSSWDNQCQCTSSATR).

In one embodiment, the anti-CD25 antibody specifically binds to an epitope of human CD25 wherein the epitope comprises at least one sequence selected from: amino acids 150-158 of SEQ ID NO:1 (YQCVQGYRA), amino acids 176-180 of SEQ ID NO:1 (RWTQP), amino acids 42-56 of SEQ ID NO:1 (KEGTMLNCECKRGFR) and amino acids 74-84 of SEQ ID NO:1 (SSWDNQCQCTS).

In one embodiment, the anti-CD25 antibody specifically binds to an epitope of human CD25 wherein the epitope comprises at least one sequence selected from amino acids wherein the epitope comprises at least one sequence selected from: amino acids 150-158 of SEQ ID NO:1 (YQCVQGYRA), amino acids 166-180 of SEQ ID NO:1 (SVCKMTHGKTRVVTQP), amino acids 176-186 of SEQ ID NO:1 (RWTQPQLICTG), amino acids 42-56 of SEQ ID NO:1 (KEGTMLNCECKRGFR) and amino acids 74-84 of SEQ ID NO:1 (SSWDNQCQCTS).

In one embodiment, the anti-CD25 antibody specifically binds to an epitope of human CD25 wherein the epitope comprises at least one sequence selected from: amino acids 42-56 of SEQ ID NO:1 (KEGTMLNCECKRGFR), amino acids 70 to 84 of SEQ ID NO: 1 (NSSHSSWDNQCQCTS) and amino acids 150 to 158 of SEQ ID NO: 1 (YQCVQGYRA In one embodiment, the anti-CD25 antibody binds to an epitope comprising the sequence of amino acids 42-56 of SEQ ID NO:1 (KEGTMLNCECKRGFR). In one embodiment the anti-CD25 antibody binds to an epitope comprising the sequence of amino acids 42-56 of SEQ ID NO:1 (KEGTMLNCECKRGFR) and amino acids 150-160 of SEQ ID NO:1 (YQCVQGYRALH). In another embodiment, the anti-CD25 antibody binds to an epitope comprising the sequence of amino acids 42-56 of SEQ ID NO:1 (KEGTMLNCECKRGFR) and amino acids 74-88 of SEQ ID NO:1 (SSWDNQCQCTSSATR). In another embodiment the anti-CD25 antibody binds to an epitope comprising the sequence of amino acids 150-163 of SEQ ID NO:1 (YQCVQGYRALHRGP), amino acids 166-180 of SEQ ID NO:1 (SVCKMTHGKTRVVTQP), amino acids 42-56 of SEQ ID NO:1 (KEGTMLNCECKRGFR) and amino acids 74-88 of SEQ ID NO:1 (SSWDNQCQCTSSATR)

In one embodiment, the anti-CD25 antibody binds to an epitope comprising the sequence of amino acids 176-180 of SEQ ID NO:1 (RWTQP). In one embodiment, the anti-CD-25 antibody binds to an epitope comprising the sequence of amino acids 166-180 of SEQ ID NO:1 (SVCKMTHGKTRVVTQP). In one embodiment, the anti-CD-25 antibody binds to an epitope comprising the sequence of amino acids 176-186 of SEQ ID NO:1 (RWTQPQLICTG).

In one embodiment, the anti-CD25 antibody specifically binds to an epitope comprising the sequence of amino acids 150-158 of SEQ ID NO:1 (YQCVQGYRA) and amino acid 176-180 of SEQ ID NO:1 (RWTQP). In one embodiment, the anti-CD25 antibody specifically binds to an epitope comprising the sequence of amino acids 150-158 of SEQ ID NO:1 (YQCVQGYRA) and amino acids 176-186 of SEQ ID NO:1 (RWTQPQLICTG). In one embodiment the anti-CD25 antibody specifically binds to an epitope comprising the sequence of amino acids 150-163 of SEQ ID NO:1 (YQCVQGYRALHRGP) and amino acids 166-180 of SEQ ID NO:1 (SVCKMTHGKTRVVTQP).

In one embodiment, the anti-CD25 antibody binds to an epitope comprising the sequence of amino acids 74-84 of SEQ ID NO:1 (SSWDNQCQCTSSATR). In one embodiment, the anti-CD25 antibody binds to an epitope comprising the sequence of amino acids 70-84 of SEQ ID NO:1 (NSSHSSWDNQCQCTS).

The present inventors having surprisingly found that antibodies that bind to particular epitopes of CD25, including those that compete with 7G7B6 and/or MA251 for binding to CD25, are useful in the treatment of cancer, in particular solid tumours. Such antibodies still permit signalling of IL-2 via the CD25 bound by the antibody, and the inventors have discovered for the first time that in addition to depleting Treg cells, the antibodies used in the present invention allow Teff cells to optimally exert their anti-cancer effects, at least in part by allowing the binding of IL-2 to, and signalling through, CD25 expressed on the Teff cells.

Such antibodies preferably have a dissociation constant ($K_d$) for CD25 of less than $10^{-7}$ M and/or a dissociation constant for at least one activating Fcγ receptor of less than about $10^{-8}$M. Preferably the antibody has a dissociation constant ($K_d$) for CD25 in the $10^{-8}$ or $10^{-9}$ or $10^{-10}$ or $10^{-11}$ or $10^{-12}$ or $10^{-13}$ range or below. Most preferably, it is a human IgG1 antibody that binds to at least one activating Fcγ receptor with high affinity and depletes tumour-infiltrating regulatory T cells. Most preferably, the anti-CD25 is characterized by other features related to Fcγ receptors, in particular:

(a) binds to Fcγ receptors with an activatory to inhibitory ratio (A/I) superior to 1; and/or
(b) binds to FcγRIIa with higher affinity than it binds to FcγRIIb.

Given the use of the anti-CD25 antibody in therapeutic methods, it can present further preferred features. The anti-CD25 antibody is preferably a monoclonal antibody, in particular a human, chimeric, or humanized antibody. The antibody may be an affinity matured variant thereof, optionally a humanised or affinity matured variant of 7G7B6 or MA251. Moreover, in view of its interactions with immune cells and/or other components of the immune system for exerting its activities, the anti-CD25 antibody may further elicit an enhanced CDC, ADCC and/or ADCP response, preferably an increased ADCC and/or ADCP response, more preferably an increased ADCC response, as compared to existing anti-human CD25 clinical antibodies, Daclizumab and Basiliximab. In some embodiments the anti-CD25 antibody may elicit a decreased CDC response, as compared to existing anti-human CD25 clinical antibodies, Daclizumab and Basiliximab, more preferably the anti-CD25 antibody does not elicit a CDC response.

The anti-CD25 antibody of the present invention (as generally defined above and in further details in the Detailed Description) can be used in methods of treating a human subject wherein said anti-CD25 antibody is administered to a subject. In one embodiment the subject has cancer. Preferably the subject has an established, solid tumour (preferably in a method further comprising the step of identifying a subject who has a solid tumour). Such methods may further comprise administering a further therapeutic agent to said subject. In one embodiment the further agent may be an immune checkpoint inhibitor to said subject, for example in the form of an antibody binding and inhibiting an immune checkpoint protein. A preferred immune checkpoint inhibitor is a PD-1 antagonist, which can be an anti-PD-1 antibody or an anti-PD-L1 antibody. More in general, an anti-CD25 antibody can be used in methods of depleting regulatory T cells in a solid tumour in a subject comprising the step of administering said anti-CD25 antibody to said subject.

In a further aspect, the anti-CD25 antibody of the invention can be used for the manufacture of a medicament for the treatment of cancer in a human subject, preferably wherein said subject has a tumour, preferably a solid tumour. Said antibody may be administered in combination with a further therapeutic agent, preferably a further cancer therapeutic agent for example with an immune checkpoint inhibitor, preferably a PD-1/PD-L1 pathway antagonist, a cancer vaccine, and/or used in combination with standard of care therapies such as chemotherapy or radiotherapy.

In a further aspect, the present invention provides a combination of an anti-CD25 antibody as defined above with another anti-cancer compound (preferably an immune checkpoint inhibitor or other compounds as indicated in the Detailed Description) for use in the treatment of cancer in a human subject, preferably wherein said subject has a solid tumour and the anti-cancer compound (for example, an immune checkpoint inhibitor such a PD-1 antagonist or a cytokine such as Interleukin 2) can be administered simultaneously, separately or sequentially. At this scope the present invention also provides a kit for use in the treatment of cancer comprising an anti-CD25 antibody, as defined above, and an anti-cancer compound (for example, an immune checkpoint inhibitor such a PD-1 antagonist).

In a further aspect, the present invention also provides a pharmaceutical composition comprising an anti-CD25 antibody as defined above in a pharmaceutically acceptable medium. Such composition may also comprise an anti-cancer compound (for example, an immune checkpoint inhibitor such a PD-1 antagonist).

In a still further aspect, the present invention also provides a bispecific antibody comprising:
(a) a first antigen binding moiety that binds to CD25; and
(b) a second antigen binding moiety that binds to another antigen;
wherein the anti-CD25 antibody does not inhibit the binding of Interleukin-2 (IL-2) to CD25, and preferably the bispecific antibody is an IgG1 antibody that binds to at least one activatory Fcγ receptor with high affinity and depletes tumour-infiltrating regulatory T cells. Preferably, such second antigen binding moiety binds to an antigen selected from an immune checkpoint protein, or a tumour-associated antigen, or may be, or be based on, an anti-human activatory Fc Receptor antibody (anti-FcgRI, anti-FcgRIIa, anti-FcgRIII), or an antagonistic anti-human FcγRIIb antibody. As such, the second antigen binding moiety may bind to FcRIIb. It may alternatively bind to FcgRI, FcgRIIa, and/or FcgRIII with antagonistic activity.

Preferably, such bispecific antibody comprises a second antigen binding moiety that binds an immune checkpoint protein that is selected from the group consisting of PD-1, CTLA-4, BTLA, KIR, LAG3, VISTA, TIGIT, TIM3, PD-L1, B7H3, B7H4, PD-L2, CD80, CD86, HVEM, LLT1, GAL9, GITR, OX40, CD137, and ICOS. Such immune checkpoint protein is preferably expressed on a tumour cell. Preferably the immune checkpoint protein is selected from PD-1, PD-L1, and CTLA-4. The second antigen binding moiety that binds to an immune checkpoint protein can be comprised in a commercially available antibody that acts as an immune checkpoint inhibitor, for example:
(a) in the case of PD-1, the anti-PD-1 antibody can be Nivolumab or Pembrolizumab.
(b) In the case of PD-L1, the anti-PD-L1 is Atezolizumab;
(c) In case of CTLA-4, the anti-CTLA-4 is Ipilimumab.

Such bispecific antibody can be provided in any commercially available format, including Duobody®, BITE® DART®, CrossMab, Knobs-in-holes, Triomab®, or other appropriate molecular format of bispecific antibody and fragments thereof.

Alternatively, such bispecific antibody comprises a second antigen binding moiety that binds to tumour-associated antigen. In this alternative embodiment. such antigens and corresponding antibodies include, without limitation CD22 (Blinatumomab), CD20 (Rituximab, Tositumomab), CD56 (Lorvotuzumab), CD66e/CEA (Labetuzumab), CD152/CTLA-4 (Ipilimumab), CD221/IGF1R (MK-0646), CD326/Epcam (Edrecolomab), CD340/HER2 (Trastuzumab, Pertuzumab), and EGFR (Cetuximab, Panitumumab).

The combination of anti-CD25 antibody of the invention with another anti-cancer compound, as well as the bispecific antibodies as defined above, can be used in a method of treating cancer, comprising the step of administering said combination or said bispecific antibody to a subject, in particular when the subject has a solid tumour, and for use in the treatment of cancer in a subject.

Further objects of the invention, including further definitions of the anti-human CD25 antibodies of the invention and of their uses in methods for treating cancer, in pharmaceutical compositions, in combinations with other anti-cancer compounds, in bispecific antibodies, are provided in the Detailed Description and in the Examples.

DETAILED DESCRIPTION OF THE INVENTION

The present invention provides a method of treating or preventing cancer, in a subject, preferably when the subject has a solid tumour, comprising the step of administering an antibody that binds to CD25 to said subject, whereby the anti-CD25 antibodies are characterized by structural elements that allow both binding CD25 without interfering in interleukin 2 binding or the signalling via CD25 and depleting efficiently Tregs, in particular within tumours. The antibody that binds to CD25 as defined in the present invention can be used in the treatment or prevention of cancer, preferably of a solid tumour. Alternatively put, the present invention provides the use of an antibody that binds to CD25 and allow both binding CD25 without interfering in interleukin 2 binding to CD25 and efficient depletion of Tregs for the manufacture of a medicament for the treatment or prevention of cancer, preferably, a solid tumour. The invention also provides the use of an antibody that binds CD25 and that allow both binding CD25 without substantially interfering in interleukin 2 binding to CD25 and depletion of Tregs in the treatment or prevention of cancer, preferably a solid tumour.

The present inventors have found for that CD25 can be targeted using an anti-CD25 antibody that does not inhibit (or does not substantially inhibit) the binding of interleukin 2 to CD25 or the signalling of IL-2 via CD25 for depletion of regulatory T cells in the therapeutic context, for example in an established solid tumour. The present inventors have found that a non-IL-2 blocking anti-CD25 antibodies having an isotype that enhances their binding to activatory Fc gamma receptors leads to effective depletion of tumour-infiltrating regulatory T cells while still allowing an optimal Teff response, a therapeutic approach that could, for example, be associated (in combination with or within bispecific antibodies) with other cancer-targeting compounds, such as those targeting an immune checkpoint protein, a tumour-associated antigen, or an inhibitory Fcγ receptor. These findings also make possible to combine the use of an anti-CD25 with interleukin-2 at appropriate doses for treating cancer.

CD25 is the alpha chain of the IL-2 receptor, and is found on activated T cells, regulatory T cells, activated B cells, some NK T cells, some thymocytes, myeloid precursors and oligodendrocytes. CD25 associates with CD122 and CD132 to form a heterotrimeric complex that acts as the high-affinity receptor for IL-2. The consensus sequence of human CD25 is shown below in SEQ ID NO:1 (Uniprot accession number P01589; the extracellular domain of mature human CD25, corresponding to amino acids 22-240, is underlined and is presented as SEQ ID NO:2):

```
          10         20         30         40
MDSYLLMWGL LTFIMVPGCQ AELCDDDPPE IPHATFKAMA 50         60         70         80
YKEGTMLNCE CKRGFRRIKS GSLYMLCTGN SSHSSWDNQC 90        100        110        120
QCTSSATRNT TKQVTPQPEE QKERKTTEMQ SPMQPVDQAS 130        140        150        160
LPGHCREPPP WENEATERIY HFVVGQMVYY QCVQGYRALH 170        180        190        200
RGPAESVCKM THGKTRWTQP QLICTGEMET SQFPGEEKPQ
```

-continued

```
        210        220        230        240
ASPEGRPESE TSCLVTTTDF QIQTEMAATM ETSIFTTEYQ 250        260        270
VAVAGCVFLL ISVLLLSGLT WQRRQRKSRR TI
```

As used herein, "an antibody that binds CD25" refers to an antibody that is capable of binding to the CD25 subunit of the IL-2 receptor. This subunit is also known as the alpha subunit of the IL-2 receptor. Such an antibody is also referred to herein as an "anti-CD25 antibody".

An anti-CD25 antibody is an antibody capable of specific binding to the CD25 subunit (antigen) of the IL-2 receptor. "Specific binding", "bind specifically", and "specifically bind" are understood to mean that the antibody has a dissociation constant ($K_d$) for the antigen of interest of less than about $10^{-6}$ M, $10^{-7}$ M, $10^{-8}$ M, $10^{-9}$ M, $10^{-10}$ M, $10^{-11}$ M, $10^{-12}$ M or $10^{-13}$ M. In a preferred embodiment, the dissociation constant is less than $10^{-8}$ M, for instance in the range of $10^{-9}$ M, $10^{-10}$ M, $10^{-11}$ M, $10^{-12}$ M or $10^{-13}$ M.

As used herein, the term "antibody" refers to both intact immunoglobulin molecules as well as fragments thereof that include the antigen-binding site, and includes polyclonal, monoclonal, genetically engineered and otherwise modified forms of antibodies, including but not limited to chimeric antibodies, humanised antibodies, heteroconjugate and/or multispecific antibodies (e.g., bispecific antibodies, diabodies, tribodies, and tetrabodies), and antigen binding fragments of antibodies, including e.g. Fab', F(ab')$_2$, Fab, Fv, rIgG, polypeptide-Fc fusions, single chain variants (scFv fragments, VHHs, Trans-bodies®, Affibodies®, shark single domain antibodies, single chain or Tandem diabodies (TandAb®), VHHs, Anticalins®, Nanobodies®, minibodies, BiTE®s, bicyclic peptides and other alternative immunoglobulin protein scaffolds). In some embodiments, an antibody may lack a covalent modification (e.g., attachment of a glycan) that it would have if produced naturally. In some embodiments, an antibody may contain a covalent modification (e.g., attachment of a glycan, a detectable moiety, a therapeutic moiety, a catalytic moiety, or other chemical group providing improved stability or administration of the antibody, such as poly-ethylene glycol). In some embodiments, the antibody may be in the form of a masked antibody (e.g. Probodies®). A masked antibody can comprise a blocking or "mask" peptide that specifically binds to the antigen binding surface of the antibody and interferes with the antibody's antigen binding. The mask peptide is linked to the antibody by a cleavable linker (e.g. by a protease). Selective cleavage of the linker in the desired environment, i.e. in the tumour environment, allows the masking/blocking peptide to dissociate, enabling antigen binding to occur in the tumour, and thereby limiting potential toxicity issues. "Antibody" may also refer to camelid antibodies (heavy-chain only antibodies) and antibody-like molecules such as anticalins (Skerra (2008) FEBS J 275, 2677-83). In some embodiments, an antibody is polyclonal or oligoclonal, that is generated as a panel of antibodies, each associated to a single antibody sequence and binding more or less distinct epitopes within an antigen (such as different epitopes within human CD25 extracellular domain that are associated to different reference anti-human CD25 antibodies). Polyclonal or oligoclonal antibodies can be provided in a single preparation for medical uses as described in the literature (Kearns J D et al., 2015. Mol Cancer Ther. 14:1625-36).

In one aspect of the invention the antibody is monoclonal. The antibody may additionally or alternatively be humanised or human. In a further aspect, the antibody is human, or in any case an antibody that has a format and features allowing its use and administration in human subjects. In aspect of the invention the antibodies may be humanised variants of affinity matured 7G7B6 or MA251. The affinity matured antibody has at least 10% higher affinity to CD25 and/or the CDR sequences are at least 80% identical, preferably 90% identical to the CDRs of the parental sequence (across all sequences). An affinity matured antibodies is an antibody with one of more altered amino acids in one or more CDRs which results in an antibody with improved affinity for CD25 compared to the parental strain not having the altered amino acids.

Antibodies (Abs) and immunoglobulins (Igs) are glycoproteins having the same structural characteristics. Immunoglobulins may be from any class such as IgA, IgD, IgG, IgE or IgM. Immunoglobulins can be of any subclass such as IgG$_1$, IgG$_2$, IgG$_3$, or IgG$_4$. In a preferred aspect of the invention the anti-CD25 antibody is from the IgG class, preferably the IgG1 subclass. In one aspect, the anti-CD25 antibody is from the human IgG1 subclass. Alternatively, in one aspect, the anti-CD25 antibody is from the human IgG2 subclass.

The Fc region of IgG antibodies interacts with several cellular Fcγ receptors (FcγR) to stimulate and regulate downstream effector mechanisms. There are five activating receptors, namely FcγRI (CD64), FcγRIIa (CD32a), FcγRIIc (0032c), FcγRIIIa (0016a) and FcγRIIIb (0016b), and one inhibitory receptor FcγRIIb (CD32b). The communication of IgG antibodies with the immune system is controlled and mediated by FcγRs, which relay the information sensed and gathered by antibodies to the immune system, providing a link between the innate and adaptive immune systems, and particularly in the context of biotherapeutics (Hayes J et al., 2016. J Inflamm Res 9: 209-219).

IgG subclasses vary in their ability to bind to FcγR and this differential binding determines their ability to elicit a range of functional responses. For example, in humans, FcγRIIIa is the major receptor involved in the activation of antibody-dependent cell-mediated cytotoxicity (ADCC) and IgG3 followed closely by IgG1 display the highest affinities for this receptor, reflecting their ability to potently induce ADCC. Whilst IgG2 have been shown to have weak binding for this receptor anti-CD25 antibody having the human IgG2 isotype have also been found to efficiently deplete Tregs.

In a preferred embodiment of the invention, the antibody binds FcγR with high affinity, preferably an activating receptor with high affinity. Preferably the antibody binds FcγRI and/or FcγRIIa and/or FcγRIIIa with high affinity. In a particular embodiment, the antibody binds to at least one activatory Fcγ receptor with a dissociation constant of less than about $10^{-6}$M, $10^{-7}$M, $10^{-8}$M, $10^{-9}$M or $10^{-10}$M.

In one aspect, the antibody is an IgG1 antibody, preferably a human IgG1 antibody, which is capable of binding to at least one Fc activating receptor. For example, the antibody may bind to one or more receptor selected from FcγRI, FcγRIIa, FcγRIIc, FcγRIIIa and FcγRIIIb. In one aspect, the antibody is capable of binding to FcγRIIIa. In one aspect, the antibody is capable of binding to FcγRIIIa and FcγRIIa and optionally FcγRI. In one aspect, the antibody is capable of binding to these receptors with high affinity, for example with a dissociation constant of less than about $10^{-7}$M, $10^{-8}$M, $10^{-9}$M or $10^{-10}$M.

In one aspect, the antibody binds an inhibitory receptor, FcγRIIb, with low affinity. In one aspect, the antibody binds FcγRIIb with a dissociation constant higher than about $10^{-7}$ M, higher than about $10^{-6}$M or higher than about $10^{-5}$M.

In a preferred embodiment of the invention, the anti-CD25 antibody is from the IgG1 subclass and preferably has ADCC and/or ADCP activity, as discussed herein, in particular with respect to cells of human origin. As previously described (Nimmerjahn F et al., 2005. Science, 310:1510-2), the mIgG2a isotype (which corresponds human IgG1 isotype) binds to all FcγR subtypes with a high activatory to inhibitory ratio (A/I), that is at least superior to 1. In contrast, other isotypes (such as rIgG1 isotype) bind with a similar affinity to a single activatory FcγR only (FcγRIII), as well as the inhibitory FcγRIIb, resulting in a low A/I ratio (<1). This lower A/I ratio can correlate with a lower in intra-tumoral Treg depletion and lower anti-tumour therapeutic activity of the isotype. Despite the known FcγR binding profile for antibodies of the human IgG2 isotype, significant Treg depletion can also be achieved with human IgG2 isotype of an anti-CD25 antibody. Therefore in one embodiment the anti-CD25 antibody is from the IgG2 subclass In a preferred embodiment, the anti-CD25 antibody as described herein binds human CD25, preferably with high affinity. Still preferably, the anti-CD25 antibody binds to the extracellular region of human CD25, as shown above. In one aspect, the invention provides an anti-CD25 antibody as described herein. In particular, the Examples provide experimental data generated with the antibody that is secreted by the 7D4 hybridoma. As indicated in the Background of the Invention, this antibody is specific for mouse CD25 which, as shown by comparing panel of monoclonal antibodies (including PC61), binds to one of the three epitopes within mouse CD25 that is distinct from the IL-2 binding site and does not block binding of IL-2 to CD25. For example, 7D4 has been shown to bind mouse CD25 at an epitope comprising amino acid 184 to 194 (REHHRFLASEE) in [Uniprot sequence P01590]). The assays involving 7D4 and mouse CD25 in the literature (for example Setiady Y et al., 2010. Eur. J. Immunol. 40: 780-6; McNeill A et al., 2007. Scand J Immunol. 65:63-9; Teege S et al., 2015, Sci Rep 5: 8959), together with those disclosed in the Examples, including recombinant antibodies comprising CD25-binding domain of 7D4 or the non-IL-2 blocking anti-human CD25 antibodies named MA-251 and 7G7B6, can be adapted for characterizing those human antibodies that recognize human CD25 having the same functional features of 7D4 both at the level of interaction with CD25 (in particular, by not blocking IL-2 binding) and with Fcγ receptors (in particular by preferably binding one or more of the human activating Fcγ receptors and depleting efficiently Treg), when the appropriate isotype is associated, as described in the Examples.

In one aspect of the invention the antibodies compete with the antibody 7G7B6 for binding to human CD25; and/or binds to the same epitope or epitopes recognised by antibody 7G7B6. 7G7B6 is a monoclonal antibody having a mouse IgG2a isotype that recognises human CD25. 7G7B6 comprises a variable heavy chain region having the sequence:

(SEQ ID NO: 3)
EVQLVESGGDLVQPRGSLKLSCAASGFTFSSYGMSWVRQTPDKRLELVAT

INGYGDTTYYPDSVKGRFTISRDNAKNTLYLQMSSLKSEDTAMYFCARDR

DYGNSYYYALDYWGQGTSVTVSS, and a variable light chain region having the sequence:

(SEQ ID NO: 4)
QIVLSQSPAILSASPGERVTMTCRASSSVSFMHWLQQKPGSSPKPWIYAT

SNLASGVSARFSGSGSGTSYSLTITRVEAEDAATYYCQQWSSNPPAFGGG

TKLEIK.

In one embodiment the antibody comprises a heavy chain comprising the amino acid sequence GFTLDSYGVS (SEQ ID NO:7) as variable heavy chain COR1; the amino acid sequence GVTSSGGSAYYADSV (SEQ ID NO:8) as variable heavy chain CDR2, the amino acid sequence DRYVYTGGYLYHYGMDL (SEQ ID NO:9) as variable heavy chain CDR3, and comprises a light chain comprising the amino acid sequence RASQSISDYLA (SEQ ID NO:11) as variable light chain COR1; the amino acid sequence YAASTLPF (SEQ ID NO:12) as variable light chain CDR2, the amino acid sequence QGTYDSSDWYWA (SEQ ID NO:13) as variable light chain CDR3. The antibody may compete with 7G7B6 for binding to human CD25. Preferably the antibody comprises a heavy chain comprising a variable heavy chain region comprising the sequence:

(SEQ ID NO: 10)
EVQLVESGGGLIQPGGSLRLSCAASGFTLDSYGVSWVRQAPGKGLEWVGV

TSSGGSAYYADSVKGRFTISRDNSKNTLYLQMNSLRAEDTAVYYCARDRY

VYTGGYLYHYGMDLWGQGTLVTVSS, and light chain comprising a variable light chain region comprising the sequence:

(SEQ ID NO: 14)
DIQMTQSPSSLSASVGDRVTITCRASQSISDYLAWYQQKPGKVPKLLIYA

ASTLPFGVPSRFSGSGSGTDFTLTISSLQPEDVATYYCQGTYDSSDWYWA

FGGGTKVEI.

In another embodiment the antibody comprises a heavy chain comprising the amino acid sequence SGFSVDIYDMS (SEQ ID NO:15) as variable heavy chain COR1; the amino acid sequence YISSSLGATYYADSV (SEQ ID NO:16) as variable heavy chain CDR2, the amino acid sequence ERIYSVYTLDYYAMDL (SEQ ID NO:17) as variable heavy chain CDR3, and comprise a light chain comprising the amino acid sequence QASQGITNNLN (SEQ ID NO:19) as variable light chain COR1; the amino acid sequence YAASTLQS (SEQ ID NO:20) as variable light chain CDR2, the amino acid sequence QQGYTTSNVDNA (SEQ ID NO:21) as variable light chain CDR3. The antibody may compete with 7G7B6 for binding to human CD25. Preferably the antibody comprises a heavy chain comprising a variable heavy chain region comprising the sequence:

(SEQ ID NO: 18)
EVQLLESGGGLVQPGGSLRLSCAASGFSVDIYDMSWVRQAPGKGLLIYAY

ISSSLGATYYADSVKGRFTISRDNSKNTLYLQMNSLRAEDTAVYYCARER

IYSVYTLDYYAMDLWGQGTLVTVSS.

and a light chain comprising a variable light chain region comprising the sequence:

(SEQ ID NO: 22)
DIQMTQSPSSLSASVGDRVTITCQASQGITNNLNWYQQKPGKVPKLLIYA

ASTLQSGVPSRFSGSGSGTDFTLTISSLQPEDVATYYCQQGYTTSNVDNA

FGGGTKVEIK.

In one embodiment the antibody that may compete with 7G7B6 for binding to human CD25 comprises a heavy chain comprising the amino acid sequence of:

(SEQ ID NO: 23)
EVQLLESGGGLVQPGGSLRLSCAASGFTFSSYGMSWVRQAPGKGLELVST

INGYGDTTYYPDSVKGRFTISRDNSKNTLYLQMNSLRAEDTAVYYCARDR

DYGNSYYYALDYWGQGTLVTVSS,
or (SEQ ID NO: 24)
EVQLLESGGGLVQPGGSLRLSCAASGFTFSSYGMSWVRQAPGKGLELVST

INGYGDTTYYPDSVKGRFTISRDNAKNTLYLQMNSLRAEDTAVYFCARDR

DYGNSYYYALDYWGQGTLVTVSS and comprises a light chain comprising the amino acid sequence of:

(SEQ ID NO: 25)
EIVLTQSPGTLSLSPGERATLSCRASSSVSFMHWLQQKPGQAPRPLIYAT

SNLASGIPDRFSGSGSGTDYTLTISRLEPEDFAVYYCQQWSSNPPAFGQG

TKLEIK,
or (SEQ ID NO: 26)
QIVLTQSPGTLSLSPGERATLSCRASSSVSFMHWLQQKPGQSPRPLIYAT

SNLASGIPDRFSGSGSGTDYTLTISRLEPEDFAVYYCQQWSSNPPAFGQG

TKLEIK.

In one aspect of the invention the antibodies compete with the antibody MA251 for binding to human CD25; and/or bind to the same epitope or epitopes recognised by antibody MA251. MA251 is a monoclonal antibody having a mouse isotype that recognises human CD25. MA251 comprises a variable heavy chain region having the sequence:

(SEQ ID NO: 5)
QVQLKESGPGLVAPSQSLSITCTVSGFSLTSYGIQWVRQPPGKGLEWLGV

IWAGGSTNYNSALMSRLSISKDNSKSQVFLKMNSLQTDDTAMYYCARAYG

YDGSWLAYWGQGTLVTVSS and a variable light chain region having the sequence:

(SEQ ID NO: 6)
QIVLSQSPAILSASPGEKVTMTCRASSSVSYMHWYQQKPGSSPKPWIFAT

SNLASGVPARFSGSGSGTSYSLTINRVEAEDADTYYCQQWSSNPPTFGGG

TKLEIK

In one embodiment the antibody that may compete with MA251 for binding to human CD25 comprises a heavy chain comprising a variable heavy chain region comprising the amino acid sequence of:

(SEQ ID NO: 27)
QVQLVESGGGVVQPGGSLRLSCAVSGFSLTSYGIQWVRQAPGKGLEWVSV

IWAGGSTNYNSALMSRFTISKDNSKSTLYLQMNSLRAEDTAVYYCARAYG

YDGSWLAYWGQGTLVTVSS;

(SEQ ID NO: 28)
QVQLQESGPGLVKPSETLSLTCTVSGFSLTSYGIQWVRQPPGKGLEWIGV

IWAGGSTNYNSALMSRVTISKDNSKSQFSLKLSSVTAADTAVYYCARAYG

YDGSWLAYWGQGTLVTVSS;
or (SEQ ID NO: 29)
QVQLVESGGGVVQPGGSLRLSCAVSGFSLTSYGIQWVRQAPGKGLEWVSV

IWAGGSTNYNSALMSRFTISKDNSKSTLYLQMNSLRAEDTAVYYCARAYG

YDGSWLAYWGQGTLVTVSS;

and comprises a light chain comprising a variable light chain region comprising the amino acid sequence of:

(SEQ ID NO: 30)
QIVLTQSPATLSLSPGERATLSCRASSSVSYMHWYQQKPGQAPRPLIFAT

SNLASGIPARFSGSGSGTDYTLTISSLEPEDFAVYYCQQWSSNPPTFGGG

TKLEIK;

(SEQ ID NO: 31)
QIVLTQSPATLSLSPGERATLSCRASSSVSYMHWYQQKPGQAPRPLIFAT

SNLASGIPARFSGSGSGTDYTLTISSLEPEDFAVYYCQQWSSNPPTFGGG

TKLEIK;

(SEQ ID NO: 32)
DIQMTQSPSSLSASVGDRVTITCRASSSVSYMHWYQQKPGKAPKPLIFAT

SNLASGVPSRFSGSGSGTDYTLTISSLQPEDFATYYCQQWSSNPPTFGGG

TKLEIK;
or (SEQ ID NO: 33)
QIQLTQSPSSLSASVGDRVTITCRASSSVSYMHWYQQKPGKSPKPLIFAT

SNLASGVPSRFSGSGSGTDYTLTISSLQPEDFATYYCQQWSSNPPTFGGG

TKLEIK.

In one embodiment the antibody comprises a heavy chain variable region comprising the amino acid sequence of SEQ ID NO: 23 and/or a light chain variable region comprising the amino acid sequence of SEQ ID NO: 25. In another embodiment the antibody comprises a heavy chain variable region comprising the amino acid sequence of SEQ ID NO: 23 and/or a light chain variable region comprising the amino acid sequence of SEQ ID NO: 26. In another embodiment the antibody comprises a heavy chain variable region comprising the amino acid sequence of SEQ ID NO: 24 and/or a light chain variable region comprising the amino acid sequence of SEQ ID NO: 25; In another embodiment the antibody comprises a heavy chain variable region comprising the amino acid sequence of SEQ ID NO: 24 and/or a light chain variable region comprising the amino acid sequence of SEQ ID NO: 26. In another embodiment the antibody comprises a heavy chain variable region comprising the amino acid sequence of SEQ ID NO:27 and/or a light chain variable region comprising the amino acid sequence of SEQ ID NO: 30. In another embodiment the antibody comprises a heavy chain variable region comprising the amino acid sequence of SEQ ID NO: 27 and/or a light chain variable region comprising the amino acid sequence of SEQ ID NO: 31. In another embodiment the antibody comprises a heavy chain variable region comprising the amino acid sequence of SEQ ID NO: 27 and/or a light chain variable region comprising the amino acid sequence of SEQ ID NO:

32. In another embodiment the antibody comprises a heavy chain variable region comprising the amino acid sequence of SEQ ID NO: 27 and/or a light chain variable region comprising the amino acid sequence of SEQ ID NO: 33. In another embodiment the antibody comprises a heavy chain variable region comprising the amino acid sequence of SEQ ID NO: 28 and/or a light chain variable region comprising the amino acid sequence of SEQ ID NO: 30. In another embodiment the antibody comprises a heavy chain variable region comprising the amino acid sequence of SEQ ID NO: 28 and/or a light chain variable region comprising the amino acid sequence of SEQ ID NO: 31. In another embodiment the antibody comprises a heavy chain variable region comprising the amino acid sequence of SEQ ID NO: 28 and/or a light chain variable region comprising the amino acid sequence of SEQ ID NO: 32. In another embodiment the antibody comprises a heavy chain variable region comprising the amino acid sequence of SEQ ID NO: 28 and/or a light chain variable region comprising the amino acid sequence of SEQ ID NO: 33. In another embodiment the antibody comprises a heavy chain variable region comprising the amino acid sequence of SEQ ID NO: 29 and/or a light chain variable region comprising the amino acid sequence of SEQ ID NO: 30. In another embodiment the antibody comprises a heavy chain variable region comprising the amino acid sequence of SEQ ID NO:29 and/or a light chain variable region comprising the amino acid sequence of SEQ ID NO: 31. In another embodiment the antibody comprises a heavy chain variable region comprising the amino acid sequence of SEQ ID NO:29 and/or a light chain variable region comprising the amino acid sequence of SEQ ID NO: 32. In another embodiment the antibody comprises a heavy chain variable region comprising the amino acid sequence of SEQ ID NO:29 and/or a light chain variable region comprising the amino acid sequence of SEQ ID NO: 33.

In one aspect, the antibodies compete with both the antibody 7G7B6 and the antibody MA251 for binding to human CD25. In one aspect, the antibodies bind to the same epitope or epitopes recognised by 7G7B6 and recognised by MA251.

Competition between the 7G7B6 antibody or MA251 antibody and a further antibody can be measured for example as discussed in the Examples and known in the art. In some embodiments competition between two antibodies, such as 7G7B6 or MA251 and a further antibody is determined by adding the further antibody to an assay and measuring the interaction between the 7G7B6 or MA251 antibody and human CD25. One such assay is an Octet® based assay into which the simultaneous binding of the 7G7B6 or MA251 antibody, the further antibody and recombinant human CD25 is determined. Octet® is a bio-layer interferometry based label free detection system for biomolecular interactions analysis sold under the trade name Octet®. If binding of the 2 antibodies to recombinant human CD25 is detected, the antibodies are non-competing. Alternatively, one such assay is an enzyme linked immunosorbent assay (ELISA) into which the binding of the 7G7B6 or MA251 antibodies to recombinant human CD25 is detected. If the observed signal decreases upon addition of the further antibody (for example decreases by at least 75%), the latter antibody is a competitor for the 7G7B6 or MA251 antibodies. The simultaneous binding of the 7G7B6 or MA251 antibodies and the further antibody to human CD25 expressing cells can also be detected using flow cytometry.

In one aspect the invention provides an anti-CD25 antibody that specifically binds to an epitope of human CD25, wherein the epitope comprises one or more amino acid residues from one or more of the amino acid stretches selected from amino acids 150-163 of SEQ ID NO:1 (YQCVQGYRALHRGP), amino acids 166-186 of SEQ ID NO:1 (SVCKMTHGKTRVVTQPQLICTG), amino acids 42-56 of SEQ ID NO:1 (KEGTMLNCECKRGFR) and amino acids 70-88 of SEQ ID NO:1 (NSSHSS-WDNQCQCTSSATR). Preferably the epitope comprises at least two, at least three, at least four, at least five, at least six, at least seven, at least eight, at least nine or more residues from the selected amino acids stretches. More preferably the epitope comprises a sequence selected from: amino acids 150-158 of SEQ ID NO:1 (YQCVQGYRA), amino acids 176-180 of SEQ ID NO:1 (RWTQP), amino acids 42-56 of SEQ ID NO:1 (KEGTMLNCECKRGFR) and amino acids 74-84 of SEQ ID NO:1 (SSWDNQCQCTS) and combinations thereof. These epitopes are distinct from the IL-2 binding site in human CD25 and antibodies binding to such an epitope, as described in the Examples, do not block the binding of IL-2 to CD25.

In a preferred embodiment, the method of treating a human subject who has a cancer comprises the step of administering an anti-CD25 antibody of the invention to a subject, wherein said subject preferably has a solid tumour, and wherein the anti-CD25 antibody preferably a human IgG1 antibody that does not inhibit the binding of interleukin 2 to CD25 and that binds to at least one activating Fcγ receptor selected from FcγRI (CD64), FcγRIIc (CD32c), and FcγRIIIa (0016a) with high affinity, and depletes tumour-infiltrating regulatory T cells depletes tumour-infiltrating regulatory T cells. Preferably the anti-CD25 antibody has a dissociation constant ($K_d$) for CD25 of less than $10^{-7}$ M, preferably less than $10^{-8}$M. More preferably, the anti-CD25 antibody binds human CD25 providing effects on IL-2 binding and Treg depletion similar to those on of 7D4 on mouse CD25 or of 7G7B6 and MA251 on human CD25. In a further embodiment, the anti-CD25 antibody binds to Fcγ receptors with an activatory to inhibitory ratio (A/I) superior to 1 and/or binds to FcγRI (CD64), FcγRIIc (0032c), FcγRIIIa (0016a) and/or FcγRIIa (CD32a) with higher affinity than it binds to FcγRIIb (CD32b).

The CD25 binding domain of 7D4 antibody has been cloned and expressed as a recombinant protein in fusion with an appropriate constant region. The sequence of the CD25 binding domain of 7D4 antibody, as well its specificity for distinct epitopes within the extracellular domain of CD25 and/or its other functional activities, can be used for comparing candidate anti-CD25 antibodies that are generated and screened by any appropriate technique (e.g. by raising panels of hybridomas from CD25-immunized rodents or generating libraries of recombinant antibodies and then screening these antibody repertoires with CD25 fragments for characterizing functionally as described herein). The anti-CD25 antibodies that are consequently identified can be produced also as recombinant antibodies, in particular as full antibodies or as fragments or variants that are described herein.

Native antibodies and immunoglobulins are usually heterotetrameric glycoproteins of about 150,000 daltons, composed of two identical light (L) chains and two identical heavy (H) chains. Each heavy chain has at the amino terminus a variable domain ($V_H$) followed by a number of constant domains. Each light chain has a variable domain at the amino terminus ($V_L$) and a constant domain at the carboxy terminus.

The variable regions are capable of interacting with a structurally complementary antigenic target and are characterized by differences in amino acid sequence from antibodies of different antigenic specificity. The variable regions of either H or L chains contain the amino acid sequences capable of specifically binding to antigenic targets. Within these sequences are smaller sequences dubbed "hypervariable" because of their extreme variability between antibodies of differing specificity. Such hypervariable regions are also referred to as "complementarity determining regions" or "CDR" regions.

These CDR regions account for the basic specificity of the antibody for a particular antigenic determinant structure. The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have 3 CDR regions, each non-contiguous with the others (termed L1, L2, L3, H1, H2, H3) for the respective light (L) and heavy (H) chains. The accepted CDR regions have been described previously (Kabat et al., 1977. J Biol Chem 252, 6609-6616).

The antibodies of the present invention may function through complement-dependent cytotoxicity (CDC) and/or antibody-dependent cell-mediated cytotoxicity (ADCC) and/or antibody-dependent cell-mediated phagocytosis (ADCP), as well as any other mechanism that allows targeting, blocking proliferation, and/or depleting Treg cells.

"Complement-dependent cytotoxicity" (CDC) refers to lysis of antigen-expressing cells by an antibody of the invention in the presence of complement.

"Antibody-dependent cell-mediated cytotoxicity" (ADCC) refers to a cell-mediated reaction in which non-specific cytotoxic cells that express Fc receptors (FcRs) (e.g. Natural Killer (NK) cells, neutrophils, and macrophages) recognize bound antibody on a target cell and thereby lead to lysis of the target cell.

"Antibody-dependent cell-mediated phagocytosis" (ADCP) refers to a cell-mediated reaction in which phagocytes (such as macrophages) that express Fc receptors (FcRs) recognize bound antibody on a target cell and thereby lead to phagocytosis of the target cell.

CDC, ADCC and ADCP can be measured using assays that are known and available in the art (Clynes et al. (1998) Proc Natl Acad Sci USA 95, 652-6), and as discussed in the examples. The constant region of an antibody is important in the ability of an antibody to fix complement and mediate cell-dependent cytotoxicity and phagocytosis. Thus, as discussed herein, the isotype of an antibody may be selected on the basis of whether it is desirable for the antibody to mediate cytotoxicity/phagocytosis.

As discussed herein, in an embodiment of the invention, an anti-CD25 antibody that does not inhibit the binding of interleukin 2 and that leads to the depletion of Treg cells is used. For example, an anti-CD25 antibody that does not inhibit the binding of interleukin 2 to CD25 and elicits a strong CDC response and/or a strong ADCC and/or a strong ADCP response may be used. Methods to increase CDC, ADCC and/or ADCP are known in the art. For example, CDC response may be increased with mutations in the antibody that increase the affinity of C1q binding (Idusogie et al. (2001) J Immunol 166, 2571-5).

References herein to "does not inhibit the binding of Interleukin-2 to CD25" may alternatively be expressed as the anti-CD25 antibody is a non-IL-2 blocking antibody or a "non-blocking" antibody (with respect to the non-blocking of IL-2 binding to CD25 in the presence of the anti-CD25 antibody), i.e. the antibody does not block the binding of Interleukin-2 to CD25 and in particular does not inhibit Interleukin-2 signalling in CD25-expressing cells. References to "non-blocking" "non-IL2 blocking", "does not block", or "without blocking" and the like (with respect to the non-blocking of IL-2 binding to CD25 in the presence of the anti-CD25 antibody) include embodiments wherein the anti-CD25 antibody of the invention does not block the signalling of IL-2 via CD25. That is the anti-CD25 antibody inhibits less than 50% of IL-2 signalling compared to IL-2 signalling in the absence of the antibodies. In particular embodiments of the invention as described herein, the anti-CD25 antibody inhibits less than about 40%, 35%, 30%, preferably less than about 25% of IL-2 signalling compared to IL-2 signalling in the absence of the antibodies. Anti-CD25 non-IL-2 blocking antibodies allow binding to CD25 without interfering with IL-2 binding to CD25, or without substantially interfering with IL-2 binding to CD25. References herein to a non-IL-2 blocking antibody may alternatively be expressed as an anti-CD25 antibody that "does not inhibit the binding of Interleukin-2 to CD25" or as an anti-CD25 antibody that "does not inhibit the signalling of IL-2".

Some anti-CD25 antibodies may allow binding of IL-2 to CD25, but still block signalling via the CD25 receptor. Such anti-CD25 antibodies are not within the scope of the present invention. Instead, the non-IL-2 blocking anti-CD25 antibodies allow binding of IL-2 to CD25 to facilitate at least 50% of the level of signalling via the CD25 receptor compared to the signalling in the absence of the anti-CD25 antibody.

IL-2 signalling via CD25 may be measured by methods as discussed in the Examples and as known in the art. Comparison of IL-2 signalling in the presence and absence of the anti-CD25 antibody agent can occur under the same or substantially the same conditions.

In some embodiments, IL-2 signalling can be determined by measuring by the levels of phosphorylated STAT5 protein in cells, using a standard Stat-5 phosphorylation assay. For example a Stat-5 phosphorylation assay to measure IL-2 signalling may involve culturing PMBC cells in the presence of the anti-CD25 antibody at a concentration of 10 ug/ml for 30 mins and then adding varying concentrations of IL-2 (for example 10U/ml or vary concentrations of 0.25 U/ml, 0.74 U/ml, 2.22 U/ml, 6.66 U/ml or 20 U/ml) for 10 mins. Cells may then be permeabilized and levels of STAT5 protein can then be measured with a fluorescent labelled antibody to a phosphorylated STAT5 peptide analysed by flow cytometry. The percentage blocking of IL-2 signalling can be calculated as follows: % blocking=100×[(% Stat5$^+$ cells No Antibody group−% Stat5$^+$ cells 10 ug/ml Antibody group)/(% Stat5$^+$ cells No Ab group)

ADCC may be increased by methods that eliminate the fucose moiety from the antibody glycan, such as by production of the antibody in a YB2/0 cell line, or though the introduction of specific mutations on the Fc portion of human IgG1 (e.g., S298A/E333A/K334A, S239D/I332E/A330L, G236A/S239D/A330L/I332E) (Lazar et al. (2006) Proc Natl Acad Sci USA 103, 2005-2010; Smith et al. (2012) Proc Natl 25 Acad Sci USA 109, 6181-6). ADCP may also be increased by the introduction of specific mutations on the Fc portion of human IgG1 (Richards et al. (2008) Mol Cancer Ther 7, 2517-27).

In a preferred embodiment of the present invention the antibody is optimised to elicit an ADCC response, that is to say the ADCC response is enhanced, increased or improved relative to other anti-CD25 antibodies, including those that do not inhibit the binding of interleukin 2 to CD25 and, for example unmodified anti-CD25 monoclonal antibodies.

In a preferred embodiment of the present invention the antibody is optimised to elicit an ADCP response, that is to say the ADCP response is enhanced, increased or improved relative to other anti-CD25 antibodies, including those that do not inhibit the binding of interleukin 2 to CD25 and, for example unmodified anti-CD25 monoclonal antibodies.

As used herein, a "chimeric antibody" can refer to an antibody having variable sequences derived from an immunoglobulin from one species, such as rat or mouse antibody, and immunoglobulin constant regions from another species, such as from a human antibody. In some embodiments, the chimeric antibody may have a constant region which is enhanced for inducing ADCC.

The antibodies according to the invention may also be partly or wholly synthetic, wherein at least part of the polypeptide chains of the antibodies are synthesized and, possibly, optimized for binding to their cognate antigen. Such antibodies may be chimeric or humanised antibodies and may be fully tetrameric in structure, or may be dimeric and comprise only a single heavy and a single light chain.

Antibodies of the present invention may also be monoclonal antibodies. As used herein, "monoclonal antibody" is not limited to antibodies produced through hybridoma technology. The term "monoclonal antibody" refers to an antibody that is derived from a single clone, including any eukaryotic, prokaryotic, or phage clone, and not the method by which it is produced.

Antibodies of the present invention may also be human antibodies. As used herein, "human antibody" refers to antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

An anti-CD25 antibody presenting the features as described herein represents a further object of the invention. The anti-CD25 antibody can be used in medicine. In a further embodiment the invention provides a method for treating a disease in a subject comprising administering an anti-CD25 antibody that does not inhibit the binding of Interleukin-2 (IL-2) to CD25 or signalling of IL-2 via CD25. Preferably the disease is a cancer, in particular for the treatment of solid tumours.

In a further embodiment, the present invention provides nucleic acid molecules encoding anti-CD25 antibodies as defined herein. In some embodiments, such provided nucleic acid molecules may contain codon-optimized nucleic acid sequences, and/or may be included in expression cassettes within appropriate nucleic acid vectors for the expression in host cells such as, for example, bacterial, yeast, insect, piscine, murine, simian, or human cells. In some embodiments, the present invention provides host cells comprising heterologous nucleic acid molecules (e.g. DNA vectors) that express the desired antibody.

In some embodiments, the present invention provides methods of preparing an isolated anti-CD25 antibody as defined above. In some embodiments, such methods may comprise culturing a host cell that comprises nucleic acids (e.g., heterologous nucleic acids that may comprise and/or be delivered to the host cell via vectors). Preferably, the host cell (and/or the heterologous nucleic acid sequences) is/are arranged and constructed so that the antibody or antigen-binding fragment or variant thereof is secreted from the host cell and isolated from cell culture supernatants.

The antibodies of the present invention may be monospecific, bispecific, or multispecific. "Multispecific antibodies" may be specific for different epitopes of one target antigen or polypeptide, or may contain antigen-binding domains specific for more than one target antigen or polypeptide (Kufer et al. (2004) Trends Biotechnol 22, 238-44).

In one aspect of the invention the antibody is a monospecific antibody. As discussed further below, in an alternative aspect the antibody is a bispecific antibody.

As used herein, "bispecific antibody" refers to an antibody having the capacity to bind to two distinct epitopes either on a single antigen or polypeptide, or on two different antigens or polypeptides.

Bispecific antibodies of the present invention as discussed herein can be produced via biological methods, such as somatic hybridization; or genetic methods, such as the expression of a non-native DNA sequence encoding the desired antibody structure in cell line or in an organism; chemical methods (e.g., by chemical coupling, genetic fusion, noncovalent association or otherwise to one or more molecular entities such as another antibody or antibody fragment); or a combination thereof.

The technologies and products that allow producing monospecific or bispecific are known in the art, as extensively reviewed in the literature, also with respect to alternative formats, antibody-drug conjugates, antibody design methods, in vitro screening methods, constant regions, post-translational and chemical modifications, improved feature for triggering cancer cell death such as Fc engineering (Tiller K and Tessier P, 2015 Annu Rev Biomed Eng. 17: 191-216; Speiss C et al., 2015. Molecular Immunology 67 95-106; Weiner G, 2015. Nat Rev Cancer, 15: 361-370; Fan G et al., 2015. J Hematol Oncol 8:130). Such bispecfic antibody can be provided in any commercially available format, including Duobody®, BiTE® DART®, CrossMab, Knobs-in-holes, Triomab®, or other appropriate molecular format and fragments thereof.

As used herein, "epitope" or "antigenic determinant" refers to a site on an antigen to which an antibody binds. As is well known in the art, epitopes can be formed both from contiguous amino acids (linear epitope) or non-contiguous amino acids juxtaposed by tertiary folding of a protein (conformational epitopes). Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes are well known in the art and include, for example, x-ray crystallography and 2-D nuclear magnetic resonance. See, for example, Epitope Mapping Protocols in Methods in Molecular Biology, Vol. 66, Glenn E. Morris, Ed (1996). For example an antibody of the invention may recognise a conformational epitope to which the antibodies 7G7B6 or MA251 bind. In one embodiment the conformational epitope comprises at least two sequences selected from amino acids 150-158 of SEQ ID NO:1 (YQCVQGYRA), amino acids 176-180 of SEQ ID NO:1 (RWTQP), amino acids 42-56 of SEQ ID NO:1 (KEGTMLNCECKRGFR) and amino acids 74-84 of SEQ ID NO:1 (SSWDNQCQCTS).

In some embodiments, the anti-CD25 antibody can be included in an agent that further comprises a conjugated payload such as a therapeutic or diagnostic agent, in particular for cancer therapy or diagnosis. Anti-CD25 antibody conjugates with radionuclides or toxins may be used. Examples of commonly used radionuclides are, for example, soy, 131I, and 67Cu, among others, and examples of commonly used toxins are doxorubicin and calicheamicin. In a further embodiment, the anti-CD25 antibody may be modified to have an altered half-life. Methods for achieving an altered half-life are known in the art. In some embodiments the anti-CD25 antibody is not conjugated to another therapeutic or diagnostic agent. In particular, in some embodiments the anti-CD25 antibody is not conjugated to a radionuclide, i.e. in some embodiments the anti-CD25 antibody is not radiolabelled.

In a preferred embodiment of the present invention, the subject of any of the aspects of the invention as described herein, is a mammal, preferably a cat, dog, horse, donkey, sheep, pig, goat, cow, hamster, mouse, rat, rabbit or guinea pig, but most preferably the subject is a human. Thus, in all aspects of the invention as described herein the subject is preferably a human.

As used herein, the terms "cancer", "cancerous", or "malignant" refer to or describe the physiological condition in mammals that is typically characterized by unregulated cell growth.

Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hepatocellular carcinoma (HCC), hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer.

In one aspect, the cancer involves a solid tumour. Examples of solid tumours are sarcomas (including cancers arising from transformed cells of mesenchymal origin in tissues such as cancellous bone, cartilage, fat, muscle, vascular, hematopoietic, or fibrous connective tissues), carcinomas (including tumours arising from epithelial cells), mesothelioma, neuroblastoma, retinoblastoma, etc. Cancers involving solid tumours include, without limitations, brain cancer, lung cancer, stomach cancer, duodenal cancer, esophagus cancer, breast cancer, colon and rectal cancer, renal cancer, bladder cancer, kidney cancer, pancreatic cancer, prostate cancer, ovarian cancer, melanoma, mouth cancer, sarcoma, eye cancer, thyroid cancer, urethral cancer, vaginal cancer, neck cancer, lymphoma, and the like.

In one aspect, the cancers involve CD25 expressing tumours, including but not limited to lymphomas, such as Hodgkin lymphomas, and lymphocytic leukemias, such as chronic lymphocytic leukemia (CLL).

In one aspect of the invention the cancer is identified by the presence of specific tumor-relevant markers and antigens such as CD20, HER2, PD-1, PD-L1, SLAM7F, CD47, CD137, CD134, TIM3, CD25, GITR, CD25, EGFR, etc or is a cancer that has been identified as having a biomarker referred to as microsatellite instability-high (MSI-H) or mismatch repair deficient (dMMR). Furthermore, the antibodies can be used when the identification of the specific tumour-relevant marker, antigen, or biomarkers has been used in defining pre-cancerous, non-invasive states of the above cancers in a patient, such as cancer in-situ, smouldering myeloma, monoclonal gammopathy of undetermined significance, cervical intra-epithelial neoplasia, MALTomas/GALTomes and various lymphoproliferative disorders. Preferably in some embodiments the subject being treated has a solid tumor.

In a one aspect of the invention the cancer is selected from melanoma, non-small cell lung cancer, renal cancer, ovarian cancer, bladder cancer, sarcoma and colon cancer. In a preferred aspect of the invention the cancer is selected from melanoma, ovarian, non-small cell lung cancer and renal cancer. In one embodiment, the cancer is not melanoma, ovarian cancer, or breast cancer. In a preferred aspect, the cancer is sarcoma, colon, melanoma or colorectal cancer, or more generally any human cancer for which the 4T1, MCA205, B16, CT26 or MC38 cell line may represent preclinical models for validating compounds as being useful for their therapeutic management.

As used herein, the term "tumour" as it applies to a subject diagnosed with, or suspected of having, a cancer refers to a malignant or potentially malignant neoplasm or tissue mass of any size, and includes primary tumours and secondary neoplasms. The terms "cancer", "malignancy", "neoplasm", "tumour", and "carcinoma can be also used interchangeably herein to refer to tumours and tumour cells that exhibit relatively abnormal, uncontrolled, and/or autonomous growth, so that they exhibit an aberrant growth phenotype characterized by a significant loss of control of cell proliferation. In general, cells of interest for detection or treatment include precancerous (e.g., benign), malignant, pre-metastatic, metastatic, and non-metastatic cells. The teachings of the present disclosure may be relevant to any and all cancers.

As used herein, "solid tumours" are an abnormal growth or mass of tissue that usually does not contain cysts or liquid areas, in particular, tumours and/or metastasis (wherever located) other than leukaemia or non-solid lymphatic cancers. Solid tumours may be benign or malignant. Different types of solid tumours are named for the type of cells that form them and/or the tissue or organ in which they are located. Examples of solid tumours are sarcomas (including cancers arising from transformed cells of mesenchymal origin in tissues such as cancellous bone, cartilage, fat, muscle, vascular, hematopoietic, or fibrous connective tissues), carcinomas (including tumours arising from epithelial cells), melanomas, lymphomas, mesothelioma, neuroblastoma, and retinoblastoma.

Particularly preferred cancers in accordance with the present invention include those characterized by the presence of a solid tumour, that is to say the subject does not have a non-solid tumour. In all aspects of the invention as discussed herein, it is preferred that the cancer is a solid tumour, i.e. that the subject has a solid tumour (and does not have a non-solid tumour).

Reference to "treat" or "treating" a cancer as used herein defines the achievement of at least one positive therapeutic effect, such as for example, reduced number of cancer cells, reduced tumour size, reduced rate of cancer cell infiltration into peripheral organs, or reduced rate of tumour metastasis or tumour growth.

Positive therapeutic effects in cancer can be measured in a number of ways (e.g. Weber (2009) J Nucl Med 50, 1S-10S). By way of example, with respect to tumour growth inhibition, according to National Cancer Institute (NCI) standards, a T/C≤42% is the minimum level of anti-tumour activity. A T/C<10% is considered a high anti-tumour activity level, with T/C (%)=Median tumour volume of the treated/Median tumour volume of the control×100. In some embodiments, the treatment achieved by a therapeutically effective amount is any of progression free survival (PFS), disease free survival (DFS) or overall survival (OS). PFS, also referred to as "Time to Tumour Progression" indicates the length of time during and after treatment that the cancer does not grow, and includes the amount of time patients have experienced a complete response or a partial response, as well as the amount of time patients have experienced stable disease. DFS refers to the length of time during and after treatment that the patient remains free of disease. OS refers to a prolongation in life expectancy as compared to naive or untreated individuals or patients.

Reference to "prevention" (or prophylaxis) as used herein refers to delaying or preventing the onset of the symptoms of the cancer. Prevention may be absolute (such that no disease occurs) or may be effective only in some individuals or for a limited amount of time.

In a preferred aspect of the invention the subject has an established tumour, that is the subject already has a tumour, e.g. that is classified as a solid tumour. As such, the invention as described herein can be used when the subject already has a tumour, such as a solid tumour. As such, the invention provides a therapeutic option that can be used to treat an existing tumour. In one aspect of the invention the subject has an existing solid tumour. The invention may be used as a prevention, or preferably as a treatment in subjects who already have a solid tumour. In one aspect the invention is not used as a preventative or prophylaxis.

In one aspect, tumour regression may be enhanced, tumour growth may be impaired or reduced, and/or survival time may be enhanced using the invention as described herein, for example compared with other cancer treatments (for example standard-of care treatments for the a given cancer).

In one aspect of the invention the method of treating or preventing cancer as described herein further comprises the step of identifying a subject who has cancer, preferably identifying a subject who has a tumour such as a solid tumour. In one embodiment the method can include identifying a subject who has a haematological cancer.

The dosage regimen of a therapy described herein that is effective to treat a cancer patient may vary according to factors such as the disease state, age, and weight of the patient, and the ability of the therapy to elicit an anti-cancer response in the subject. Selection of an appropriate dosage will be within the capability of one skilled in the art. For example 0.01, 0.1, 0.3, 0.5, 1, 2, 3, 4, 5, 6, 7, 8, 9, 10, 20, 30, 40, or 50 mg/kg. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

The antibody according to any aspect of the invention as described herein may be in the form of a pharmaceutical composition which additionally comprises a pharmaceutically acceptable carrier, diluent or excipient. These compositions include, for example, liquid, semi-solid and solid dosage formulations, such as liquid solutions (e.g., injectable and infusible solutions), dispersions or suspensions, tablets, pills, or liposomes. In some embodiments, a preferred form may depend on the intended mode of administration and/or therapeutic application. Pharmaceutical compositions containing the antibody can be administered by any appropriate method known in the art, including, without limitation, oral, mucosal, by-inhalation, topical, buccal, nasal, rectal, or parenteral (e.g. intravenous, infusion, intratumoural, intranodal, subcutaneous, intraperitoneal, intramuscular, intradermal, transdermal, or other kinds of administration involving physical breaching of a tissue of a subject and administration of the pharmaceutical composition through the breach in the tissue). Such a formulation may, for example, be in a form of an injectable or infusible solution that is suitable for intradermal, intratumoural or subcutaneous administration, or for intravenous infusion. The administration may involve intermittent dosing. Alternatively, administration may involve continuous dosing (e.g., perfusion) for at least a selected period of time, simultaneously or between the administration of other compounds.

In some embodiments, the antibody can be prepared with carriers that protect it against rapid release and/or degradation, such as a controlled release formulation, such as implants, transdermal patches, and microencapsulated delivery systems. Biodegradable, biocompatible polymers can be used.

Those skilled in the art will appreciate, for example, that route of delivery (e.g., oral vs intravenous vs subcutaneous vs intratumoural, etc) may impact dose amount and/or required dose amount may impact route of delivery. For example, where particularly high concentrations of an agent within a particular site or location (e.g., within a tumour) are of interest, focused delivery (e.g., in this example, intratumoural delivery) may be desired and/or useful. Other factors to be considered when optimizing routes and/or dosing schedule for a given therapeutic regimen may include, for example, the particular cancer being treated (e.g., type, stage, location, etc.), the clinical condition of a subject (e.g., age, overall health, etc.), the presence or absence of combination therapy, and other factors known to medical practitioners.

The pharmaceutical compositions typically should be sterile and stable under the conditions of manufacture and storage. The composition can be formulated as a solution, microemulsion, dispersion, liposome, or other ordered structure suitable to high drug concentration. Sterile injectable solutions can be prepared by incorporating the antibody in the required amount in an appropriate solvent with one or a combination of ingredients enumerated above, as required, followed by filtered sterilization. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent. Each pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers are non-toxic to the subjects at the dosages and concentrations employed. Preferably, such a composition can further comprise a pharmaceutically acceptable carrier or excipient for use in the treatment of cancer that that is compatible with a given method and/or site of administration, for instance for parenteral (e.g. subcutaneous, intradermal, or intravenous injection), intratumoral, or peritumoral administration.

While an embodiment of the treatment method or compositions for use according to the present invention may not be effective in achieving a positive therapeutic effect in every subject, it should do so in a using pharmaceutical compositions and dosing regimens that are consistently with good medical practice and statistically significant number of subjects as determined by any statistical test known in the art such as the Student's t-test, the $\chi^2$-test, the U-test according to Mann and Whitney, the Kruskal-Wallis test (H-test), Jonckheere-Terpstra test and the Wilcoxon-test.

Where hereinbefore and subsequently a tumour, a tumour disease, a carcinoma or a cancer is mentioned, also metastasis in the original organ or tissue and/or in any other location are implied alternatively or in addition, whatever the location of the tumour and/or metastasis is.

As discussed herein, the present invention relates to depleting regulatory T cells (Tregs). Thus, in one aspect of the invention, the anti-CD25 antibody that does not inhibit the binding of interleukin 2 to CD25, also depletes or reduces tumour-infiltrating regulatory T cells. In one aspect, the depletion is via ADCC. In another aspect, the depletion is via ADCP.

As such, the invention provides a method for depleting regulatory T cells in a tumour in a subject, comprising administering to said subject an anti-CD25 antibody that does not inhibit the binding of interleukin 2 to CD25. In a preferred embodiment Tregs are depleted in a solid tumour. By "depleted" it is meant that the number, ratio or percentage of Tregs is decreased relative to when an anti-CD25 antibody that does not inhibit the binding of interleukin 2 to CD25, is not administered. In particular embodiments of the invention as described herein, over about 5%, 10%, 20%, 30%, 40%, 50%, 60%, 70%, 80%, 90% or 99% of the tumour-infiltrating regulatory T cells are depleted.

As used herein, "regulatory T cells" ("Treg", "Treg cells", or "Tregs") refer to a lineage of CD4+T lymphocytes specialized in controlling autoimmunity, allergy and infection. Typically, they regulate the activities of T cell populations, but they can also influence certain innate immune system cell types. Tregs are usually identified by the expression of the biomarkers CD4, CD25 and Foxp3. Naturally occurring Treg cells normally constitute about 5-10% of the peripheral CD4+T lymphocytes. However, within a tumour microenvironment (i.e. tumour-infiltrating Treg cells), they can make up as much as 20-30% of the total CD4+T lymphocyte population.

Activated human Treg cells may directly kill target cells such as effector T cells and APCs through perforin- or granzyme B-dependent pathways; cytotoxic T-lymphocyte-associated antigen 4 (CTLA4+) Treg cells induce indoleamine 2,3-dioxygenase (IDO) expression by APCs, and these in turn suppress T-cell activation by reducing tryptophan; Treg cells, may release interleukin-10 (IL-10) and transforming growth factor (TGFβ) in vivo, and thus directly inhibit T-cell activation and suppress APC function by inhibiting expression of MHC molecules, CD80, CD86 and IL-12. Treg cells can also suppress immunity by expressing high levels of CTLA4 which can bind to CD80 and CD86 on antigen presenting cells and prevent proper activation of effector T cells.

In a preferred embodiment of the present invention the ratio of effector T cells to regulatory T cells in a solid tumour is increased. In some embodiments, the ratio of effector T cells to regulatory T cells in a solid tumour is increased to over 5, 10, 15, 20, 40 or 80.

An immune effector cell refers to an immune cell which is involved in the effector phase of an immune response. Exemplary immune cells include a cell of a myeloid or lymphoid origin, e.g., lymphocytes (e.g., B cells and T cells including cytolytic T cells (CTLs)), killer cells, natural killer cells, macrophages, monocytes, eosinophils, neutrophils, polymorphonuclear cells, granulocytes, mast cells, and basophils.

Immune effector cells involved in the effector phase of an immune response express specific Fc receptors and carry out specific immune functions. An effector cell can induce antibody-dependent cell-mediated cytotoxicity (ADCC), e.g., a neutrophil capable of inducing ADCC. For example, monocytes, macrophages, neutrophils, eosinophils, and lymphocytes which express FcαR are involved in specific killing of target cells and presenting antigens to other components of the immune system, or binding to cells that present antigens. An effector cell can also phagocytose a target antigen, target cell, or microorganism. As discussed herein, antibodies according to the present invention may be optimised for ability to induce ADCC.

In some embodiments, a different agent against cancer may be administered in combination with the antibody via the same or different routes of delivery and/or according to different schedules. Alternatively or additionally, in some embodiments, one or more doses of a first active agent is administered substantially simultaneously with, and in some embodiments via a common route and/or as part of a single composition with, one or more other active agents. Those skilled in the art will further appreciate that some embodiments of combination therapies provided in accordance with the present invention achieve synergistic effects; in some such embodiments, dose of one or more agents utilized in the combination may be materially different (e.g., lower) and/or may be delivered by an alternative route, than is standard, preferred, or necessary when that agent is utilized in a different therapeutic regimen (e.g., as monotherapy and/or as part of a different combination therapy).

In some embodiments, where two or more active agents are utilized in accordance with the present invention, such agents can be administered simultaneously or sequentially. In some embodiments, administration of one agent is specifically timed relative to administration of another agent. For example, in some embodiments, a first agent is administered so that a particular effect is observed (or expected to be observed, for example based on population studies showing a correlation between a given dosing regimen and the particular effect of interest). In some embodiments, desired relative dosing regimens for agents administered in combination may be assessed or determined empirically, for example using ex vivo, in vivo and/or in vitro models; in some embodiments, such assessment or empirical determination is made in vivo, in a patient population (e.g., so that a correlation is established), or alternatively in a particular patient of interest.

In another aspect of the invention, an anti-CD25 antibody that does not inhibit the binding of interleukin 2 to CD25 has improved therapeutic effects when combined with an immune checkpoint inhibitor. A combination therapy with an anti-CD25 antibody that does not inhibit the binding of interleukin 2 to CD25 and an immune checkpoint inhibitor can have synergistic effects in the treatment of established tumours. The data in respect of PD-1/PD-L1 in the present Examples relates to interfering with PD-1/PD-L1 interaction. As such, the interaction between the PD-1 receptor and the PD-L1 ligand may be blocked, resulting in "PD-1 blockade". In one aspect, the combination may lead to enhanced tumour regression, enhanced impairment or reduction of tumour growth, and/or survival time may be enhanced using the invention as described herein, for example compared with either anti-CD25 antibodies or PD-1/PD-L1 blockade alone (directly, using an anti-PD1 antibody, or indirectly, using an anti-PD-L1 antibody). When since the anti-CD25 antibody does not inhibit the binding of interleukin 2 to CD25, a combination therapy with an anti-CD25 antibody and immune checkpoint inhibitor may also further include the administration of Interleukin-2 at a dosage that is appropriate for the treatment of cancer.

As used herein, "immune checkpoint" or "immune checkpoint protein" refer to proteins belonging to inhibitory pathways in the immune system, in particular for the modulation of T-cell responses. Under normal physiological conditions, immune checkpoints are crucial to preventing autoimmunity, especially during a response to a pathogen. Cancer cells can alter the regulation of the expression of immune checkpoint proteins in order to avoid immune surveillance.

Examples of immune checkpoint proteins include but are not limited to PD-1, CTLA-4, BTLA, KIR, LAG3, TIGIT, CD155, B7H3, B7H4, VISTA and TIM3, and also OX40, GITR, ICOS, 4-1BB and HVEM. Immune checkpoint proteins may also refer to proteins which bind to other immune checkpoint proteins. Such proteins include PD-L1, PD-L2, CD80, CD86, HVEM, LLT1, and GAL9.

"Immune checkpoint protein inhibitors" refer to any protein that can interfere with the signalling and/or proteinprotein interactions mediated by an immune checkpoint protein. In one aspect of the invention the immune checkpoint protein is PD-1 or PD-L1. In a preferred aspect of the invention as described herein the immune checkpoint inhibitor interferes with PD-1/PD-L1 interactions via anti-PD-1 or anti PD-L1 antibodies.

As such, the present invention also provides a method of treating cancer, comprising administering an anti-CD25 antibody that does not inhibit the binding of interleukin 2 to CD25 and a further therapeutic agent, preferably a checkpoint inhibitor, to a subject. The invention also provides an anti-CD25 antibody that does not inhibit the binding of interleukin 2 to CD25 and a further therapeutic agent, preferably an immune checkpoint inhibitor, for use in the treatment of cancer.

The present invention additionally provides the use of an anti-CD25 antibody that does not inhibit the binding of interleukin-2 to CD25, and a further therapeutic agent, preferably an immune checkpoint inhibitor, for the manufacture of a medicament for the treatment of cancer. Administration of the anti-CD25 antibody that does not inhibit the binding of interleukin-2 to CD25 and further therapeutic agent, such as the immune checkpoint inhibitor may be simultaneous, separate or sequential.

The present invention provides a combination of an anti-CD25 that does not inhibit the binding of interleukin-2 to CD25 and a further therapeutic agent, preferably an immune checkpoint inhibitor, for use in the treatment of cancer in a subject, wherein the anti-CD25 antibody that does not inhibit the binding of interleukin-2 to CD25 and further therapeutic agent, such as the immune checkpoint inhibitor, are administered simultaneously, separately or sequentially. Such a anti-human CD25 antibody that does not inhibit the binding of interleukin-2 to CD25 and present the human IgG1 isotype can be used specifically in combination with antibodies targeting immune checkpoints but lacking sequences that allow ADCC, ADCP, and/or CDC.

In an alternative aspect, the invention provides an anti-CD25 antibody that does not inhibit the binding of interleukin 2 to CD25 for use in the treatment of cancer, wherein said antibody is for administration in combination with a further therapeutic agent, preferably an immune checkpoint inhibitor. The invention also provides the use of an anti-CD25 that does not inhibit the binding of interleukin 2 to CD25 in the manufacture of a medicament for treating cancer, wherein said medicament is for administration in combination with a further therapeutic agent, preferably an immune checkpoint inhibitor.

The present invention provides a pharmaceutical composition comprising an anti-CD25 antibody that does not inhibit the binding of interleukin 2 to CD25, and optionally a further therapeutic agent, preferably an immune checkpoint inhibitor, in a pharmaceutically acceptable medium. As discussed above, the immune checkpoint inhibitor may be an inhibitor of PD-1, i.e. a PD-1 antagonist.

PD-1 (Programmed cell Death protein 1), also known as CD279, is a cell surface receptor expressed on activated T cells and B cells. Interaction with its ligands has been shown to attenuate T-cell responses both in vitro and in vivo. PD-1 binds two ligands, PD-L1 and PD-L2. PD-1 belongs to the immunoglobulin superfamily. PD-1 signalling requires binding to a PD-1 ligand in close proximity to a peptide antigen presented by major histocompatibility complex (MHC) (Freeman (2008) Proc Natl Acad Sci USA 105, 10275-6). Therefore, proteins, antibodies or small molecules that prevent co-ligation of PD-1 and TCR on the T cell membrane are useful PD-1 antagonists.

In one embodiment, the PD-1 receptor antagonist is an anti-PD-1 antibody, or an antigen binding fragment thereof, which specifically binds to PD-1 and blocks the binding of PD-L1 to PD-1. The anti-PD-1 antibody may be a monoclonal antibody. The anti-PD-1 antibody may be a human or humanised antibody. An anti-PD-1 antibody is an antibody capable of specific binding to the PD-1 receptor. Anti-PD-1 antibodies known in the art include Nivolumab and Pembrolizumab.

PD-1 antagonists of the present invention also include compounds or agents that either bind to and/or block a ligand of PD-1 to interfere with or inhibit the binding of the ligand to the PD-1 receptor, or bind directly to and block the PD-1 receptor without inducing inhibitory signal transduction through the PD-1 receptor. In particular PD-1 antagonists include small molecules inhibitors of the PD-1/PD-L1 signalling pathway. Alternatively, the PD-1 receptor antagonist can bind directly to the PD-1 receptor without triggering inhibitory signal transduction and also binds to a ligand of the PD-1 receptor to reduce or inhibit the ligand from triggering signal transduction through the PD-1 receptor. By reducing the number and/or amount of ligands that bind to PD-1 receptor and trigger the transduction of an inhibitory signal, fewer cells are attenuated by the negative signal delivered by PD-1 signal transduction and a more robust immune response can be achieved.

In one embodiment, the PD-1 receptor antagonist is an anti-PD-L1 antibody, or an antigen binding fragment thereof, which specifically binds to PD-L1 and blocks the binding of PD-L1 to PD-1. The anti-PD-L1 antibody may be a monoclonal antibody. The anti-PD-L1 antibody may be a human or humanised antibody, such as Atezolizumab (MPDL3280A).

The present invention also provides a method of treating cancer, comprising administering an anti-CD25 antibody that does not inhibit the binding of interleukin 2 to CD25 and an antibody which is an agonist of a T cell activating costimulatory pathway to a subject. Antibody agonists of a T cell activating costimulatory pathway include, without limitation, agonist antibodies against ICOS, GITR, OX40, CD40, LIGHT and 4-1BB.

A further method of treating cancer comprises administering an anti-CD25 antibody that does not inhibit the binding of interleukin 2 to CD25 and a compound that decreases, blocks, inhibits, and/or antagonizes FcγRIIb (CD32b). Such FcγRIIb antagonist can be a small molecule interfering for FcγRIIb-induced intracellular signalling, modified antibodies that do not engage inhibitory FcγRIIb receptor, or an anti-human FcγRIIb (anti-CD32b antibody. For example, antagonistic anti-human FcγRIIb antibodies have been characterized also for their anti-tumour properties (Roghanian A et al., 2015, Cancer Cell. 27, 473-488; Rozan C et al., 2013, Mol Cancer Ther. 12:1481-91; WO2015173384; WO2008002933).

In a further aspect, the present invention provides a bispecific antibody comprising:
  (a) a first antigen binding moiety that binds to CD25; and
  (b) a second antigen binding moiety that binds to an immune checkpoint protein, a tumour-associated antigen, an anti-human activatory Fc Receptor antibody (FcgRI, FcgRIIa, FcgRIII), or an antagonistic anti-human FcγRIIb antibody;
wherein the wherein the anti-CD25 antibody does not inhibit the binding of Interleukin-2 (IL-2) to CD25, and preferably is an IgG1 bispecific antibody that binds to at least one activatory Fcγ receptor with high affinity, and depletes tumour-infiltrating regulatory T cells. In a preferred embodiment, the second antigen binding moiety binds to PD-L1.

As used herein, "tumour-associated antigen" refers to antigens expressed on tumour cells, making them distinguishable from non-cancer cells adjacent to them, and include, without limitation, CD20, CD38, PD-L1, EGFR, EGFRV3, CEA, TYRP1 and HER2. Various review articles have been published that describe relevant tumour-associated antigens and the corresponding therapeutically useful antitumor antibody agents (see, for example, Sliwkowski & Mellman (2013) Science 341, 192-8). Such antigens and corresponding antibodies include, without limitation CD22 (Blinatumomab), CD20 (Rituximab, Tositumomab), CD56 (Lorvotuzumab), CD66e/CEA (Labetuzumab), CD152/CTLA-4 (Ipilimumab), CD221/IGF1R (MK-0646), CD326/Epcam (Edrecolomab), CD340/HER2 (Trastuzumab, Pertuzumab), and EGFR (Cetuximab, Panitumumab).

In one aspect, the bispecific antibody according to the invention as described herein leads to ADCC, or, in one aspect, enhanced ADCC.

The bispecific antibody may bind to a specific epitope on CD25 that does not affect the binding of IL-2 to CD25, and a specific epitope on the immune checkpoint protein or tumour-associated antigen as defined herein. In a preferred embodiment, the second antigen binding moiety binds to PD-L1. In a preferred aspect, the present invention provides a bispecific antibody comprising:
  (a) a first antigen binding moiety that binds to CD25 and that does not affect the binding of IL-2 to CD25; and
  (b) a second antigen binding moiety that binds to an immune checkpoint protein expressed on a tumour cell.

In a particular embodiment, the immune checkpoint protein expressed on a tumour cell is PD-L1, VISTA, GAL9, B7H3 or B7H4. Still preferably, the anti-CD25 antibody an IgG1 antibody that does not affect the binding of IL-2 to CD25 and that binds to at least one activatory Fcγ receptors with high affinity, and depletes tumour-infiltrating regulatory T cells. Alternatively the anti-CD25 antibody is a human IgG2 antibody that depletes tumour-infiltrating regulatory T cells. In one particular embodiment, the anti-CD25 antibody is a human IgG2 antibody that binds to at least one activatory Fcγ receptors with high affinity, preferably FcγRIIa.

One skilled in the art would be able to produce a bispecific antibody using known methods. The bispecific antibody according to the invention may be used in any of the aspects of the invention as described herein. Preferably, the second antigen binding moiety within the bispecific antibody according to the invention binds to human PD-1, human PD-L1, or human CTLA-4.

In one aspect the bispecific antibody may bind to CD25 and to immune modulatory receptors expressed at high levels on tumour infiltrating Tregs, for example CTLA4, ICOS, GITR, 4-1 BB or OX40.

The present invention also provides a kit which comprises an anti-CD25 antibody as described herein, and a further therapeutic agent, preferably an immune checkpoint inhibitor, preferably a PD-1 antagonist (directly, using an anti-PD1 antibody, or indirectly, using an anti-PD-L1 antibody) as discussed herein. In one aspect the immune checkpoint inhibitor is anti-PD-L1. In an alternative embodiment the kit comprises an anti-CD25 antibody as described herein, and an antibody which is an agonist of a T cell activating costimulatory pathway. The kit may comprise instructions for use.

Any aspect of the invention as described herein may be performed in combination with additional therapeutic agents, in particular additional cancer therapies. In particular, the anti-CD25 antibody and, optionally, the immune checkpoint inhibitor according to the present invention may be administered in combination with co-stimulatory antibodies, chemotherapy and/or radiotherapy (by applying irradiation externally to the body or by administering radioconjugated compounds), cytokine-based therapy, targeted therapy, monoclonal antibody therapy, a vaccine, or an adjuvant, or any combination thereof.

A chemotherapeutic entity as used herein refers to an entity which is destructive to a cell, that is the entity reduces the viability of the cell. The chemotherapeutic entity may be a cytotoxic drug. A chemotherapeutic agent contemplated includes, without limitation, alkylating agents, anthracyclines, epothilones, nitrosoureas, ethylenimines/methylmelamine, alkyl sulfonates, alkylating agents, antimetabolites, pyrimidine analogs, epipodophylotoxins, enzymes such as L-asparaginase; biological response modifiers such as IFNα, IFN-γ, IL-2, IL-12, G-CSF and GM-CSF; platinum coordination complexes such as cisplatin, oxaliplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

The additional cancer therapy may also include the administration of a cancer vaccine. "Cancer vaccines" as used herein refer to therapeutic cancer vaccines administrated to cancer patients and designed to eradicate cancer cells through strengthening patient's own immune responses. Cancer vaccines include tumour cell vaccines (autologous and allogenic), dendritic cell vaccines (ex vivo generated and peptide-activated), protein/peptide-based cancer vaccines and genetic vaccines (DNA, RNA and viral based vaccines). Accordingly, therapeutic cancer vaccines, in principle, may be utilized to inhibit further growth of advanced cancers and/or relapsed tumours that are refractory to conventional therapies, such as surgery, radiation therapy and chemotherapy. Tumour cell based vaccines (autologous and allogeneic) include those genetically modified to secrete soluble immune stimulatory agents such as cytokines (IL-2, IFN-g, IL12, GMCSF, FLT3L), single chain Fv antibodies against immune modulatory receptors (PD-1, CTLA-4, GITR, ICOS, OX40, 4-1 BB) and/or to express on their membrane the ligand for immune-stimulatory receptors such as ICOS-ligand, 4-1BB ligand, GITR-ligand, and/or OX40 ligand amongst others. In one embodiment the cancer vaccine may be a GVAX anti-tumour vaccine.

The additional cancer therapy may be other antibodies or small molecule reagents that reduce immune regulation in the periphery and within the tumour microenvironment, for example molecules that target TGFbeta pathways, IDO (indoleamine deoxigenase), Arginase, and/or CSF1R.

'In combination' may refer to administration of the additional therapy before, at the same time as or after administration of any aspect according to the present invention.

The invention will now be further described by way of the following Examples, which are meant to serve to assist one of ordinary skill in the art in carrying out the invention and are not intended in any way to limit the scope of the invention, with reference to the drawings.

BRIEF DESCRIPTION OF FIGURES

FIG. 1—shows the characterization of 7D4 and PC61 anti-mouse CD25 antibodies as used in the Examples. Effect on IL-2 binding was performed using a tandem format cross-blocking assay. Biotinylated mouse CD25 was loaded onto SA sensors. The sensors were then exposed to 100 nM mouse IL-2 followed by either anti-mouse CD25 antibody at time 150 sec. Additional binding by the antibody after IL-2 association indicates an anti-mouse CD25 that does not block IL-2 binding, while no further binding indicates ligand blocking. PC-61 mIgG2a shows interference of the mouse IL-2—mouse CD25 interaction, in contrast the 7D4 (A). The mouse IL-2/mouse CD25 interaction in presence of the recombinant anti-mouse CD25 7D4(mIgG1) was evaluated using a standard sandwich format cross-blocking assay. 7D4(mIgG1) was loaded onto AHQ sensors and unoccupied Fc-binding sites on the sensor were blocked with an irrelevant human IgG1 antibody. The sensors were then exposed to 100 nM of recombinant mouse CD25 (R&D Systems; cat. no. 2438-RM-050) followed by recombinant mouse IL-2 (Peprotech; cat. no. 212-12). Additional binding by the mouse IL-2 after 7D4(mIgG1)-mouse CD25 association indicates an unoccupied epitope, with both 7D4(mIgG1) and mouse IL-2 that do not compete for the epitope within mouse CD25 since binding is simultaneously to mouse CD25 (B). Binding to mouse CD25 was determined using CHO cells expressing mouse CD25 for the anti-human CD25-binding antibodies Daclizumab (DAC), the P061 (mIgG2a) antibody (the original anti-CD25 obtained from clone PC-61 with murine IgG2a and κ constant regions that are associated with ADCC) and a7D4(mIgG1) antibody (an anti-D25 obtained from clone 7D4 with murine IgG1 and κ constant regions). anti-mouse CD25 IgG bind to cellular expressed mCD25. CHO-mCD25 were aliquoted in 96-well assay plates (50000 cells/well) and incubated with 0.1 mL antibody-containing solution (antibody at 100 nM concentration in PBS+0.1% bovine serum albumin) at 25° C. for 15 minutes. The cells were washed three times with ice-cold PBS+0.1% bovine serum albumin) and then labeled with goat Anti-Human IgG (γ chain specific) R-PE (Southern Biotech, catalog number 2040-09) and analyzed using a flow cytometry (propidium iodide was used to distinguish dead cells). No binding was detected for DAC, while both PC61 (mIgG2a) and 7D4(mIgG1) show clear binding to such cells (C).

FIG. 10: shows the consensus sequence of human CD25 (Uniprot code P01589), referred to as SEQ ID NO:1 herein. The extracellular domain of mature CD25, corresponding to amino acids 22-240, is underlined. The position of epitopes from non-IL blocking anti-CD25 antibodies as preliminarily identified: epitopes 1 (full and short epitopes), epitope 2 (full and short epitopes), epitope 3 and epitope 4 (full and short epitopes)) are indicated. The position of the basiliximab and daclizumab epitope (indicated as DAC) is also identified.

FIG. 11: Characterization of (A) 7D4, (B) PC61 and (C) 2E4 binding to CD25 expressed on CHO cells expressing CD25 at increasing antibody concentrations and comparing with mouse IgG2a isotype control.

FIG. 12: SPR based analysis of purified antibodies (mIgG2a) to rmCD25 his tagged on the Biacore 2000, (A) 7D4, (B) 2E4.

FIG. 25: In vivo model showing suppression of tumour growth after dosing with: vehicle (A) and (C); or Antibody 1 (B), (D) and (E).

FIG. 26: Affinity determination by SPR based analysis of purified antibodies (IgG1) to rhCD25 his tagged on the Biacore 2000. A) 7g7B6ch, B) MA251ch, C) Antibody 1, D) Antibody 3 and E) Daclizumab (control) or by biolayer interferometry on the Octet® Red 96 instrument (F).

FIG. 27: Characterization of Antibody 1 binding to CD25 expressed on human in vitro differentiated Treg cells (A), SU-DHL-1 cells (B), or SR-786 cells (C) at increasing antibody concentrations and comparing with human IgG1 isotype control.

FIG. 28: Characterization of Antibody 1 binding to CD25 expressed on CD3/CD28 bead activated Human (A) and (B) Pan T cells, then gated on CD4+ and CD8+ T cells, at increasing antibody concentration and comparing with human IgG1 isotype control.

FIG. 29: Shows non-competitive binding of Antibody 1 and IL-2 (A) and competitive binding of a IL-2 competing antibody with IL-2 (B) by biolayer interferometry on the Octet® Red384 using a standard sandwich format binning assay. The anti-human CD25 antibody, Antibody 1, was loaded onto AHQ sensors. The sensors were then exposed to 100 nM human CD25 followed by human IL-2. Additional binding by human IL2 after antigen association indicates an unoccupied epitope (non-competitor), while no binding indicates epitope blocking (competitor).

FIG. 30: Shows non-competitive binding of Antibody 1 and Daclizumab to CD25 by biolayer interferometry on the Octet® Red384 system using a standard sandwich format binning assay. The reference monoclonal anti-human CD25 antibody Daclizumab was loaded onto AHQ sensors. The sensors were then exposed to 100 nM human CD25 antigen followed by the anti-human CD25 antibody (Antibody 1). Additional binding by the second antibody after antigen association indicates an unoccupied epitope (non-competitor), while no binding indicates epitope blocking (competitor).

FIG. 35: Characterization of Antibody 3 binding to CD25 expressed on human in vitro differentiated Treg cells (A), SU-DHL-1 cells (B), or SR-786 cells (C) at increasing antibody concentrations and comparing with human IgG1 isotype control FIG. 36: Characterization of Antibody 3 binding to CD25 expressed on CD3/CD28 bead activated Human (A) and (B) or Cynomolgus Monkey (C) and (D) Pan T cells, then gated on CD4+ and CD8+ T cells, at increasing antibody concentration and comparing with human IgG1 isotype control.

FIG. 40: Functional characterization of Antibody 3 compared to human IgG1 isotype control, Daclizumab, or commercially available mouse anti-human IL-2 neutralizing antibody as a positive control, (clone: AB12-3G4) using Pan T cells. Cells were incubated with 10 ug/ml antibody then activated with CD3/0028 beads for 72 hours before flow cytometry analysis. Results show percentage of granzyme B positive proliferating CD4 (A) or CD8 (B) T cells.

FIG. 41: Functional characterization of Antibody 3 compared to human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.

FIG. 42: Functional characterization of Antibody 3 compared to human IgG1 isotype control in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye+/CD14−. Dual-labelled cells (eFluor™ 450-dye+/0014+) were considered to represent phagocytosis of targets by Macrophages. Phagocytosis of target cells was calculated with the following equation: % Phagocytosis=100×[(percent dual positive)/(percent dual positive+percent residual targets)].

FIG. 43: Characterization of Antibody 4 binding to CD25 expressed on human in vitro differentiated Treg cells (A), SU-DHL-1 cells (B), or SR-786 cells (C) at increasing antibody concentrations and comparing with human IgG1 isotype control.

FIG. 48: Functional characterization of Antibody 4 compared to human IgG1 isotype control, Daclizumab, or commercially available mouse anti-human IL-2 neutralizing antibody as a positive control, (clone: AB12-3G4) using Pan T cells. Cells were incubated with 10 ug/ml antibody then activated with CD3/CD28 beads for 72 hours before flow cytometry analysis. Results show percentage of granzyme B positive proliferating CD4 (A) or CD8 (B) T cells.

FIG. 51: Characterization of Antibody 2 binding to CD25 expressed on human in vitro differentiated Treg cells (A), SU-DHL-1 cells (B), or SR-786 cells (C) at increasing antibody concentrations and comparing with human IgG1 isotype control.

FIG. 52: Characterization of Antibody 2 binding to CD25 expressed on CD3/CD28 bead activated Human (A) and (B) or Cynomolgus Monkey (C) and (D) Pan T cells, then gated on CD4$^+$ and CD8$^+$ T cells, at increasing antibody concentration and comparing with human IgG1 isotype control.

FIG. 56: Functional characterization of Antibody 2 compared to human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.

FIG. 57: Functional characterization of Antibody 2 compared to human IgG1 isotype control in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye$^+$/CD14$^-$. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

FIG. 63: Characterization of Antibody 6, Antibody 7, Antibody 8 and antibody 9, binding to CD25 expressed on Karpas 299 cells at increasing antibody concentrations and comparing with human IgG1 isotype control.

FIG. 64: Competition assays in the Octet®. Binding the first Ab (Antibody 7) to the immobilized rhCD25 followed by either the first Ab again (as control) or a second Ab Daclizumab (A) or Basiliximab (B).

FIG. 68: Characterization of Antibody 10, Antibody 11, Antibody 12, Antibody 12, Antibody 13, Antibody 14, Antibody 15, Antibody 16, Antibody 17, antibody 18, Antibody 19, Antibody 20 and Antibody 21, binding to CD25 expressed on Karpas 299 cells at increasing antibody concentrations and comparing with human IgG1 isotype control.

FIG. 69: Competition assays in the Octet®. Binding the first Ab (Antibody 19) to the immobilized rhCD25 followed by either the first Ab again (as control) or a second Ab Daclizumab (A) or Basiliximab (B).

FIG. 72: Functional characterization of Antibody 19 compared to an anti-human CD25 Fc silent control antibody in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye$^+$/CD14$^-$. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

FIG. 73: Functional characterization of Antibody 19, Antibody 12 and Antibody 20 compared to an anti-human CD25 Fc silent control antibody in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye$^+$/CD14$^-$. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

FIG. 74: Therapeutic activity of non-IL-2 blocking anti-CD25 antibody, 7D4 mouse IgG2a, in combination with GVAX in a B161316 immune therapy resistant model. Individual mice were treated with Gvax alone or in combination with, 7D4.

EXAMPLES

Figure 2:
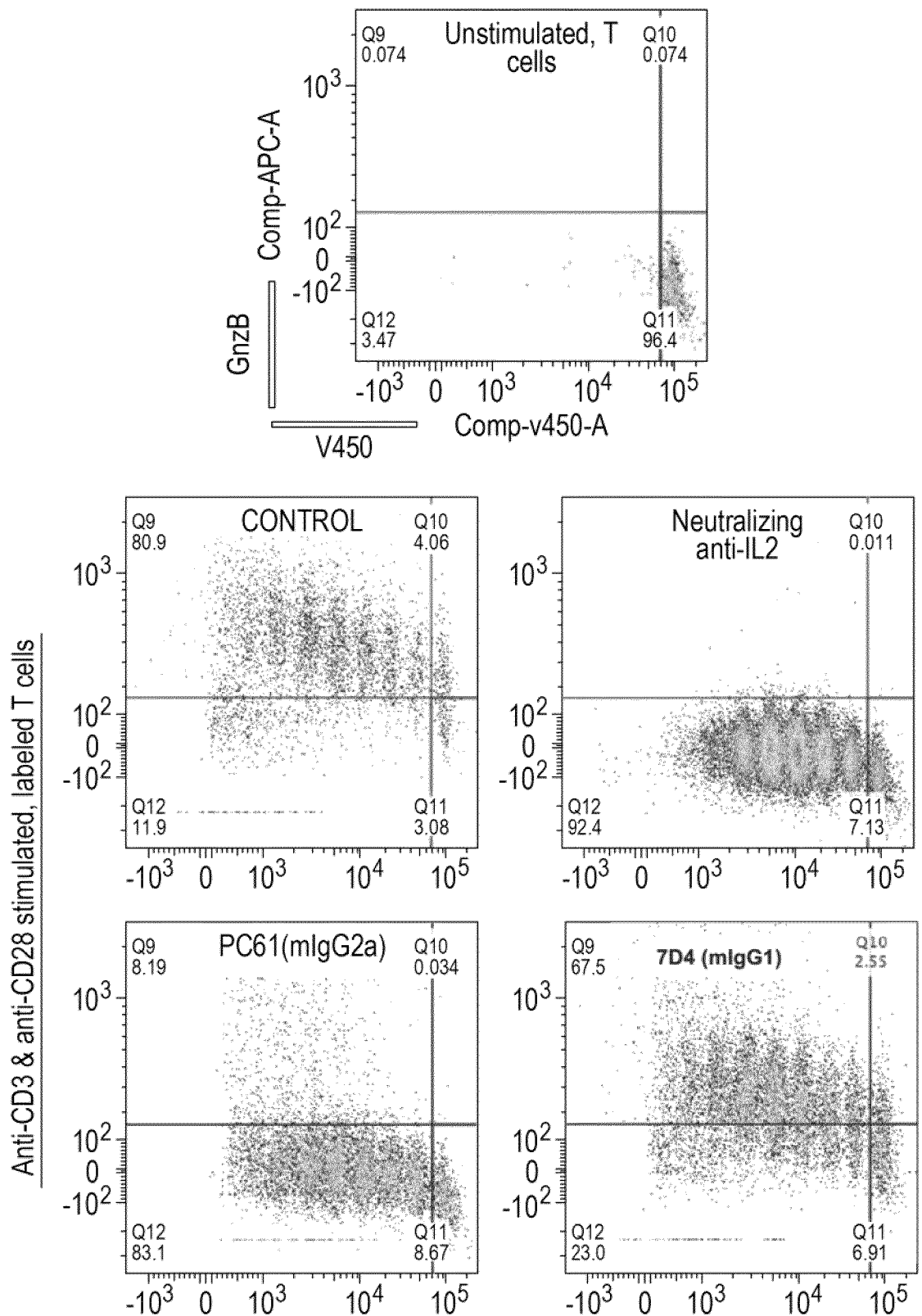
FIG. 2—shows the effect of anti-mouse CD25 antibodies on the induction of Granzyme B expression by CD4 T cells upon stimulation with anti-CD3 and anti-CD28, Total CD4-positive T cells were isolated using CD4 MicroBeads from mouse lymph nodes and spleen and labelled with Cell-Trace™ Violet dyes (ThermoFisher) for measuring cell proliferation. The labeled T cells (105) have been seeded with feeder cells (105; CD90.2negative fraction, using mouse pan T Dynabeads™ kit) in 96-well plate. Anti-CD3 (clone 145-2011, BioXcell Cat No. BE0001-1; 1 µg/ml) and anti-CD28 (clone 37.51 Cat No. BioXcell BE0015-1; 0.5 µg/ml) were added to the wells (with the exception of the control sample of unstimulated, labeled T cells) to activate the CD4 T cells and induce proliferation and Granzyme B production. The following antibodies were then further added (at 25 µg/mL) to the wells containing labelled CD4 T cells and anti-CD3 and anti-CD28 antibodies (wells containing labelled T cells and anti-CD3 and anti-CD28 antibodies only were used as negative control): PC61(mIgG2a), 7D4(mIgG1), or a neutralizing anti-mouse IL-2 antibody (clone Jes6-1A12, BioXcell 6032988564) used as a positive control, to show the impact of blocking the interaction between IL-2 and its receptor on T cell activation. The samples of labeled T cells were then incubated for approx. 84 hrs. Cells were then fixed and permeabilized before being stained with anti-mouse Granzyme B antibody (clone GB11, Invitrogen). Cells were then analyzed by flow cytometry for granzyme B expression and CellTrace™ violet dyes dilutions (BV450). The percentage of labeled T cells that are both proliferating and expressing Granzyme B (GnzB) is shown in top left quadrant of each treatment-specific graph (Q9), while the percentage of labeled T cells that are proliferating but not expressing GnzB is shown in the bottom left quadrant of each treatment-specific graph (Q12).

Example 1—In Vitro Characterization and Preparation of Recombinant Anti-Mouse CD25, Treg-Depleting Antibodies that are Either Non-IL-2 Blocking or IL-2 Blocking Materials & Methods
Origin of Antibody and their Recombinant Production The sequence of the variable regions of the heavy and light chains of rat anti-murine CD25 PC61 were resolved from PC-61.5.3 hybridoma (ATCC cat no. TIB-222) by rapid amplification of cDNA ends (RACE) and then cloned into the constant regions of murine IgG2a and K chains (or corresponding mouse IgG1 sequences that were isolated from the commercial plasmids (Invivogen).

Each antibody chain was then sub-cloned into a murine leukemia virus (MLV)-derived retroviral vector. For preliminary experiments, antibody was produced using K562 cells transduced with vectors encoding both the heavy and the light chains. The antibody was purified from supernatants using a protein G HiTrap MabSelect column (GE Healthcare), dialyzed in phosphate-buffered saline (PBS), concentrated and filter-sterilized.

The re-cloned, anti-mouse CD25 heavy variable chain DNA sequence from PC-61.5.3 antibody (mouse IgG2a) encodes for the following protein sequence:

METDTLLLWVLLLWVPGSTGEVQLQQSGAELVRPGTSVKLSCKVSGDTIT

AYYIHFVKQRPGQGLEWIGRIDPEDDSTEYAEKFKNKATITANTSSNTAH

LKYSRLTSEDTATY FCTTDNMGATEFVYWGQGTLVTVSS

The re-cloned, anti-mouse CD25 light variable chain DNA sequence from PC-61.5.3 antibody (mouse IgG2a) encodes for the following protein sequence:

METDTLLLWVLLLWVPGSTGQVVLTQPKSVSASLESTVKLSCKLNSGNIG

SYYMHWYQQREGRSPTNLIYRDDKRPDGAPDRFSGSIDISSNSAFLTINN

VQTEDEAMYFCHSYDGRMYIFGGGTKLTV

7D4-IgM sequencing was performed on the 7D4 hybridoma (ECACC, 88111402). Total RNA or mRNA was extracted and reverse transcription performed to obtain cDNA for the antibody heavy and light chains. The variable heavy and variable light chains were amplified using degenerate forward primers that bound either in the signal peptide or framework region 1 and a reverse primer that bound in the antibody constant region. The amplified genes were cloned and sequenced following a standard approach. cDNA was generated by reverse transcription and a homopolymeric tail added to the 3' end of the cDNA. The antibody variable domain genes were then amplified using gene specific primers followed by a standard cloning and sequencing approach. DNA was sequenced by conventional Sanger sequencing and data analysed using DNASTAR Lasergene software. Signal peptide and variable domain sequences were identified by comparison with known sequences in the IMGT database.

Genes encoding the variable heavy and variable light domains were codon optimized for expression in a human cell line and synthesised with NheI and AvaI restriction sites 5' and 3' of the gene. Restriction digest cloning was performed to insert 7D4 variable heavy domain gene into separate expression vectors containing mouse IgG1 and IgG2a constant domains. Restriction digest cloning was performed to insert the 7F4 variable light domain gene into an expression vector containing the mouse kappa constant domain. Suspension HEK293 cells cultured in serum-free media were chemically co-transfected with heavy and light chain expression vector and cultured for a further 6 days at 37° C. in a 5% CO2 environment and with shaking at 140 rpm. Cultures were harvested by centrifugation at 4000 rpm and further clarified by filtration through a 0.22 µM filter. Supernatant was loaded onto a Protein A column pre-equilibrated with PBS pH 7.2, eluted with sodium citrate pH 3.5 and equilibrated with 10% (v/v) 0.5 M Tris pH 9.0. The neutralised antibody solution was buffer exchanged into PBS pH 7.2 using a desalting column and concentrated as required using a centrifugal concentrator with a 30 kDa molecular weight cut-off. Protein concentration was determined by measurement of absorbance at 280 nm and purity was determined by SDS-PAGE.

The re-cloned, anti-mouse CD25 heavy chain DNA sequence from 7D4 antibody (mouse IgG1) encodes for the following protein sequence:

EVQLQQSGAALVKPGASVKMSCKASGYSFPDSWVTWVKQSHGKSLEWIGD

IFPNSGATNFNEKFKGKATLTVDKSTSTAYMELSRLTSEDSAIYYCTRLD

YGYWGQGVMVTVSSAKTTPPSVYPLAPGSAAQTNSMVTLGCLVKGYFPEP

VTVTWNSGSLSSGVHTFPAVLQSDLYTLSSSVTVPSSTWPSQTVTCNVAH

PASSTKVDKKIVPRDCGCKPCICTVPEVSSVFIFPPKPKDVLMISLTPKV

TCVVVDISKDDPEVQFSWFVDDVEVHTAQTKPREEQINSTERSVSELPIL

HQDWLNGKEFKCRVNSAAFPAPIEKTISKTKGRPKAPQVYTIPPPKEQMA

KDKVSLTCMITNEFPEDITVEWQWNGQPAENYKNTQPIMDTDGSYFVYSK

LNVQKSNWEAGNTFTCSVLHEGLHNHHTEKSLSHSPGK

The re-cloned, anti-mouse CD25 heavy variable chain DNA sequence from 7D4 antibody (mouse IgG2a) encodes for the following protein sequence:

EVQLQQSGAALVKPGASVKMSCKASGYSFPDSWVTWVKQSHGKSLEWIGD

IFPNSGATNFNEKFKGKATLTVDKSTSTAYMELSRLTSEDSAIYYCTRLD

YGYWGQGVMVTVSSAKTTAPSVYPLAPVCGDTTGSSVTLGCLVKGYFPEP

VTLTWNSGSLSSGVHTFPAVLQSDLYTLSSSVTVTSSTWPSQSITCNVAH

PASSTKVDKKIEPRGPTIKPCPPCKCPAPNLLGGPSVFIFPPKIKDVLMI

SLSPIVTCVVVDVSEDDPDVQISWFVNNVEVHTAQTQTHREDYNSTLRVV

SALPIQHQDWMSGKEFKCKVNNKDLPAPIERTISKPKGSVRAPQVYVLPP

PEEEMTKKQVTLTCMVTDFMPEDIYVEWTNNGKTELNYKNTEPVLDSDGS

YFMYSKLRVEKKNWVERNSYSCSVVHEGLHNHHTTKSFSRTPGK

The re-cloned, anti-mouse CD25 kappa light chain DNA sequence for both 7D4 (mIg1) and 7D4(mIg2a) antibody (mouse IgG2a) encodes for the following protein sequence:

DVVLTQTPPTLSATIGQSVSISCRSSQSLLHSNGNTYLNWLLQRPGQPPQ

LLIYLASRLESGVPNRFSGSGSGTDFTLKISGVEAEDLGVYYCVQSSHFP

-continued
NTFGVGTKLEIKRADAAPTVSIFPPSSEQLTSGGASVVCFLNNFYPKDIN

VKWKIDGSERQNGVLNSWTDQDSKDSTYSMSSTLTLTKDEYERHNSYTCE

ATHKTSTSPIVKSFNRNEC

2E4 was generated from the 2E4 hybridoma (Gift from Dr Ethan M. Shevach, National Institute of Health). Hybridoma sequencing was performed by proprietary next generation sequencing (NGS) based technology to. RNA samples were used to generate a cDNA library. Libraries were sequenced on an Illumina platform. De novo assembly was used to reconstruct the sample transcriptome from raw data. Variable domain sequences were identified by comparison with known sequences.

The variable heavy domain protein sequence for anti-mouse CD25 2E4 antibody (mouse IgG1) has the following protein sequence:

EVQLVESGGGLVQPGRSLKLSCAASGFTFSDYGMAWVRQAPTKGLEWVAS

ITNGGLNTYYRDSVKGRFTISRDNAKCTLYLQMDSLRSEDTATYYCATGG

FSFWGQGTLVTVSS

The variable light domain protein sequence for anti-mouse CD25 2E4 (mIg1) has the following protein sequence:

DIVMTQSPTSMSISVGDRVTMNCKASQNVDSNVDWYQQKTGQSPKLLIYK

ASNRYTGVPDRFTGSGSGTDFTFTIRNMQAEDLAVYYCMQSNSYPLTFGS

GTKLEIK

Assessing the Affinity of the Recombinant Antibodies for Mouse CD25

ForteBio affinity measurements were performed on an Octet® RED384 generally as previously described (see, e.g., Estep P et al., 2013. Mabs. 5(2), 270-8). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. All kinetics were analyzed using the 1:1 binding model.

Results

Two mouse hybridomas have been selected as reference antibody for evaluating CD25 binding and Treg depleting properties of anti-mouse CD25, that are either non-IL-2 blocking or IL-2 blocking: 7D4 (mouse IgM isotype) and PC61 (mouse IgG1 isotype), respectively. The IL-2 binding-related properties that were described in the literature have been preliminarily confirmed using the original, non-recombinant antibodies and recombinant mouse IL-2 (FIG. 1A). The recombinant variants of such antibodies have been produced for testing antibodies in which the isotype is more active and relevant for functional studies (such as for Treg depletion or effects on other immune cells). Moreover, in the case of 7D4, the change of isotype is required since the antibody aggregation properties of IgM antibodies may affect the results of the assays. The recombinant 7D4 (mIgG1), as the original non-recombinant IgM isotype antibody, still allows the binding mouse IL-2 to mouse CD25 (FIG. 1B). 7D4(mIgG1) also binds mouse CD25 on cell surface, similarly to recombinant PC61(IgG2a) while a reference anti-human CD25 antibody does not bind (FIG. 10).

The DNA sequence encoding for the variable domain of 7D4 heavy chain (as well as of PC61) has been also cloned within a vector that allow expressing the mouse CD25 binding domain with the mouse IgG2a isotype (functionally corresponding to human IgG1). In this manner, it is possible to compare two recombinant anti-mouse CD25 antibody with optimized ADCC activity that may efficiently deplete intra-tumoral Treg but presenting distinctive properties with respect to mouse IL-2 binding to mouse CD25. The resulting recombinant anti-mouse CD25 antibodies have been tested for their CD25 affinity. The different isotype (mouse IgG2a or mouse IgG1) does not affect this property since the Kd is similar between 7D4-based recombinant antibodies (around 1 nM) and comparable to the one of PC61(mIgG2a), that is measured as 4.6 nM.

The functional properties of these recombinant antibodies were also compared in an in vitro assay for determining their effect on Granzyme B production in response to anti-CD3 and anti-CD28 stimulation (FIG. 2). Granzyme B (GnzB) is a serine proteinase expressed by memory T cells and NK cells as well as activated CD4 and CD8 T cells, which strongly express and secrete GnzB during immunological reactions. This enzyme is an important mediator of cell death, tissue pathology and disease. The in vitro stimulation and proliferation of T cells with anti-CD3 and anti-CD28 antibodies (with >80% of CD4 T cells both proliferating and expressing GnzB) can be affected by cytokines and antibodies. When this stimulation is performed in combination with a neutralizing anti-IL-2 antibody Granzyme B production, but not proliferation, is inhibited: the frequency of cell both proliferating and producing GnzB drops from >80% to <1%, while the frequency of proliferating cells remains >90%. This indicates that the production of Granzyme B, but not cell proliferation, is dependent on IL-2 signalling. A similar drop in Granzyme B producing T cells is observed when PC61 (mIgG1) is added to the stimulated T cells. However, 7D4 (mIgG1) mostly preserves the ability of CD4 T cells to respond to anti-CD3 and anti-CD28 stimulation by producing GnzB (>65% of cells still producing GnzB and proliferating). These results confirm that PC61-based antibodies block the IL-2 signalling, while 7D4 has only little effect on this signalling and can thus be used as a surrogate antibody to evaluate the therapeutic potential of an anti-human CD25 antibody, in particular with respect to Treg depletion and tumour-specific properties, that would not impact on the IL-2 signalling.

Example 2—Treg Depleting and Anti-Cancer Properties of Recombinant Anti-Mouse CD25, Treg-Depleting Antibodies that are Either Non-IL-2 Blocking or IL-2 Blocking Materials & Method Mice In vivo studies were performed by Charles River Discovery Services North Carolina (CR Discovery Services). Female BALB/c mice (BALB/c AnNcr1, Charles River) and Female C57BL/6 mice (C57BL/6Ncr1, Charles River), were between seven and nine weeks old at the start of the study. CR Discovery Services specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International, which assures compliance with accepted standards for the care and use of laboratory animals.

Cell Lines and Tissue Culture

MCA205 tumour cells (3-methylcholanthrene-induced weakly immunogenic fibrosarcoma cells; from G. Kroemer, Gustave Roussy Cancer Institute) were cultured in Dulbecco's modified Eagle medium (DMEM, Sigma) supplemented with 10% fetal calf serum (FCS, Sigma), 100 U/mL penicillin, 100 µg/mL streptomycin and 2 mM L-glutamine (all from Gibco). MC38 murine colon carcinoma cells (CR discovery services) were grown to mid-log phase in Dulbecco's Modified Eagle's Medium (DMEM) containing 10% fetal bovine serum, 2 mM glutamine, 100 units/mL, penicillin G, 100 µg/mL streptomycin sulphate and 25 µg/mL gentamicin. CT26 murine colon carcinoma cells (CR discovery services) were grown in RPMI-1640 medium containing 10% fetal bovine serum, 2 mM glutamine, 100 units/mL penicillin G sodium, 100 µg/mL streptomycin sulphate, and 25 µg/mL gentamicin. All tumor cells were cultured in tissue culture flasks in a humidified incubator at 37° C., in an atmosphere of 5% CO2 and 95% air. K562 cells used for antibody production were cultured in phenol red-free Iscove modified Dulbecco medium (IMDM) supplemented with 10% IgG-depleted FCS (Life Technologies).

In Vivo Tumour Experiments

Cultured tumour cells were trypsinized (MCA205) or not (MC38 and CT26), washed and resuspended in PBS and injected subcutaneously s.c.) in the flank ($5\times10^5$ cells for MCA205 and MC38 models in C57BL/6 mice; $3\times10^5$ 15 cells for CT26 models in BALB/c mice). Antibodies were injected intraperitoneally (i.p.) at the time points described in the figure legends. For functional experiments, 12 days after tumour implantation the tumors and draining lymph nodes were harvested and processed for analysis by flow cytometry as described (Simpson et al. (2013) J Exp Med 210, 1695-710). For therapeutic experiments, tumours were measured twice weekly and volumes calculated as the product of three orthogonal diameters.

Flow Cytometry

Acquisition was performed with a BD LSR II Fortessa (BD Biosciences). The following antibodies were used: anti-CD3 (clone 145-2C11, ebioscience, 25003182), anti-CD4 (clone RM4-5, BD biosciences, 560782), anti-CD8 (clone 53-6.7, Biolegend, 100750), anti-Granzyme B (clone GB11, Invitrogen), anti-FoxP3 (Clone FJK-16s, eBiosciences) and Ki67 (Clone SolA15, eBiosciences, 48569882). Lymph nodes (inguinal, axillary, and brachial) and tumors from mice were dissected into serum-free RPMI. Lymph nodes were dispersed through a 70-µm filter whereas tumors were mechanically disrupted using gentleMACS (Miltenyl Biotech) and digested with a mixture of 0.33 mg/ml DNase (Sigma-Aldrich) and 0.27 mg/ml Liberase TL (Roche) in serum-free RPMI for 30 min at 37 C. Tumours were filtered through a 70-µm filter and the resulting tumour single cell suspensions were enriched for leukocytes by passage through a Ficoll-paque (GE Healthcare) gradient. Tumours and LN were washed in complete RPMI, re-suspended in FACS buffer (500 mL PBS, 2% FCS, 2 mM EDTA) and placed in round-bottomed 96 well plates. A mastermix of surface antibodies was prepared at the manufacturer's recommended dilution: anti-CD3 (clone 145-2C11, ebioscience, 25003182), anti-CD4 (clone RM4-5, BD biosciences, 560782), anti-CD8 (clone 53-6.7, Biolegend, 100750). A fixable viability dye (eFluor780™, eBioscience, an organic dye that can be excited by the red (633 nm) laser line) was also included the surface mastermix. Following permeabilisation for 20 minutes with use of an intracellular fixation and permeabilization buffer set (eBioscience), an intracellular staining panel was applied consisting of the following antibodies used at the manufacturers recommended dilution: anti-Granzyme B (clone GB11, Invitrogen), anti-FoxP3 (Clone FJK-16s, eBiosciences) and Ki67 (Clone SolA15, eBiosciences, 48569882).

Results

The MCA205 sarcoma murine model allows generating mice in which the immunological response and overall efficacy against a solid tumour can be evaluated for a panel of immunomodulatory compounds in a short time. In particular, the recombinant, mouse IgG2a-based anti-mouse CD25 antibodies were tested for evaluating the changes in the T cell sub-populations that present as Tumour-infiltrating lymphocytes or within peripheral lymph nodes, as well as the tumour growth and viability of mice exposed to MCA205. A further antibody (anti-mouse PD1) is included in the study as negative control for immunological effects on Treg.

Figure 3:
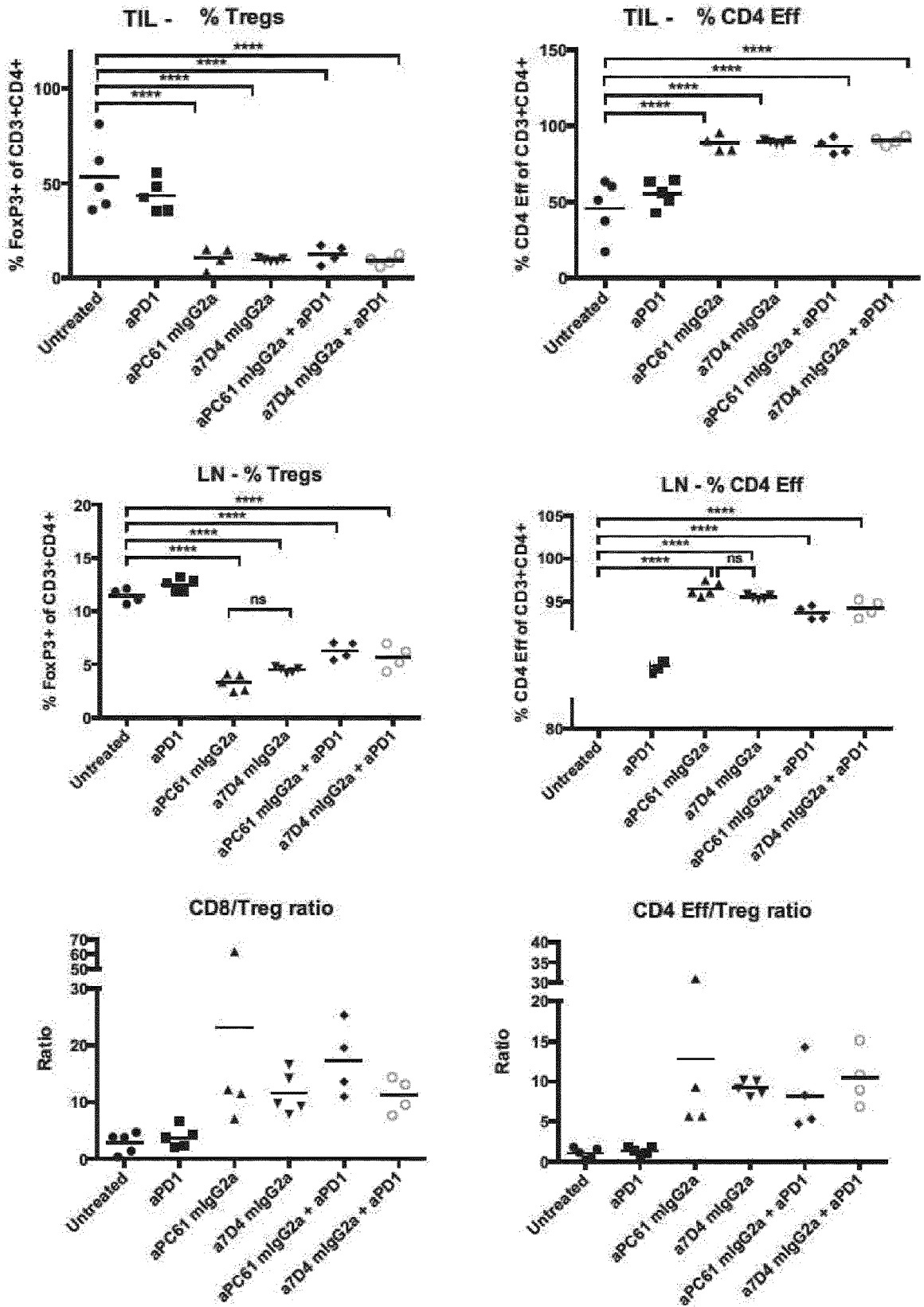
FIG. 3—shows the in vivo effect of anti-mouse CD25 antibodies having the same isotype (mouse IgG2a) that are either blocking or non-blocking the interaction between CD25 and IL-2, when administered in presence or not of anti-mouse PD1 (aPD1; clone RMP1-14), on immune cells. Six groups of mice were injected sub-cutaneously with MCA205 tumor cells ($5\times10^5$ 15) at Day0 and treated separately as indicated in the graphs. In four groups, the anti-mouse CD25 antibody (either aPC61 mIgG2a or a7D4 mIgG2a; 200 µg) is injected intra-peritoneally at Day5. In three groups, aPD1 (100 µg) is injected intra-peritoneally at Day6 and Day9. The tumors and Lymph Nodes are harvested at Day12 and then processed for staining cells according to the desired type and analysed by flow cytometry as indicated in each panel, using the following antibodies: anti-CD3 (clone 17A2, Biolegend), anti-CD4 (clone RM4-5, BD biosciences), anti-CD8 (clone 53-6.7, Biolegend) and anti-FoxP3 (Clone FJK-16s, eBiosciences). Intranuclear staining of FoxP3 was performed using the FoxP3 Transcription Factor Staining Buffer Set (eBioscience). Percentage of CD4-positive/Foxp3-positive regulatory T cells and CD4-positive/FoxP3-negative effector CD4 T cells (CD4 Teff) in LN and TIL as well as ratio of effector CD8-positive T cell/Treg cells and CD4 Teff/Treg cells is shown. Data analysis was performed in Flowjo version 10.0.8 (Tree Star Inc.). Statistical analyses were performed in Prism 6 (GraphPad Software, Inc.); p values were calculated using Kruskall-Wallis analysis of variance and Dunn's post-hoc test (ns=p>0.05; ****=p<0.0001).

The immunological analysis shows that the 7D4 antibody, when cloned into a mouse IgG2a backbone, shows a similar ability as PC61 (mouse IgG2a) at depleting Treg and subsequently increasing the ratio of Teff to Treg in both tumour and periphery, while anti-PD1 is ineffective either alone or in combination (FIG. 3) Thus, any further effect that is measured using 7D4(mIgG2a) as a surrogate antibody to a non-IL-2-blocking, anti-human CD25 antibody does not appear associated to changes in the Treg depletion properties.

Figure 4:
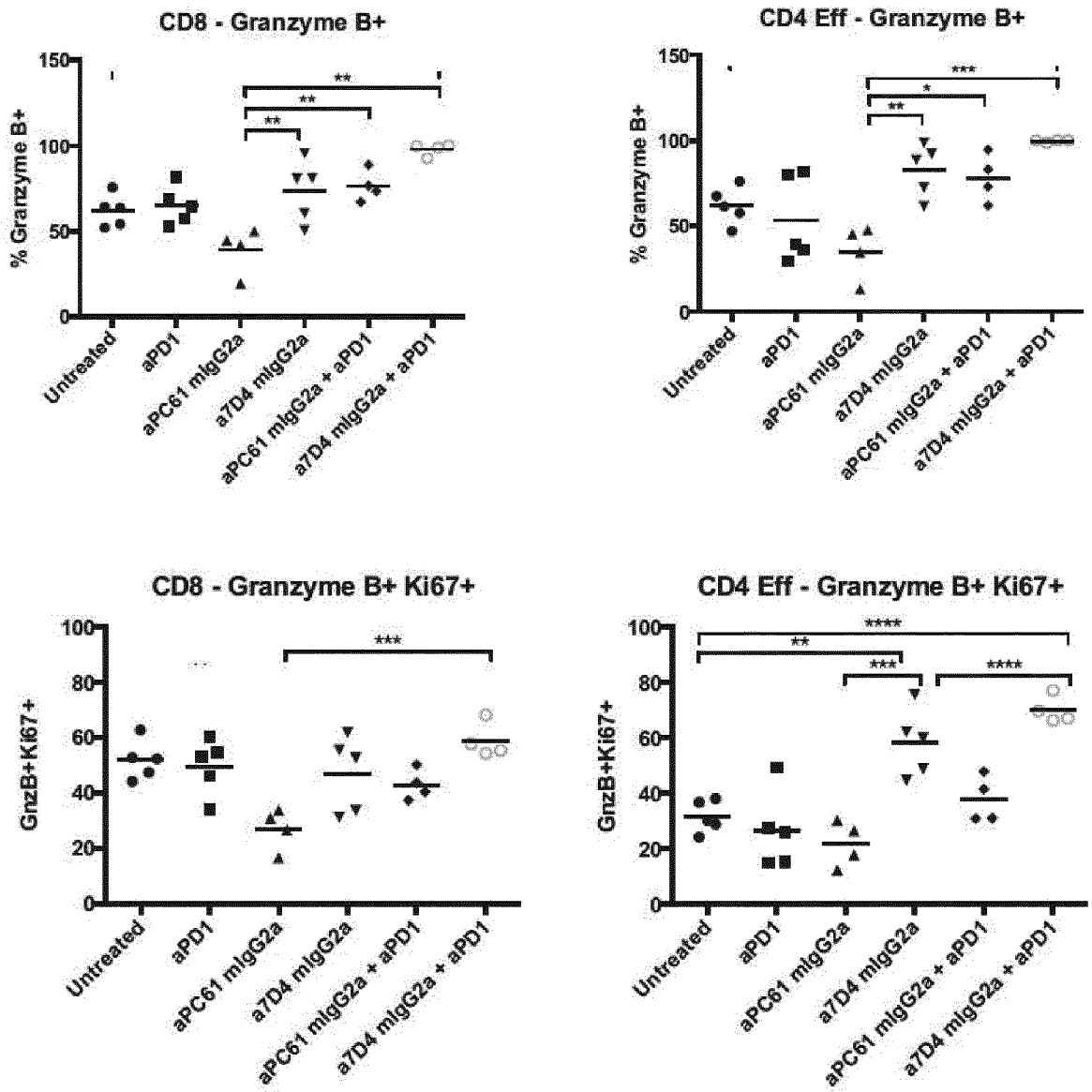
FIG. 4—shows the effect of anti-mouse CD25 antibodies having the same isotype (IgG2a) that are either blocking or non-blocking the interaction between CD25 and IL-2, in presence or not of anti-mouse PD1 (aPD1; clone RMP1-14) on the production of Granzyme B by proliferating T cells in vivo. Sample of cells were generated using the MCA205-based model in six treatment groups as indicated in the FIG. 3. Tumour cells were stained according to the desired type and analysed by flow cytometry as indicated in each panel, using the following antibodies: anti-CD3 (PeCy7, clone 145-2011, Ebioscience, 25003182), anti-CD4 (V500, clone RM4-5, BD biosciences, 560782), anti-CD8 (BV785, clone 53-6.7, Biolegend, 100750), anti-Granzyme B (APC, clone GB11; Invitrogen, grb05) and Ki67 (V450, Clone SolA15; eBiosciences, 48569882). Intranuclear staining of Ki67 and Granzyme B was performed using the FoxP3 Transcription Factor Staining Buffer Set (eBioscience, 00-5523-00). The percentage of GnzB-positive well as the total number of GnzB-positive proliferating (as indicated by Ki67 positivity) CD4-positive or CD8-positive T cells were compared. Statistical analyses were performed as for FIG. 3 (ns=p>0.05; *=p<0.05; =p<0.01; *=p<0.001; ****=p<0.0001).
Figure 5:
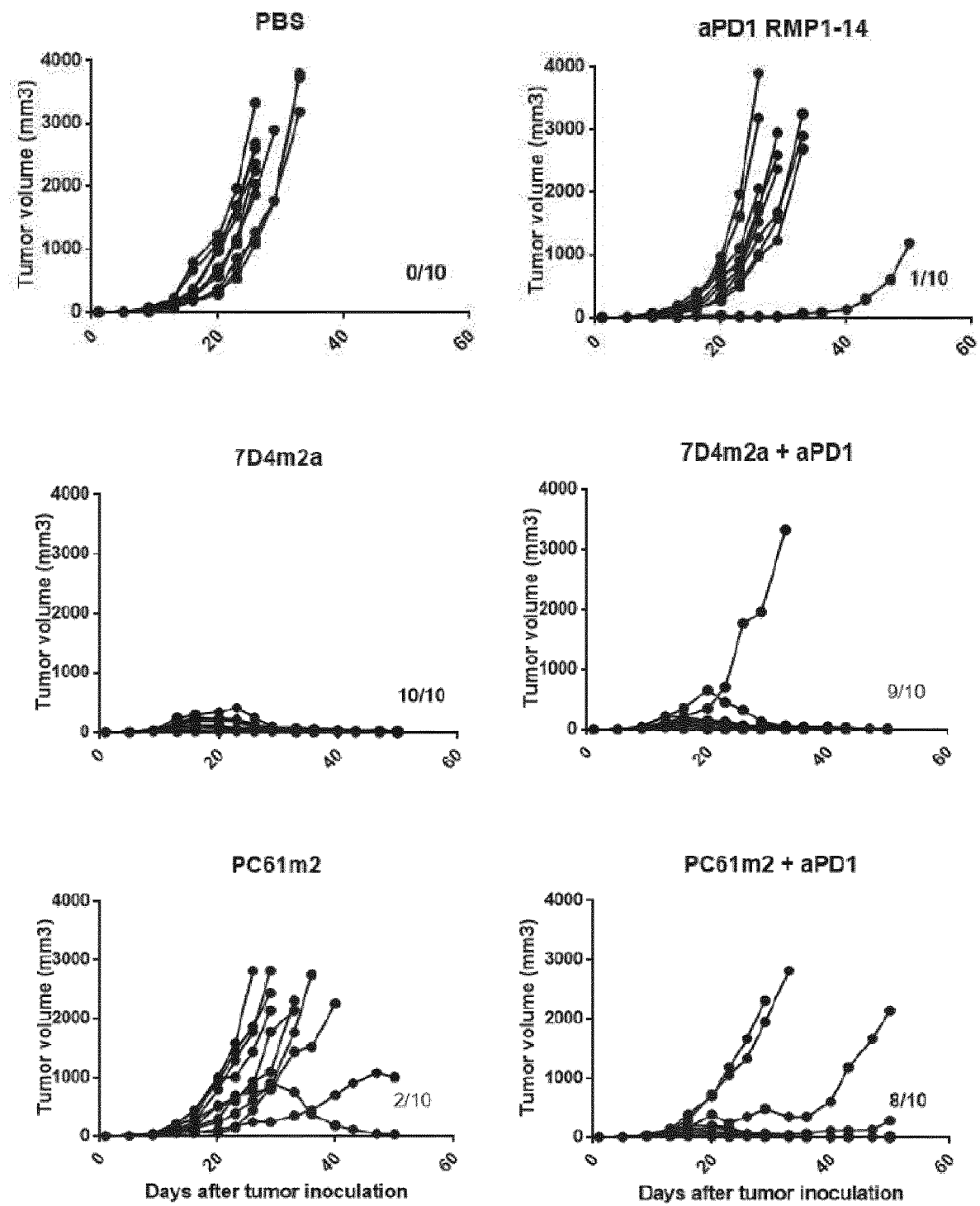
FIG. 5—shows the effect of anti-mouse CD25 (IgG2a isotype) that is administered with or without the combination with an anti-PD-1 (clone RMP1-14) on the eradication of established tumours in the CT26 mouse model. Both 7D4m2a and PC61 m2a are anti-mouse CD25, Treg-depleting antibodies but either non-IL-2 blocking (7D4m2a) or IL-2 blocking (PC61 m2). Growth curves of individual mice were established for each treatment group over time. The number of tumour-free survivors after 50 days is indicated in each graph. CT26 cells used for implantation were harvested during log phase growth and resuspended in cold PBS. On day 1 (D1) of the study, each mouse was injected subcutaneously in the right flank with $3\times10^5$ cells (0.1 mL cell suspension). The anti-mouse CD25 was injected i.p. (10 mg/kg) at Day 6 (when palpable tumors were detected). The anti-mouse PD1 was injected i.p. (100 µg/injection) at Day 7, Day 10, Day 14, and Day 17. Tumors were calipered in two dimensions twice weekly to monitor growth. Tumor size, in $mm^3$, was calculated from: Tumor Volume=(w2×l)/2 where w=width and l=length, in mm, of the tumor. The study endpoint was a tumor volume of 4000 $mm^3$ or 50 days, whichever came first (data point stopping at different, earlier days are due to death of mice; the number of animal surviving at the end of the experiment is indicated within each panel).

MCA205 model mice that are treated with 7D4 show also a higher percentage of GnzB-positive cells, such as proliferating CD4-positive and CD8-positive T cells, with respect not only to anti-PD1 treatment but also 11-2 blocking PC61(mIg2a). In such treated mice, not only 7D4(mIg2a), as PC61(mIg2a), does not affect Teff cells, but it also increases the frequency of Teff cells as compared to PC61(mIg2a), suggesting an even higher anti-tumour activity of an anti-human CD25 antibody that would not block the IL-2/CD25 interaction (FIG. 4).

The use of anti-human CD25 functionally equivalent to 7D4(mIg2a) for cancer immunotherapy, in particular for solid tumours, can be tested in MCA205 murine model but also other models such CT26 and MC38(colon carcinoma) or B16 (melanoma) models. Both IgG2a, anti-mouse CD25 antibodies show therapeutic activity against established CT26 tumours when administered in combination with anti-PD1 antibodies. Interestingly, when used as monotherapy, the non-IL-2 blocking 7D4(mIg2a) antibody shows a clearly higher therapeutic activity than the PC61-based antibody having the same isotype. At the end of the experiment, all mice treated with 7D4(mIg2a) only show a control of tumour growth to a volume lower than 50 mm$^3$, while none of the mice treated with PC61(mIg2a) show tumour smaller than 50 mm$^3$, with tumours in 8 out of 10 mice even reaching the 2000 mm$^3$ endpoint. This is also illustrated by a difference in survival, with all mice treated with 7D4 (mIg2a) still alive on day 50, versus only 2 out of 10 mice treated with PC61(mIg2a). Indeed, if PC61(mIg2a) efficacy results largely improving by the combination with anti-PD1, the efficacy of 7D4(mIg2a) is not further improved, at least when using this antibody at this concentration.

Figure 6:
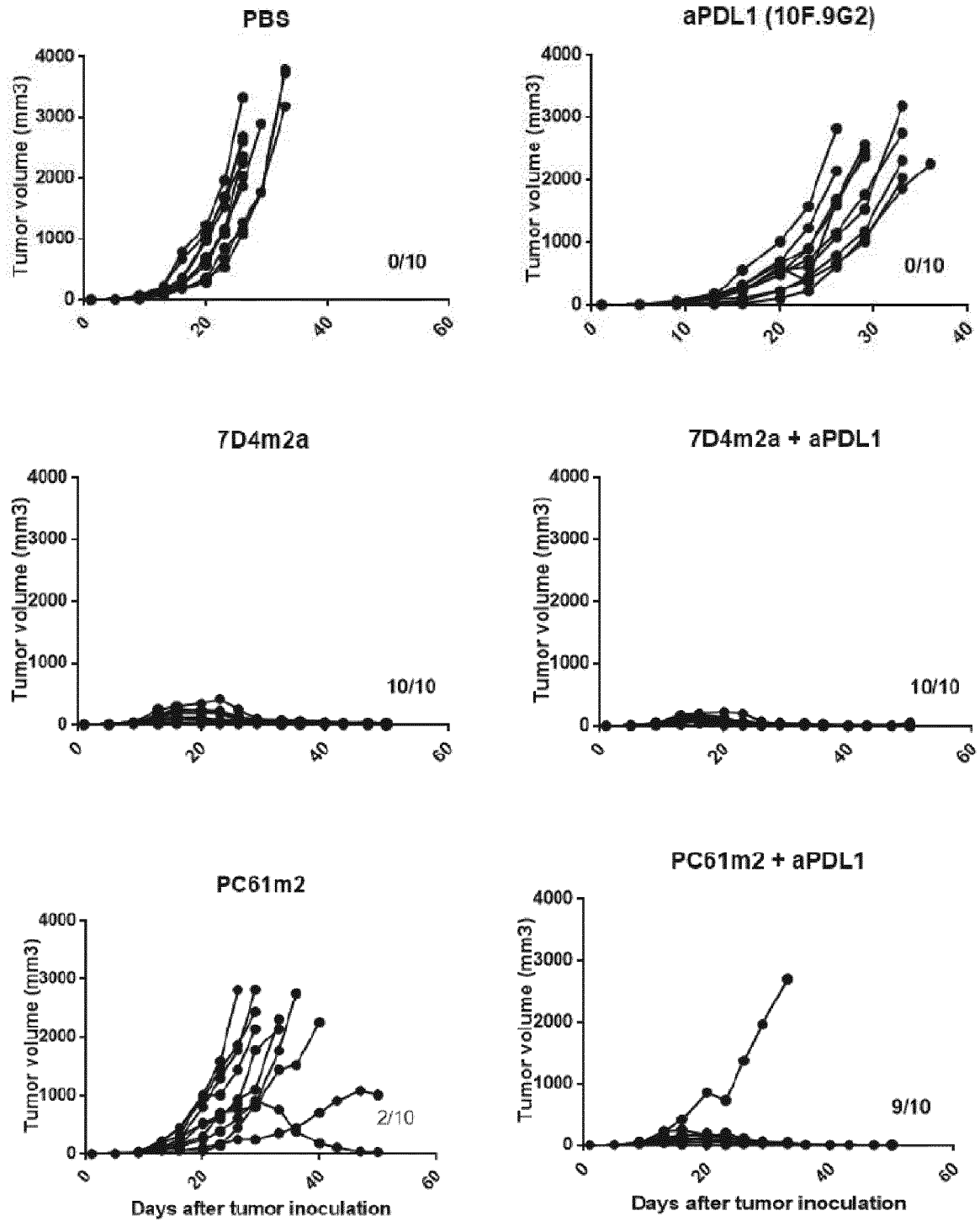
FIG. 6—shows CT26 tumour growth curves of individual mice not treated (PBS, vehicle only) or treated with anti-mouse CD25 IgG2a antibodies, both Treg depleting but either non-IL-2 blocking (7D4m2a) or IL-2 blocking (PC61m2), and further combined or not with anti-mouse PD-L1 clone 10F.9G2 (aPDL1; clone 10F.9G2). Model, regimen, and data analysis are the same as for FIG. 5.
Figure 7:
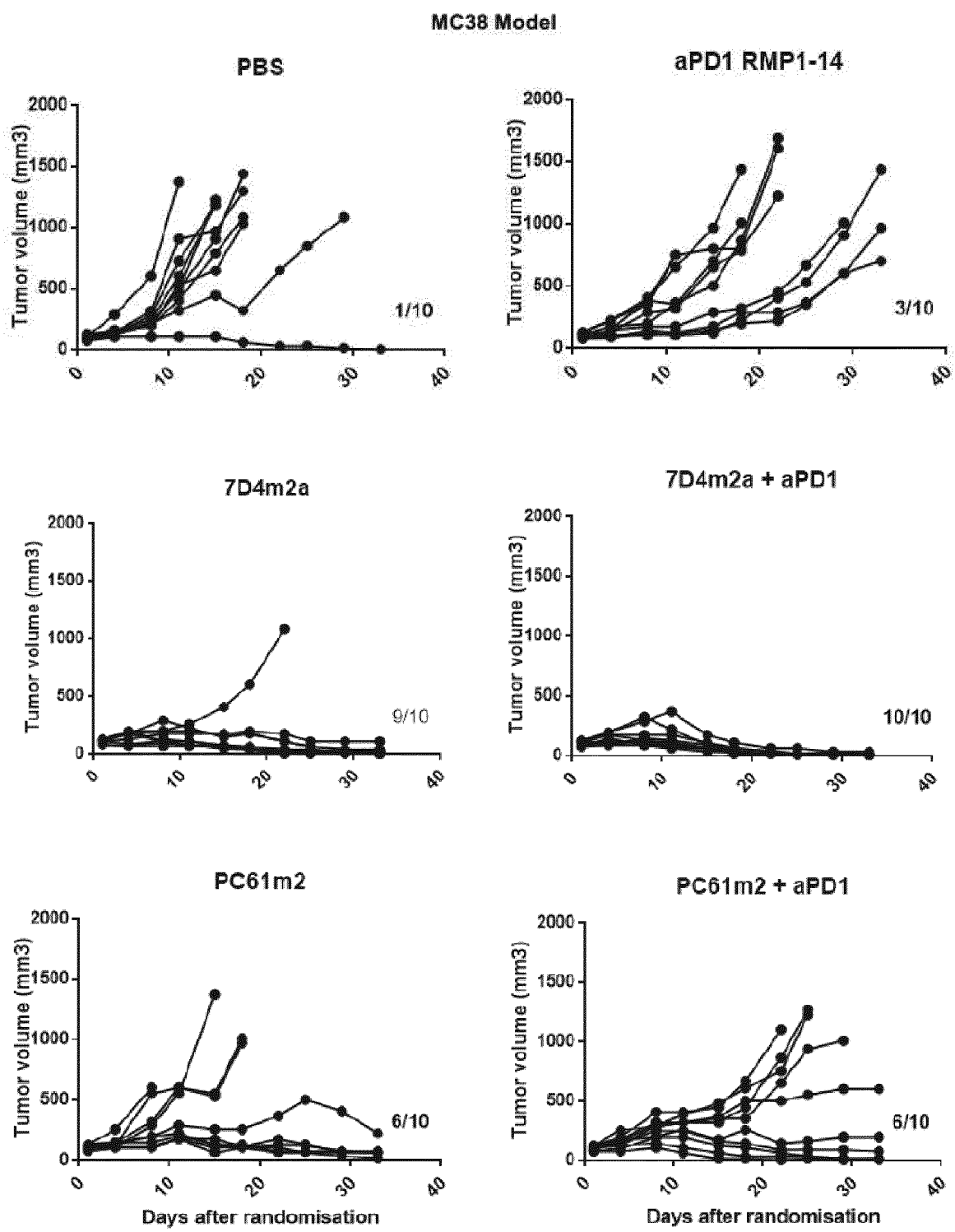
FIG. 7—shows the effect of anti-mouse CD25 (IgG2a isotype) that is administered with or without the combination with an anti-PD-1 (clone RMP1-14) on the eradication of established tumours in the MC38 mouse model. The tested antibodies are those described in FIG. 5. Growth curves of individual mice were established for each treatment group over time. The number of tumour-free survivors after 35 days is indicated in each graph. The MC38 colon carcinoma cells used for implantation were harvested during log phase growth and re-suspended in cold PBS. Each mouse was injected subcutaneously in the right flank with $5\times10^5$ tumor cells (0.1 mL cell suspension). Tumors were monitored as their volumes approached the target range of 100 to 150 $mm^3$. Twenty-two days after tumor implantation, on Day 1 of the study, animals with individual tumor volumes ranging from 75-126 $mm^3$ were sorted into nine groups (n=10) with group mean tumor volumes of about 106 $mm^3$. Treatments began on Day 1 in mice bearing established MC38 tumors. The effects of each treatment were compared to a vehicle-treated control group that received PBS intraperitoneally (i.p.) on Day 1, Day 2, Day 5, Day 9, and Day 12. Anti-PD1 was administered i.p. at 100 µg/animal, twice weekly for two weeks (biwk×2) beginning on Day 2. 7D4m2a and PC61m2a were administered i.p. once on Day 1 at 200 µg/animal. Tumor measurements were taken twice weekly. The study endpoint was a tumor volume of 4000 $mm^3$ or 35 days, whichever came first (data point stopping at different, earlier days are due to death of mice; the number of animal surviving at the end of the experiment is indicated with each panel).
Figure 8:
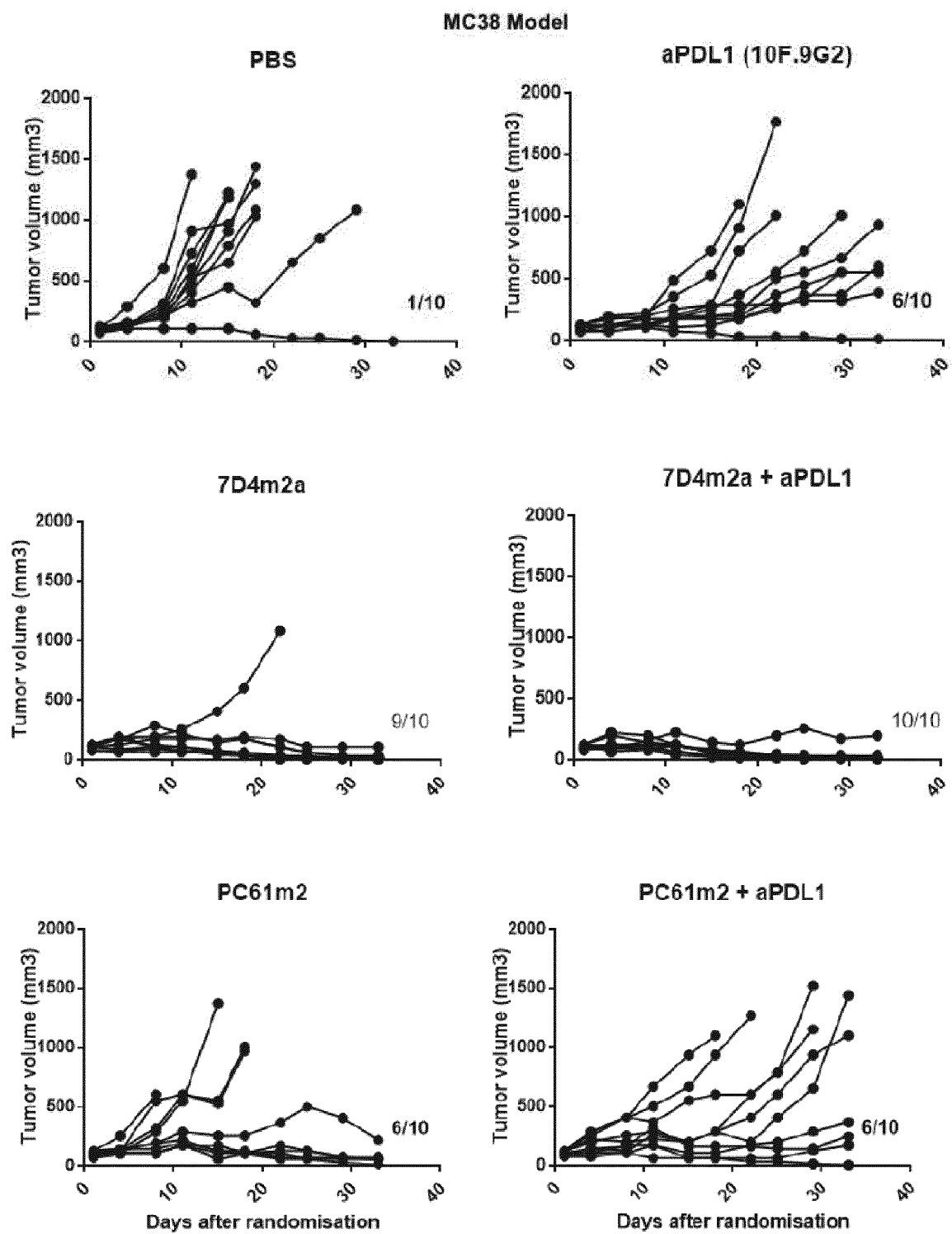
FIG. 8—shows MC38 tumour growth curves of individual mice not treated (PBS, vehicle only), treated with anti-mouse CD25 IgG2a antibodies, both Treg depleting but either non-IL-2 blocking (7D4m2a) or IL-2 blocking (PC61m2), and further combined or not with anti-mouse PD-L1 clone 10F.9G2 (aPDL1; clone 10F.9G2). Model, regimen, and data analysis are the same of FIG. 7.
Figure 9:
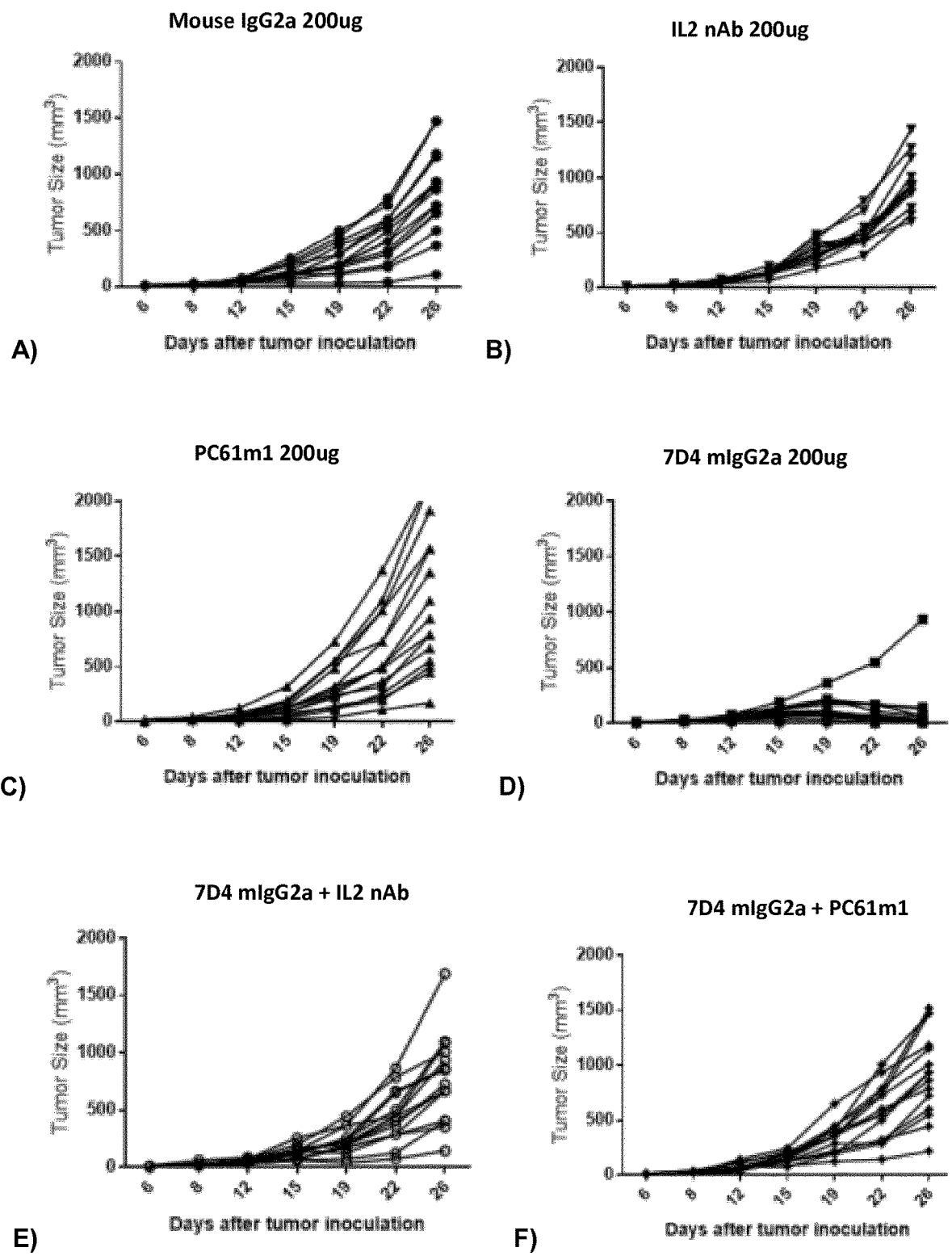
FIG. 9: Evaluation of the therapeutic activity of 7D4 mIgG2a, an anti-mouse CD25 non-IL-2 blocking, Treg depleting antibody alone (D) and in combination with an IL-2 neutralizing antibody (ThermoFisher; JES6-1A12) (E), or an IL-2 blocking non depleting anti-mouse CD25 antibody of the mouse IgG1 isotype (PC61 mouse IgG1) (F), in mice bearing CT26 syngeneic colon tumors in female BALB/c mice. The activity of mouse IgG2s control (A), an IL-2 neutralizing antibody alone (B), and an IL-2 blocking anti-CD25 antibody alone (C) were tested for comparison.

Since these 7D4- and PC61-based antibodies show a similar ability to deplete Treg (see FIG. 3), such a difference in efficacy could be explained, at least in part, by the lower impact of 7D4(mIg2a) on the interaction between IL-2 and its receptor. This shows that not only the absence of IL-2/IL-2 receptor blocking activity is not detrimental for therapeutic activity but it could also provide a therapeutic advantage. This data therefore supports the selection of a non-IL-2/IL-2 receptor blocking CD25 targeting antibody for use in cancer therapy. These advantageous properties of 7D4 (mIg2a) antibody were confirmed also when an anti-mouse PD-L1 is used in the same CT26 murine model (FIG. 6) or when the MC38 murine model is used with the same combinations of antibodies (FIG. 7 and FIG. 8).

These data show that Treg depleting, CD25-binding properties of antibodies based on 7D4 properties and with appropriate isotype can be exploited in combination with other anti-cancer compounds such as antibodies targeting immune checkpoint proteins (e.g. against PD-1 and anti-PD-L1) or against other cancer-relevant targets. This approach can be pursued by producing and administering the two products as a novel mixture of monospecific antibodies or as novel bispecific antibodies. This approach that involves the construction of bispecific antibodies combining the two antigen-binding properties and therapeutically relevant isotype (e.g. human IgG1) can be validated by using Duobody® technology that allow the efficient association of single heavy and light chain from two distinct monospecific antibodies that are produced separately and contain single matching point mutations in the CH3 domain, thus allowing Fab exchange within a single heteromeric protein (Labrijn A F et al., Nat Protoc. 2014, 9:2450-63). The functional properties of such 7D4-based Duobody® products (for example including an anti-PD1 or an anti-PD-L1) can be evaluated by using models of cell interaction and depletion that were used for validating 7D4-based antibodies and antibody combinations as described above.

These results also indicate that 7D4 binding properties with respect to mouse CD25, without interfering with the interaction of IL-2 with its receptor and IL-2 signalling in CD25-expressing cells, can be exploited in anti-human CD25 in which the isotype is selected consistently with this mechanism of action (e.g. human IgG1). Indeed, several other properties can be considered for screening anti-human CD25 antibody candidates with further improved properties with respect to their preparation, use, and/or administration for treating cancer, and in particular solid tumours.

These properties can be defined also with respect to features of known anti-human CD25 such as Humax-TAC, Basiliximab or Daclizumab, all having Kd in the nanomolar range for human CD25, but all blocking the binding of human IL-2 to human CD25 (using clone M-A251 as potential reference non-IL-2 blocking, anti-human CD25 to be included in the selection of anti-human CD25 of the invention).

These features can be one or more of the following ones:
Affinity for recombinant, isolated monomeric human CD25 with a $K_D$ inferior to 25 nM, preferentially below 10 nM and even more preferred below 1 nM (as established using technologies such as Octet®, KinExA, ELISA or others);
cross-reactivity for recombinant, isolated monomeric Cynomolgous CD25 with a $K_D$ inferior to 75 nM, preferentially below 30 nM and even more preferred below 3 nM (as established using technologies such as Octet®, KinExA, ELISA or others);
Affinity for recombinant, monomeric human CD25 on the surface of CHO or MJ cells with a $K_D$ inferior to 100 nM, preferentially below 10 nM and even more preferred below 1 nM (as established using technologies such as flow cytometry, cell-based ELISA or others);
Affinity for recombinant, monomeric rhesus CD25 on the surface of CHO cells with a $K_D$ inferior to 300 nM, preferentially below 30 nM and even more preferred below 3 nM (as established using technologies such as flow cytometry, cell-based ELISA or others);
Human Treg cells binding with a KD inferior to 100 nM, preferentially below 10 nM and even more preferred below 1 nM (as established using technologies such as flow cytometry, cell-based ELISA or others);
Cynomolgus Treg cells binding with a KD inferior to 300 nM, preferentially below 30 nM and even more preferred below 3 nM (as established using technologies such as flow cytometry, cell-based ELISA or others);
Lack of inhibition of the interaction between human recombinant IL-2 and human recombinant CD25 in biochemical assay (less than 25% of the IL-2 binding to CD25 is blocked in screening as described in Example 1);
Lack of IL-2 induced signalling in cell-based assay, such as STAT5 phosphorylation in activated CD8-positive or CD4-positive T cell or CD25-expressing cell line, or Granzyme B upregulation following activation of CD4-positive T cell assay (less than 25% of the base line signal is inhibited, as described in Example 1); and/or
Relevant potency evaluation in cell-based assays, such as ADCC, ADCP, and/or CDC assay in cell lines expressing human CD25 or primary Treg cells (with EC50 below 10 nM, preferentially below 1 nM and even more preferred below 0.1 nM).

Example 3—Further In Vivo Mouse Model Experiments with Non IL2 Blocking Anti-Mouse CD25 Antibodies Materials and Methods Therapeutic activity of a non-IL-2 blocking antibody: Female BALB/c mice obtained from Charles River were injected with $3 \times 10^5$ CT26 tumour cells in 0% Matrigel subcutaneously in the flank, n=15 per group. Animals were randomized into treatment groups based on Day 1 bodyweight. Treatment was started on Day 6 and mice were treated with one injection of each antibody (mouse IgG2a isotype, IL-2 neutralizing antibody, PC61 mIgG1, an anti-mouse CD25 blocking IL-2 signalling of mouse IgG1 isotype, and 7D4 mIgG2a, an anti-mouse CD25 non-blocking IL-2 signalling of mouse IgG2a isotype) at 200 µg/animal. Animals received either monotherapy treatments, with one group per antibody, or combination treatment of 7D4 mIgG2a and the IL-2 neutralizing antibody or 7D4 mIgG2a and PC61 mIgG1 antibody. Mice were sacrificed when the tumour volume reached 2000 mm$^3$ or 50 days, whichever was reached first.

Therapeutic Activity of a Non-IL-2 Blocking Antibodies in Comparison to Blocking Antibody $3 \times 10^5$ CT26 cells were implanted subcutaneously in the flank. A pair match was performed at day 0 when the tumours reached between 30-60 mm$^3$ and treatment commenced. At day 1 and biweekly thereafter, 10 mg/kg treatment was dosed i.p. Groups were treated with IL-2 neutralizing antibody PC61-m2a, non-IL-2 blocking antibody 7D4, non-IL-2 blocking antibody 2E4 or were untreated.

Therapeutic Activity of a Non-IL-2 Blocking Antibody in Combination with aPDL1 Therapy Mice were injected with 50,000 MCA205 tumour cells subcutaneously, n=10 per group or n=5 as indicated in the figures. Animals were randomized into treatment groups. Animals received either monotherapy treatments, of either 7D4 mIgG2a or aPD-L1 (clone 10F.9G2), combination treatment of 7D4 mIgG2a with aPD-L1 (clone 10F.9G2) or were untreated. Groups received either: a7D4 mIgG2a alone—day 10 (200 ug), aPD-L1 rIgG2b (10F.9G2)—day 6, 9 and 12 (200 ug), aPD-L1+a7D4 combo (aPDL-1 at day 6, 9 and 12 and a7D4 at day 10), or aPD-L1+a7D4 combo (aPDL-1 at day 6, 9 and 12 and a7D4 at day 10), — extra shot of a7D4 day 15+aPD-L1 day 18 (5 mice only).

Results

Figure 13:
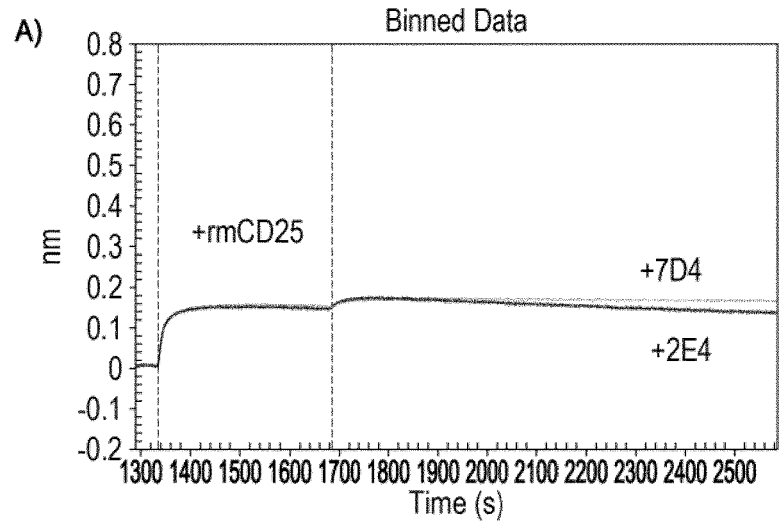
FIG. 13: Competition analysis of anti mCD25 antibodies to rmCD25 his tagged on the Octet® 96. Showing the binding by a second antibody after 7D4 capture on the sensor and antigen association steps. Competitive binding to mCD25 is observed between 7D4 and 2E4 (A) but not between 7D4 and PC61 (B)

The anti-CD25 depleting non-IL-2 blocking antibody 7D4 mIgG2a induced tumour rejection in treated mice, while the other antibodies showed no effect as monotherapy when compared to the isotype control mouse IgG2a. Combination with IL2-blocking antibodies, either PC61 mIgG1 or IL2 nAb, abrogates the therapeutic activity of the non-IL-2 blocking antibody 7D4 mIgG2a (FIG. 13). This demonstrates that the non-IL-2 blocking feature of 7D4 mIgG2a is key for therapeutic activity. It also suggests that the therapeutic activity of this antibody relies on anti-tumor immune response mediated by T effector cells, which are dependent on IL-2 signalling for optimal activity. These results show that the absence of IL-2/CD25 blocking activity is required for an optimal therapeutic activity of the CD25 targeting antibody and supports the use of an anti-CD25 non-IL-2 blocking antibody as described herein in cancer therapy.

These results further show that the absence of IL-2/CD25 blocking activity is not detrimental to the antibodies therapeutic activity and supports the use of an anti-CD25 non-IL-2 blocking antibody as described herein in cancer therapy.

Figure 75:
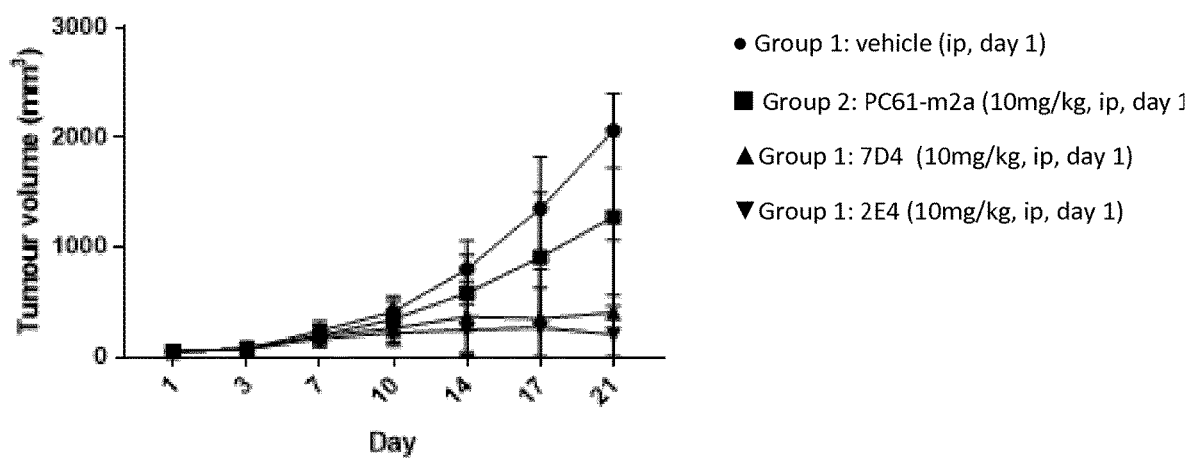
FIG. 75: Therapeutic activity of non-IL-2 blocking anti-CD25 antibodies (7D4 and 2E4) compared to an IL-2 blocking antibody (PC61) in a CT26 tumour model using female BALB/c mice. Anti-CD25 non-blocking antibodies 7D4 and 2E4 exert potent therapeutic activity against solid tumours. Both 7D4 and 2E4 are more potent than the IL-2 blocking antibody, PC61

These results further showed that the non-IL-2 blocking antibodies, 7D4 and 2E4 are more potent than IL-2 blocking antibody, PC61. The anti-CD25 non-blocking antibodies 7D4 and 2E4 exert potent therapeutic activity against solid tumours (FIG. 75).

Figure 76:
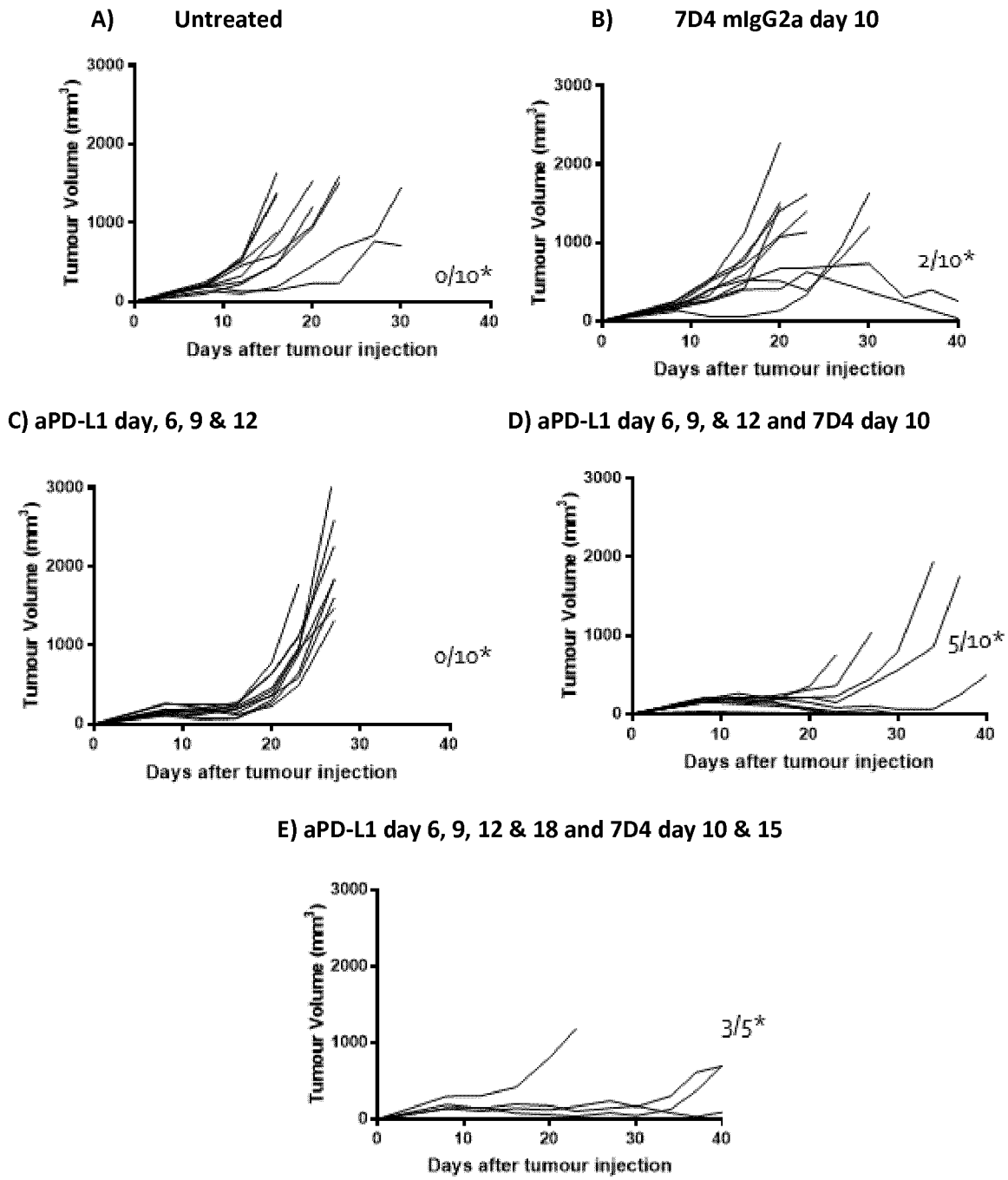
FIG. 76: Evaluation of therapeutic activity of non-IL-2 blocking anti-CD25 antibody 7D4 mIgG2a in an MCA205 model, at single and repeated injections in combination with anti-mouse PD-L1. * indicates mice alive at the end of the experiment.

The results showed single or repeated injections of non-IL2 blocking aCD25 antibody 7D4 after initiation of aPDL1 therapy boosts anti-tumour responses. Teff cells activated upon aPDL1 treatment are spared and boosted by aCD25 antibody (FIG. 76).

Example 4—Epitope Characterization of Anti-CD25 Non-IL-2 Blocking Antibodies

Epitope Binning

Epitope binning of the antibodies was performed on a Forte Bio Octet® Red384 system (Pall Forte Bio Corporation, Menlo Park, CA) using a standard sandwich format binning assay. Anti-mouse CD25 PC61 antibody was loaded onto AMC sensors and unoccupied Fc-binding sites on the sensor were blocked with a non-relevant mouse IgG1 antibody. The sensors were then exposed to 15 nM target antigen followed by the 7D4 antibody. Data was processed using ForteBio's Data Analysis Software 7.0. Additional binding by the second antibody after antigen association indicates an unoccupied epitope (non-competitor), while no binding indicates epitope blocking (competitor).

Epitope Mapping of Anti-CD25 Non-IL-2 Blocking Antibodies

Different sets of linear, single loop, β-turn mimics, disulfide bridge mimics, discontinuous disulfide bridges, discontinuous epitope mimics peptides representing the human CD25 sequence (Uniprot record no. P01589) were synthesized using solid-phase Fmoc synthesis (Pepscan BV, The Netherlands; Timmermann P et al., 2007 J. Mol. Recognit., 20, 283-99; Langedijk J P et al., 2011, Analytical Biochemistry. 417:149-155). The binding of the antibodies to each of the synthesized peptides was tested in an ELISA (Pepscan, The Netherlands). The peptide arrays were incubated with primary antibody solution (overnight at 4° C.). After washing, the peptide arrays were incubated with a 1/1000 dilution of an appropriate antibody peroxidase conjugate (2010-05; Southern Biotech) for one hour at 25° C. After washing, the peroxidase substrate 2,2'-azino-di-3-ethylbenzthiazoline sulfonate (ABTS) and 20 µl/ml of 3 percent $H_2O_2$ were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader. To verify the quality of the synthesized peptides, a separate set of positive and negative control peptides was synthesized in parallel and screened with irrelevant, control antibodies.

Results

Epitope binning was performed to determine whether the antibodies bind to epitopes overlapping with those of the commercially available mouse anti-human non-IL-2 blocking CD25 antibody, 7G7B6. The antibodies were further characterised to determine the epitopes for the non-IL-2 blocking antibodies. The epitope of the anti-mouse CD25 blocking antibody, PC61, was determined for comparison a control. The results of the epitope mapping are shown in Table 1 for anti-human CD25 antibodies and Table 2 for anti-mouse CD25 antibodies:

TABLE 1

| anti-human CD25 antibodies: | | | | |
|---|---|---|---|---|
| Antibody | Epitope 1 | Epitope 2 | Epitope 3 | Epitope 4 |
| 7G7B6 and Antibodies 6 to 9 | $_{150}$YQCVQGYRALHRGP$_{163}$ | $_{166}$SVCKMTHGKTRWTQP$_{180}$ | $_{42}$KEGTMLNCECKRGFR$_{56}$* | $_{74}$SSWDNQCQCTSSATR$_{88}$* |
| MA251 and antibodies 10 to 21 | $_{150}$YQCVQGYRALHRGP163 | $_{166}$SVCKMTHGKTRWTQP$_{180}$ | $_{42}$KEGTMLNCECKRGFR$_{56}$* | $_{74}$SSWDNQCQCTSSATR$_{88}$* |
| Antibody 1 | | | | $_{70}$NSSHSSWDNQCQCTS$_{84}$ |
| Antibody 2 | $_{150}$YQCVQGYRA$_{158}$ | $_{176}$RWTQPQLICTG$_{186}$ | | |
| Antibody 3 | | | $_{42}$KEGTMLNCECKRGFR$_{56}$* | |

TABLE 1-continued anti-human CD25 antibodies:

| Antibody | Epitope 1 | Epitope 2 | Epitope 3 | Epitope 4 |
|---|---|---|---|---|
| Antibody 4 | $_{150}$YQCVQGYRALH$_{160}$ | | $_{42}$KEGTMLNCECKR GFR$_{56}$* | |

*secondary epitope

The amino acid (aa) sequence numbering is based on human CD25 taken from the sequence published under the Uniprot accession number P01589 (SEQ ID NO: 1).

TABLE 2 anti-mouse CD25 antibodies:

| Antibody | Epitope | |
|---|---|---|
| 2E4 | $_{146}$YECIPGYKA$_{154}$ | $_{178}$LTCVDER$_{184}$ |
| 7D4 | $_{184}$REHHRFLASEE$_{194}$ | |
| PC61 | $_{47}$LNCECKRGFRR$_{57}$ | $_{78}$TSNSHDKSRKQ$_{88}$ |

The amino acid (aa) sequence numbering is based on mouse CD25 taken from the sequence published under the Uniprot accession number P01590.

The epitope mapping study that has been performed using Pepscan technology indicates that the anti-human antibodies bind human CD25 at an epitope that does not overlap with the IL-2 binding site on CD25. The anti-human antibodies bind to a different epitope than basiliximab and daclizumab. The epitope for Basiliximab and Daclizumab comprises residues in the region of amino acids 137-143 (of SEQ ID NO: 1), which overlaps with interaction side of CD25 to IL-2 (Binder M et al, Cancer Res 2007 vol 67(8): 3518-23). The anti-mouse CD25 non-blocking antibodies, 2E4 and 7D4, recognise a different epitope than PC61.

Example 5: Characterisation of Mouse Anti-CD25 Antibodies

Binding of Antibodies to CHO Cells Expressing Mouse CD25

Binding to CD25 expressing CHO cells was examined by staining test articles (anti-CD25 primary antibodies, 701, PC61 and 2E4) with 30 mg/ml antibodies followed by semi-log dilution series (7-point) for 30 minutes on ice. This was followed by staining with a secondary antibody (Alexa Fluor 647-AffiniPure Fab Fragment Goat Anti-Human IgG (H+L)—(Jackson ImmunoResearch)) concentration of 1 mg/ml for 30 minutes on ice. All samples were stained in duplicates. Live cells were gated using FSC vs SSC parameters by flow cytometry during sample acquisition. Mean fluorescence intensity (MFI) of stained cells were plotted on an XY chart, graphing MFI against the log of the concentration, and the data fit to a non-linear regression curve from which the EC50 is calculated. The results as shown in FIG. 11, confirmed that the anti-mouse CD25 antibodies bind to CHO cells expressing mouse CD25.

Affinity Measurements of Anti-mCD25 Antibodies.

The affinity for the anti-mouse CD25 antibodies, 7D4, PC61 and 2E4, was determined by measuring their $K_D$ by SPR in a Biacore 2000 using a CM-5 Sensor chip with an ambient experiment temperature of 25° C. Anti-mouse antibody was initially immobilised across all flow cells in a analysis buffer (pH 7.4, 10 mM HEPES, 150 mM NaCl, 3 mM EDTA, 0.05% Tween 20) to an RU of between 16,000-18,000 over 10 minutes. The ligand (antibody test articles) was sub sequentially loaded to a capture level between 119-163RU. The analyte (recombinant mouse CD25 his tagged) was then associated in analysis buffer from a 2-fold dilution starting at 800 nM with a lowest concentration of 3.13 nM for 6 minutes. Dissociation was performed in analysis buffer over 10 minutes. Regeneration steps between sample concentrations were performed in 10 mM Glycin pH1.7 for 10 minutes. A flow rate of 25 µl/min was maintained throughout the process. Kinetics data were fit using a global model bivalent analyte analysis software provided by Biacore with reference subtraction. The SPR based analysis is shown in FIG. 12. The $K_d$ values that were established in this assay for the anti-mouse CD25 antibodies are the following: for 7D4, $2.6 \times 10^{-9}$M; for 2E4 $114 \times 10^{-9}$M, and for PC61 $3.6 \times 10^{-9}$M (result not shown).

Anti-Mouse Antibody Competition in the Octet®

Antibody competitions were performed on a Forte Bio Octet® Red96 system (Pall Forte Bio Corp., USA) using a standard sandwich binning assay. 10 nM anti-mouse CD25 antibody was be loaded onto AMC sensors for 900 s and unoccupied Fc-binding sites on the sensor were blocked with a non-relevant mouse IgG2a antibody. Sensors were exposed to 15 nM target antigen (mouse CD25 his tagged) for 600 s followed by a second anti-CD25 antibody (also at 10 nM). Data was processed using Forte Bio Data Analysis Software 9.0. Additional binding by a second antibody after antigen association indicates an unoccupied epitope, while no binding indicates epitope blocking.

Competitive binding to mCD25 is observed between 7D4 and 2E4 (FIG. 13(A)) but not between 7D4 and PC61 (FIG. 13(B).

In-Vitro IL-2 Signalling by STAT5 Phosphorylation Assay:

Pan T cells were isolated from splenocytes using the Dynabeads® FlowComp™ Mouse Pan T (CD90.2) kit from Invitrogen (Cat: 11465D). 200,000 cells were plated and rested for 2 hours at 37° C. Antibodies were added at 50 ug/ml and incubated with the cells for 30 mins at 37° C., following which cells were stimulated with IL2 (50 U/ml) for 10 mins at 37° C.

IL-2 induced STAT5 phosphorylation was stopped when the cells were fixed and permeabilized with the eBioscience™ Foxp3/Transcription Factor Staining Buffer Set (Invitrogen) and treated with the BD Phosflow Perm Buffer III (BD Biosciences). Cells were then simultaneously stained with surface and intracellular fluorochrome labelled antibodies (STAT5-Alexa Fluor 647 clone 47/stat5/pY694 BD Bioscience, CD3-PerCP-Cy5.5 clone 17A2 Biolegend, CD4-PE clone RM4-5 Biolegend, FoxP3-AF488 clone FJK-16s Ebioscience) and samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. CD3$^+$ T cells were defined using a CD3 PerCP-Cy5.5-A versus FCS-A plot and a gate was drawn on a histogram showing count versus STAT5 Alexa Fluor 647-A to determine the population of STAT5$^+$CD3$^+$ T cells. The percentage blocking of IL-2 signalling was calculated as follows: % blocking=100×[(% Stat5$^+$ cells No Ab group–% Stat5$^+$ cells 50 ug/ml Ab group)/(% Stat5$^+$ cells No Ab group)]. Further analysis of STAT5 phosphorylation by different T cell subsets (CD4$^+$, CD8$^+$, CD4$^+$FoxP3–) was also be assessed by gating on the respective subsets and analysed as above. Graphs and statistical analysis was performed using GraphPad Prism v7 (results not shown). The results are shown in FIG. 14.

Results:

The anti-mouse antibodies, 7D4 and 2E4, were further evaluated with respect to its ability to bind CD25 and to not interfere with IL-2 signalling of CD25 expressing target cells. 7D4 and 2E4, non IL-2 blockers, compete for the binding to CD25 while PC61 (an IL-2 signalling blocker) does not compete with 2E4 or 7D4 to bind CD25 (FIG. 12).

Figure 14:
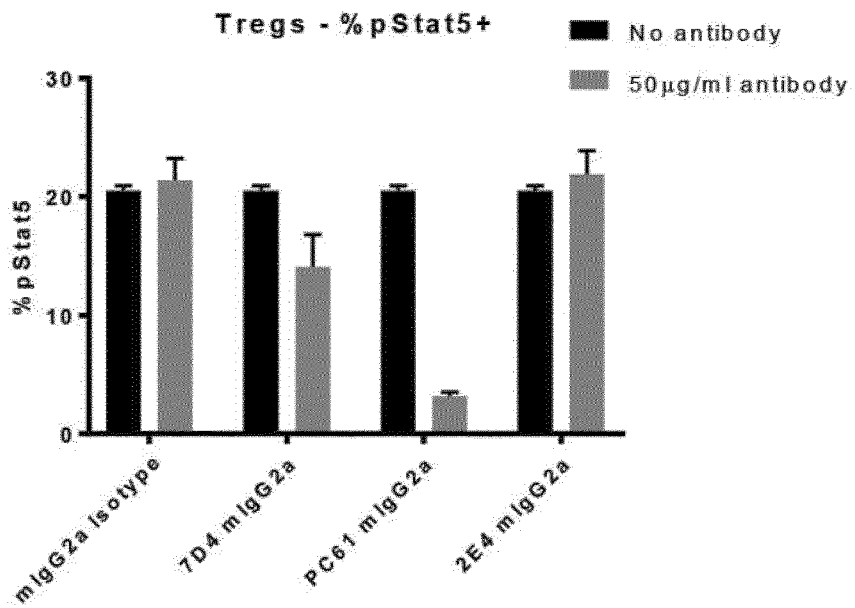
FIG. 14: Characterization of 7D4, PC61 and 2E4 compared to mouse IgG2a isotype control or in absence of a primary antibody in respect to blocking IL-2 signalling in a STAT5 phosphorylation assay using T cells isolated from C57BL/6 splenocytes. Cells were incubated with 50 µg/ml antibody followed by 50 U/ml IL-2. Analysis was restricted to percentage of Treg cells phosphorylating STAT5.

The STAT5 assay confirmed that 7D4 and 2E4 did not block IL-2 signalling while IL-2 signalling was blocked by the "blocking" antibody PC61 (FIG. 14)

Example 6: In Vivo Depletion of Treg

1×10$^5$ 4T1 cells in 200 µl RPMI 1640 media were implanted in the 2$^{nd}$ thoracic fat pad tissue of Balb/c mice. When tumours reached 50-100 mm$^3$ the mice were randomised and a single intraperitoneal flat dose of either 2 µg, 20 µg or 200 µg mouse anti-mouse CD25 (7D4) antibody was administered per mouse. At day 3 and day 9, tumour tissues and whole blood was isolated for immunophenotyping.

Figure 15:
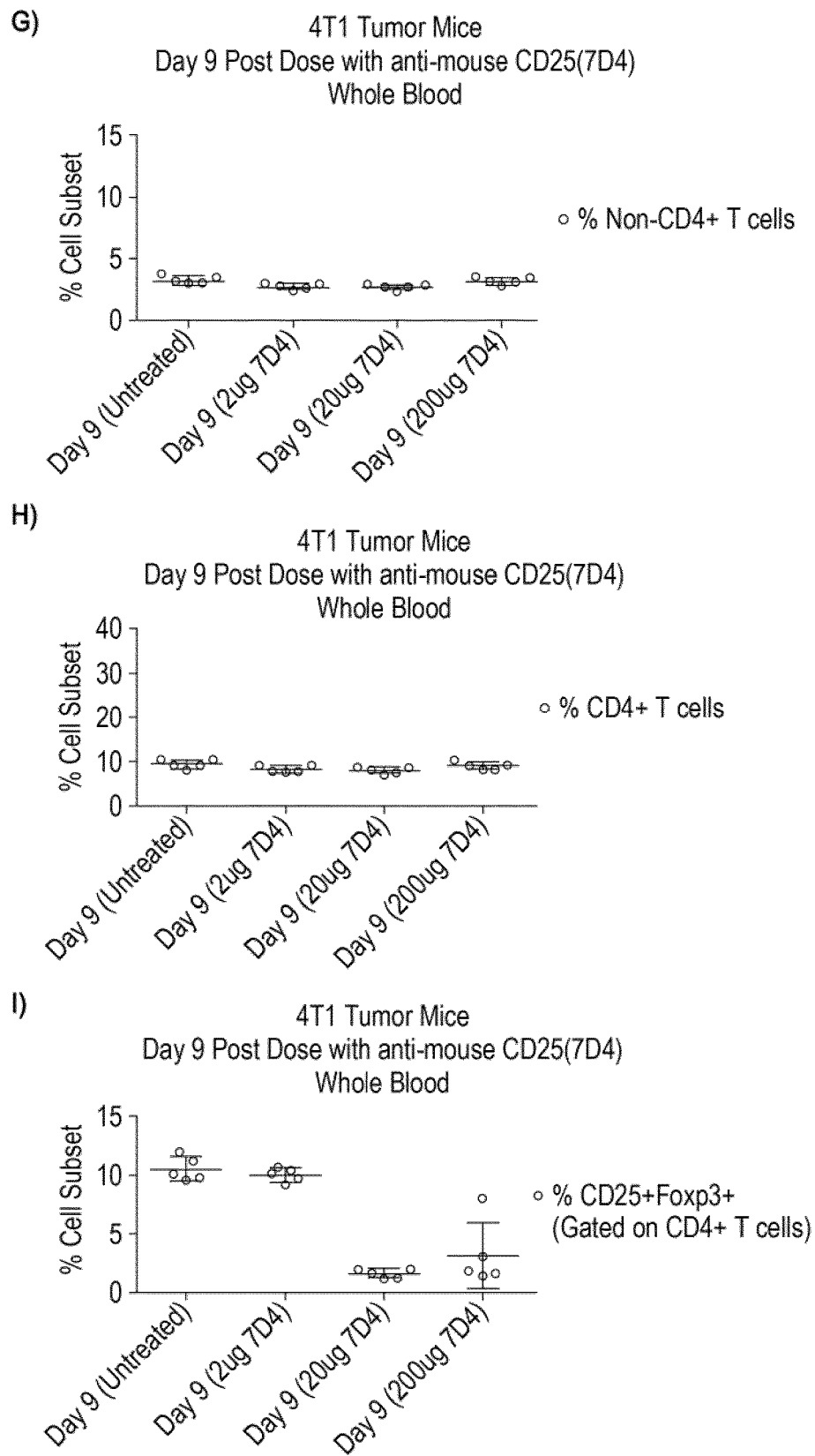
FIG. 15: In vivo depletion of Treg in 4T1 tumour bearing balb/c mice after dosing with mouse anti-mouse CD25 (7D4) antibody. (A)-(C): % non-CD4, CD4+ and CD25+ FoxP3+ cells, respectively in whole blood at day 3 post-dose. (D)-(F): % non-CD4, CD4+ and CD25+FoxP3+ cells, respectively in tumour at day 3 post-dose. (G)-(I): % non-CD4, CD4+ and CD25+FoxP3+ cells, respectively in whole blood at day 9 post-dose. (J)-(L): % non-CD4, CD4+ and CD25+FoxP3+ cells, respectively in tumour at day 9 post-dose.

Results:

Antibody 7D4 exhibited Treg depleting activity in both whole blood and tumour tissue based on day 3 and day 9 post-dose analysis by immunophenotyping (FIG. 15).

Example 7: Characterisation of Anti-CD25 Antibody 7G76B

Binding of Anti-CD25 Antibodies to Human CD25-Expressing Cells:

The 7G76B is evaluated by binding to lymphoma human cell lines, Karpas 299, SU-DHL-1 and SR-786 and the in-vitro differentiated Tregs cells. Binding to CD25 expressing human cell lines (SU-DHL-1 and SR-786) was examined by firstly blocking the cells with Trustain (Biolegend) prior to incubation with anti-CD25 antibodies titrated in a semi-log dilution series from a top concentration of 20 µg/ml, for 30 mins at 4° C. before being washed and incubated with PE conjugated anti-human IgG Fc antibody (Biolegend). Cells were washed again and resuspended in FACS buffer containing DAPI and acquired on the Intellicyt iQue. Live cells were gated using FSC vs SSC parameters by flow cytometry during sample acquisition. Geo Mean Intensity of stained cells were plotted on an XY chart, graphing Geo Mean Intensity against the log of the concentration, and the data fit to a non-linear regression curve from which the EC50 is calculated.

Figure 16:
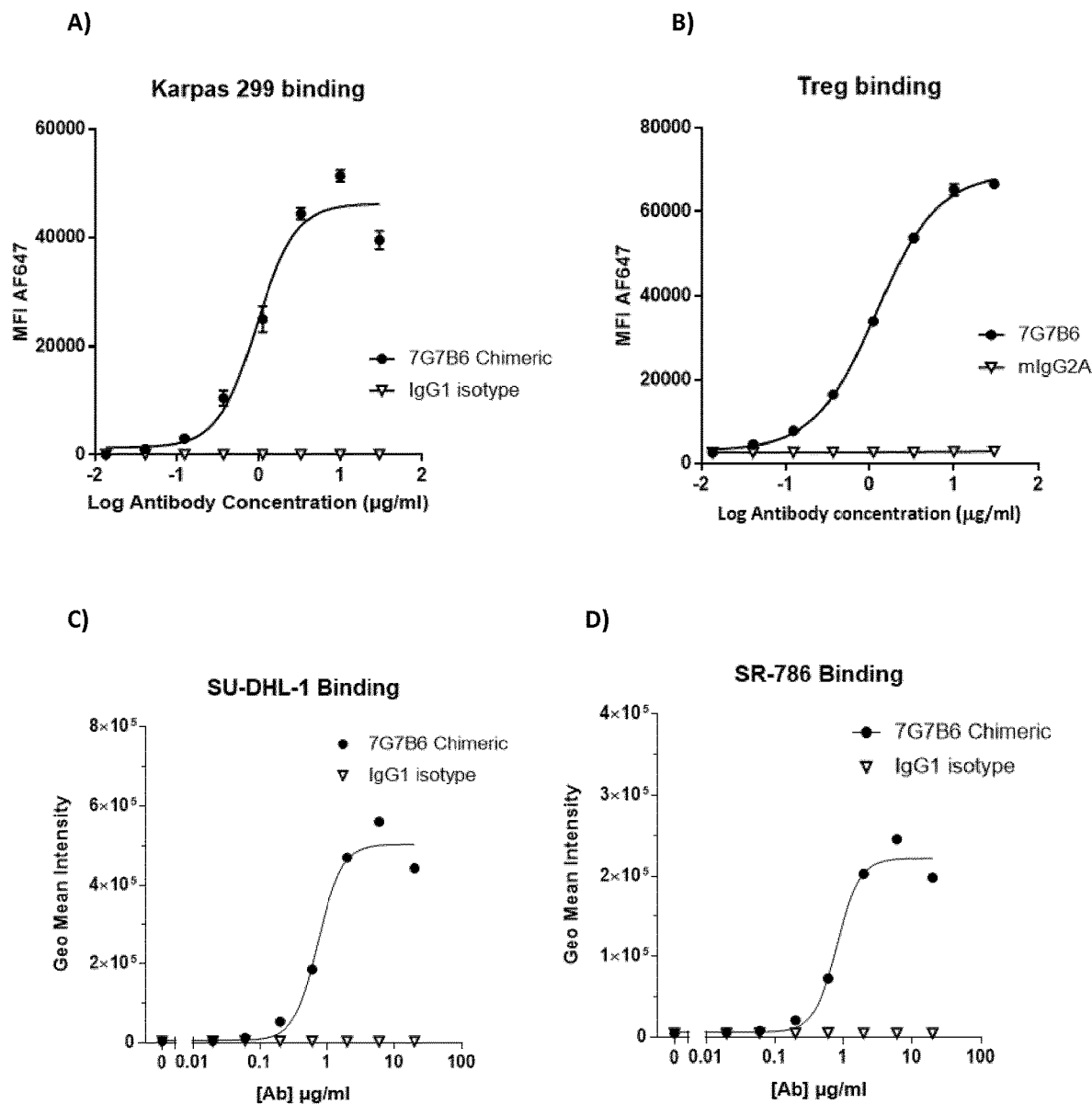
FIG. 16: Characterization of mouse (B) or chimeric (A, C and D) anti-human CD25 clone 7G7B6 binding to CD25 expressed on Karpas 299 cells (A), human in vitro differentiated Treg cells (B), SU-DHL-1 cells (C), or SR-786 cells (D) at increasing antibody concentrations and comparing with human IgG1 isotype control.
Figure 21:
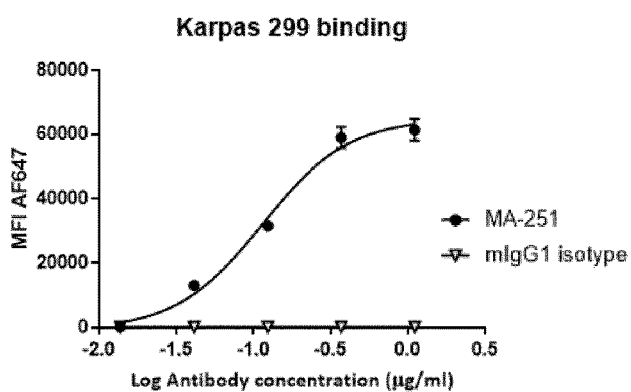
FIG. 21: Characterization of MA-251 binding to CD25 expressed on Karpas 299 cells at increasing antibody concentrations and comparing with mouse IgG1 isotype control.

Binding to CD25 expressing Karpas 299 cells and in vitro differentiated Tregs was examined by staining test articles (anti-CD25 primary antibodies) with 30 mg/ml antibodies followed by semi-log dilution series (7-point) for 30 minutes on ice. This was followed by staining with a secondary antibody (Alexa Fluor 647-AffiniPure Fab Fragment Goat Anti-Human IgG (H+L)—(Jackson ImmunoResearch)) concentration of 1 mg/ml for 30 minutes on ice. All samples were stained in duplicates. Live cells were gated using FSC vs SSC parameters by flow cytometry during sample acquisition. Mean fluorescence intensity (MFI) of stained cells were plotted on an XY chart, graphing MFI against the log of the concentration, and the data fit to a non-linear regression curve from which the EC50 is calculated. The results as shown in FIG. 16 and FIG. 21, confirmed that the anti-CD25 antibodies binds to CD25 expressing cells.

Figure 17:
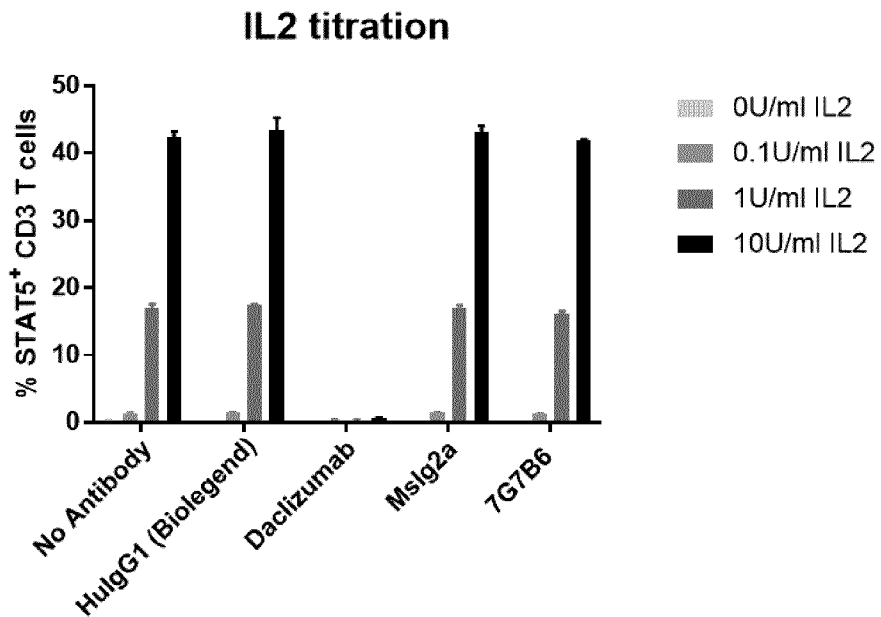
FIG. 17: Characterization of 7G7B6 compared to mouse IgG2a isotype control, human IgG1 isotype control, Daclizumab, or in absence of a primary antibody in respect to blocking IL-2 signalling in a STAT5 phosphorylation assay using PBMCs of human origin. Cells were incubated with 10 µg/ml antibody followed by increasing concentrations of IL-2 (as shown in the Figures). Analysis was restricted to percentage of CD3-positive cells phosphorylating STAT5.
Figure 22:
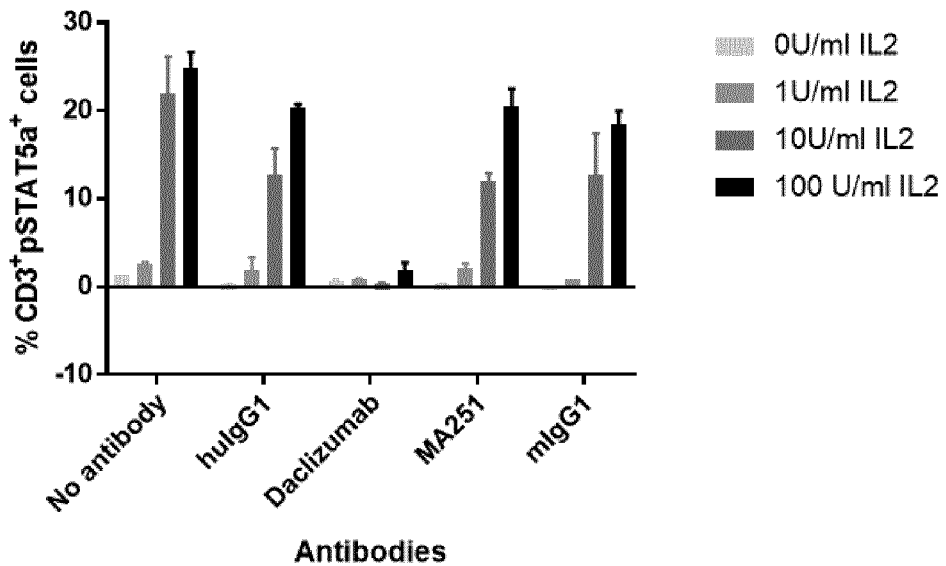
FIG. 22: Characterization of MA-251 compared to mouse IgG1 isotype control, human IgG1 isotype control, Daclizumab, or in absence of a primary antibody. Blocking of IL-2 signalling in a STAT5 phosphorylation assay was assessed using PBMCs of human origin. Cells were incubated with 10 µg/ml antibody followed by increasing concentrations of IL-2 (as shown in the Figures). Analysis was restricted to percentage of CD3-positive cells phosphorylating STAT5.

In-Vitro IL-2 Signalling by STAT5 Phosphorylation Assay:

IL-2-blocking was characterised using a STAT5 phosphorylation assay, in which IL-2 signalling was examined. Previously frozen PBMC (Stemcell Technologies) were cultured in 96-U-bottom well plates in the presence of 10 µg/ml anti-CD25 antibodies for 30 minutes before adding IL-2 (Peprotech) at varying concentrations of 0.1 U/ml, 1 U/ml, or 10 U/ml for 10 minutes in RPMI 1640 (Life Technologies) containing 10% FBS (Sigma), 2 mM L-Glutamine (Life Technologies) and 10,000 U/ml Pen-Strep (Sigma). IL-2 induced STAT5 phosphorylation was stopped when the cells were fixed and permeabilized with the eBioscience™ Foxp3/Transcription Factor Staining Buffer Set (Invitrogen) and treated with the BD Phosflow Perm Buffer III (BD Biosciences). Cells were then simultaneously stained with surface and intracellular fluorochrome labelled antibodies (STAT5-Alexa Fluor 647 clone 47/stat5/pY694 BD Bioscience, CD3-PerCP-Cy5.5 clone UCHT1 Biolegend, CD4-BV510 clone SK3 BD Bioscience, CD8-Alexa Fluor 700 clone RPA-T8 Invitrogen, CD45RA-PE-Cy7 clone HI100 Invitrogen, FoxP3-Alexa Fluor 488 clone 236A/E7 Invitrogen) and samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. CD3$^+$ T cells were defined using a CD3 PerCP-Cy5.5-A versus FCS-A plot and a gate was drawn on a histogram showing count versus STAT5 Alexa Fluor 647-A to determine the population of STAT5$^+$CD3$^+$ T cells. The percentage blocking of IL-2 signalling was calculated as follows: % blocking=100×[(% Stat5$^+$ cells No Ab group–% Stat5$^+$ cells 10 ug/ml Ab group)/(% Stat5$^+$ cells No Ab group)]. Further analysis of STAT5 phosphorylation by different T cell subsets (CD4$^+$, CD8$^+$, CD4$^+$FoxP3$^+$, naïve and memory T cells) was also be assessed by gating on the respective subsets and analyzed as above. Graphs and statistical analysis was performed using GraphPad Prism v7 (results not shown). The results are shown in FIG. 17 and FIG. 22.

In-Vitro T Cell Activation Assay:

Impact of IL-2 signalling on Teff responses were characterised in a T cell activation assay, in which intracellular granzyme B (GrB) upregulation and proliferation were examined. Previously frozen primary human Pan T cells (Stemcell Technologies) were labelled with eFluor™ 450 cell proliferation dye (Invitrogen) according to manufacturer's recommendation, and added to 96-U-bottom well plates at 1×10$^5$ cells/well in RPMI 1640 (Life Technologies) containing 10% FBS (Sigma), 2 mM L-Glutamine (Life Technologies) and 10,000 U/ml Pen-Strep (Sigma). The cells were then treated with 10 µg/ml anti-CD25 antibodies or control antibodies followed by Human T-Activator CD3/CD28 (20:1 cell to bead ratio; Gibco) and incubated for 72 hrs in a 37° C., 5% CO2 humidified incubator. To assess T cell activation, cells were stained with the eBioscience Fixable Viability Dye eFluor™ 780 (Invitrogen), followed by fluorochrome labelled antibodies for surface T cell markers (CD3-PerCP-Cy5.5 clone UCHT1 Biolegend, CD4-

Figure 18:
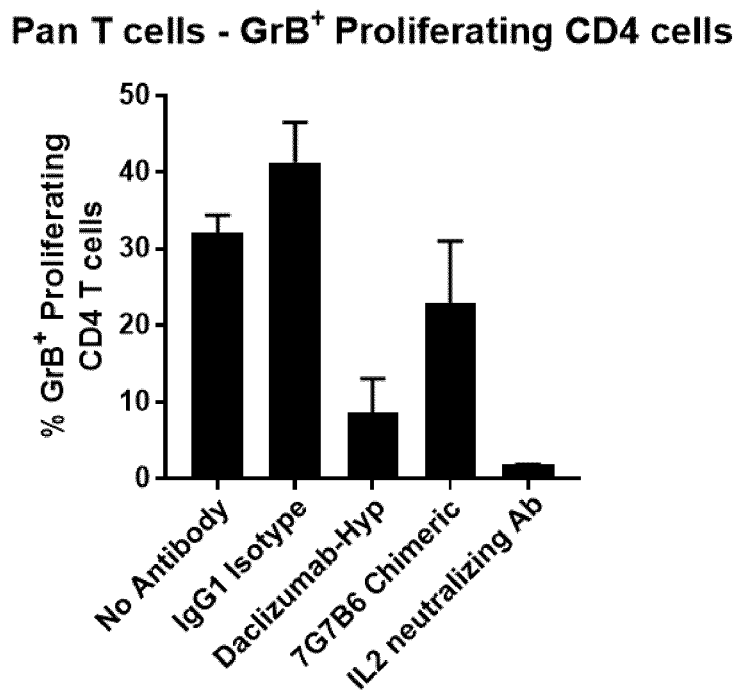
FIG. 18: Functional characterization of chimeric 7G7B6 compared to human IgG1 isotype control, Daclizumab, or commercially available mouse anti-human IL-2 neutralizing antibody as a positive control, (clone: AB12-3G4) using Pan T cells. Cells were incubated with 10 ug/ml antibody then activated with CD3/CD28 beads for 72 hours before flow cytometry analysis. Results show percentage of granzyme B positive proliferating CD4 T cells.

BV510 clone SK3 BD Bioscience, CD8-Alexa Fluor 700 clone RPA-T8 Invitrogen, CD45RA-PE-Cy7 clone HI100 Invitrogen, CD25-BUV737 clone 2A3 BD Bioscience) and then fixed and permeabilized with the eBioscience™ Foxp3/Transcription Factor Staining Buffer Set (Invitrogen) before staining for intracellular GrB and intranuclear FoxP3 (Granzyme B-PE clone GB11 BD Bioscience, FoxP3-APC clone 236A/E7). Samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. $CD4^+$ and $CD8^+$ T cell subsets gated from the live $CD3^+$ lymphocytes were assessed using a GrB-PE-A versus proliferation eFluor™ 450-A plot. Results were presented as percentage of proliferating GrB positive cells from the whole $CD4^+$ T cell population. Graphs and statistical analysis was performed using GraphPad Prism v7. The results are shown in FIG. 18.

Figure 19:
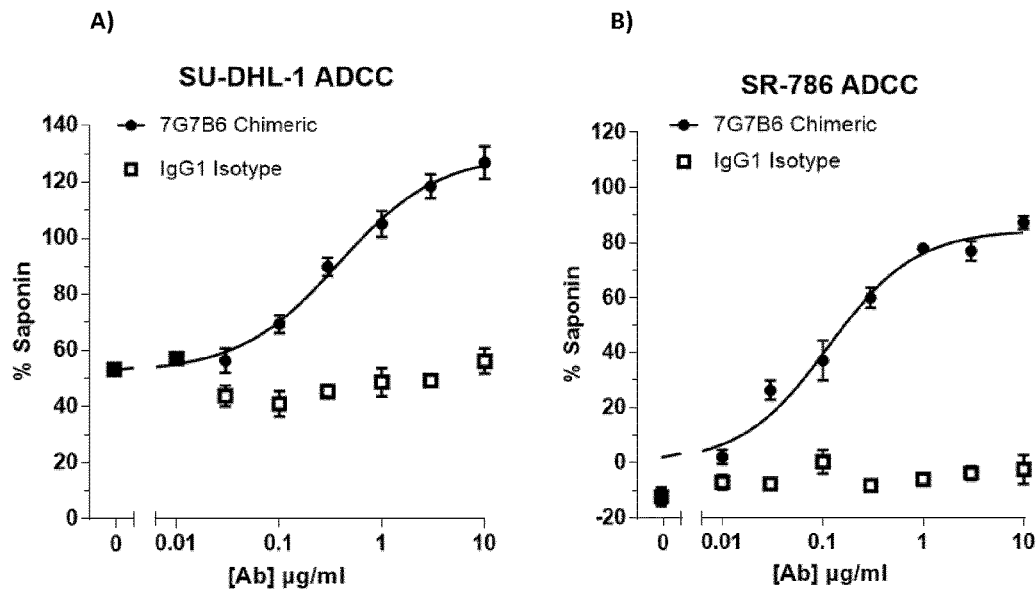
FIG. 19: Functional characterization of chimeric 7G7B6 compared to human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.

In Vitro ADCC Assay:

Antibody-dependent cell-mediated cytotoxicity assays (ADCC assays) were performed for the characterization of anti-human CD25 antibodies using SU-DHL-1, or SR-786 (CD25 positive) human cell lines as target cells with human NK cells as the source of effector cells. NK cells were isolated from PBMCs of healthy donors using NK cell negative isolation kit (Stemcell Technologies). NK cells were cultured overnight in the presence of and 2 ng/mL IL-2 (Peprotech). SU-DHL-1, or SR-786 target cells were loaded with Calcein-AM (Thermofisher) and plated, 4 replicates per condition, in the presence of anti-CD25 or isotype antibodies for 30 mins at 37° C. 5% $CO_2$. Following incubation, NK cells were added to wells at a Target:Effector (T:E) ratio of 1:10 (10,000 target cells and 100,000 effector cells) and incubated for 4 hrs at 37° C. 5% CO2. Readout of calcein fluorescence in the supernatant was performed on BMG Fluostar plate reader. The percentage of specific lysis was calculated relative to target cells alone (0% lysis) and target cells treated with 0.1% Saponin (100% lysis). Graphs of the raw data were produced using Graphpad Prism v7 to generate dose response curves. Percentage target cell lysis was plotted on an XY chart, graphing normalized Calcein AM percentage release against the log of the concentration, and the data fit to a no-linear regression curve from which the EC50 was calculated. The results are shown in FIG. 19.

Figure 20:
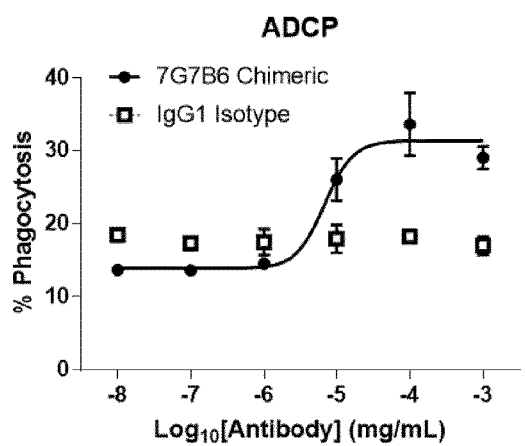
FIG. 20: Functional characterization of chimeric 7G7B6 compared to human IgG1 isotype control in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. eFluor™ 450 is an organic dye that can be excited by the 405 nm violet laser. Residual target cells were defined as cells that were eFluor™ 450-dye+/CD14−. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

In Vitro ADCP Assay:

Antibody-dependent cell-mediated phagocytosis (ADCP) assays were performed using in-vitro differentiated Tregs as target cells and monocyte-derived macrophages as the effector cells. PBMCs were isolated from leucocyte cones by Ficoll gradient centrifugation. Monocytes (CD14+ cells) were isolated using CD14 Microbeads (Miltenyi Biotec). Monocytes were cultured for 5 days in the presence of 50 ng/ml M-CSF in RPMI 1640 (Life Technologies) containing 10% FBS (Sigma), 2 mM L-Glutamine (Life Technologies) and 10,000 U/ml Pen-Strep (Sigma), fresh media containing M-CSF is added after 3 days. Regulatory T cells (Treg) were isolated using the Human Treg Cell Differentiation Kit (R&D Systems). These cells were incubated in a 37° C., 5% CO2 humidified incubator for 5 days and labelled with eFluor™ 450-dye (Invitrogen), as per manufacturer recommendations. At day 5, macrophages and eFluor™ 450-dye labelled Tregs are cocultured for 4 hours at a 10 to 1 effector to target ratio in the presence of anti-CD25 antibodies or controls, as describe thereafter. Target cells (Treg) were added at $1\times10^4$ cells/well while the effector cells (macrophages) were added at $1\times10^5$ cells/well, for a effector to target ratio of 10 to 1. The anti-CD25 antibodies were then added at a top concentration of 1 μg/ml followed by a log series (7 points) in duplicates. Cells and antibodies were incubated for 4 hours at 37° C. 5% $CO_2$. To assess ADCP, cells were placed on ice, stained with the cell surface marker CD14 (CD14-PerCP-Cy5.5 clone MfP9 BD Biosciences) and fixed with the eBioscience fixation buffer. Two colour flow cytometric analysis was performed using the Fortessa LSR X20. Residual target cells were defined as cells that were eFluor™ 450-dye$^+$/CD14$^-$. Macrophages were defined as CD14+. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)]. The results are shown in FIG. 20.

Statistics:

Prism software (GraphPad) was used to perform curve fitting to determine EC50 values and maximal activity.

Human Antibodies do not Block IL2-CD25 Interaction

Interference with IL2 Ligand binding to CD25 was performed on a Forte Bio Octet® Red384 system (Pall Forte Bio Corp., USA) using a standard sandwich binning assay. The MA251 antibody was loaded onto AHQ sensors and unoccupied Fc-binding sites on the sensor were blocked with a non-relevant human IgG1 antibody. Sensors were exposed to 100 nM human CD25 followed by 100 nM human IL-2. Data was processed using Forte Bio Data Analysis Software 7.0. Additional binding by human 1L2 after antigen association indicates an unoccupied epitope (non-competitor), while no binding indicates epitope blocking (competitor).

Figure 24:
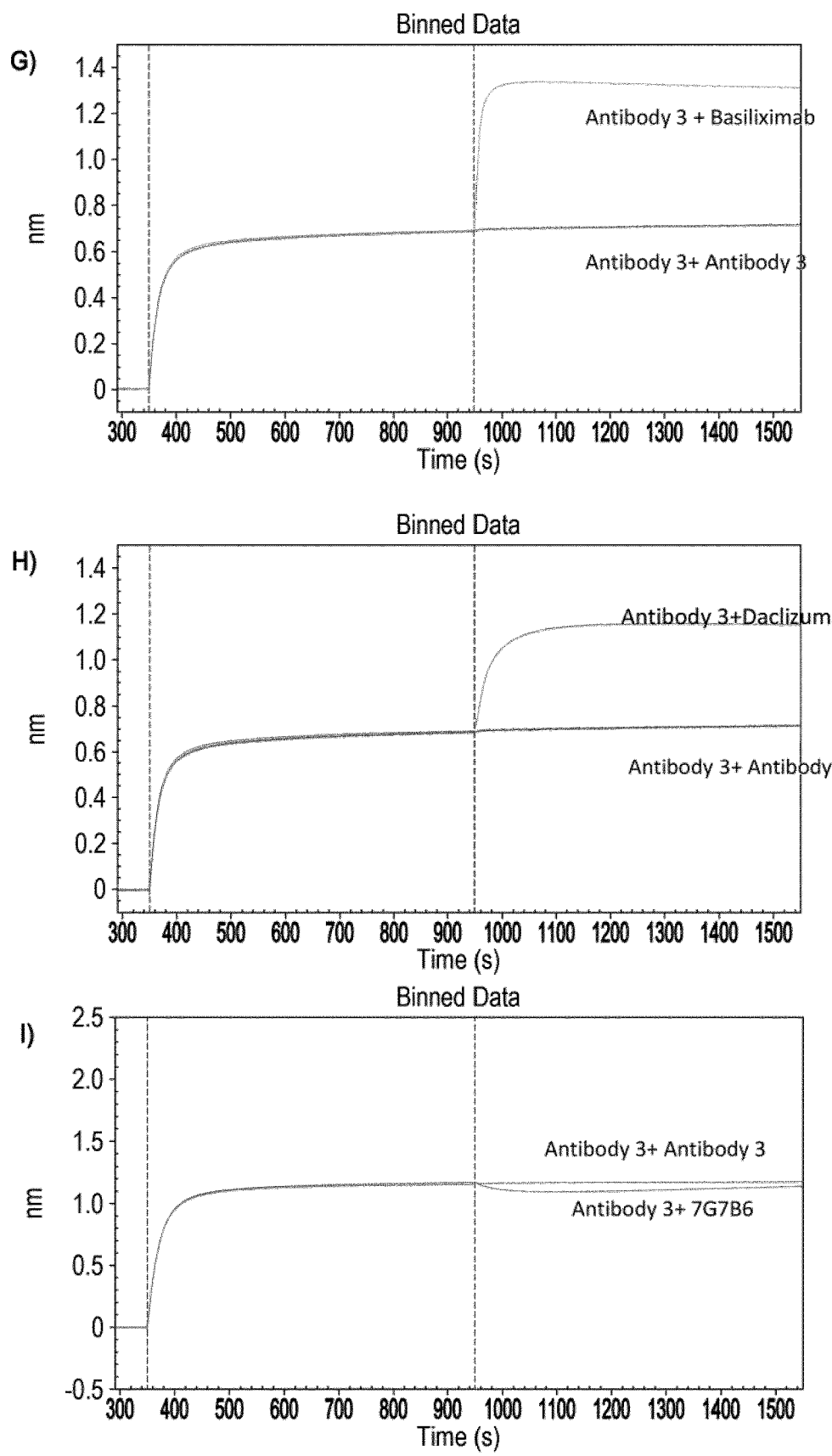
FIG. 24: Competition analysis of anti-CD25 antibodies in the Octet®. Binding the first Ab to the immobilized rhCD25 followed by either the first Ab again (as control) or a second Ab. mAbs which are non blockers of IL-2 signal compete with each other or with 7G7B6 and MA251 and do not compete with research Daclizumab or research Basiliximab (FIGS. 24(A) to (N)). (A) to (C) competition analysis of 7G7B6; (D)-(F) competition analysis of MA251; (G) to (I) and (N) competition analysis of Antibody 3; (J) to (M) competition analysis of Antibody 1. mAbs which are IL-2 signalling blockers (TSK031) do compete with the research Daclizumab and research Basiliximab and not compete with 7G7B6 (FIGS. 24(O) to (Q).
Figure 24:
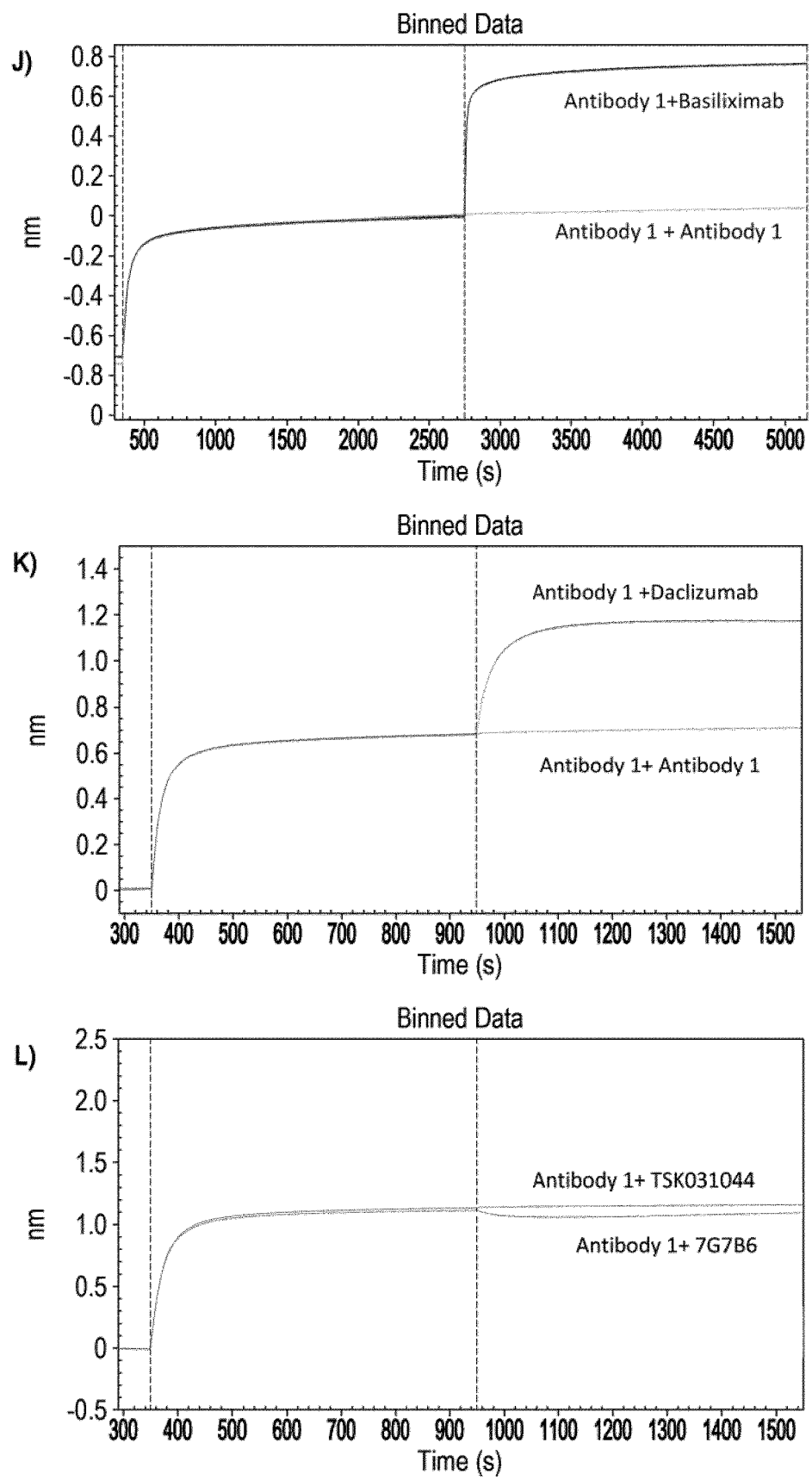
Figure 24:
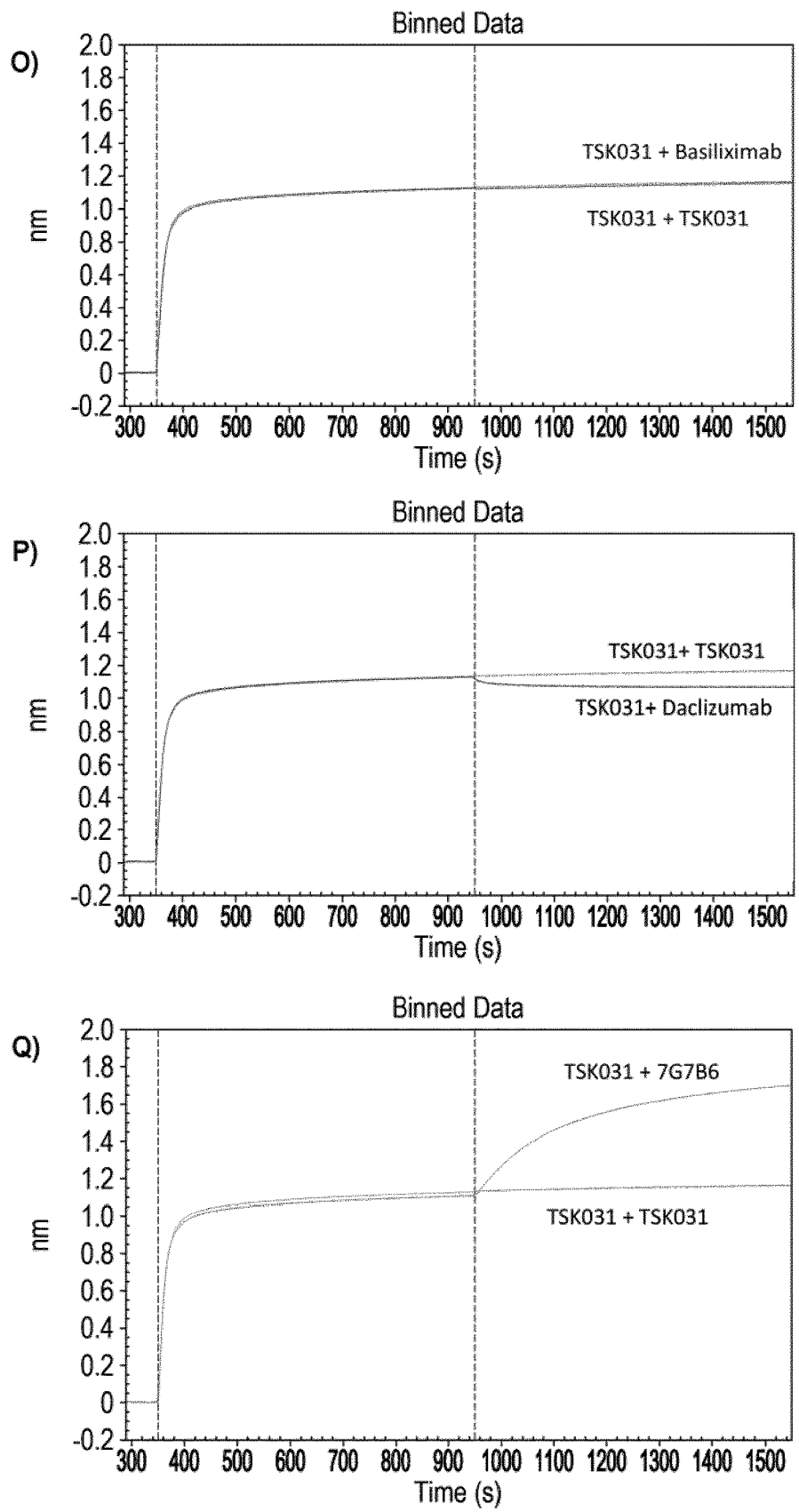

Results:

The 7G7B6 antibody, was further evaluated with respect to its ability to not interfere with IL-2 signalling and its capacity to kill CD25 expressing target cells. In the STAT5 assay, 7G7B6 did not block IL-2 signalling regardless of IL-2 concentrations tested while IL-2 signalling was completely blocked by the reference antibody Daclizumab (FIG. 17). Daclizumab, which has been shown to block the interaction of CD25 with IL-2 via the so-called "Tac" epitope (Queen C et al, 1989, PNAS. 86(24)10029-10033, and Bielekova B, 2013, Neurotherapeutics, 10(1):55-67) binds to a different epitope than 7G7B6 (FIG. 10 and FIG. 24B), which can explain why Daclizumab blocks IL-2 signalling and the 7G7B6 does not block the IL-2 signalling in the STAT5 phosphorylation assay (FIG. 17). Additionally, Daclizumab reduces effector responses of activated T cells, probably due to its blocking of IL-2 signalling, while 7G7B6, which does not block IL-2 signalling, does not have a negative impact on T cell responses (FIG. 18). Finally, 7G7B6 chimeric antibody kills CD25 expressing cells, tumor cells or regulatory T cells, via ADCC (FIG. 19) and ADCP (FIG. 20) when compared to the IgG1 isotype antibody.

In conclusion, 7G7B6 as a chimeric antibody has been characterized and demonstrates potent killing of CD25 positive cells (Tregs or cancer cell lines) and does not interfere with IL-2 signalling and consequently does not inhibit T effector responses. 7G7B6 is thus a Treg depleting antibody which could be applied for the treatment of cancer, as monotherapy or in combination.

Figure 23:
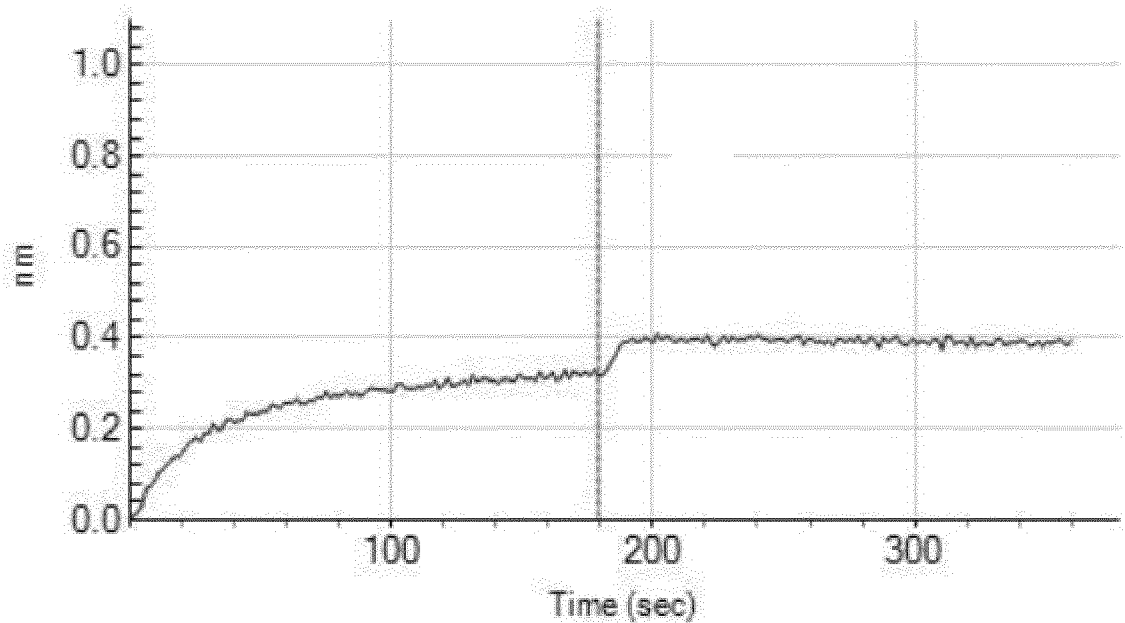
FIG. 23: Characterization of MA-251 and IL2 binding to CD25. Interference with IL2 Ligand binding to CD25 was performed on a Forte Bio Octet® Red384 system (Pall Forte Bio Corp., USA) using a standard sandwich binning assay. The MA251 antibody was loaded onto AHQ sensors and unoccupied Fc-binding sites on the sensor were blocked with a non-relevant human IgG1 antibody. Sensors were exposed to 100 nM human CD25 followed by 100 nM human IL-2. Data was processed using Forte Bio Data Analysis Software 7.0. Additional binding by human IL2 after antigen association indicates an unoccupied epitope (non-competitor), while no binding indicates epitope blocking (competitor).

The MA-251 antibody was further evaluated with respect to its ability to not interfere with IL-2 signalling. The MA251 antibody was assessed in the IL2-CD25 Octet® competition assay. Simultaneous IL2 binding and MA251 binding to CD25 was observed (FIG. 23), showing that the MA251 binds in a non-competitive manner. In the STAT5 assay, MA-251 did not block IL-2 signalling regardless of IL-2 concentrations tested while IL-2 signalling was completely blocked by the reference antibody Daclizumab (FIG. 22). Daclizumab, which has been shown to block the interaction of CD25 with IL-2 via the so-called "Tac" epitope (Queen C et al, 1989 and Bielekova B, 2013) binds to a different epitope than MA-251 (FIG. 10 and FIG. 24(E)), which can explain why Daclizumab blocks IL-2 signalling and the MA-251 does not block the IL-2 signalling in the STAT5 phosphorylation assay (FIG. 22).

Example 8: Anti Human CD25 Ab Competition Assay

Antibody competitions were performed on a Forte Bio Octet® Red96 system (Pall Forte Bio Corp., USA) using a standard sequential binding assay. 26.8 nM recombinant human CD25his tagged was loaded onto Ni-NTA Biosensors for 200s. After base line step on kinetic buffer sensors were exposed to 66.6 nM of first antibody for either 600s or 1800s followed by a second anti-CD25 antibody (also at 66.6 nM for either 600s or 1800s). Data was processed using Forte Bio Data Analysis Software 9.0. Additional binding by a second antibody indicates an unoccupied epitope (no competition for the epitope), while no binding indicates epitope blocking (competition for the epitope).
Results
Non blockers of IL-2 signal mAbs (Antibody 1 and Antibody 3) compete with each other or with 7G7B6 and MA251 while they do not compete with research Daclizumab or research Basiliximab (examples (A) to (N), FIG. 24). IL-2 signalling blockers (i.e. TSK031) do compete with the research Daclizumab and research Basiliximab and do not compete with 7G7B6 (examples (O) to (Q), FIG. 24).

Example 9: Therapeutic Analysis of a Non-Blocking Antibody

At day 0, 1×10$^7$ SU-DHL-1 cells in 200 µl RPMI 1640 were implanted into the right flank. At day 12, the mice with palpable tumours were randomised into either treatment with vehicle or Antibody 1 at 2 mg/kg, twice weekly. At day 15, mice with a tumour size of 100-200 mm$^3$ were randomised and dosed with either vehicle, Antibody 1 at 2 mg/kg, twice weekly or a single dose of antibody 1 at 10 mg/kg.
Results
Antibody 1 prevented growth in 9/10 mice with palpable tumours dosed at 2 mg/kg, twice weekly (FIG. 25(A)-(B)). In mice with a tumour size of 100-200 mm$^3$, Antibody 1 also prevented tumour growth at doses of 2 mg/kg, twice weekly and 10 mg/kg single dose (FIG. 25(C)-(E)).

Example 10: Affinity Measurements of Anti-Human CD25 Antibodies

The affinity for the anti-human CD25 antibodies was determined by measuring their $K_D$ by SPR in a Biacore 2000 using a CM-5 Sensor chip with an ambient experiment temperature of 25° C. Anti-human antibody was initially immobilised across all flow cells in analysis buffer (pH 7.4, 10 mM HEPES, 150 mM NaCl, 3 mM EDTA, 0.05% Tween 20) to an RU of between 12,000-14,000 over 10 minutes. The ligand (antibody test articles) was sub sequentially loaded to a capture level between 145-190RU. The analyte (recombinant human CD25 his tagged) was then associated in analysis buffer from a 2-fold dilution starting at 400 nM with a lowest concentration of 3.13 nM for 6 minutes. Dissociation was performed in analysis buffer over 10 minutes. Regeneration steps between sample concentrations were performed in 10 mM Glycin pH1.7 for 10 minutes. A flow rate of 25 µl/min was maintained throughout the process. Kinetics data were fit using a global two state reaction conformational change analysis software provided by Biacore with reference subtraction for FIG. 26(C) and FIG. 26(D). A 1:1 Langmuir model with reference subtraction was used for FIG. 26(A), FIG. 26(B) and FIG. 26(E).

ForteBio affinity measurements were performed on an Octet® RED384 generally as previously described (see, e.g., Estep P et al., 2013. Mabs. 5(2), 270-8).

Alternatively, the affinity for the antihuman CD25 antibodies was determined by measuring their $K_D$ by biolayer interferometry on the Octet® Red 96 system (Pall Forte Bio Corp., USA). Sensors were equilibrated off-line in kinetic buffer for 10 minutes and then monitored on-line for 60 seconds for baseline establishment. 13.32 nM of antibody was loaded to the AHC biosensor for 200s followed by varying concentrations of the rhCD25his tagged (1:3 serial dilutions, from 50 nM to 0.54 nM) for 600s and let them to dissociate in kinetics buffer for 400s. Kinetics data were fit using a global 1:1 analysis software provided by Pall Forte Bio with reference subtraction. Results are shown in FIG. 26(F).
Results:
The results are shown FIG. 26. The $K_d$ values that were established in this assay for the anti-CD25 antibodies are the following: for Antibody 1, 3.2×10$^{-9}$M; for Antibody 3, 3.8×10$^{-9}$M, and for Daclizumab 0.61×10$^{-9}$M.

Example 11: Characterisation of Anti-CD25 Antibodies—Antibody 1 to, Antibody 21

Binding of Anti-CD25 Antibodies to CD25-Expressing Cells:

The candidate hits are evaluated by binding to lymphoma human cell lines such as Karpas 299, SU-DHL-1 and SR-786 cells, in-vitro differentiated Tregs cells, activated human or cyno PBMC, the HSC-F Cynomolgus monkey T cell line, and CHO cells.

Binding to CD25 expressing human cell lines (SU-DHL-1 and SR-786 cells) was examined by firstly blocking the cells with Trustain (Biolegend) prior to incubation with anti-CD25 antibodies titrated in a semi-log dilution series from a top concentration of 20 µg/ml, for 30 mins at 4° C. before being washed and incubated with PE conjugated anti-human IgG Fc antibody (Biolegend). Cells were washed again and resuspended in FACS buffer containing DAPI and acquired on the Intellicyt iQue. Live cells were gated using FSC vs SSC parameters by flow cytometry during sample acquisition. Geo Mean Intensity of stained cells were plotted on an XY chart, graphing Geo Mean Intensity against the log of the concentration, and the data fit to a non-linear regression curve from which the EC50 is calculated.

Binding to CD25 expressing Karpas 299 cells and in vitro differentiated Tregs was examined by staining test articles (anti-CD25 primary antibodies) with 30 mg/ml antibodies followed by semi-log dilution series (7-point) for 30 minutes on ice. This was followed by staining with a secondary antibody (Alexa Fluor 647-AffiniPure Fab Fragment Goat Anti-Human IgG (H+L) or Alexa Fluor 647-AffiniPure F(ab')2 Fragment Rabbit Anti-Human IgG Fcγ fragment—(Jackson ImmunoResearch)) concentration of 1 mg/ml for 30 minutes on ice. All samples were stained in duplicates. Live cells were gated using FSC vs SSC parameters by flow cytometry during sample acquisition. Mean fluorescence intensity (MFI) of stained cells were plotted on an XY chart, graphing MFI against the log of the concentration, and the data fit to a non-linear regression curve from which the EC50 is calculated.

Binding to CD25 expressing activated human and Cynomolgus monkey PMBC was examined by staining test articles (anti-CD25 primary antibodies) with 20 mg/ml antibodies followed by semi-log dilution series (7-point) for 30 minutes on ice. This was followed by staining with a secondary antibody (rabbit anti-human Fcg F(ab')2—(Jackson ImmunoResearch)) concentration of 5 mg/ml for 30 minutes on ice. All samples were stained in triplicates. To minimize cross-linking induced cell death mediated by binding of the secondary antibody, cell lines were examined in staining cohorts of 4 test articles at a time. Live lymphocytes were gated using FSC vs SSC parameters by flow cytometry during sample acquisition. Mean fluorescence intensity (MFI) of gated $CD4^+$ and $CD8^+$ T cell subsets were plotted on an XY chart, graphing MFI against the log of the concentration, and the data fit to a non-linear regression curve from which the EC50 was calculated.

Binding to CD25 expressing HSC-F Cynomolgus monkey T cell line was examined by staining test articles (anti-CD25 primary antibodies) with 20 mg/ml antibodies followed by semi-log dilution series (7-point) for 30 minutes on ice. This was followed by staining with a secondary antibody (rabbit anti-human Fcg F(ab')2—(Jackson ImmunoResearch)) concentration of 5 mg/ml for 30 minutes on ice. All samples were stained in triplicates. To minimize cross-linking induced cell death mediated by binding of the secondary antibody, cell lines were examined in staining cohorts of 4 test articles at a time. Live lymphocytes were gated using FSC vs SSC parameters by flow cytometry during sample acquisition. Mean fluorescence intensity (MFI) live cells was plotted on an XY chart, graphing MFI against the log of the concentration, and the data fit to a non-linear regression curve from which the EC50 was calculated.

Binding to CD25 expressing CHO cells was also examined. Approximately 100,000 cells overexpressing the antigen were washed with wash buffer and incubated with 100 μl 100 nM IgG for 15 minutes at room temperature. Cells were then washed twice with wash buffer and incubated with 100 μl of 1:100 Human-PE for 15 minutes on ice. Cells were then washed twice with wash buffer and analyzed on a FACS Canto II analyzer (BD Biosciences.) An unmodified CHO cell line was also used as a negative control In-Vitro IL-2 Signalling by STAT5 Phosphorylation Assay:

IL-2-blocking was characterised using a STAT5 phosphorylation assay, in which IL-2 signalling was examined. Previously frozen PBMC (Stemcell Technologies) were cultured in 96-U-bottom well plates in the presence of 10 μg/ml anti-CD25 antibodies for 30 minutes before adding IL-2 (Peprotech) at varying concentrations of 10 U/ml or 0.25 U/ml, 0.74 U/ml, 2.22 U/ml, 6.66 U/ml or 20 U/ml for 10 minutes in RPMI 1640 (Life Technologies) containing 10% FBS (Sigma), 2 mM L-Glutamine (Life Technologies) and 10,000 U/ml Pen-Strep (Sigma). IL-2 induced STAT5 phosphorylation was stopped when the cells were fixed and permeabilized with the eBioscience™ Foxp3/Transcription Factor Staining Buffer Set (Invitrogen) and treated with the BD Phosflow Perm Buffer III (BD Biosciences). Cells were then simultaneously stained with surface and intracellular fluorochrome labelled antibodies (STAT5-Alexa Fluor 647 clone 47/stat5/pY694 BD Bioscience, CD3-PerCP-Cy5.5 clone UCHT1 Biolegend, CD4-BV510 clone SK3 BD Bioscience, CD8-Alexa Fluor 700 clone RPA-T8 Invitrogen, CD45RA-PE-Cy7 clone HI100 Invitrogen, FoxP3-Alexa Fluor 488 clone 236A/E7 Invitrogen) and samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. CD3+ T cells were defined using a CD3 PerCP-Cy5.5-A versus FCS-A plot and a gate was drawn on a histogram showing count versus STAT5 Alexa Fluor 647-A to determine the population of STAT5+CD3+ T cells. The percentage blocking of IL-2 signalling was calculated as follows: % blocking=100×[(% Stat5+ cells No Ab group−% Stat5+ cells 10 ug/ml Ab group)/(% Stat5+ cells No Ab group)]. Further analysis of STAT5 phosphorylation by different T cell subsets (CD4+, CD8+, CD4+FoxP3+, naïve and memory T cells) was also be assessed by gating on the respective subsets and analyzed as above. Graphs and statistical analysis was performed using GraphPad Prism v7.

In-Vitro T Cell Activation Assay:

Impact of IL-2 signalling on Teff responses were characterised in a T cell activation assay, in which intracellular granzyme B (GrB) upregulation and proliferation were examined. Previously frozen primary human Pan T cells (Stemcell Technologies) were labelled with eFluor™ 450 cell proliferation dye (Invitrogen) according to manufacturer's recommendation, and added to 96-U-bottom well plates at $1\times10^5$ cells/well in RPMI 1640 (Life Technologies) containing 10% FBS (Sigma), 2 mM L-Glutamine (Life Technologies) and 10,000 U/ml Pen-Strep (Sigma). The cells were then treated with 10 μg/ml anti-CD25 antibodies or control antibodies followed by Human T-Activator CD3/CD28 (20:1 cell to bead ratio; Gibco) and incubated for 72 hrs in a 37° C., 5% $CO_2$ humidified incubator. To assess T cell activation, cells were stained with the eBioscience Fixable Viability Dye eFluor™ 780 (Invitrogen), followed by fluorochrome labelled antibodies for surface T cell markers (CD3-PerCP-Cy5.5 clone UCHT1 Biolegend, CD4-BV510 clone SK3 BD Bioscience, CD8-Alexa Fluor 700 clone RPA-T8 Invitrogen, CD45RA-PE-Cy7 clone HI100 Invitrogen, CD25-BUV737 clone 2A3 BD Bioscience) and then fixed and permeabilized with the eBioscience™ Foxp3/Transcription Factor Staining Buffer Set (Invitrogen) before staining for intracellular GrB and intranuclear FoxP3 (Granzyme B-PE clone GB11 BD Bioscience, FoxP3-APC clone 236A/E7). Samples were acquired on the Fortessa LSR X20 Flow Cytometer (BD Bioscience) and analysed using the BD FACSDIVA software. Doublets were excluded using FCS-H versus FCS-A, and lymphocytes defined using SSC-A versus FCS-A parameters. CD4+ and CD8+ T cell subsets gated from the live CD3+ lymphocytes were assessed using a GrB-PE-A versus proliferation eFluor™ 450-A plot. Results were presented as percentage of proliferating GrB positive cells from the whole CD4+ or CD8+ T cell populations. Graphs and statistical analysis was performed using GraphPad Prism v7.

In Vitro ADCC Assay:

Antibody-dependent cell-mediated cytotoxicity assays (ADCC assays) were performed for the characterization of anti-human CD25 antibodies using SU-DHL-1, or SR-786 (CD25 positive) human cell lines as target cells with human NK cells as the source of effector cells. NK cells were isolated from PBMCs of healthy donors using NK cell negative isolation kit (Stemcell Technologies). NK cells were cultured overnight in the presence of and 2 ng/mL IL-2 (Peprotech). SU-DHL-1, or SR-786 target cells were loaded with Calcein-AM (Thermofisher) and plated, 4 replicates per condition, in the presence of anti-CD25 or isotype antibodies for 30 mins at 37° C. 5% $CO_2$. Following incubation, NK cells were added to wells at a Target:Effector (T:E) ratio of 1:10 (10,000 target cells and 100,000 effector cells) and incubated for 4 hrs at 37° C. 5% $CO_2$. Readout of calcein fluorescence in the supernatant was performed on BMG Fluostar plate reader. The percentage of specific lysis was calculated relative to target cells alone (0% lysis) and target cells treated with 0.1% Saponin (100% lysis). Graphs of the raw data were produced using Graphpad Prism v7 to generate dose response curves. Percentage target cell lysis was plotted on an XY chart, graphing normalized Calcein AM percentage release against the log of the concentration, and the data fit to a no-linear regression curve from which the EC50 was calculated.

ADDC was also determined in a luciferase reporter system assay. CD25-expressing SR786 cells, herein called target (T) cells, are incubated for 20 minutes at 37° C. with different concentrations of mAbs against CD25 (or control IgG) in a low-IgG FBS-supplemented medium (4% FBS in RPMI). ADCC effector (E) cells are then added to the cell-mAbs mixture at an E:T ratio of 1:1. The effector cells are Jurkat cells stably transfected with a luciferase reporter system and over-expressing CD16/FcgammaRIIIA (Promega). After overnight incubation at 37 C, the cells are lysed and luciferase activity is measured by mean of luminescence release from the hydrolysis of a specific luciferase substrate, following manufacturer instruction (Promega Bio-Glow protocol).

In Vitro ADCP Assay Using In Vitro Differentiated Macrophages and Treg Cells:

Antibody-dependent cell-mediated phagocytosis (ADCP) assays were performed using in-vitro differentiated Tregs as target cells and monocyte-derived macrophages as the effector cells. PBMCs were isolated from leucocyte cones by Ficoll gradient centrifugation. Monocytes (0014+ cells) were isolated using CD14 Microbeads (Miltenyi Biotec). Monocytes were cultured for 5 days in the presence of 50 ng/ml M-CSF in RPMI 1640 (Life Technologies) containing 10% FBS (Sigma), 2 mM L-Glutamine (Life Technologies) and 10,000 U/ml Pen-Strep (Sigma), fresh media containing M-CSF is added after 3 days. Regulatory T cells (Treg) were isolated using the Human Treg Cell Differentiation Kit (R&D Systems). These cells were incubated in a 37° C., 5% $CO_2$ humidified incubator for 5 days and labelled with eFluor™ 450-dye (Invitrogen), as per manufacturer recommendations. At day 5, macrophages and eFluor™ 450-dye labelled Tregs are cocultured for 4 hours at a 10 to 1 effector to target ratio in the presence of anti-CD25 antibodies or controls, as describe thereafter. Target cells (Treg) were added at $1\times10^4$ cells/well while the effector cells (macrophages) were added at $1\times10^5$ cells/well, for an effector to target ratio of 10 to 1. The anti-CD25 antibodies were then added at a top concentration of 1 µg/ml followed by a log series (7 points) in duplicates. Cells and antibodies were incubated for 4 hours at 37° C. 5% 002. To assess ADCP, cells were placed on ice, stained with the cell surface marker CD14 (0014-PerCP-Cy5.5 clone MfP9 BD Biosciences) and fixed with the eBioscience fixation buffer. Two colour flow cytometric analysis was performed using the Fortessa LSR X20. Residual target cells were defined as cells that were eFluor™ 450-dye+/CD14−. Macrophages were defined as CD14+. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

In Vitro ADCP Assay Using FcγRIIa-H Reporter Assay

ADCP Bioassay Effector Cells (FcγRIIa-H) were obtained from Promega (Cat #G9881/5; Lot #0000261099). 5,000 cells/well of SUDHL-1 target cells were plated (25 µl/well) using a 96 well white polystyrene plate (Costar; Cat #3917). Test antibodies were serially diluted using 3 fold dilutions and 25 µl added to the cells. 50,000 effector cells were added per well in 25 µl volume to result in a 10:1 ratio of effector and target cells. All target cells, antibodies, and effector cells were plated using cell culture media. The plate was incubated for 18 hours at 37° C. Plates were then removed from the incubator and kept at room temperature for 20 minutes. 60 µl of Bio-Glo Luciferase assay Substrate buffer was added to each well followed by 30 minutes incubation and Luminescence was measured using the GloMax Multi Detection System (Promega).

Statistics:

Prism software (GraphPad) was used to perform curve fitting to determine EC50 values and maximal activity.

Results

Figure 31:
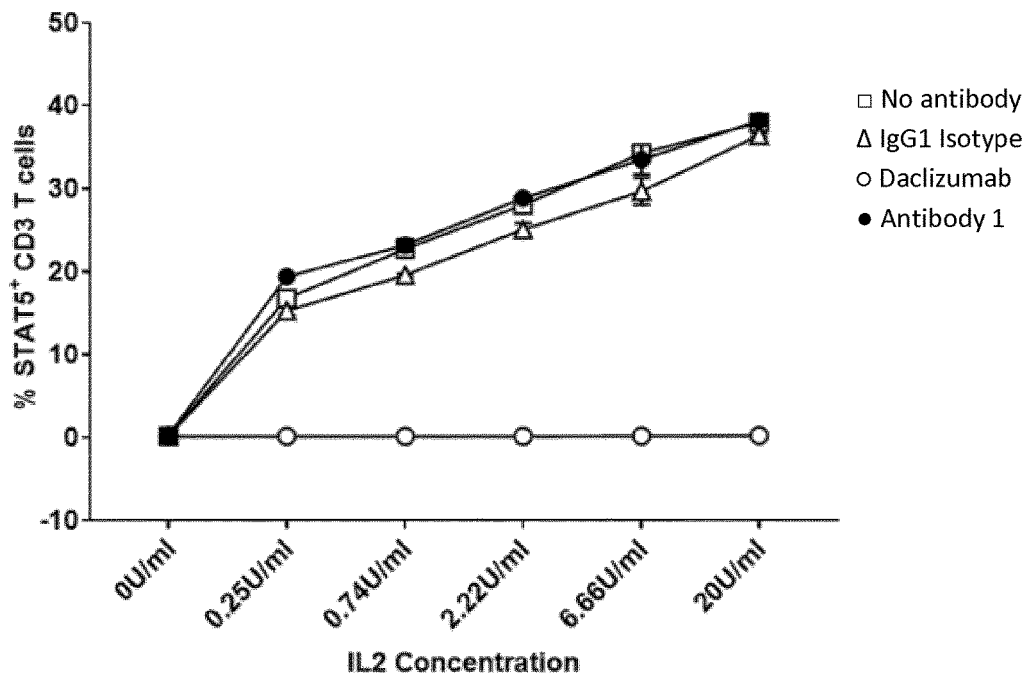
FIG. 31: characterization of Antibody 1 compared to human IgG1 isotype control, Daclizumab, or in absence of a primary antibody in respect to blocking IL-2 signalling in a STAT5 phosphorylation assay using PBMCs of human origin. Cells were incubated with 10 µg/ml antibody followed by increasing concentrations of IL-2 (as shown in the Figures). Analysis was restricted to percentage of CD3-positive cells phosphorylating STAT5.
Figure 32:
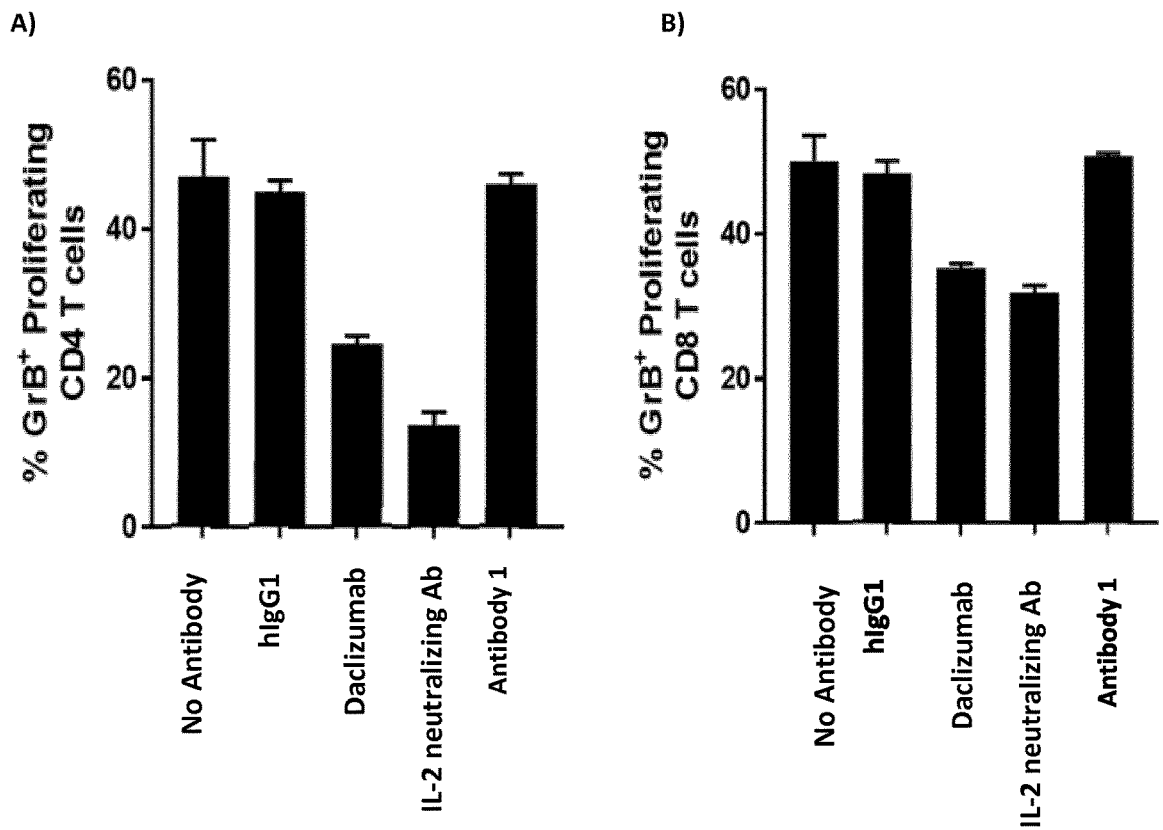
FIG. 32: Functional characterization of Antibody 1 compared to human IgG1 isotype control, Daclizumab, or commercially available mouse anti-human IL-2 neutralizing antibody as a positive control, (clone: AB12-3G4) using Pan T cells. Cells were incubated with 10 ug/ml antibody then activated with CD3/CD28 beads for 72 hours before flow cytometry analysis. Results show percentage of granzyme B positive proliferating CD4 (A) or CD8 (B) T cells.
Figure 33:
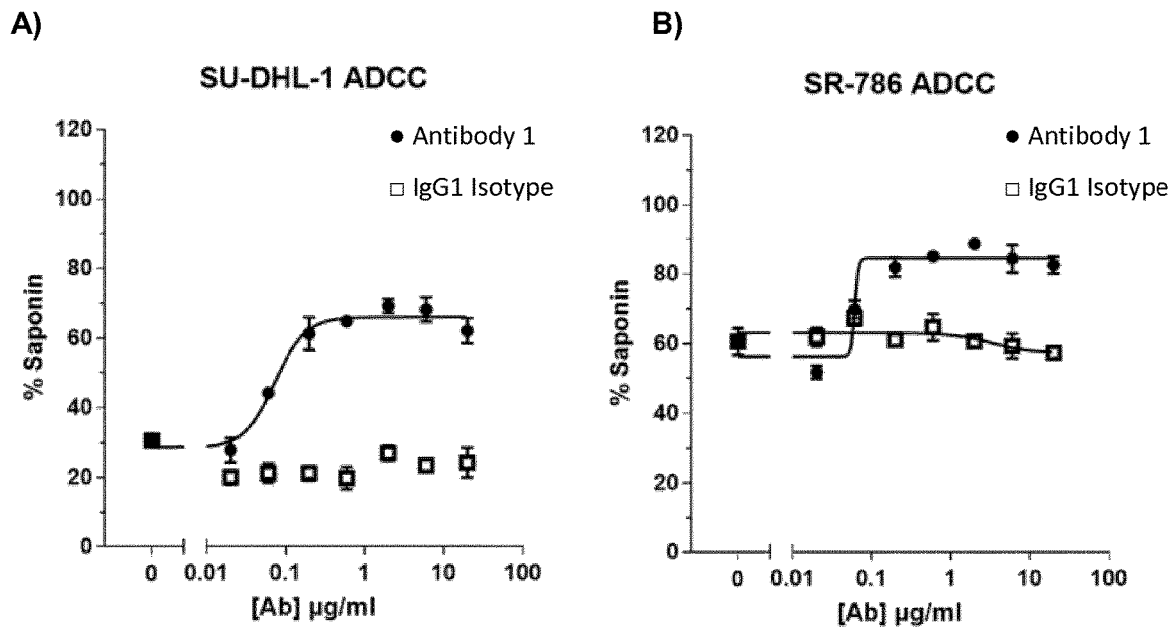
FIG. 33: Functional characterization of Antibody 1 compared to human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.
Figure 34:
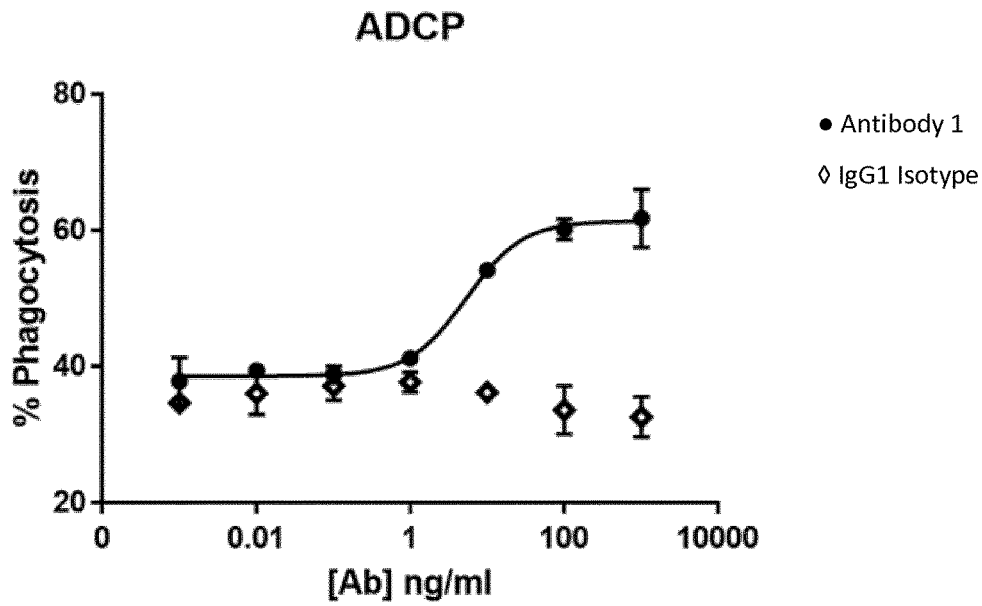
FIG. 34: Functional characterization of Antibody 1 compared to human IgG1 isotype control in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye+/CD14−. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

The Antibody 1 antibody, was evaluated with respect to its ability to not interfere with IL-2 signalling and its capacity to kill CD25 expressing target cells. The results of the binding to rhCD25, and IL-2 competitive binding analysis are shown in FIGS. 27 and 28. The ligand binding assay using the Octet® showed that Antibody 1 does not affect IL-2 binding to CD25 (FIG. 29). This was confirmed in the STAT5 assay where Antibody 1 did not block IL-2 signalling regardless of IL-2 concentrations tested while IL-2 signalling was completely blocked by the reference antibody Daclizumab (FIG. 31). Daclizumab, which has been shown to block the interaction of CD25 with IL-2 via the so-called "Tac" epitope (Queen C et al, 1989 and Bielekova B, 2013) binds to a different epitope than Antibody 1 (FIG. 30), which can explain why Daclizumab blocks IL-2 signalling and the Antibody 1 does not block the IL-2 signalling in the STAT5 phosphorylation assay (FIG. 31). Additionally, Daclizumab reduces effector responses of activated T cells, probably due to its blocking of IL-2 signalling, while Antibody 1, which does not block IL-2 signalling, does not have a negative impact on T cell responses (FIG. 32). Finally, Antibody 1 kills CD25 expressing cells, tumor cells or regulatory T cells, via ADCC (FIG. 33) and ADCP (FIG. 34) when compared to the IgG1 isotype antibody.

In conclusion, Antibody 1 has been characterized and demonstrates potent killing of CD25 positive cells (Tregs or cancer cell lines) and does not interfere with IL-2 signalling and consequently does not inhibit T effector responses. Antibody 1 is thus a Treg depleting antibody which could be applied for the treatment of cancer, as monotherapy or in combination.

Figure 37:
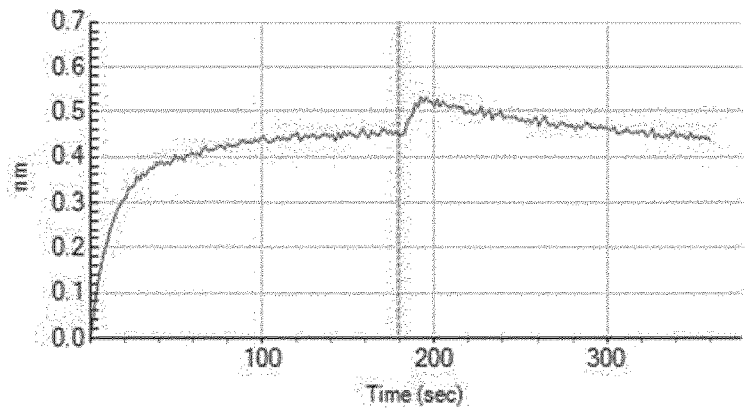
FIG. 37: Shows non-competitive binding of Antibody 3 and IL-2 by biolayer interferometry on the Octet® Red384 using a standard sandwich format binning assay. The anti-human CD25 antibody, Antibody 3, was loaded onto AHQ sensors. The sensors were then exposed to 100 nM human CD25 followed by human IL-2. Additional binding by human IL2 after antigen association indicates an unoccupied epitope (non-competitor).
Figure 39:
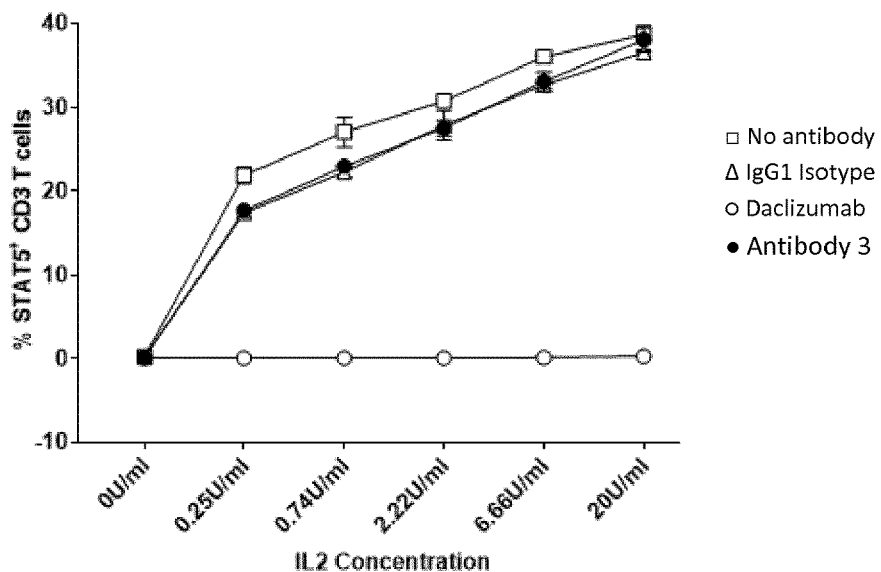
FIG. 39: characterization of Antibody 3 compared to human IgG1 isotype control, Daclizumab, or in absence of a primary antibody in respect to blocking IL-2 signalling in a STAT5 phosphorylation assay using PBMCs of human origin. Cells were incubated with 10 µg/ml antibody followed by increasing concentrations of IL-2 (as shown in the Figures). Analysis was restricted to percentage of CD3-positive cells phosphorylating STAT5.

The Antibody 3 antibody was evaluated with respect to its ability to not interfere with IL-2 signalling and its capacity to kill of CD25 expressing target cells. The results of the binding to rhCD25, and IL-2 competitive binding analysis are shown in FIGS. 35 and 36. The ligand binding assay using the Octet® showed that Antibody 3 does not affect IL-2 binding to CD25 (FIG. 37). This was confirmed in the STAT5 assay where Antibody 3 did not block IL-2 signalling regardless of IL-2 concentrations tested while IL-2 signalling was completely blocked by the reference antibody Daclizumab (FIG. 39). Daclizumab, which has been shown to block the interaction of CD25 with IL-2 via the so-called "Tac" epitope binds to a different epitope than Antibody 3

Figure 38:
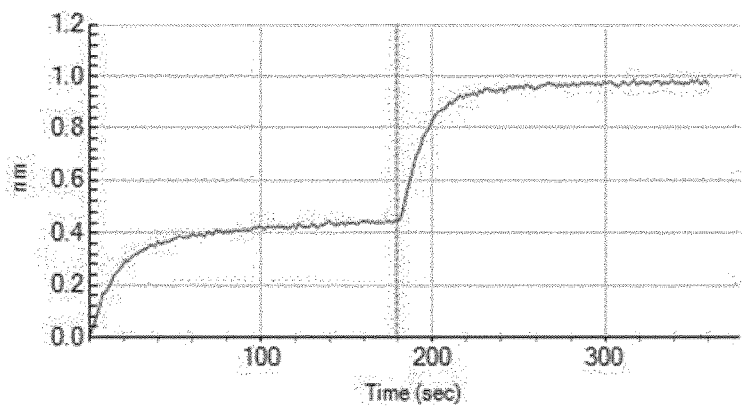
FIG. 38: Shows non-competitive binding of Antibody 3 and Daclizumab to CD25 by biolayer interferometry on the Octet® Red384 system using a standard sandwich format binning assay. The reference monoclonal anti-human CD25 antibody Daclizumab was loaded onto AHQ sensors. The sensors were then exposed to 100 nM human CD25 antigen followed by the anti-human CD25 antibody (Antibody 3). Additional binding by the second antibody after antigen association indicates an unoccupied epitope (non-competitor), while no binding indicates epitope blocking (competitor).

(FIG. 38), which can explain why Daclizumab blocks IL-2 signalling and the Antibody 3 does not block the IL-2 signalling in the STAT5 phosphorylation assay (FIG. 39). Additionally, Daclizumab reduces effector responses of activated T cells, probably due to its blocking of IL-2 signalling, while Antibody 3, which does not block IL-2 signalling, has only minimal impact, if any, on T cell responses when compared to the condition without antibody or with isotype control (FIG. 40). Finally, Antibody 3 kills CD25 expressing cells, tumor cells or regulatory T cells, via ADCC (FIG. 41) and ADCP (FIG. 42) when compared to the IgG1 isotype antibody.

In conclusion, Antibody 3 has been characterized and demonstrates potent killing of CD25 positive cells (Tregs or cancer cell lines) and does not interfere with IL-2 signalling and consequently does not inhibit T effector responses. Antibody 3 is thus a Treg depleting antibody which could be applied for the treatment of cancer, as monotherapy or in combination.

Figure 44:
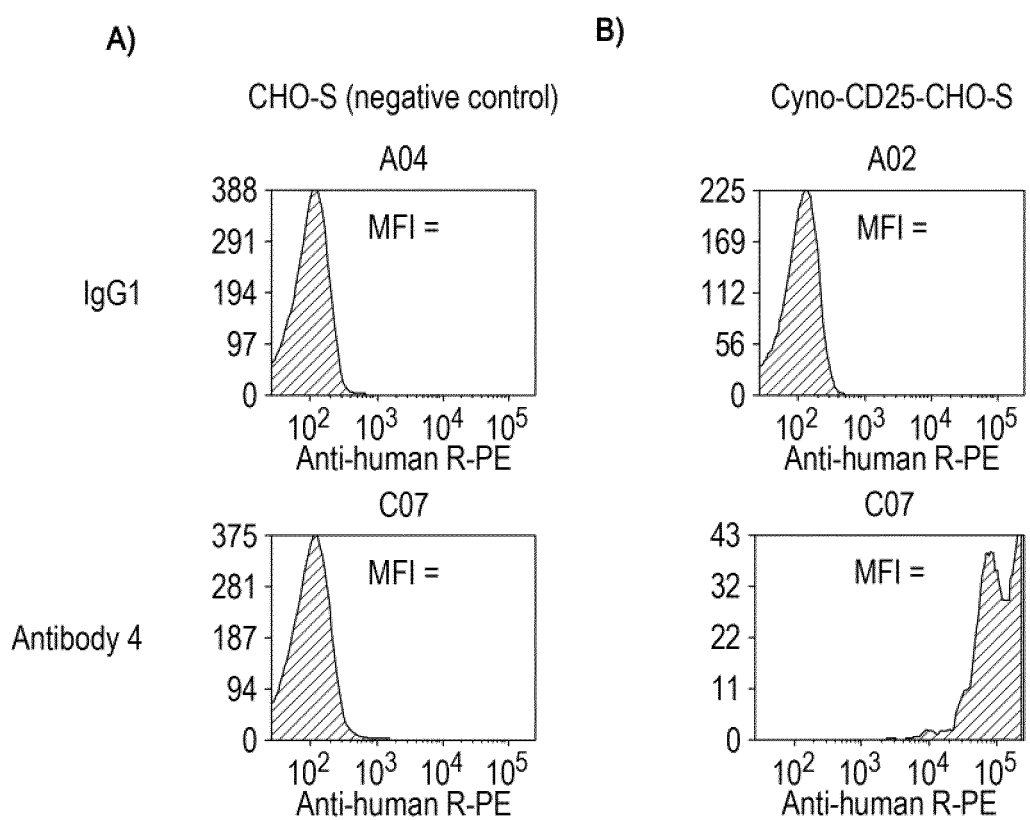
FIG. 44: Characterization of Antibody 4 binding to unmodified CHO-S cells, (negative control) (A), or cyno-CD25-CHO-S cells (B), at 100 nM antibody concentration and comparing with human IgG1 isotype control.
Figure 45:
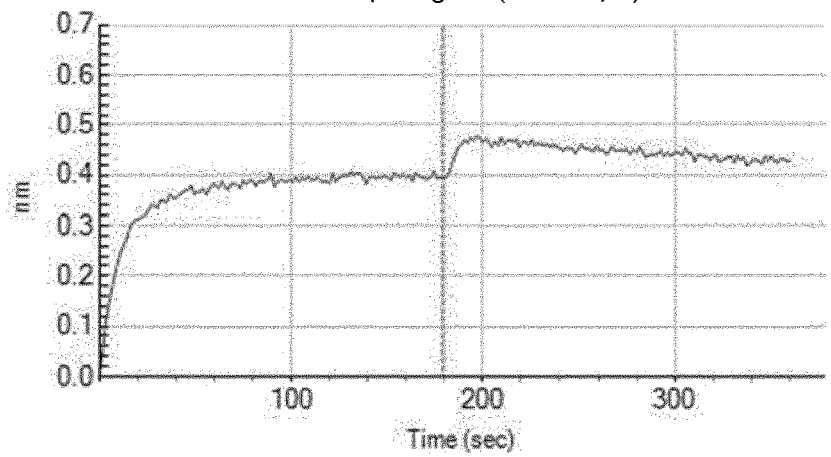
FIG. 45: Shows non-competitive binding of Antibody 4 and IL-2 by biolayer interferometry on the Octet® Red384 using a standard sandwich format binning assay. The anti-human CD25 antibody, Antibody 4, was loaded onto AHQ sensors. The sensors were then exposed to 100 nM human CD25 followed by human IL-2. Additional binding by human IL2 after antigen association indicates an unoccupied epitope (non-competitor).
Figure 46:
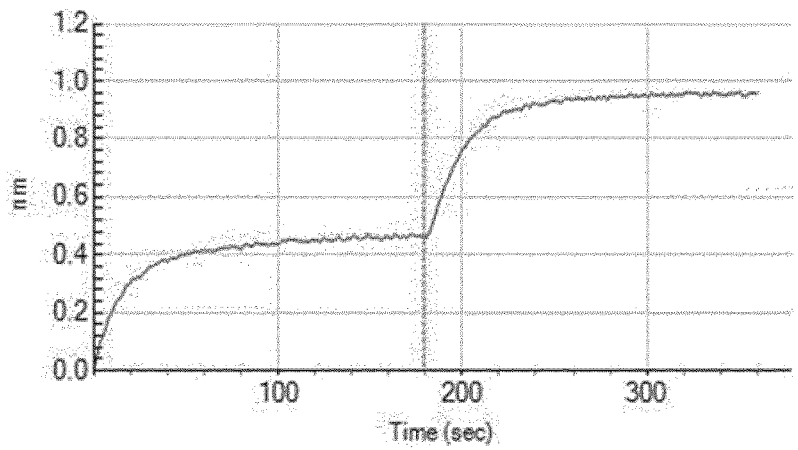
FIG. 46: Shows non-competitive binding of Antibody 4 and Daclizumab to CD25 by biolayer interferometry on the Octet® Red384 system using a standard sandwich format binning assay. The reference monoclonal anti-human CD25 antibody Daclizumab was loaded onto AHQ sensors. The sensors were then exposed to 100 nM human CD25 antigen followed by the anti-human CD25 antibody (Antibody 4). Additional binding by the second antibody after antigen association indicates an unoccupied epitope (non-competitor), while no binding indicates epitope blocking (competitor).
Figure 47:
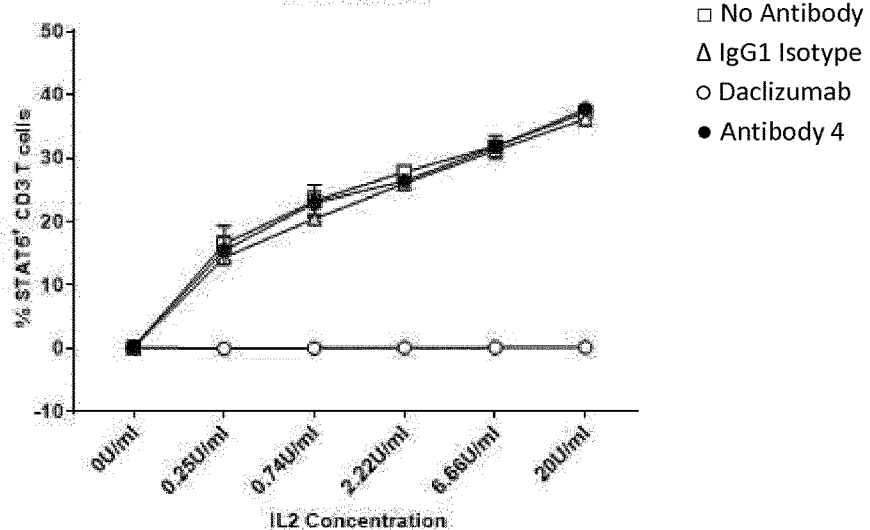
FIG. 47: characterization of Antibody 4 compared to human IgG1 isotype control, Daclizumab, or in absence of a primary antibody in respect to blocking IL-2 signalling in a STAT5 phosphorylation assay using PBMCs of human origin. Cells were incubated with 10 µg/ml antibody followed by increasing concentrations of IL-2 (as shown in the Figures). Analysis was restricted to percentage of CD3-positive cells phosphorylating STAT5.
Figure 49:
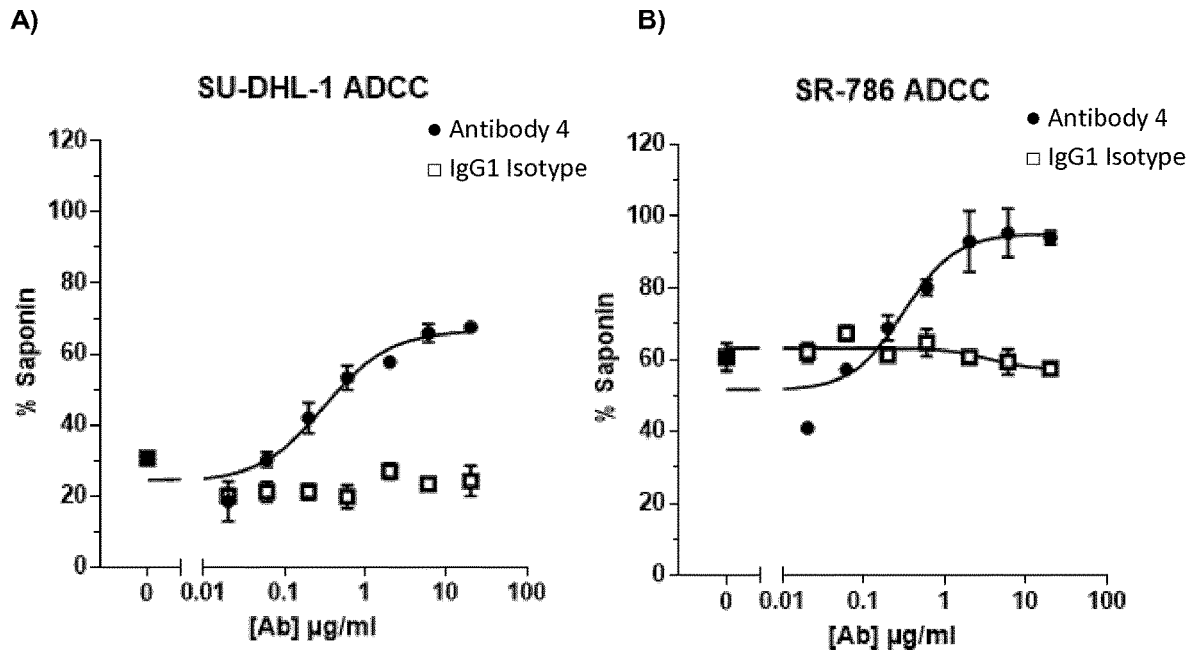
FIG. 49: Functional characterization of Antibody 4 compared to human IgG1 isotype control in respect to killing of CD25-positive cell lines in an ADCC assay. CD25-high or -low expressing cells, SU-DHL-1 (A) or SR-786 cells (B) respectively, were co-cultured with purified NK cells in the presence of varying concentrations of antibodies (as shown in the Figures). Target cell lysis was measured by calcein release into the supernatant at four hours post addition to NK cells. Data was normalised to saponin treated controls.
Figure 50:
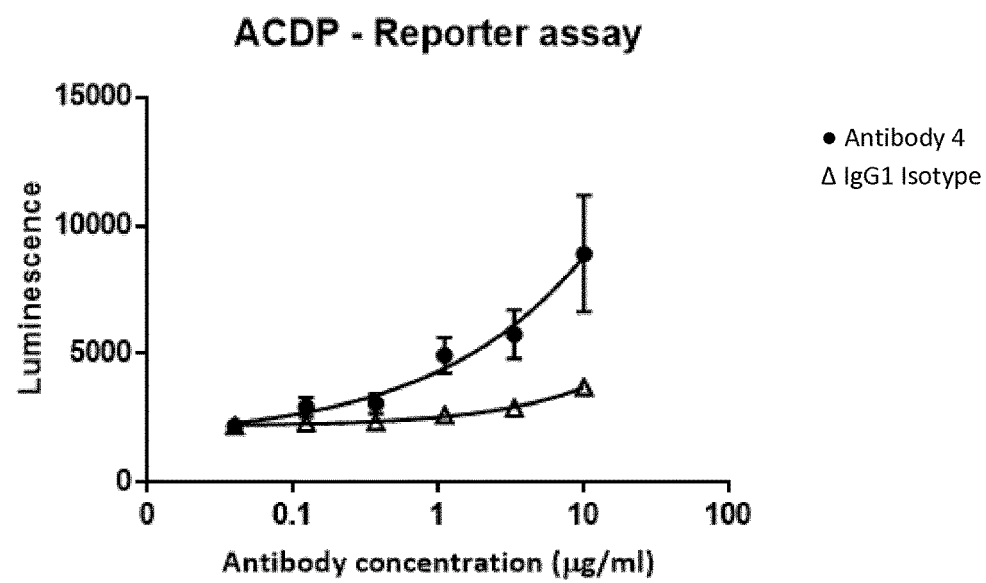
FIG. 50: Functional characterization of Antibody 4 compared to human IgG1 isotype control in respect to inducing ADCP in a Reporter Bioassay. CD25 expressing SU-DHL-1 cells were co-cultured with Jurkat T cells genetically engineered to express FcγRIIa and an NFAT-response element that drives luciferase expression (NFAT-RE-luc2) in the presence of varying concentrations of antibodies (as shown in the Figures).

The Antibody 4 antibody, was evaluated with respect to its ability to not interfere with IL-2 signalling and its capacity to kill CD25 expressing target cells. The results of the binding to rhCD25, and IL-2 competitive binding analysis are shown in FIGS. 43 and 44. The ligand binding assay using the Octet® showed that Antibody 4 does not affect IL-2 binding to CD25 (FIG. 45). This was confirmed in the STAT5 assay where Antibody 4 did not block IL-2 signalling regardless of IL-2 concentrations tested while IL-2 signalling was completely blocked by the reference antibody Daclizumab (FIG. 47). Daclizumab, which has been shown to block the interaction of CD25 with IL-2 via the so-called "Tac" epitope binds to a different epitope than Antibody 4 (FIG. 46), which can explain why Daclizumab blocks IL-2 signalling and the Antibody 4 does not block the IL-2 signalling in the STAT5 phosphorylation assay (FIG. 47). Additionally, Daclizumab reduces effector responses of activated T cells, probably due to its blocking of IL-2 signalling, while Antibody 4, which does not block IL-2 signalling, does not have a negative impact on T cell responses (FIG. 48). Finally, Antibody 4 kills CD25 expressing cells, tumor cells or regulatory T cells, via ADCC (FIG. 49) and ADCP (FIG. 50) when compared to the IgG1 isotype antibody.

In conclusion, Antibody 4 has been characterized and demonstrates potent killing of CD25 positive cells (Tregs or cancer cell lines) and does not interfere with IL-2 signalling and consequently does not inhibit T effector responses. Antibody 4 is thus a Treg depleting antibody which could be applied for the treatment of cancer, as monotherapy or in combination.

Figure 53:
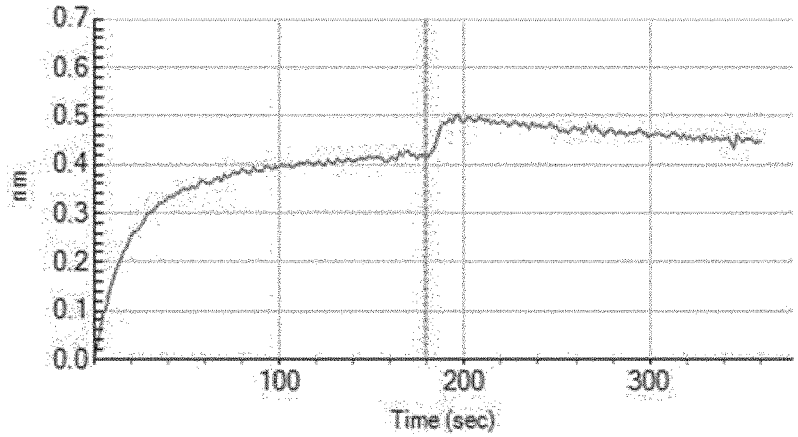
FIG. 53: Shows non-competitive binding of Antibody 2 and IL-2 (A) and competitive binding of a IL-2 competing antibody with IL-2 (B) by biolayer interferometry on the Octet® Red384 using a standard sandwich format binning assay. The anti-human CD25 antibody, Antibody 2, was loaded onto AHQ sensors. The sensors were then exposed to 100 nM human CD25 followed by human IL-2. Additional binding by human IL2 after antigen association indicates an unoccupied epitope (non-competitor).
Figure 54:
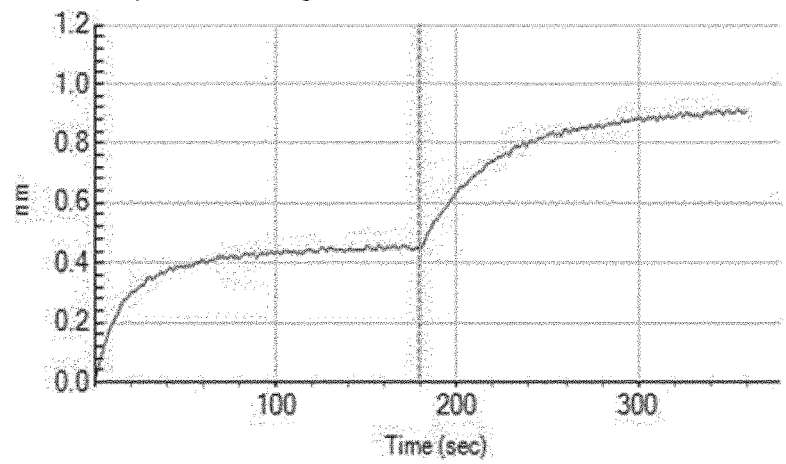
FIG. 54: Shows non-competitive binding of Antibody 2 and Daclizumab to CD25 by biolayer interferometry on the Octet® Red384 system using a standard sandwich format binning assay. The reference monoclonal anti-human CD25 antibody Daclizumab was loaded onto AHQ sensors. The sensors were then exposed to 100 nM human CD25 antigen followed by the anti-human CD25 antibody (Antibody 2). Additional binding by the second antibody after antigen association indicates an unoccupied epitope (non-competitor), while no binding indicates epitope blocking (competitor).
Figure 55:
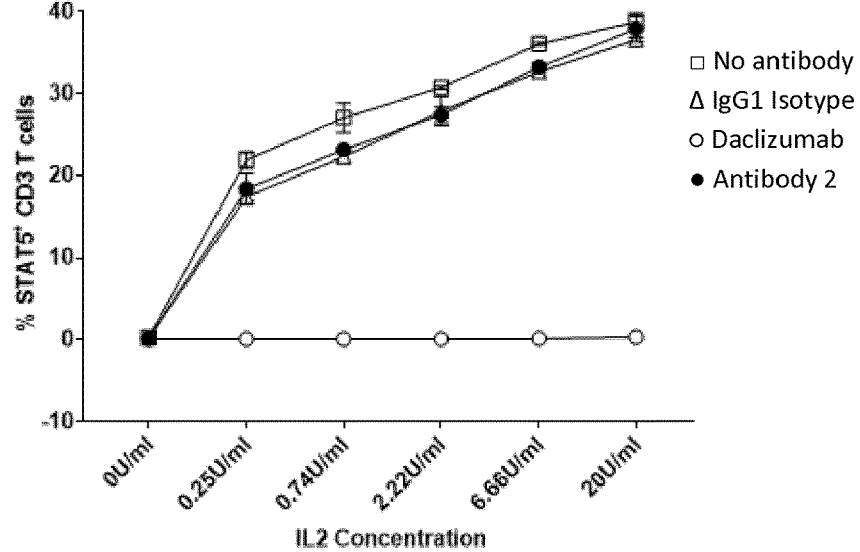
FIG. 55: Characterization of Antibody 2 compared to human IgG1 isotype control, Daclizumab, or in absence of a primary antibody in respect to blocking IL-2 signalling in a STAT5 phosphorylation assay using PBMCs of human origin. Cells were incubated with 10 µg/ml antibody followed by increasing concentrations of IL-2 (as shown in the Figures). Analysis was restricted to percentage of CD3-positive cells phosphorylating STAT5.

The Antibody 2 antibody was evaluated with respect to its ability to not interfere with IL-2 signalling and its capacity to kill CD25 expressing target cells. The results of the binding to rhCD25, and IL-2 competitive binding analysis are shown in FIGS. 51 and 52. The ligand binding assay using the Octet® showed that Antibody 2 does not affect IL-2 binding to CD25 (FIG. 53). This was confirmed in the STAT5 assay where Antibody 2 did not block IL-2 signalling regardless of IL-2 concentrations tested while IL-2 signalling was completely blocked by the reference antibody Daclizumab (FIG. 55). Daclizumab, which has been shown to block the interaction of CD25 with IL-2 via the so-called "Tac" epitope binds to a different epitope than Antibody 2 (FIG. 54), which can explain why Daclizumab blocks IL-2 signalling and the Antibody 2 does not block the IL-2 signalling in the STAT5 phosphorylation assay (FIG. 55). Finally, Antibody 2 kills CD25 expressing cells, tumor cells or regulatory T cells, via ADCC (FIG. 56) and ADCP (FIG. 57) when compared to the IgG1 isotype antibody.

In conclusion, Antibody 2 has been characterized and demonstrates potent killing of CD25 positive cells (Tregs or cancer cell lines) and does not interfere with IL-2 signalling and consequently does not inhibit T effector responses. Antibody 2 is thus a Treg depleting antibody which could be applied for the treatment of cancer, as monotherapy or in combination.

The Antibody 5 antibody is characterised as comprising a heavy chain variable region comprising the sequence of:

(SEQ ID NO: 10)
EVQLVESGGGLIQPGGSLRLSCAASGFTLDSYGVSWVRQAPGKGLEWVGV

TSSGGSAYYADSVKGRFTISRDNSKNTLYLQMNSLRAEDTAVYYCARDRY

VYTGGYLYHYGMDLWGQGTLVTVSS and a variable light chain comprising the sequence:

(SEQ ID NO: 14)
DIQMTQSPSSLSASVGDRVTITCRASQSISDYLAWYQQKPGKVPKLLIYA

ASTLPFGVPSRFSGSGSGTDFTLTISSLQPEDVATYYCQGTYDSSDWYWA

FGGGTKVEIK.

The sequences of the complementarity determining regions (CDRs; i.e., COR1, CDR2, and CDR3), as indicated above, and framework regions (FRs) were defined according to Kabat numbering scheme.

Figure 58:
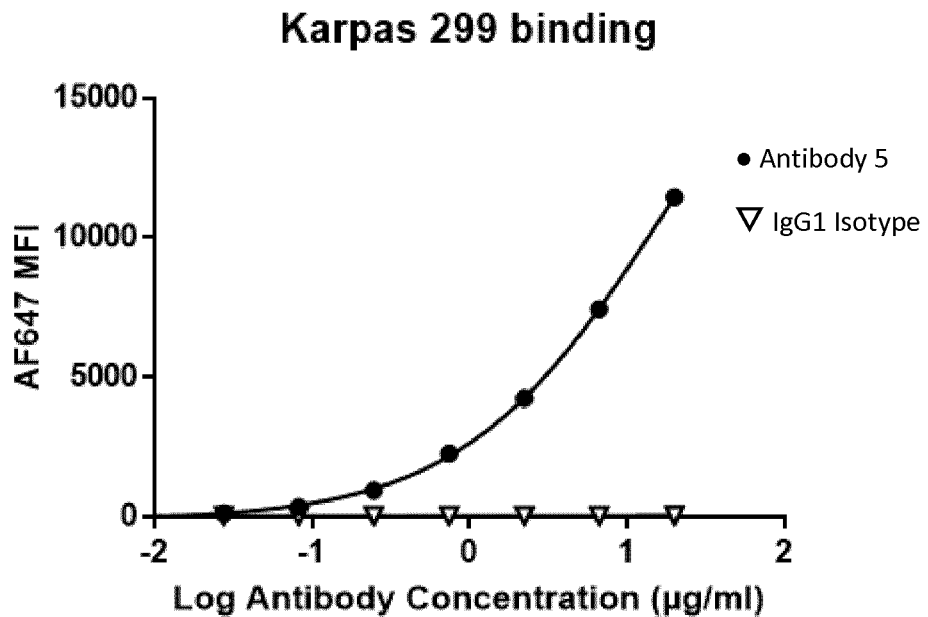
FIG. 58: Characterization of Antibody 5 binding to CD25 expressed on Karpas 299 cells at increasing antibody concentrations and comparing with human IgG1 isotype control.
Figure 59:
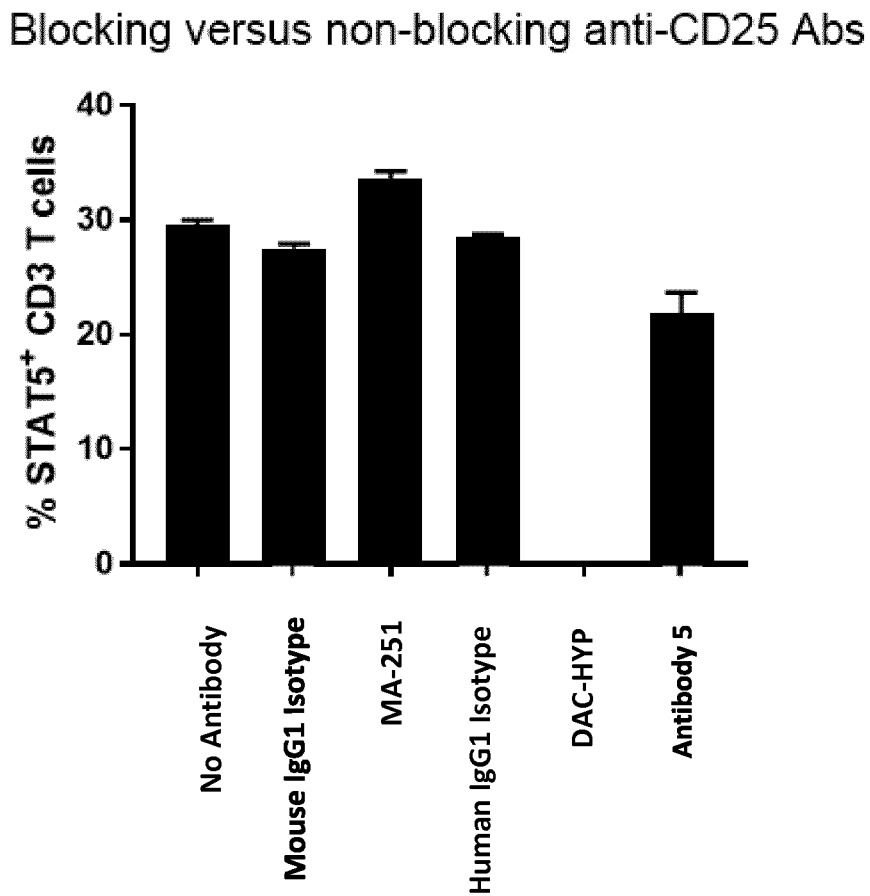
FIG. 59: Characterization of Antibody 5 in respect to blocking IL-2 signalling in a STAT5 phosphorylation assay using PBMCs of human origin. The mouse anti-human antibody MA-251 was used as a non-blocking control while the clinical Daclizumab High Yield Process (DAC HYP) was used as a blocking control compared to mouse IgG1 isotype control, human IgG1 isotype controls or in absence of a primary antibody, respectively. Cells were incubated with 10 µg/ml antibody followed by 10 U/ml IL-2. Analysis was restricted to percentage of CD3-positive cells phosphorylating STAT5.
Figure 60:
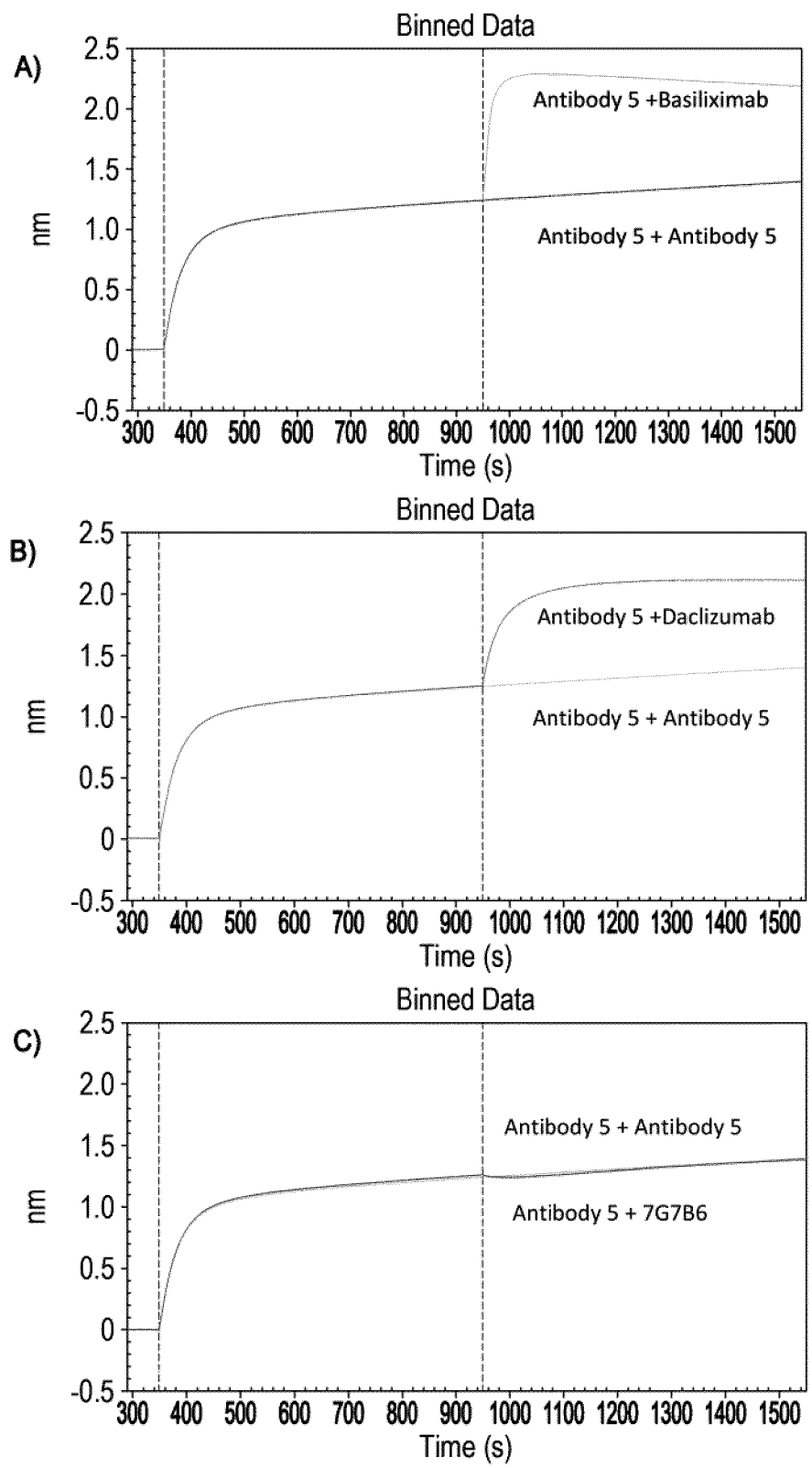
FIG. 60: Competition assays in the Octet®. Binding Antibody 1 to the immobilized rhCD25 followed by either the first Ab again (Antibody 1 as control) or a second Ab, either an IL-2 competitor e.g. Daclizumab and Basiliximab research or an IL-2 no competitor e.g. 7G7B6). Antibody 1 does not compete with the IL-2 signal blockers research Basiliximab (A) Daclizumab (B) while it does compete with 7G7B6 (non-IL-2 blocker) (C).
Figure 61:
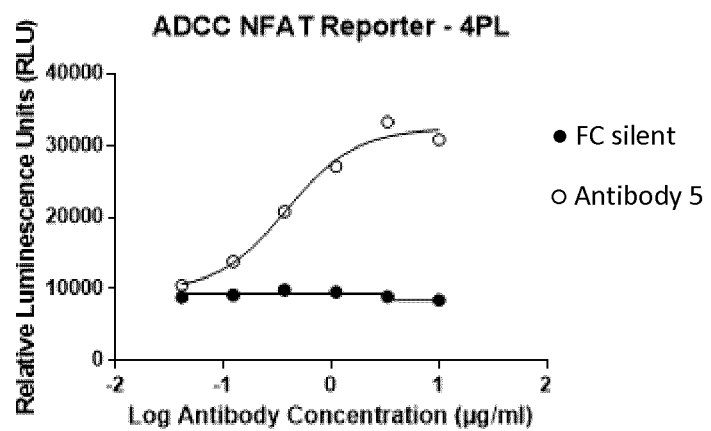
FIG. 61: Characterization of Antibody 5 compared to an anti-human CD25 Fc silent control antibody in respect to inducing ADCC in a Reporter Bioassay. CD25 expressing SR-786 cells were co-cultured with Jurkat T cells genetically engineered to express FcγRIIIa and an NFAT-response element that drives luciferase expression (NFAT-RE-luc2) in the presence of varying concentrations of antibodies (as shown in the Figures).
Figure 62:
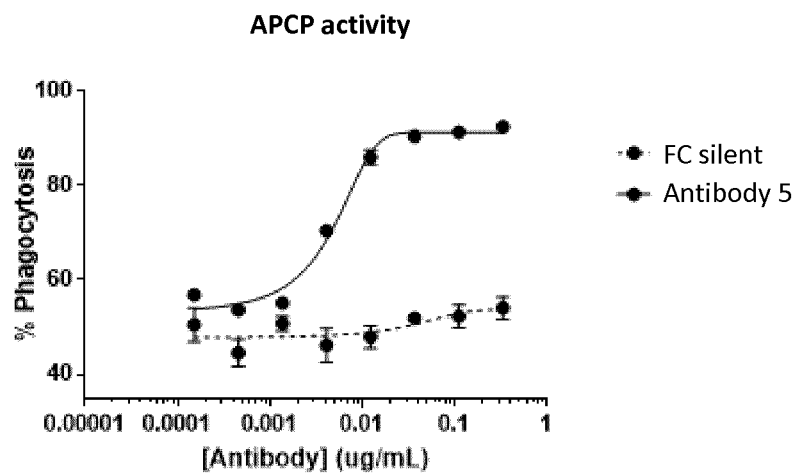
FIG. 62: Functional characterization of Antibody 5 compared to human IgG1 isotype control in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye$^+$/CD14$^-$. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

The Antibody 5 was evaluated with respect to its ability to not interfere with IL-2 signalling and its capacity to kill of CD25 expressing target cells. The results of the binding to rhCD25, are shown in FIG. 58. The STAT5 assay showed that Antibody 5 did not block IL-2 signalling tested while IL-2 signalling was completely blocked by the antibody Daclizumab (FIG. 59). The competition assay showed that Antibody 5 does not compete with the IL-2 signal blockers Daclizumab or Basiliximab FIGS. 60(A) and (B) while it does compete with 7G7B6 (non-IL-2 blocker) (FIG. 60(C)). Finally, Antibody5 kills CD25 expressing cells, tumor cells or regulatory T cells, via ADCC (FIG. 61) and ADCP (FIG. 61) when compared to an anti-human CD25 Fc silent control antibody.

In conclusion, Antibody 5 has been characterized and demonstrates potent killing of CD25 positive cells (Tregs or cancer cell lines) and does not interfere with IL-2 signalling and consequently does not inhibit T effector responses. Antibody 5 is thus a Treg depleting antibody which could be applied for the treatment of cancer, as monotherapy or in combination.

The Antibody 6, Antibody 7, Antibody 8 and Antibody 9 antibodies are characterised as comprising the following sequences:

Antibody 6 comprises a heavy chain variable region comprising the sequence of:

(SEQ ID NO: 23)
EVQLLESGGGLVQPGGSLRLSCAASGFTFSSYGMSWVRQAPGKGLELVST

INGYGDTTYYPDSVKGRFTISRDNSKNTLYLQMNSLRAEDTAVYYCARDR

DYGNSYYYALDYWGQGTLVTVSS and a variable light chain comprising the sequence:

(SEQ ID NO: 25)
EIVLTQSPGTLSLSPGERATLSCRASSSVSFMHWLQQKPGQAPRPLIYAT
SNLASGIPDRFSGSGSGTDYTLTISRLEPEDFAVYYCQQWSSNPPAFGQG
TKLEIK.

Antibody 7 comprises a heavy chain variable region comprising the sequence of:

(SEQ ID NO: 23)
EVQLLESGGGLVQPGGSLRLSCAASGFTFSSYGMSWVRQAPGKGLELVST
INGYGDTTYYPDSVKGRFTISRDNSKNTLYLQMNSLRAEDTAVYYCARDR
DYGNSYYYALDYWGQGTLVTVSS and a variable light chain comprising the sequence:

(SEQ ID NO: 26)
QIVLTQSPGTLSLSPGERATLSCRASSSVSFMHWLQQKPGQSPRPLIYAT
SNLASGIPDRFSGSGSGTDYTLTISRLEPEDFAVYYCQQWSSNPPAFGQG
TKLEIK.

Antibody 8 comprises a heavy chain variable region comprising the sequence of:

(SEQ ID NO: 24)
EVQLLESGGGLVQPGGSLRLSCAASGFTFSSYGMSWVRQAPGKGLELVST
INGYGDTTYYPDSVKGRFTISRDNAKNTLYLQMNSLRAEDTAVYFCARDR
DYGNSYYYALDYWGQGTLVTVSS and a variable light chain comprising the sequence:

(SEQ ID NO: 25)
EIVLTQSPGTLSLSPGERATLSCRASSSVSFMHWLQQKPGQAPRPLIYAT
SNLASGIPDRFSGSGSGTDYTLTISRLEPEDFAVYYCQQWSSNPPAFGQG
TKLEIK.

Antibody 9 comprises a heavy chain variable region comprising the sequence of:

(SEQ ID NO: 24)
EVQLLESGGGLVQPGGSLRLSCAASGFTFSSYGMSWVRQAPGKGLELVST
INGYGDTTYYPDSVKGRFTISRDNAKNTLYLQMNSLRAEDTAVYFCARDR
DYGNSYYYALDYWGQGTLVTVSS and a variable light chain comprising the sequence:

(SEQ ID NO: 26)
QIVLTQSPGTLSLSPGERATLSCRASSSVSFMHWLQQKPGQSPRPLIYAT
SNLASGIPDRFSGSGSGTDYTLTISRLEPEDFAVYYCQQWSSNPPAFGQG
TKLEIK.

The sequences of the complementarity determining regions (CDRs; i.e., CDR1, CDR2, and CDR3), as indicated above, and framework regions (FRs) were defined according to Kabat numbering scheme.

The results of the epitope mapping indicated that Antibody 6, Antibody 7, Antibody 8 and Antibody 9 bind human CD25 in the region from amino acids 150 to 163 (YQCVQGYRALHRGP) and amino acids 166 to 180 (SVCKMTHGKTRVVTQP) of SEQ ID NO: 1, and binds human CD25 extracellular protein sequences with a Kd value in the $10^{-8}$ M to $10^{-10}$ M range.

Figure 65:
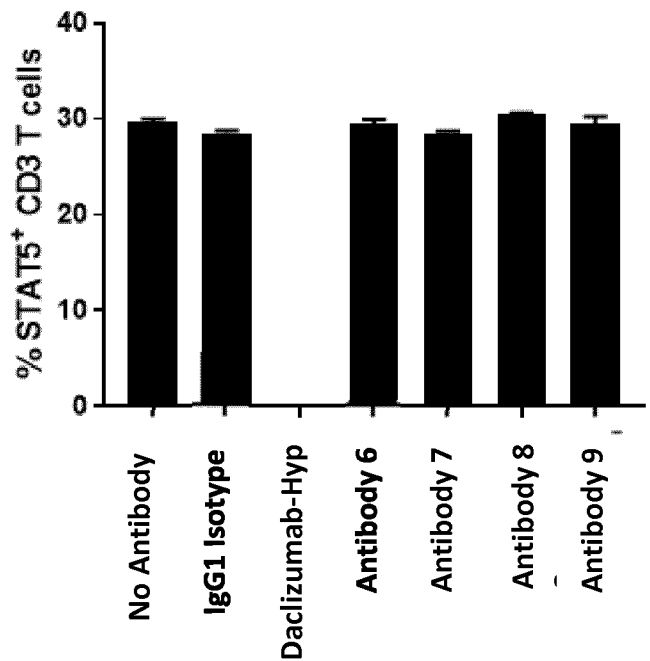
FIG. 65: Characterization of Antibody 7 compared to human IgG1 isotype control, Daclizumab-Hyp, or in the absence of a primary antibody in respect to blocking IL-2 signalling in a STAT5 phosphorylation assay using PBMCs of human origin. Cells were incubated with 10 μg/ml antibody followed by 10 U/ml of IL-2. Analysis was restricted to percentage of CD3-positive cells phosphorylating STAT5.

The Antibody 6, Antibody 7, Antibody 8 and Antibody 9 were evaluated with respect to their ability to not interfere with IL-2 signalling and its capacity to kill of CD25 expressing target cells. The results of the binding to rhCD25, are shown in FIG. 63. The STAT5 assay showed that antibodies did not block IL-2 signalling tested while IL-2 signalling was completely blocked by the antibody Daclizumab (FIG. 65).

Figure 66:
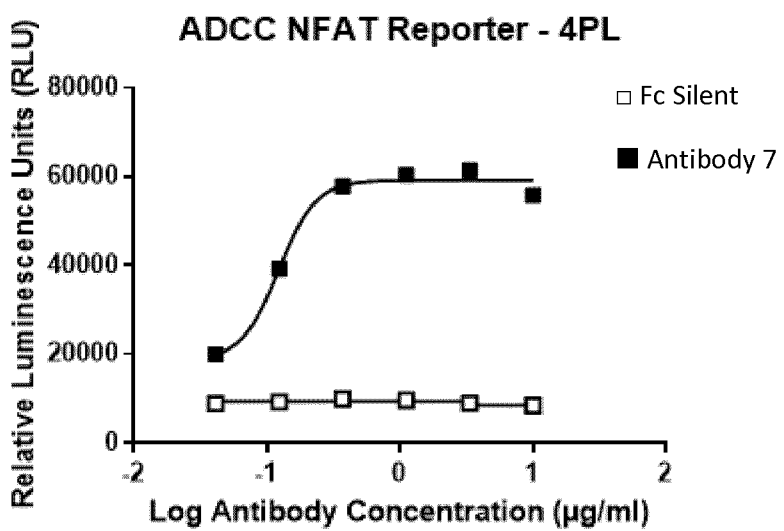
FIG. 66: Functional characterization of Antibody 7 compared to an anti-human CD25 Fc silent control antibody in respect to inducing ADCC in a Reporter Bioassay. CD25 expressing SR-786 cells were co-cultured with Jurkat T cells genetically engineered to express FcγRIIIa and an NFAT-response element that drives luciferase expression (NFAT-RE-luc2) in the presence of varying concentrations of antibodies (as shown in the Figures).
Figure 67:
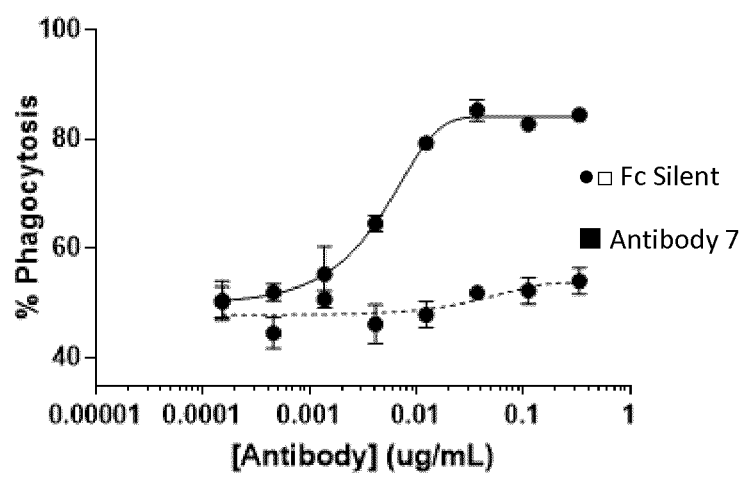
FIG. 67: Functional characterization of Antibody 7 compared to an anti-human CD25 Fc silent control antibody in respect to phagocytosis of in-vitro differentiated Treg cells in an ADCP assay. Tregs were co-cultured with MCSF differentiated Macrophages in the presence of varying concentrations of antibodies (as shown in the Figures). Two colour flow cytometric analysis was performed with CD14+ stained Macrophages and eFluor™ 450-dye labelled Tregs. Residual target cells were defined as cells that were eFluor™ 450-dye$^+$/CD14$^-$. Dual-labelled cells (eFluor™ 450-dye+/CD14+) were considered to represent phagocytosis of targets by Macrophages. Phagocytosis of target cells was calculated with the following equation: % Phagocytosis=100×[(percent dual positive)/(percent dual positive+percent residual targets)].

The competition assay showed that Antibody 7 does not compete with the IL-2 signal blockers Daclizumab or Basiliximab FIGS. 64(A) and (B). Finally, Antibody 7 kills CD25 expressing cells, tumor cells or regulatory T cells, via ADCC (FIG. 66) and ADCP (FIG. 67) when compared to an anti-human CD25 Fc silent control antibody.

In conclusion, Antibody 6, Antibody 7, Antibody 8 and Antibody 9 have been characterized and demonstrates potent killing of CD25 positive cells (Tregs or cancer cell lines) and does not interfere with IL-2 signalling and consequently does not inhibit T effector responses. The antibodies are thus a Treg depleting antibodies which could be applied for the treatment of cancer, as monotherapy or in combination.

Antibody 10, Antibody 11, Antibody 12, Antibody 12, Antibody 13, Antibody 14, Antibody 15, Antibody 16, Antibody 17, antibody 18, Antibody 19, Antibody 20, Antibody 21, antibodies are characterised as comprising a heavy chain variable region comprising the sequence of:

|      | VH Protein | VL Protein |
| --- | --- | --- |
| Ab10 | QVQLQESGPGLVKPSETLSLTCTVSGFSLTSYG IQWIRQPPGKGLEWIGVIWAGGSTNYNSALMSR VTISKDNSKNQFSLKLSSVTAADTAVYYCARAY GYDGSWLAYWGQGTLVTVSS (SEQ ID NO: 27) | EIVLTQSPATLSLSPGERATLSCRASSSVSYM HWYQQKPGQAPRPLIFATSNLASGIPARFSGS GSGTDFTLTISSLEPEDFAVYYCQQWSSNPPT FGGGTKLEIK SEQ ID NO: 30) |
| Ab11 | QVQLQESGPGLVKPSETLSLTCTVSGFSLTSYG IQWIRQPPGKGLEWIGVIWAGGSTNYNSALMSR VTISKDNSKNQFSLKLSSVTAADTAVYYCARAY GYDGSWLAYWGQGTLVTVSS (SEQ ID NO: 27) | QIVLTQSPATLSLSPGERATLSCRASSSVSYM HWYQQKPGQAPRPLIFATSNLASGIPARFSGS GSGTDYTLTISSLEPEDFAVYYCQQWSSNPPT FGGGTKLEIK (SEQ ID NO: 31) |

-continued

| | VH Protein | VL Protein |
|---|---|---|
| Ab12 | QVQLQESGPGLVKPSETLSLTCTVSGFSLTSYGIQWIRQPPGKGLEWIGVIWAGGSTNYNSALMSR VTISKDNSKNQFSLKLSSVTAADTAVYYCARAY GYDGSWLAYWGQGTLVTVSS (SEQ ID NO: 27) | DIQMTQSPSSLSASVGDRVTITCRASSSVSYM HWYQQKPGKAPKPLIFATSNLASGVPSRFSGS GSGTDYTLTISSLQPEDFATYYCQQWSSNPPT FGGGTKLEIK (SEQ ID NO: 32) |
| Ab13 | QVQLQESGPGLVKPSETLSLTCTVSGFSLTSYGIQWIRQPPGKGLEWIGVIWAGGSTNYNSALMSR VTISKDNSKNQFSLKLSSVTAADTAVYYCARAY GYDGSWLAYWGQGTLVTVSS SEQ ID NO: 27) | QIQLTQSPSSLSASVGDRVTITCRASSSVSYM HWYQQKPGKSPKPLIFATSNLASGVPSRFSGS GSGTDYTLTISSLQPEDFATYYCQQWSSNPPT FGGGTKLEIK (SEQ ID NO: 33) |
| AB14 | QVQLQESGPGLVKPSETLSLTCTVSGFSLTSYGIQWVRQPPGKGLEWIGVIWAGGSTNYNSALMSR VTISKDNSKSQFSLKLSSVTAADTAVYYCARAY GYDGSWLAYWGQGTLVTVSS (SEQ ID NO: 28) | EIVLTQSPATLSLSPGERATLSCRASSSVSYM HWYQQKPGQAPRPLIFATSNLASGIPARFSGS GSGTDFTLTISSLEPEDFAVYYCQQWSSNPPT FGGGTKLEIK (SEQ ID NO: 30) |
| Ab15 | QVQLQESGPGLVKPSETLSLTCTVSGFSLTSYGIQWVRQPPGKGLEWIGVIWAGGSTNYNSALMSR VTISKDNSKSQFSLKLSSVTAADTAVYYCARAY GYDGSWLAYWGQGTLVTVSS (SEQ ID NO: 28) | QIVLTQSPATLSLSPGERATLSCRASSSVSYM HWYQQKPGQAPRPLIFATSNLASGIPARFSGS GSGTDYTLTISSLEPEDFAVYYCQQWSSNPPT FGGGTKLEIK (SEQ ID NO: 31) |
| Ab16 | QVQLQESGPGLVKPSETLSLTCTVSGFSLTSYGIQWVRQPPGKGLEWIGVIWAGGSTNYNSALMSR VTISKDNSKSQFSLKLSSVTAADTAVYYCARAY GYDGSWLAYWGQGTLVTVSS (SEQ ID NO: 28) | DIQMTQSPSSLSASVGDRVTITCRASSSVSYM HWYQQKPGKAPKPLIFATSNLASGVPSRFSGS GSGTDYTLTISSLQPEDFATYYCQQWSSNPPT FGGGTKLEIK (SEQ ID NO: 32) |
| Ab17 | QVQLQESGPGLVKPSETLSLTCTVSGFSLTSYGIQWVRQPPGKGLEWIGVIWAGGSTNYNSALMSR VTISKDNSKSQFSLKLSSVTAADTAVYYCARAY GYDGSWLAYWGQGTLVTVSS (SEQ ID NO: 28) | QIQLTQSPSSLSASVGDRVTITCRASSSVSYM HWYQQKPGKSPKPLIFATSNLASGVPSRFSGS GSGTDYTLTISSLQPEDFATYYCQQWSSNPPT FGGGTKLEIK (SEQ ID NO: 33) |
| Ab18 | QVQLVESGGGVVQPGGSLRLSCAVSGFSLTSYGIQWVRQAPGKGLEWVSVIWAGGSTNYNSALMSR FTISKDNSKSTLYLQMNSLRAEDTAVYYCARAY GYDGSWLAYWGQGTLVTVSS (SEQ ID NO: 29) | EIVLTQSPATLSLSPGERATLSCRASSSVSYM HWYQQKPGQAPRPLIFATSNLASGIPARFSGS GSGTDFTLTISSLEPEDFAVYYCQQWSSNPPT FGGGTKLEIK (SEQ ID NO: 30) |
| Ab19 | QVQLVESGGGVVQPGGSLRLSCAVSGFSLTSYGIQWVRQAPGKGLEWVSVIWAGGSTNYNSALMSR FTISKDNSKSTLYLQMNSLRAEDTAVYYCARAY GYDGSWLAYWGQGTLVTVSS (SEQ ID NO: 29) | QIVLTQSPATLSLSPGERATLSCRASSSVSYM HWYQQKPGQAPRPLIFATSNLASGIPARFSGS GSGTDYTLTISSLEPEDFAVYYCQQWSSNPPT FGGGTKLEIK (SEQ ID NO: 31) |
| Ab20 | QVQLVESGGGVVQPGGSLRLSCAVSGFSLTSYGIQWVRQAPGKGLEWVSVIWAGGSTNYNSALMSR FTISKDNSKSTLYLQMNSLRAEDTAVYYCARAY GYDGSWLAYWGQGTLVTVSS (SEQ ID NO: 29) | DIQMTQSPSSLSASVGDRVTITCRASSSVSYM HWYQQKPGKAPKPLIFATSNLASGVPSRFSGS GSGTDYTLTISSLQPEDFATYYCQQWSSNPPT FGGGTKLEIK (SEQ ID NO: 32) |
| Ab21 | QVQLVESGGGVVQPGGSLRLSCAVSGFSLTSYGIQWVRQAPGKGLEWVSVIWAGGSTNYNSALMSR FTISKDNSKSTLYLQMNSLRAEDTAVYYCARAY GYDGSWLAYWGQGTLVTVSS (SEQ ID NO: 29) | QIQLTQSPSSLSASVGDRVTITCRASSSVSYM HWYQQKPGKSPKPLIFATSNLASGVPSRFSGS GSGTDYTLTISSLQPEDFATYYCQQWSSNPPT FGGGTKLEIK (SEQ ID NO: 33) |

The sequences of the complementarity determining regions (CDRs; i.e., CDR1, CDR2, and CDR3), as indicated above, and framework regions (FRs) were defined according to Kabat numbering scheme.

The results of the epitope mapping indicated that Antibody 10, Antibody 11, Antibody 12, Antibody 12, Antibody 13, Antibody 14, Antibody 15, Antibody 16, Antibody 17, antibody 18, Antibody 19, Antibody 20, Antibody 21 bind human CD25 in the region from amino acids 150 to 163 (YQCVQGYRALHRGP) and amino acids 166 to 180 (SVCKMTHGKTRVVTQP) of SEQ ID NO: 1, and binds human CD25 extracellular protein sequences with a Kd value in the $10^{-8}$ M to $10^{-10}$ M range.

Figure 70:
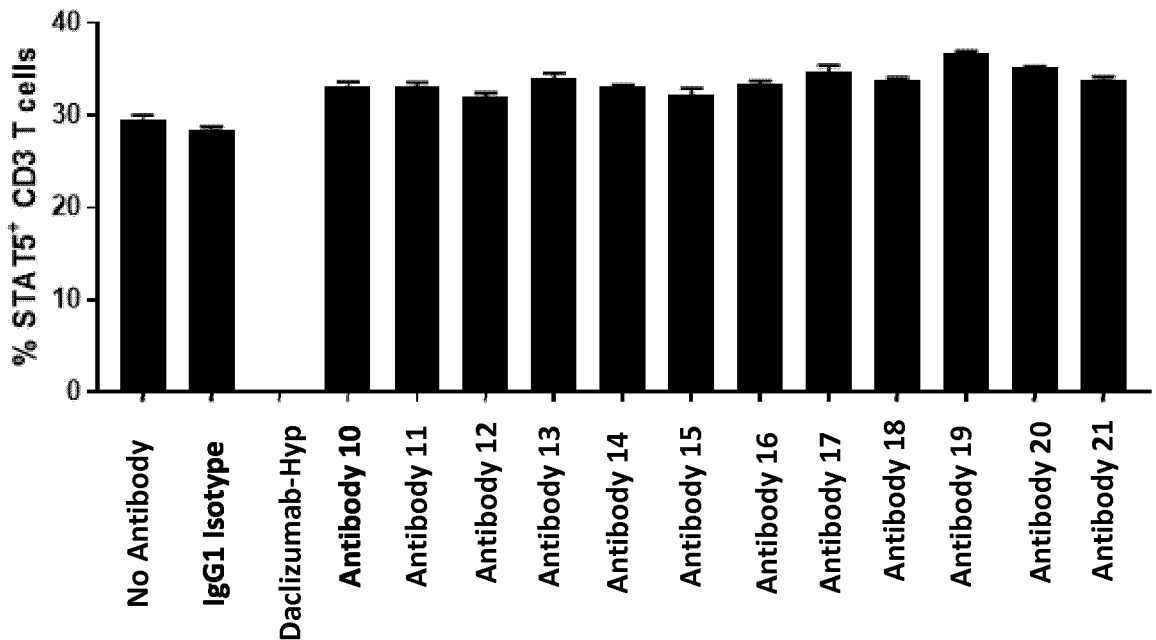
FIG. 70: Characterization of Antibody 10, Antibody 11, Antibody 12, Antibody 12, Antibody 13, Antibody 14, Antibody 15, Antibody 16, Antibody 17, antibody 18, Antibody 19, Antibody 20 and Antibody 21 compared to human IgG1 isotype control, Daclizumab-Hyp, or in the absence of a primary antibody in respect to blocking IL-2 signalling in a STAT5 phosphorylation assay using PBMCs of human origin. Cells were incubated with 10 μg/ml antibody followed by 10 U/ml of IL-2. Analysis was restricted to percentage of CD3-positive cells phosphorylating STAT5.
Figure 71:
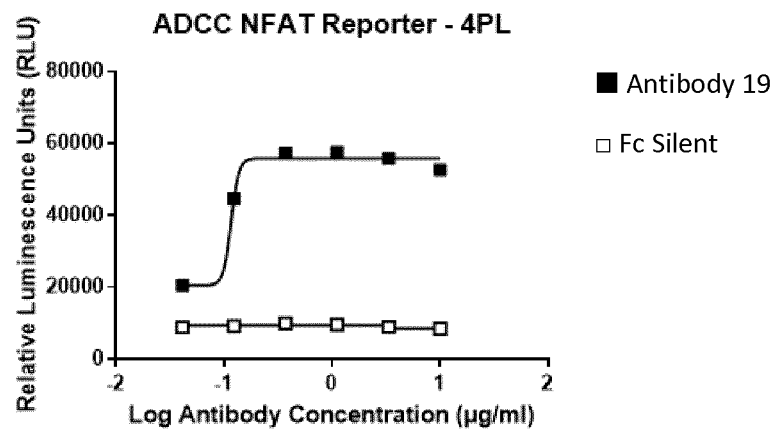
FIG. 71: Functional characterization of Antibody 19 compared to an anti-human CD25 Fc silent control antibody in respect to inducing ADCC in a Reporter Bioassay. CD25 expressing SR-786 cells were co-cultured with Jurkat T cells genetically engineered to express FcγRIIIa and an NFAT-response element that drives luciferase expression (NFAT-RE-luc2) in the presence of varying concentrations of antibodies (as shown in the Figures).

The Antibodies were evaluated with respect to its ability to not interfere with IL-2 signalling and its capacity to kill of CD25 expressing target cells. The results of the binding to rhCD25, are shown in FIG. 68. The STAT5 assay showed that the Antibodies did not block IL-2 signalling tested while IL-2 signalling was completely blocked by the antibody Daclizumab (FIG. 70). The competition assay showed that Antibody 19 does not compete with the IL-2 signal blockers Daclizumab or Basiliximab FIGS. 69(A) and (B). Finally, Antibody 12, Antibody 19 and Antibody 20 kill CD25 expressing cells, tumor cells or regulatory T cells, via ADCC (FIG. 71) and ADCP (FIGS. 72 and 73) when compared to an anti-human CD25 Fc silent control antibody.

In conclusion, Antibody 10, Antibody 11, Antibody 12, Antibody 12, Antibody 13, Antibody 14, Antibody 15, Antibody 16, Antibody 17, antibody 18, Antibody 19, Antibody 20, Antibody 21 have been characterized and demonstrates potent killing of CD25 positive cells (Tregs or cancer cell lines) and does not interfere with IL-2 signalling and consequently does not inhibit T effector responses. The Antibodies are thus Treg depleting antibodies which could be applied for the treatment of cancer, as monotherapy or in combination.

Example 12: Therapeutic Analysis in Combination with a Cancer Vaccine

The therapeutic activity of a non-IL-2 blocking anti-CD25 antibody, 7D4 mouse IgG2a, in combination with GVAX in a B16B16 immune therapy resistant mice model was determined. At day 0, $50 \times 10^3$ B16B16 cells were implanted i.d. At day 5, 200 µg non-IL-2 blocking anti-CD25 antibody was dosed i.p, or not. At days 6, 9 and 12 mice were treated, or not, with $1 \times 10^6$ irradiated (150 Gy) B16B16 cells adjuvanted with GM-CSF (GVAX). Tumour growth and mice survival was monitored until day 33. The results are shown in FIG. 74.

A synergistic effect was seen with a combination of GVAX and 7D4 non-blocking anti-CD25 antibody in a B161316 model. Therefore, the administration of 7D4 with a cancer vaccine boosted the vaccine-induced anti-tumour response. These results show that a non-IL2 blocking anti-CD25 depleting antibody can be use in combination with cancer vaccines for the treatment of cancer in human. Furthermore, this data shows that a non-IL2 blocking depleting antibody is able to enhance vaccine-induced immune responses, with potentially broader applications than cancer.

All publications mentioned in the above specification are herein incorporated by reference. Various modifications and variations of the described methods and system of the invention will be apparent to those skilled in the art without departing from the scope and spirit of the invention. Although the invention has been described in connection to specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

---

The invention claimed is:

1. A method of treating cancer in a human subject comprising the step of administering a human IgG1 anti-CD25 antibody to a subject, wherein said subject has a solid tumour, wherein said antibody does not inhibit the binding of Interleukin-2 (IL-2) to CD25.

2. The method according to claim 1 wherein the anti-CD25 antibody competes with the antibody 7G7B6 for binding to human CD25; and/or competes with the antibody MA251 for binding to human CD25.

3. The method according to claim 1 or claim 2 wherein the anti-CD25 antibody binds to the same epitope recognised by antibody 7G7B6 and/or the epitope recognised by antibody MA251.

4. The method according to claim 1 wherein the anti-CD25 antibody specifically binds to an epitope of human CD25 wherein the epitope comprises one or more amino acid residues comprised in one or more of the amino acid stretches selected from amino acids 150-163 of SEQ ID NO:1 (YQCVQGYRALHRGP), amino acids 166-186 of SEQ ID NO:1 (SVCKMTHGKTRWTQPQLICTG), amino acids 42-56 of SEQ ID NO:1 (KEGTMLNCECKRGFR) and amino acids 70-88 of SEQ ID NO:1 (NSSHSS-WDNQCQCTSSATR).

5. The method according to claim 1, wherein the anti-CD25 antibody is an IgG1 antibody that binds to at least one activating Fcγ receptor selected from FcγRI, FcγRIIc, and/or FcγRIIIa with high affinity, and depletes tumour-infiltrating regulatory T cells.

6. The method according to claim 1, wherein the anti-CD25 antibody:
  (a) binds to Fcγ receptors with an activatory to inhibitory ratio (A/I) superior to 1; and/or
  (b) binds to FcγRI, FcγRIIc, and/or FcγRIIIa with higher affinity than it binds to FcγRIIb.

7. The method according to claim 1, wherein the antibody is selected from the group consisting of:
  (a) an antibody comprising a heavy chain comprising the amino acid sequence of SEQ ID NO: 3 and the light chain comprising the amino acid sequence of SEQ ID NO:4;
  (b) an antibody comprising a heavy chain comprising the amino acid sequence of SEQ ID NO: 5 and the light chain comprising the amino acid sequence of SEQ ID NO: 6;
  (c) an antibody comprising a heavy chain comprising the amino acid sequence of SEQ ID NO: 10 and the light chain comprising the amino acid sequence of SEQ ID NO: 14;
  (d) an antibody comprising a heavy chain comprising the amino acid sequence of SEQ ID NO: 18 and the light chain comprising the amino acid sequence of SEQ ID NO: 22;
  (d) an antibody comprising a heavy chain comprising the amino acid sequence of SEQ ID NO: 23 and the light chain comprising the amino acid sequence of SEQ ID NO: 25;
  (e) an antibody comprising a heavy chain comprising the amino acid sequence of SEQ ID NO: 23 and the light chain comprising the amino acid sequence of SEQ ID NO: 26;
  (f) an antibody comprising a heavy chain comprising the amino acid sequence of SEQ ID NO: 24 and the light chain comprising the amino acid sequence of SEQ ID NO: 25;
  (g) an antibody comprising a heavy chain comprising the amino acid sequence of SEQ ID NO: 24 and the light chain comprising the amino acid sequence of SEQ ID NO: 26;
  (h) an antibody comprising a heavy chain comprising the amino acid sequence of SEQ ID NO: 27 and the light chain comprising the amino acid sequence of SEQ ID NO: 30;
  (i) an antibody comprising a heavy chain comprising the amino acid sequence of SEQ ID NO: 27 and the light chain comprising the amino acid sequence of SEQ ID NO: 31;
  (j) an antibody comprising a heavy chain comprising the amino acid sequence of SEQ ID NO: 27 and the light chain comprising the amino acid sequence of SEQ ID NO: 32;
  (k) an antibody comprising a heavy chain comprising the amino acid sequence of SEQ ID NO: 27 and the light chain comprising the amino acid sequence of SEQ ID NO: 33;
  (l) an antibody comprising a heavy chain comprising the amino acid sequence of SEQ ID NO: 28 and the light chain comprising the amino acid sequence of SEQ ID NO: 30;
  (m) an antibody comprising a heavy chain comprising the amino acid sequence of SEQ ID NO: 28 and the light chain comprising the amino acid sequence of SEQ ID NO: 31;
  (n) an antibody comprising a heavy chain comprising the amino acid sequence of SEQ ID NO: 28 and the light chain comprising the amino acid sequence of SEQ ID NO: 32;
  (o) an antibody comprising a heavy chain comprising the amino acid sequence of SEQ ID NO: 28 and the light chain comprising the amino acid sequence of SEQ ID NO: 33;
  (p) an antibody comprising a heavy chain comprising the amino acid sequence of SEQ ID NO: 29 and the light chain comprising the amino acid sequence of SEQ ID NO: 30;
  (q) an antibody comprising a heavy chain comprising the amino acid sequence of SEQ ID NO: 29 and the light chain comprising the amino acid sequence of SEQ ID NO: 31;
  (r) an antibody comprising a heavy chain comprising the amino acid sequence of SEQ ID NO: 29 and the light chain comprising the amino acid sequence of SEQ ID NO: 32; and (s) an antibody comprising a heavy chain comprising the amino acid sequence of SEQ ID NO: 29 and the light chain comprising the amino acid sequence of SEQ ID NO: 33.

8. The method according to claim 1, wherein the anti-CD25 antibody has a dissociation constant (Kd) for CD25 of between $10^{-7}$ M and $10^{-13}$ M.

9. The method according to claim 1, wherein the anti-CD25 antibody inhibits IL-2 signalling by less than 50%.

10. The method according to claim 1, wherein the anti-CD25 antibody is a monoclonal antibody.

11. The method according to claim 1, wherein the anti-CD25 antibody is a human, chimeric, or humanized antibody.

12. The method according to claim 1, wherein the anti-CD25 antibody is an affinity-matured variant thereof.

13. The method according to claim 1, wherein said method further comprises administering an immune checkpoint inhibitor to said subject.

14. The method according to claim 1, wherein said method further comprises administering a cancer vaccine.

15. The method according to claim 14 wherein the cancer vaccine is a GVAX cancer vaccine.

16. A method of depleting regulatory T cells in a subject comprising the step of administering an anti-CD25 antibody to the subject wherein the subject has a solid tumor, wherein the antibody is as defined claim 1.

* * * * *

SEQUENCE LISTING

```
<160> NUMBER OF SEQ ID NOS: 45

<210> SEQ ID NO 1
<211> LENGTH: 272
<212> TYPE: PRT
<213> ORGANISM: homosapien

<400> SEQUENCE: 1

Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
        50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
        115                 120                 125

Pro Pro Trp Glu Asn Glu Ala Thr Glu Arg Ile Tyr His Phe Val Val
    130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
        195                 200                 205
```

```
Ser Glu Thr Ser Cys Leu Val Thr Thr Thr Asp Phe Gln Ile Gln Thr
    210             215                 220
Glu Met Ala Ala Thr Met Glu Thr Ser Ile Phe Thr Thr Glu Tyr Gln
225                 230                 235                 240
Val Ala Val Ala Gly Cys Val Phe Leu Leu Ile Ser Val Leu Leu Leu
            245                 250                 255
Ser Gly Leu Thr Trp Gln Arg Arg Gln Arg Lys Ser Arg Arg Thr Ile
            260                 265                 270

<210> SEQ ID NO 2
<211> LENGTH: 219
<212> TYPE: PRT
<213> ORGANISM: homosapien

<400> SEQUENCE: 2

Glu Leu Cys Asp Asp Asp Pro Pro Glu Ile Pro His Ala Thr Phe Lys
1               5                   10                  15
Ala Met Ala Tyr Lys Glu Gly Thr Met Leu Asn Cys Glu Cys Lys Arg
            20                  25                  30
Gly Phe Arg Arg Ile Lys Ser Gly Ser Leu Tyr Met Leu Cys Thr Gly
        35                  40                  45
Asn Ser Ser His Ser Ser Trp Asp Asn Gln Cys Gln Cys Thr Ser Ser
    50                  55                  60
Ala Thr Arg Asn Thr Thr Lys Gln Val Thr Pro Gln Pro Glu Glu Gln
65                  70                  75                  80
Lys Glu Arg Lys Thr Thr Glu Met Gln Ser Pro Met Gln Pro Val Asp
                85                  90                  95
Gln Ala Ser Leu Pro Gly His Cys Arg Glu Pro Pro Pro Trp Glu Asn
            100                 105                 110
Glu Ala Thr Glu Arg Ile Tyr His Phe Val Val Gly Gln Met Val Tyr
        115                 120                 125
Tyr Gln Cys Val Gln Gly Tyr Arg Ala Leu His Arg Gly Pro Ala Glu
    130                 135                 140
Ser Val Cys Lys Met Thr His Gly Lys Thr Arg Trp Thr Gln Pro Gln
145                 150                 155                 160
Leu Ile Cys Thr Gly Glu Met Glu Thr Ser Gln Phe Pro Gly Glu Glu
                165                 170                 175
Lys Pro Gln Ala Ser Pro Glu Gly Arg Pro Glu Ser Glu Thr Ser Cys
            180                 185                 190
Leu Val Thr Thr Thr Asp Phe Gln Ile Gln Thr Glu Met Ala Ala Thr
        195                 200                 205
Met Glu Thr Ser Ile Phe Thr Thr Glu Tyr Gln
    210                 215

<210> SEQ ID NO 3
<211> LENGTH: 123
<212> TYPE: PRT
<213> ORGANISM: murine

<400> SEQUENCE: 3

Glu Val Gln Leu Val Glu Ser Gly Gly Asp Leu Val Gln Pro Arg Gly
1               5                   10                  15
Ser Leu Lys Leu Ser Cys Ala Ala Ser Gly Phe Thr Phe Ser Ser Tyr
            20                  25                  30
Gly Met Ser Trp Val Arg Gln Thr Pro Asp Lys Arg Leu Glu Leu Val
        35                  40                  45
```

Ala Thr Ile Asn Gly Tyr Gly Asp Thr Thr Tyr Tyr Pro Asp Ser Val
            50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Phe Cys
                85                  90                  95

Ala Arg Asp Arg Asp Tyr Gly Asn Ser Tyr Tyr Tyr Ala Leu Asp Tyr
            100                 105                 110

Trp Gly Gln Gly Thr Ser Val Thr Val Ser Ser
            115                 120

<210> SEQ ID NO 4
<211> LENGTH: 106
<212> TYPE: PRT
<213> ORGANISM: murine

<400> SEQUENCE: 4

Gln Ile Val Leu Ser Gln Ser Pro Ala Ile Leu Ser Ala Ser Pro Gly
1               5                   10                  15

Glu Arg Val Thr Met Thr Cys Arg Ala Ser Ser Ser Val Ser Phe Met
            20                  25                  30

His Trp Leu Gln Gln Lys Pro Gly Ser Ser Pro Lys Pro Trp Ile Tyr
        35                  40                  45

Ala Thr Ser Asn Leu Ala Ser Gly Val Ser Ala Arg Phe Ser Gly Ser
    50                  55                  60

Gly Ser Gly Thr Ser Tyr Ser Leu Thr Ile Thr Arg Val Glu Ala Glu
65                  70                  75                  80

Asp Ala Ala Thr Tyr Tyr Cys Gln Gln Trp Ser Ser Asn Pro Pro Ala
                85                  90                  95

Phe Gly Gly Gly Thr Lys Leu Glu Ile Lys
            100                 105

<210> SEQ ID NO 5
<211> LENGTH: 119
<212> TYPE: PRT
<213> ORGANISM: murine

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Ile Gln Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Ala Tyr Gly Tyr Asp Gly Ser Trp Leu Ala Tyr Trp Gly Gln Gly
            100                 105                 110

Thr Leu Val Thr Val Ser Ser
        115

<210> SEQ ID NO 6

```
<211> LENGTH: 106
<212> TYPE: PRT
<213> ORGANISM: murine

<400> SEQUENCE: 6

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Phe
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Asn Arg Val Glu Ala Glu
65                  70                  75                  80

Asp Ala Asp Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 7
<211> LENGTH: 10
<212> TYPE: PRT
<213> ORGANISM: murine

<400> SEQUENCE: 7

Gly Phe Thr Leu Asp Ser Tyr Gly Val Ser
1               5                   10

<210> SEQ ID NO 8
<211> LENGTH: 15
<212> TYPE: PRT
<213> ORGANISM: murine

<400> SEQUENCE: 8

Gly Val Thr Ser Ser Gly Gly Ser Ala Tyr Tyr Ala Asp Ser Val
1               5                   10                  15

<210> SEQ ID NO 9
<211> LENGTH: 17
<212> TYPE: PRT
<213> ORGANISM: murine

<400> SEQUENCE: 9

Asp Arg Tyr Val Tyr Thr Gly Gly Tyr Leu Tyr His Tyr Gly Met Asp
1               5                   10                  15

Leu

<210> SEQ ID NO 10
<211> LENGTH: 125
<212> TYPE: PRT
<213> ORGANISM: murine

<400> SEQUENCE: 10

Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Leu Asp Ser Tyr
            20                  25                  30

Gly Val Ser Trp Val Arg Gln Ala Pro Gly Lys Gly Leu Glu Trp Val
        35                  40                  45
```

```
Gly Val Thr Ser Ser Gly Ser Ala Tyr Tyr Ala Asp Ser Val Lys
    50              55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Arg Tyr Val Tyr Thr Gly Tyr Leu Tyr His Tyr Gly Met
            100                 105                 110

Asp Leu Trp Gly Gln Gly Thr Leu Val Thr Val Ser Ser
            115                 120                 125
```

<210> SEQ ID NO 11
<211> LENGTH: 11
<212> TYPE: PRT
<213> ORGANISM: murine

<400> SEQUENCE: 11

```
Arg Ala Ser Gln Ser Ile Ser Asp Tyr Leu Ala
1               5                   10
```

<210> SEQ ID NO 12
<211> LENGTH: 8
<212> TYPE: PRT
<213> ORGANISM: murine

<400> SEQUENCE: 12

```
Tyr Ala Ala Ser Thr Leu Pro Phe
1               5
```

<210> SEQ ID NO 13
<211> LENGTH: 12
<212> TYPE: PRT
<213> ORGANISM: murine

<400> SEQUENCE: 13

```
Gln Gly Thr Tyr Asp Ser Ser Asp Trp Tyr Trp Ala
1               5                   10
```

<210> SEQ ID NO 14
<211> LENGTH: 109
<212> TYPE: PRT
<213> ORGANISM: murine

<400> SEQUENCE: 14

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
                20                  25                  30

Leu Ala Trp Tyr Gln Gln Lys Pro Gly Lys Val Pro Lys Leu Leu Ile
            35                  40                  45

Tyr Ala Ala Ser Thr Leu Pro Phe Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gly Thr Tyr Asp Ser Ser Asp
                85                  90                  95

Trp Tyr Trp Ala Phe Gly Gly Gly Thr Lys Val Glu Ile
            100                 105
```

<210> SEQ ID NO 15

```
<211> LENGTH: 11
<212> TYPE: PRT
<213> ORGANISM: murine

<400> SEQUENCE: 15

Ser Gly Phe Ser Val Asp Ile Tyr Asp Met Ser
1               5                   10

<210> SEQ ID NO 16
<211> LENGTH: 15
<212> TYPE: PRT
<213> ORGANISM: murine

<400> SEQUENCE: 16

Tyr Ile Ser Ser Ser Leu Gly Ala Thr Tyr Tyr Ala Asp Ser Val
1               5                   10                  15

<210> SEQ ID NO 17
<211> LENGTH: 16
<212> TYPE: PRT
<213> ORGANISM: murine

<400> SEQUENCE: 17

Glu Arg Ile Tyr Ser Val Tyr Thr Leu Asp Tyr Tyr Ala Met Asp Leu
1               5                   10                  15

<210> SEQ ID NO 18
<211> LENGTH: 125
<212> TYPE: PRT
<213> ORGANISM: murine

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Val Asp Ile Tyr
            20                  25                  30

Asp Met Ser Trp Val Arg Gln Ala Pro Gly Lys Gly Leu Glu Trp Val
        35                  40                  45

Ala Tyr Ile Ser Ser Ser Leu Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Tyr Ser Val Tyr Thr Leu Asp Tyr Tyr Ala Met
            100                 105                 110

Asp Leu Trp Gly Gln Gly Thr Leu Val Thr Val Ser Ser
        115                 120                 125

<210> SEQ ID NO 19
<211> LENGTH: 11
<212> TYPE: PRT
<213> ORGANISM: murine

<400> SEQUENCE: 19

Gln Ala Ser Gln Gly Ile Thr Asn Asn Leu Asn
1               5                   10

<210> SEQ ID NO 20
<211> LENGTH: 8
<212> TYPE: PRT
<213> ORGANISM: murine
```

```
<400> SEQUENCE: 20

Tyr Ala Ala Ser Thr Leu Gln Ser
1               5

<210> SEQ ID NO 21
<211> LENGTH: 12
<212> TYPE: PRT
<213> ORGANISM: murine

<400> SEQUENCE: 21

Gln Gln Gly Tyr Thr Thr Ser Asn Val Asp Asn Ala
1               5                   10

<210> SEQ ID NO 22
<211> LENGTH: 110
<212> TYPE: PRT
<213> ORGANISM: murine

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Thr Asn Asn
            20                  25                  30

Leu Asn Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Thr Thr Ser Asn
                85                  90                  95

Val Asp Asn Ala Phe Gly Gly Gly Thr Lys Val Glu Ile Lys
            100                 105                 110

<210> SEQ ID NO 23
<211> LENGTH: 123
<212> TYPE: PRT
<213> ORGANISM: murine

<400> SEQUENCE: 23

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ser Thr Ile Asn Gly Tyr Gly Asp Thr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Asp Tyr Gly Asn Ser Tyr Tyr Ala Leu Asp Tyr
            100                 105                 110

Trp Gly Gln Gly Thr Leu Val Thr Val Ser Ser
        115                 120
```

```
<210> SEQ ID NO 24
<211> LENGTH: 123
<212> TYPE: PRT
<213> ORGANISM: murine

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Leu Val
        35                  40                  45

Ser Thr Ile Asn Gly Tyr Gly Asp Thr Thr Tyr Tyr Pro Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Asp Arg Asp Tyr Gly Asn Ser Tyr Tyr Tyr Ala Leu Asp Tyr
            100                 105                 110

Trp Gly Gln Gly Thr Leu Val Thr Val Ser Ser
        115                 120

<210> SEQ ID NO 25
<211> LENGTH: 106
<212> TYPE: PRT
<213> ORGANISM: murine

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Phe Met
            20                  25                  30

His Trp Leu Gln Gln Lys Pro Gly Gln Ala Pro Arg Pro Leu Ile Tyr
        35                  40                  45

Ala Thr Ser Asn Leu Ala Ser Gly Ile Pro Asp Arg Phe Ser Gly Ser
50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Ser Asn Pro Pro Ala
                85                  90                  95

Phe Gly Gln Gly Thr Lys Leu Glu Ile Lys
            100                 105

<210> SEQ ID NO 26
<211> LENGTH: 106
<212> TYPE: PRT
<213> ORGANISM: murine

<400> SEQUENCE: 26

Gln Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Phe Met
            20                  25                  30

His Trp Leu Gln Gln Lys Pro Gly Gln Ser Pro Arg Pro Leu Ile Tyr
        35                  40                  45

Ala Thr Ser Asn Leu Ala Ser Gly Ile Pro Asp Arg Phe Ser Gly Ser
50                  55                  60
```

```
Gly Ser Gly Thr Asp Tyr Thr Leu Thr Ile Ser Arg Leu Glu Pro Glu
65                  70                  75                  80

Asp Phe Ala Val Tyr Tyr Cys Gln Gln Trp Ser Ser Asn Pro Pro Ala
                85                  90                  95

Phe Gly Gln Gly Thr Lys Leu Glu Ile Lys
            100                 105
```

<210> SEQ ID NO 27
<211> LENGTH: 119
<212> TYPE: PRT
<213> ORGANISM: homosapien

<400> SEQUENCE: 27

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile Gln Trp Ile Arg Gln Pro Pro Gly Lys Gly Leu Glu Trp Ile
        35                  40                  45

Gly Val Ile Trp Ala Gly Gly Ser Thr Asn Tyr Asn Ser Ala Leu Met
    50                  55                  60

Ser Arg Val Thr Ile Ser Lys Asp Asn Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Tyr Asp Gly Ser Trp Leu Ala Tyr Trp Gly Gln Gly
            100                 105                 110

Thr Leu Val Thr Val Ser Ser
        115
```

<210> SEQ ID NO 28
<211> LENGTH: 119
<212> TYPE: PRT
<213> ORGANISM: murine

<400> SEQUENCE: 28

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Ile Gln Trp Val Arg Gln Pro Pro Gly Lys Gly Leu Glu Trp Ile
        35                  40                  45

Gly Val Ile Trp Ala Gly Gly Ser Thr Asn Tyr Asn Ser Ala Leu Met
    50                  55                  60

Ser Arg Val Thr Ile Ser Lys Asp Asn Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Ala Tyr Gly Tyr Asp Gly Ser Trp Leu Ala Tyr Trp Gly Gln Gly
            100                 105                 110

Thr Leu Val Thr Val Ser Ser
        115
```

<210> SEQ ID NO 29
<211> LENGTH: 119
<212> TYPE: PRT
<213> ORGANISM: murine

<400> SEQUENCE: 29

Gln Val Gln Leu Val Glu Ser Gly Gly Val Val Gln Pro Gly Gly
1               5                   10                  15

Ser Leu Arg Leu Ser Cys Ala Val Ser Gly Phe Ser Leu Thr Ser Tyr
            20                  25                  30

Gly Ile Gln Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Ser Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Tyr Gly Tyr Asp Gly Ser Trp Leu Ala Tyr Trp Gly Gln Gly
            100                 105                 110

Thr Leu Val Thr Val Ser Ser
        115

<210> SEQ ID NO 30
<211> LENGTH: 106
<212> TYPE: PRT
<213> ORGANISM: murine

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Leu Ile Phe
        35                  40                  45

Ala Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 31
<211> LENGTH: 106
<212> TYPE: PRT
<213> ORGANISM: murine

<400> SEQUENCE: 31

Gln Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Pro Leu Ile Phe
        35                  40                  45

Ala Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

```
Asp Phe Ala Val Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 32
<211> LENGTH: 106
<212> TYPE: PRT
<213> ORGANISM: murine

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Pro Leu Ile Phe
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 33
<211> LENGTH: 106
<212> TYPE: PRT
<213> ORGANISM: murine

<400> SEQUENCE: 33

Gln Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ser Pro Lys Pro Leu Ile Phe
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 34
<211> LENGTH: 139
<212> TYPE: PRT
<213> ORGANISM: murine

<400> SEQUENCE: 34

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Ala Glu Leu Val
            20                  25                  30

Arg Pro Gly Thr Ser Val Lys Leu Ser Cys Lys Val Ser Gly Asp Thr
```

```
            35                  40                  45
Ile Thr Ala Tyr Tyr Ile His Phe Val Lys Gln Arg Pro Gly Gln Gly
    50                  55                  60

Leu Glu Trp Ile Gly Arg Ile Asp Pro Glu Asp Asp Ser Thr Glu Tyr
65                  70                  75                  80

Ala Glu Lys Phe Lys Asn Lys Ala Thr Ile Thr Ala Asn Thr Ser Ser
                85                  90                  95

Asn Thr Ala His Leu Lys Tyr Ser Arg Leu Thr Ser Glu Asp Thr Ala
            100                 105                 110

Thr Tyr Phe Cys Thr Thr Asp Asn Met Gly Ala Thr Glu Phe Val Tyr
        115                 120                 125

Trp Gly Gln Gly Thr Leu Val Thr Val Ser Ser
        130                 135

<210> SEQ ID NO 35
<211> LENGTH: 129
<212> TYPE: PRT
<213> ORGANISM: murine

<400> SEQUENCE: 35

Met Glu Thr Asp Thr Leu Leu Leu Trp Val Leu Leu Leu Trp Val Pro
1               5                   10                  15

Gly Ser Thr Gly Gln Val Val Leu Thr Gln Pro Lys Ser Val Ser Ala
            20                  25                  30

Ser Leu Glu Ser Thr Val Lys Leu Ser Cys Lys Leu Asn Ser Gly Asn
        35                  40                  45

Ile Gly Ser Tyr Tyr Met His Trp Tyr Gln Gln Arg Glu Gly Arg Ser
    50                  55                  60

Pro Thr Asn Leu Ile Tyr Arg Asp Asp Lys Arg Pro Asp Gly Ala Pro
65                  70                  75                  80

Asp Arg Phe Ser Gly Ser Ile Asp Ile Ser Ser Asn Ser Ala Phe Leu
                85                  90                  95

Thr Ile Asn Asn Val Gln Thr Glu Asp Glu Ala Met Tyr Phe Cys His
            100                 105                 110

Ser Tyr Asp Gly Arg Met Tyr Ile Phe Gly Gly Gly Thr Lys Leu Thr
        115                 120                 125

Val

<210> SEQ ID NO 36
<211> LENGTH: 438
<212> TYPE: PRT
<213> ORGANISM: murine

<400> SEQUENCE: 36

Glu Val Gln Leu Gln Gln Ser Gly Ala Ala Leu Val Lys Pro Gly Ala
1               5                   10                  15

Ser Val Lys Met Ser Cys Lys Ala Ser Gly Tyr Ser Phe Pro Asp Ser
            20                  25                  30

Trp Val Thr Trp Val Lys Gln Ser His Gly Lys Ser Leu Glu Trp Ile
        35                  40                  45

Gly Asp Ile Phe Pro Asn Ser Gly Ala Thr Asn Phe Asn Glu Lys Phe
    50                  55                  60

Lys Gly Lys Ala Thr Leu Thr Val Asp Lys Ser Thr Ser Thr Ala Tyr
65                  70                  75                  80

Met Glu Leu Ser Arg Leu Thr Ser Glu Asp Ser Ala Ile Tyr Tyr Cys
                85                  90                  95
```

```
Thr Arg Leu Asp Tyr Gly Tyr Trp Gly Gln Gly Val Met Val Thr Val
            100                 105                 110

Ser Ser Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Gln
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220

Val Pro Glu Val Ser Ser Val Phe Ile Phe Pro Pro Lys Pro Lys Asp
225                 230                 235                 240

Val Leu Met Ile Ser Leu Thr Pro Lys Val Thr Cys Val Val Val Asp
                245                 250                 255

Ile Ser Lys Asp Asp Pro Glu Val Gln Phe Ser Trp Phe Val Asp Asp
            260                 265                 270

Val Glu Val His Thr Ala Gln Thr Lys Pro Arg Glu Glu Gln Ile Asn
        275                 280                 285

Ser Thr Phe Arg Ser Val Ser Glu Leu Pro Ile Leu His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Lys Glu Gln Met Ala Lys Asp
            340                 345                 350

Lys Val Ser Leu Thr Cys Met Ile Thr Asn Phe Phe Pro Glu Asp Ile
        355                 360                 365

Thr Val Glu Trp Gln Trp Asn Gly Gln Pro Ala Glu Asn Tyr Lys Asn
    370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His Thr Glu Lys Ser Leu
            420                 425                 430

Ser His Ser Pro Gly Lys
        435

<210> SEQ ID NO 37
<211> LENGTH: 444
<212> TYPE: PRT
<213> ORGANISM: murine

<400> SEQUENCE: 37

Glu Val Gln Leu Gln Gln Ser Gly Ala Ala Leu Val Lys Pro Gly Ala
1               5                   10                  15

Ser Val Lys Met Ser Cys Lys Ala Ser Gly Tyr Ser Phe Pro Asp Ser
```

-continued

```
            20                  25                  30
Trp Val Thr Trp Val Lys Gln Ser His Gly Lys Ser Leu Glu Trp Ile
         35                  40                  45
Gly Asp Ile Phe Pro Asn Ser Gly Ala Thr Asn Phe Asn Glu Lys Phe
 50                  55                  60
Lys Gly Lys Ala Thr Leu Thr Val Asp Lys Ser Thr Ser Thr Ala Tyr
 65                  70                  75                  80
Met Glu Leu Ser Arg Leu Thr Ser Glu Asp Ser Ala Ile Tyr Tyr Cys
                 85                  90                  95
Thr Arg Leu Asp Tyr Gly Tyr Trp Gly Gln Gly Val Met Val Thr Val
                100                 105                 110
Ser Ser Ala Lys Thr Thr Ala Pro Ser Val Tyr Pro Leu Ala Pro Val
                115                 120                 125
Cys Gly Asp Thr Thr Gly Ser Ser Val Thr Leu Gly Cys Leu Val Lys
                130                 135                 140
Gly Tyr Phe Pro Glu Pro Val Thr Leu Thr Trp Asn Ser Gly Ser Leu
145                 150                 155                 160
Ser Ser Gly Val His Thr Phe Pro Ala Val Leu Gln Ser Asp Leu Tyr
                165                 170                 175
Thr Leu Ser Ser Ser Val Thr Val Thr Ser Ser Thr Trp Pro Ser Gln
                180                 185                 190
Ser Ile Thr Cys Asn Val Ala His Pro Ala Ser Ser Thr Lys Val Asp
                195                 200                 205
Lys Lys Ile Glu Pro Arg Gly Pro Thr Ile Lys Pro Cys Pro Pro Cys
                210                 215                 220
Lys Cys Pro Ala Pro Asn Leu Leu Gly Gly Pro Ser Val Phe Ile Phe
225                 230                 235                 240
Pro Pro Lys Ile Lys Asp Val Leu Met Ile Ser Leu Ser Pro Ile Val
                245                 250                 255
Thr Cys Val Val Val Asp Val Ser Glu Asp Asp Pro Asp Val Gln Ile
                260                 265                 270
Ser Trp Phe Val Asn Asn Val Glu Val His Thr Ala Gln Thr Gln Thr
                275                 280                 285
His Arg Glu Asp Tyr Asn Ser Thr Leu Arg Val Val Ser Ala Leu Pro
                290                 295                 300
Ile Gln His Gln Asp Trp Met Ser Gly Lys Glu Phe Lys Cys Lys Val
305                 310                 315                 320
Asn Asn Lys Asp Leu Pro Ala Pro Ile Glu Arg Thr Ile Ser Lys Pro
                325                 330                 335
Lys Gly Ser Val Arg Ala Pro Gln Val Tyr Val Leu Pro Pro Pro Glu
                340                 345                 350
Glu Glu Met Thr Lys Lys Gln Val Thr Leu Thr Cys Met Val Thr Asp
                355                 360                 365
Phe Met Pro Glu Asp Ile Tyr Val Glu Trp Thr Asn Asn Gly Lys Thr
                370                 375                 380
Glu Leu Asn Tyr Lys Asn Thr Glu Pro Val Leu Asp Ser Asp Gly Ser
385                 390                 395                 400
Tyr Phe Met Tyr Ser Lys Leu Arg Val Glu Lys Asn Trp Val Glu
                405                 410                 415
Arg Asn Ser Tyr Ser Cys Ser Val Val His Glu Gly Leu His Asn His
                420                 425                 430
His Thr Thr Lys Ser Phe Ser Arg Thr Pro Gly Lys
                435                 440
```

<210> SEQ ID NO 38
<211> LENGTH: 219
<212> TYPE: PRT
<213> ORGANISM: murine

<400> SEQUENCE: 38

Asp Val Val Leu Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Asn Gly Asn Thr Tyr Leu Asn Trp Leu Leu Gln Arg Pro Gly Gln Pro
        35                  40                  45

Pro Gln Leu Leu Ile Tyr Leu Ala Ser Arg Leu Glu Ser Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Ser
                85                  90                  95

Ser His Phe Pro Asn Thr Phe Gly Val Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 39
<211> LENGTH: 114
<212> TYPE: PRT
<213> ORGANISM: murine

<400> SEQUENCE: 39

Glu Val Gln Leu Val Glu Ser Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Gly Met Ala Trp Val Arg Gln Ala Pro Thr Lys Gly Leu Glu Trp Val
        35                  40                  45

Ala Ser Ile Thr Asn Gly Gly Leu Asn Thr Tyr Tyr Arg Asp Ser Val
    50                  55                  60

Lys Gly Arg Phe Thr Ile Ser Arg Asp Asn Ala Lys Cys Thr Leu Tyr
65                  70                  75                  80

Leu Gln Met Asp Ser Leu Arg Ser Glu Asp Thr Ala Thr Tyr Tyr Cys
                85                  90                  95

Ala Thr Gly Gly Phe Ser Phe Trp Gly Gln Gly Thr Leu Val Thr Val
            100                 105                 110

-continued

Ser Ser

<210> SEQ ID NO 40
<211> LENGTH: 107
<212> TYPE: PRT
<213> ORGANISM: murine

<400> SEQUENCE: 40

Asp Ile Val Met Thr Gln Ser Pro Thr Ser Met Ser Ile Ser Val Gly
1               5                   10                  15

Asp Arg Val Thr Met Asn Cys Lys Ala Ser Gln Asn Val Asp Ser Asn
            20                  25                  30

Val Asp Trp Tyr Gln Gln Lys Thr Gly Gln Ser Pro Lys Leu Leu Ile
        35                  40                  45

Tyr Lys Ala Ser Asn Arg Tyr Thr Gly Val Pro Asp Arg Phe Thr Gly
    50                  55                  60

Ser Gly Ser Gly Thr Asp Phe Thr Phe Thr Ile Arg Asn Met Gln Ala
65                  70                  75                  80

Glu Asp Leu Ala Val Tyr Tyr Cys Met Gln Ser Asn Ser Tyr Pro Leu
                85                  90                  95

Thr Phe Gly Ser Gly Thr Lys Leu Glu Ile Lys
            100                 105

<210> SEQ ID NO 41
<211> LENGTH: 9
<212> TYPE: PRT
<213> ORGANISM: murine

<400> SEQUENCE: 41

Tyr Glu Cys Ile Pro Gly Tyr Lys Ala
1               5

<210> SEQ ID NO 42
<211> LENGTH: 7
<212> TYPE: PRT
<213> ORGANISM: murine

<400> SEQUENCE: 42

Leu Thr Cys Val Asp Glu Arg
1               5

<210> SEQ ID NO 43
<211> LENGTH: 11
<212> TYPE: PRT
<213> ORGANISM: murine

<400> SEQUENCE: 43

Arg Glu His His Arg Phe Leu Ala Ser Glu Glu
1               5                   10

<210> SEQ ID NO 44
<211> LENGTH: 11
<212> TYPE: PRT
<213> ORGANISM: murine

<400> SEQUENCE: 44

Leu Asn Cys Glu Cys Lys Arg Gly Phe Arg Arg
1               5                   10

<210> SEQ ID NO 45
<211> LENGTH: 11

```
<212> TYPE: PRT
<213> ORGANISM: murine

<400> SEQUENCE: 45

Thr Ser Asn Ser His Asp Lys Ser Arg Lys Gln
1               5                   10
```